(12) United States Patent
Simon et al.

(10) Patent No.: US 9,416,141 B2
(45) Date of Patent: Aug. 16, 2016

(54) COMPOUNDS AND METHODS FOR PREVENTING, TREATING AND/OR PROTECTING AGAINST SENSORY HAIR CELL DEATH

(71) Applicants: University of Washington through its Center for Commercialization, Seattle, WA (US); Fred Hutchinson Cancer Research Center, Seattle, WA (US)

(72) Inventors: Julian Simon, Seattle, WA (US); Graham Johnson, Sanbornton, NH (US); Edwin Rubel, Seattle, WA (US); Sarwat Chowdhury, Seattle, WA (US); R. Jason Herr, Voorheesville, NY (US); Qin Jiang, Latham, NY (US); Xinchao Chen, Schenectady, NY (US); Kelly N Owens, Lake Forest Park, WA (US); David Raible, Seattle, WA (US)

(73) Assignees: University of Washington through its Center for Commercialization, Seattle, WA (US); Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 14/431,025

(22) PCT Filed: Sep. 27, 2013

(86) PCT No.: PCT/US2013/062440
§ 371 (c)(1),
(2) Date: Mar. 25, 2015

(87) PCT Pub. No.: WO2014/052914
PCT Pub. Date: Apr. 3, 2014

(65) Prior Publication Data
US 2015/0232476 A1 Aug. 20, 2015

Related U.S. Application Data

(60) Provisional application No. 61/784,410, filed on Mar. 14, 2013, provisional application No. 61/707,767, filed on Sep. 28, 2012.

(51) Int. Cl.
| | | |
|---|---|---|
| *A01N 43/42* | (2006.01) |
| *A61K 31/44* | (2006.01) |
| *C07D 495/04* | (2006.01) |
| *A61K 31/4365* | (2006.01) |
| *A61K 31/496* | (2006.01) |
| *A61K 31/5377* | (2006.01) |
| *C07D 495/08* | (2006.01) |
| *A61K 45/06* | (2006.01) |
| *A61K 31/70* | (2006.01) |

(52) U.S. Cl.
CPC .......... *C07D 495/04* (2013.01); *A61K 31/4365* (2013.01); *A61K 31/496* (2013.01); *A61K 31/5377* (2013.01); *A61K 31/70* (2013.01); *A61K 45/06* (2013.01); *C07D 495/08* (2013.01)

(58) Field of Classification Search
None
See application file for complete search history.

(56) References Cited

U.S. PATENT DOCUMENTS

| | | | |
|---|---|---|---|
| 4,174,396 A | 11/1979 | Jargue et al. |
| 4,327,725 A | 5/1982 | Cortese et al. |
| 4,624,848 A | 11/1986 | Lee |
| 4,871,549 A | 10/1989 | Ueda et al. |
| 4,968,509 A | 11/1990 | Radebaugh et al. |
| 5,011,692 A | 4/1991 | Fujioka et al. |
| 5,017,381 A | 5/1991 | Maruyama et al. |
| 5,229,135 A | 7/1993 | Philippon et al. |
| 5,260,068 A | 11/1993 | Chen |
| 5,260,069 A | 11/1993 | Chen |
| 5,456,923 A | 10/1995 | Nakamichi et al. |
| 5,461,140 A | 10/1995 | Heller et al. |
| 5,508,040 A | 4/1996 | Chen |
| 5,516,527 A | 5/1996 | Curatolo |
| 5,567,441 A | 10/1996 | Chen |
| 5,622,721 A | 4/1997 | Dansereau et al. |
| 5,686,105 A | 11/1997 | Kelm et al. |
| 5,700,410 A | 12/1997 | Nakamichi et al. |
| 5,837,284 A | 11/1998 | Mehta et al. |
| 5,840,329 A | 11/1998 | Bai et al. |
| 5,977,175 A | 11/1999 | Lin |
| 6,465,014 B1 | 10/2002 | Moroni et al. |
| 6,932,983 B1 | 8/2005 | Straub et al. |
| 2006/0188445 A1 | 8/2006 | Ou et al. |

FOREIGN PATENT DOCUMENTS

| | | | |
|---|---|---|---|
| ES | 462993 A1 | 6/1978 |
| GB | 1582688 A | 1/1981 |
| WO | WO 03/002569 A1 | 1/2003 |
| WO | WO 2005/023818 A2 | 3/2005 |
| WO | WO 2005/044008 A2 | 5/2005 |
| WO | WO 2005/048948 A2 | 6/2005 |
| WO | WO 2009/009550 A1 | 1/2009 |
| WO | WO 2012/082331 A1 | 6/2012 |

OTHER PUBLICATIONS

Allen, et al. Transient-evoked otoacoustic emissions in children after cisplatin chemotherapy. Otolaryngol Head Neck Surg. May 1998;118(5):584-8.
Berge, et al. Pharmaceutical salts. J Pharm Sci. Jan. 1977;66(1):1-19.
Bundgaard. Design of Prodrugs. Elsevier, Amsterdam. 1985.
Claessen, et al. Quinine pharmacokinetics: ototoxic and cardiotoxic effects in healthy Caucasian subjects and in patients with falciparum malaria. Trop Med Int Health. Jun. 1998;3(6):482-9.

(Continued)

*Primary Examiner* — Patrick Lewis
(74) *Attorney, Agent, or Firm* — Wilson Sonsini Goodrich & Rosati

(57) ABSTRACT

Disclosed herein are compounds, and pharmaceutical compositions that include such compounds, for preventing, treating, and/or protecting against sensory hair cell death. Methods of using the compounds, alone or in combination with other therapeutic agents, are also disclosed.

20 Claims, 5 Drawing Sheets

(56) References Cited

OTHER PUBLICATIONS

Dhanireddy, et al. Vestibular toxic effects induced by once-daily aminoglycoside therapy. Arch Otolaryngol Head Neck Surg. Jan. 2005;131(1):46-8.

Formann, et al. Sudden hearing loss in patients with chronic hepatitis C treated with pegylated interferon/ribavirin. Am J Gastroenterol. May 2004;99(5):873-7.

Greenberg. Diuretic complications. Am J Med Sci. Jan. 2000;319(1):10-24.

International search report and written opinion dated Nov. 13, 2013 for PCT/US2013/062440.

Liberman, et al. Pharmaceutical Dosage Forms, 2 Ed., vol. 1. 1990.

Matz. Clinical perspectives on ototoxic drugs. Ann Otol Rhinol Laryngol Suppl. Jun. 1990;148:39-41.

Singh, et al. Encyclopedia of Pharmaceutical Technology, 2nd Ed. 2002; 754-757.

Smith, et al. Controlled comparison of amikacin and gentamicin. N Engl J Med. Feb. 17, 1977;296(7):349-53.

Theopold. Comparative surface studies of ototoxic effects of various aminoglycoside antibiotics on the organ of Corti in the guinea pig. A scanning electron microscopic study. Acta Otolaryngol. Jul.-Aug. 1977;84(1-2):57-64.

Toovey, et al. Audiometric changes associated with the treatment of uncomplicated falciparum malaria with co-artemether. Trans R Soc Trop Med Hyg. May 2004;98(5):261-7; discussion 268-9.

Alvarez, et al. Benzomorphan related compounds. V. Synthesis of thienomorphans. Journal of Heterocyclic Chemistry. 1978; 15(2):193-201.

Bosch, et al. Compuestos relacionados con los benzomorfanos IX (1). Aplicacion del metodo de grewe a la sintesis de furomorfanos. Analas de Quimica 1979; 75(5):360-365. (in Spanish with English abstract).

Devani, et al. Synthesis of 2-aminothiophenes and thieno [2, 3-D] pyrimidines. Indian Journal of Chemistry Section B-Organic Chemistry including Medicinal Chemistry. 1976; 14B(5):357-360.

COMPOUNDS AND METHODS FOR PREVENTING, TREATING AND/OR PROTECTING AGAINST SENSORY HAIR CELL DEATH

CROSS REFERENCE

The present application is a U.S. National Phase Application under 35 U.S.C. §371 of International Application No. PCT/US2013/062440, filed Sep. 27, 2013, which claims the benefit of priority from U.S. provisional application Ser. No. 61/784,410, filed Mar. 14, 2013, and U.S. provisional application Ser. No. 61/707,767, filed Sep. 28, 2012; both of which are incorporated by reference in their entirety.

STATEMENT AS TO FEDERALLY SPONSORED RESEARCH

This invention was made with government support under Grants 5U01 NS074506, and 1R01 DC009807 awarded by the National Institutes of Health. The government has certain rights in the invention.

BACKGROUND

Aminoglcosides are clinically used drugs that cause dose-dependent sensorineural hearing loss (Smith et al., New Engl J Med, (1977) 296:349-53) and are known to kill hair cells in the mammalian inner ear (Theopold, Acta Otolaryngol (1977) 84:57-64). In the U.S. over 2,000,000 people receive treatment with aminoglycosides per year. The clinical efficacy of these drugs in treating resistant bacterial infections and their low cost globally account for their continued use and need. Cisplatin, a chemotherapeutic agent is also used for its benefit to life despite its toxic effects on the hair cells of the inner ear. High frequency hearing loss (>8 kHZ) has been reported to be as high as 90% in children undergoing cisplatin therapy (Allen, et al, Otolaryngol Head Neck Surg (1998) 118:584-588). The incidence of vestibulotoxic effects of such drugs on patient populations has been less well studied. Estimates range between 3% and 6% with continued reports in the literature of patients with aminoglycoside induced vestibulotoxicity (Dhanireddy et al., Arch Otolarngol Head Neck Surg (2005) 131:46-48). Other clinically important and commonly used drugs also have documented ototoxic effects, including loop diuretics (Greenberg, Am J Med Sci, (2000) 319:10-24), antimalarial sesquiterpene lactone endoperoxides (i.e., artemesinins) (Toovey and Jamieson, Trans R Soc Trop Med Hyg (2004) 98:261-7), antimalarial quinines (Claessen, et al., Trop Med Int Health, (1998) 3:482-9), salicylates (Matz, Ann Otol Rhinol Laryngol Suppl (1990) 148:39-41), and interferon polypeptides (Formann, et al., Am J Gastroenterol (2004) 99:873-77).

BRIEF SUMMARY OF THE INVENTION

Described herein are compounds of Formula (I), Formula (II), Formula (III), Formula (IV), Formula (V), Formula (VI), or Formula (VII) (hereinafter compounds of Formula (I)-(VII)), pharmaceutical compositions comprising said compounds, and methods of use thereof, for preventing, treating, and/or protecting against sensory hair cell death. In one aspect, compounds of Formula (I)-(VII) prevent sensory hair cell death. In another aspect, compounds of Formula (I)-(VII) treat sensory hair cell death. In another aspect, compounds of Formula (I)-(VII) protect against sensory hair cell death.

In another aspect, provided herein is a compound of Formula (I):

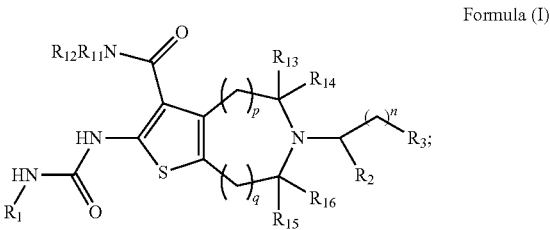

Formula (I)

wherein:
$R_1$ is $C_6$-$C_{10}$aryl or $C_3$-$C_9$heteroaryl, wherein $C_6$-$C_{10}$aryl and $C_3$-$C_9$heteroaryl are optionally substituted with one or more $R_4$;
$R_2$ is H, $C_1$-$C_4$alkyl, or $C_2$-$C_4$alkenyl;
$R_3$ is $C_2$-$C_6$alkyl, $C_2$-$C_6$alkenyl, $C_1$-$C_4$haloalkyl, optionally substituted $C_3$-$C_6$cycloalkyl, optionally substituted $C_2$-$C_7$heterocycloalkyl, optionally substituted $C_6$-$C_{10}$aryl, —$OR_6$, —$NR_5R_6$, —$C(O)R_7$, —$CO_2R_6$, —$C(O)NR_5R_6$, —$N(R_5)C(O)R_7$, —$N(R_5)CO_2R_7$, —$NHS(O)_2R_7$, —$S(O)_2NR_5R_6$,

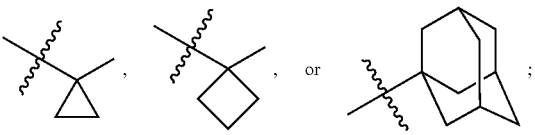

or
$R_2$ and $R_3$ together form an optionally substituted $C_2$-$C_7$heterocycloalkyl ring;
each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, $C_6$-$C_{10}$aryl, and $C_3$-$C_9$heteroaryl;
$R_5$ is H, or $C_1$-$C_6$alkyl;
$R_6$ is H, $C_1$-$C_6$alkyl, optionally substituted $C_3$-$C_6$cycloalkyl, optionally substituted $C_2$-$C_7$heterocycloalkyl, optionally substituted $C_6$-$C_{10}$aryl, optionally substituted $C_3$-$C_9$heteroaryl, optionally substituted $C_1$-$C_6$alkyl$C_6$-$C_{10}$aryl, or optionally substituted $C_1$-$C_6$alkyl$C_3$-$C_9$heteroaryl;
$R_7$ is $C_1$-$C_6$alkyl, optionally substituted $C_3$-$C_6$cycloalkyl, optionally substituted $C_2$-$C_7$heterocycloalkyl, optionally substituted $C_6$-$C_{10}$aryl, $C_3$-$C_9$heteroaryl, optionally substituted $C_1$-$C_6$alkyl$C_6$-$C_{10}$aryl, or optionally substituted $C_1$-$C_6$alkyl$C_3$-$C_9$heteroaryl;
$R_8$ is H, or $C_1$-$C_6$alkyl;
$R_9$ is H, $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;
$R_{10}$ is $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;
$R_{11}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl; or $R_{11}$ and $R_{12}$ together with the nitrogen to which they are attached form an optionally substituted $C_2$-$C_7$heterocycloalkyl ring;

$R_{13}$, $R_{14}$, $R_{15}$, and $R_{16}$ are each independently H, or $C_1$-$C_4$alkyl;

n is an integer selected from 0-4;

p is an integer selected from 0-3; and q is an integer selected from 0-3;

or a pharmaceutically acceptable salt, pharmaceutically acceptable solvate or hydrate, pharmaceutically acceptable salt hydrate, or pharmaceutically acceptable prodrug thereof.

In another aspect, provided herein is a compound of Formula (II):

Formula (II)

wherein:

$X^-$ is a pharmaceutically acceptable counterion;

$R_1$ is $C_6$-$C_{10}$aryl or $C_3$-$C_9$heteroaryl, wherein $C_6$-$C_{10}$aryl and $C_3$-$C_9$heteroaryl are optionally substituted with one or more $R_4$;

$R_2$ is $C_1$-$C_6$alkyl, $C_1$-$C_6$alkyl-$OR_5$, or $C_1$-$C_6$alkyl$C_3$-$C_6$cycloalkyl;

$R_3$ is $C_1$-$C_6$alkyl, $C_1$-$C_6$haloalkyl, $C_1$-$C_6$alkyl-$OR_5$, optionally substituted $C_1$-$C_6$alkyl$C_3$-$C_6$cycloalkyl, optionally substituted $C_2$-$C_7$heterocycloalkyl, $C_1$-$C_6$alkyl-$CO_2R_6$, $C_1$-$C_6$alkyl-$C(O)NR_5R_6$, , , or

;

or $R_2$ and $R_3$ together with the nitrogen to which they are attached form an optionally substituted $C_2$-$C_7$heterocycloalkyl ring;

each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, $C_6$-$C_{10}$aryl, and $C_3$-$C_9$heteroaryl;

each $R_5$ is independently H, or $C_1$-$C_6$alkyl;

$R_6$ is H, or $C_1$-$C_6$alkyl;

$R_8$ is H, or $C_1$-$C_6$alkyl;

$R_9$ is H, $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

$R_{10}$ is $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

$R_{11}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

or $R_{11}$ and $R_{12}$ together with the nitrogen to which they are attached form an optionally substituted $C_2$-$C_7$heterocycloalkyl ring;

$R_{13}$, $R_{14}$, $R_{15}$, and $R_{16}$ are each independently H, or $C_1$-$C_4$alkyl;

p is an integer selected from 0-3; and q is an integer selected from 0-3;

or a pharmaceutically acceptable salt, pharmaceutically acceptable solvate or hydrate, pharmaceutically acceptable salt hydrate, or pharmaceutically acceptable prodrug thereof.

In another aspect, provided herein is a compound of Formula (III):

Formula (III)

wherein:

X is a single bond, double bond, —$CH_2$—, or —O—;

$R_1$ is $C_6$-$C_{10}$aryl or $C_3$-$C_9$heteroaryl, wherein $C_6$-$C_{10}$aryl and $C_3$-$C_9$heteroaryl are optionally substituted with one or more $R_4$;

$R_2$ is H, $C_1$-$C_6$alkyl, $C_1$-$C_6$alkyl-$OR_6$, $C_1$-$C_6$alkyl$C_3$-$C_6$cycloalkyl, $C_1$-$C_6$alkyl$C_2$-$C_7$heterocycloalkyl, $C_1$-$C_6$alkyl-$CO_2R_6$, optionally substituted $C_1$-$C_6$alkyl$C_6$-$C_{10}$aryl, or optionally substituted $C_1$-$C_6$alkyl$C_3$-$C_9$heteroaryl;

$R_3$ are $R_5$ are each independently H, or $C_1$-$C_6$alkyl; or $R_3$ and $R_5$ together form an optionally substituted $C_3$-$C_6$cycloalkyl ring, optionally substituted $C_2$-$C_7$heterocycloalkyl ring, optionally substituted $C_6$-$C_{10}$aryl ring, or an optionally substituted $C_3$-$C_9$heteroaryl ring;

each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, $C_6$-$C_{10}$aryl, and $C_3$-$C_9$heteroaryl;

$R_6$ is H, or $C_1$-$C_6$alkyl;

$R_8$ is H, or $C_1$-$C_6$alkyl;

$R_9$ is H, $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

R₁₀ is $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

R₁₁ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

R₁₂ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

or R₁₁ and R₁₂ together with the nitrogen to which they are attached form an optionally substituted $C_2$-$C_7$heterocycloalkyl ring; and R₁₃ are R₁₄ are each independently H, or $C_1$-$C_6$alkyl;

or a pharmaceutically acceptable salt, pharmaceutically acceptable solvate or hydrate, pharmaceutically acceptable salt hydrate, or pharmaceutically acceptable prodrug thereof.

In another aspect, provided herein is a compound of Formula (IV):

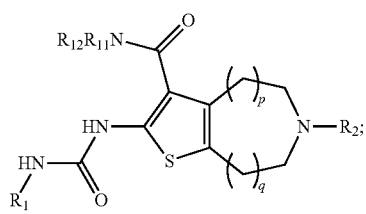

Formula (IV)

wherein:

R₁ is $C_6$-$C_{10}$aryl or $C_3$-$C_9$heteroaryl, wherein $C_6$-$C_{10}$aryl and $C_3$-$C_9$heteroaryl are optionally substituted with one or more R₄;

R₂ is H, —CH₃, —CH₂CH₃, or —CH(CH₃)₂;

each R₄ is independently selected from F, Br, I, —CN, —NO₂, —OR₉, —OCF₃, —NR₈R₉, —C(O)NR₈R₉, —N(R₈)C(O)R₁₀, —N(R₈)CO₂R₁₀, —NHS(O)₂R₁₀, —S(O)₂NR₈R₉, $C_2$-$C_6$alkyl, $C_3$-$C_6$cycloalkyl, $C_1$-$C_6$heteroalkyl, $C_2$-$C_7$heterocycloalkyl, $C_6$-$C_{10}$aryl, and $C_3$-$C_9$heteroaryl;

R₈ is H, or $C_1$-$C_6$alkyl;

R₉ is H, $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

R₁₀ is $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

R₁₁ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

R₁₂ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

or R₁₁ and R₁₂ together with the nitrogen to which they are attached form an optionally substituted $C_2$-$C_7$heterocycloalkyl ring;

p is an integer selected from 0-3; and q is an integer selected from 0-3;

or a pharmaceutically acceptable salt, pharmaceutically acceptable solvate, or pharmaceutically acceptable prodrug thereof.

In another aspect, provided herein is a compound of Formula (V):

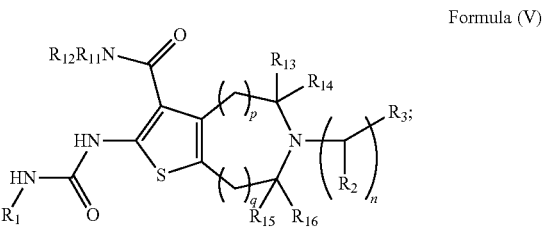

Formula (V)

wherein:

R₁ is $C_6$-$C_{10}$aryl or $C_3$-$C_9$heteroaryl, wherein $C_6$-$C_{10}$aryl and $C_3$-$C_9$heteroaryl are optionally substituted with one or more R₄;

each R₂ is independently H, or $C_1$-$C_4$alkyl;

R₃ is H, $C_1$-$C_6$alkyl, $C_1$-$C_6$haloalkyl, optionally substituted $C_3$-$C_6$cycloalkyl, optionally substituted $C_2$-$C_7$heterocycloalkyl, optionally substituted $C_6$-$C_{10}$aryl, optionally substituted $C_3$-$C_9$heteroaryl, —OR₆, —NR₅R₆, —C(O)R₇, —CO₂R₆, —C(O)NR₅R₆, —N(R₅)C(O)R₇, —N(R₅)CO₂R₇, —NHS(O)₂R₇, —S(O)₂NR₅R₆,

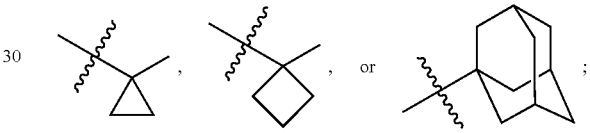

or

R₂ and R₃ together form an optionally substituted $C_2$-$C_7$heterocycloalkyl ring; each R₄ is independently selected from F, Cl, Br, I, —CN, —NO₂, —CF₃, —OR₉, —OCF₃, —NR₈R₉, —C(O)R₁₀, —CO₂R₉, —C(O)NR₈R₉, —N(R₈)C(O)R₁₀, —N(R₈)CO₂R₁₀, —NHS(O)₂R₁₀, —S(O)₂NR₈R₉, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, $C_6$-$C_{10}$aryl, and $C_3$-$C_9$heteroaryl;

R₅ is H, or $C_1$-$C_6$alkyl;

R₆ is H, $C_1$-$C_6$alkyl, optionally substituted $C_3$-$C_6$cycloalkyl, optionally substituted $C_2$-$C_7$heterocycloalkyl, optionally substituted $C_6$-$C_{10}$aryl, optionally substituted $C_3$-$C_9$heteroaryl, optionally substituted $C_1$-$C_6$alkyl$C_6$-$C_{10}$aryl, or optionally substituted $C_1$-$C_6$alkyl$C_3$-$C_9$heteroaryl;

R₇ is $C_1$-$C_6$alkyl, optionally substituted $C_3$-$C_6$cycloalkyl, optionally substituted $C_2$-$C_7$heterocycloalkyl, optionally substituted $C_6$-$C_{10}$aryl, $C_3$-$C_9$heteroaryl, optionally substituted $C_1$-$C_6$alkyl$C_6$-$C_{10}$aryl, or optionally substituted $C_1$-$C_6$alkyl$C_3$-$C_9$heteroaryl;

R₈ is H, or $C_1$-$C_6$alkyl;

R₉ is H, $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

R₁₀ is $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

R₁₁ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

or $R_{11}$ and $R_{12}$ together with the nitrogen to which they are attached form an optionally substituted $C_2$-$C_7$heterocycloalkyl ring;

$R_{13}$, $R_{14}$, $R_{15}$, and $R_{16}$ are each independently H, or $C_1$-$C_4$alkyl, wherein at least one of $R_{13}$, $R_{14}$, $R_{15}$, and $R_{16}$ is not H; or $R_3$ and $R_{13}$ together form an optionally substituted $C_2$-$C_7$heterocycloalkyl ring; or $R_3$ and $R_{15}$ together form an optionally substituted $C_2$-$C_7$heterocycloalkyl ring; and n is an integer selected from 0-5;
p is an integer selected from 0-3; and
q is an integer selected from 0-3;

or a pharmaceutically acceptable salt, pharmaceutically acceptable solvate or hydrate, pharmaceutically acceptable salt hydrate, or pharmaceutically acceptable prodrug thereof.

In another aspect, provided herein is a compound of Formula (VI):

Formula (VI)

wherein:

X is a single bond, double bond, —$CH_2$—, or —O—;

$R_1$ is $C_6$-$C_{10}$aryl or $C_3$-$C_9$heteroaryl, wherein $C_6$-$C_{10}$aryl and $C_3$-$C_9$heteroaryl are optionally substituted with one or more $R_4$;

$R_{2a}$ is $C_1$-$C_6$alkyl, $C_1$-$C_6$alkyl-$OR_5$, or $C_1$-$C_6$alkyl$C_3$-$C_6$cycloalkyl;

$R_2$ is $C_1$-$C_6$alkyl, $C_1$-$C_6$alkyl-$OR_6$, $C_1$-$C_6$alkyl$C_3$-$C_6$cycloalkyl, or $C_1$-$C_6$alkyl-$CO_2R_6$;

$R_3$ are $R_5$ are each independently H, or $C_1$-$C_6$alkyl; or $R_3$ and $R_5$ together form an optionally substituted $C_3$-$C_6$cycloalkyl ring, optionally substituted $C_2$-$C_7$heterocycloalkyl ring, optionally substituted $C_6$-$C_{10}$aryl ring, or an optionally substituted $C_3$-$C_9$heteroaryl ring;

each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, $C_6$-$C_{10}$aryl, and $C_3$-$C_9$heteroaryl;

$R_6$ is H, or $C_1$-$C_6$alkyl;
$R_8$ is H, or $C_1$-$C_6$alkyl;
$R_9$ is H, $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

$R_{10}$ is $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

$R_{11}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

or $R_{11}$ and $R_{12}$ together with the nitrogen to which they are attached form an optionally substituted $C_2$-$C_7$heterocycloalkyl ring; and $R_{13}$ are $R_{14}$ are each independently H, or $C_1$-$C_6$alkyl;

or a pharmaceutically acceptable salt, pharmaceutically acceptable solvate or hydrate, pharmaceutically acceptable salt hydrate, or pharmaceutically acceptable prodrug thereof.

In another aspect, provided herein is a compound of Formula (VII):

Formula (VII)

wherein:

$R_1$ is $C_6$-$C_{10}$aryl or $C_3$-$C_9$heteroaryl, wherein $C_6$-$C_{10}$aryl and $C_3$-$C_9$heteroaryl are optionally substituted with one or more $R_4$;

$R_2$ is H, $C_1$-$C_6$alkyl, $C_1$-$C_6$alkyl-$NR_5R_6$, $C_1$-$C_6$alkyl-$OR_5$, or $C_1$-$C_6$alkyl$C_3$-$C_6$cycloalkyl;

$R_3$ is —$NR_5R_6$, $C_1$-$C_6$alkyl-$NR_5R_6$, $C_1$-$C_6$haloalkyl, $C_1$-$C_6$alkyl-$OR_5$, optionally substituted $C_1$-$C_6$alkyl$C_3$-$C_6$cycloalkyl, optionally substituted $C_2$-$C_7$heterocycloalkyl, $C_1$-$C_6$alkyl-$CO_2R_6$, $C_1$-$C_6$alkyl-$C(O)NR_5R_6$, or $R_2$ and $R_3$ together with the carbon atom to which they are attached form an optionally substituted $C_2$-$C_7$heterocycloalkyl ring;

each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, $C_6$-$C_{10}$aryl, and $C_3$-$C_9$heteroaryl;

each $R_5$ is independently H, or $C_1$-$C_6$alkyl;
$R_6$ is H, or $C_1$-$C_6$alkyl;
$R_8$ is H, or $C_1$-$C_6$alkyl;
$R_9$ is H, $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

$R_{10}$ is $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

$R_{11}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

or $R_{11}$ and $R_{12}$ together with the nitrogen to which they are attached form an optionally substituted $C_2$-$C_7$heterocycloalkyl ring;

$R_{13}$, $R_{14}$, $R_{15}$, and $R_{16}$ are each independently H, or $C_1$-$C_4$alkyl;

p is an integer selected from 0-3; and q is an integer selected from 0-3;

or a pharmaceutically acceptable salt, pharmaceutically acceptable solvate or hydrate, pharmaceutically acceptable salt hydrate, or pharmaceutically acceptable prodrug thereof.

In another aspect is a pharmaceutical composition comprising a compound of Formula (I)-(VII) and a pharmaceutically acceptable excipient. In another embodiment is a pharmaceutical composition comprising a compound of Formula (I)-(VII) and a pharmaceutically acceptable excipient further comprising an aminoglycoside antibiotic. In another embodiment is a pharmaceutical composition comprising a compound of Formula (I)-(VII) and a pharmaceutically acceptable excipient further comprising an aminoglycoside antibiotic wherein the aminoglycoside antibiotic is selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin. In some embodiments is a pharmaceutical composition comprising a compound of Formula (I)-(VII) and a pharmaceutically acceptable excipient further comprising an aminoglycoside antibiotic wherein the aminoglycoside antibiotic is streptomycin. In some embodiments is a pharmaceutical composition comprising a compound of Formula (I)-(VII) and a pharmaceutically acceptable excipient further comprising an aminoglycoside antibiotic wherein the aminoglycoside antibiotic is neomycin. In some embodiments is a pharmaceutical composition comprising a compound of Formula (I)-(VII) and a pharmaceutically acceptable excipient further comprising an aminoglycoside antibiotic wherein the aminoglycoside antibiotic is amikacin. In some embodiments is a pharmaceutical composition comprising a compound of Formula (I)-(VII) and a pharmaceutically acceptable excipient further comprising an aminoglycoside antibiotic wherein the aminoglycoside antibiotic is gentamicin. In some embodiments is a pharmaceutical composition comprising a compound of Formula (I)-(VII) and a pharmaceutically acceptable excipient further comprising an aminoglycoside antibiotic wherein the aminoglycoside antibiotic is kanamycin. In some embodiments is a pharmaceutical composition comprising a compound of Formula (I)-(VII) and a pharmaceutically acceptable excipient further comprising an aminoglycoside antibiotic wherein the aminoglycoside antibiotic is tobramycin. In another embodiment of the aforementioned embodiments is a pharmaceutical composition formulated for intravenous, intramuscular, or subcutaneous administration.

In another aspect is a method for preventing, treating, and/or protecting against sensory hair cell death in an individual comprising administering to the individual a therapeutically effective amount of a compound of Formula (I)-(VII). In another embodiment is a method for preventing, treating, and/or protecting against sensory hair cell death in an individual comprising administering to the individual a therapeutically effective amount of a compound of Formula (I)-(VII) wherein the sensory hair cell death is associated with exposure to an ototoxic agent. In another embodiment is a method for preventing, treating, and/or protecting against sensory hair cell death in an individual comprising administering to the individual a therapeutically effective amount of a compound of Formula (I)-(VII) wherein the sensory hair cell death is associated with exposure to an ototoxic agent and the ototoxic agent is an aminoglycoside antibiotic, chemotherapeutic agent, loop diuretic, antimalarial sesquiterpene lactone endoperoxide, antimalarial quinine, salicylate, or interferon polypeptide. In another embodiment is a method for preventing, treating, and/or protecting against sensory hair cell death in an individual comprising administering to the individual a therapeutically effective amount of a compound of Formula (I)-(VII) wherein the sensory hair cell death is associated with exposure to an aminoglycoside antibiotic. In another embodiment is a method for preventing, treating, and/or protecting against sensory hair cell death in an individual comprising administering to the individual a therapeutically effective amount of a compound of Formula (I)-(VII) wherein the sensory hair cell death is associated with exposure to an aminoglycoside antibiotic and the aminoglycoside antibiotic is selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin. In another embodiment is a method for preventing, treating, and/or protecting against sensory hair cell death in an individual comprising administering to the individual a therapeutically effective amount of a compound of Formula (I)-(VII) wherein the sensory hair cell death is associated with exposure to streptomycin. In another embodiment is a method for preventing, treating, and/or protecting against sensory hair cell death in an individual comprising administering to the individual a therapeutically effective amount of a compound of Formula (I)-(VII) wherein the sensory hair cell death is associated with exposure to neomycin. In another embodiment is a method for preventing, treating, and/or protecting against sensory hair cell death in an individual comprising administering to the individual a therapeutically effective amount of a compound of Formula (I)-(VII) wherein the sensory hair cell death is associated with exposure to amikacin. In another embodiment is a method for preventing, treating, and/or protecting against sensory hair cell death in an individual comprising administering to the individual a therapeutically effective amount of a compound of Formula (I)-(VII) wherein the sensory hair cell death is associated with exposure to gentamicin. In another embodiment is a method for preventing, treating, and/or protecting against sensory hair cell death in an individual comprising administering to the individual a therapeutically effective amount of a compound of Formula (I)-(VII) wherein the sensory hair cell death is associated with exposure to kanamycin. In another embodiment is a method for preventing, treating, and/or protecting against sensory hair cell death in an individual comprising administering to the individual a therapeutically effective amount of a compound of Formula (I)-(VII) wherein the sensory hair cell death is associated with exposure to tobramycin. In another embodiment is a method for preventing, treating, and/or protecting against sensory hair cell death in an individual comprising administering to the individual a therapeutically effective amount of a compound of Formula (I)-(VII) wherein the sensory hair cell death is associated with exposure to a chemotherapeutic agent. In another embodiment is a method for preventing, treating, and/or protecting against sensory hair cell death in an individual comprising administering to the individual a therapeutically effective amount of a compound of Formula (I)-(VII) wherein the sensory hair cell death is associated with exposure to a chemotherapeutic agent and the chemotherapeutic agent is selected from cisplatin or carboplatin.

In another aspect is a compound with a maximum hair cell protection of greater than 50% in the assay described in Example 231.

In another aspect is the use of the assay described in Example 231 for the testing of a compound of Formula (I)-(VII).

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
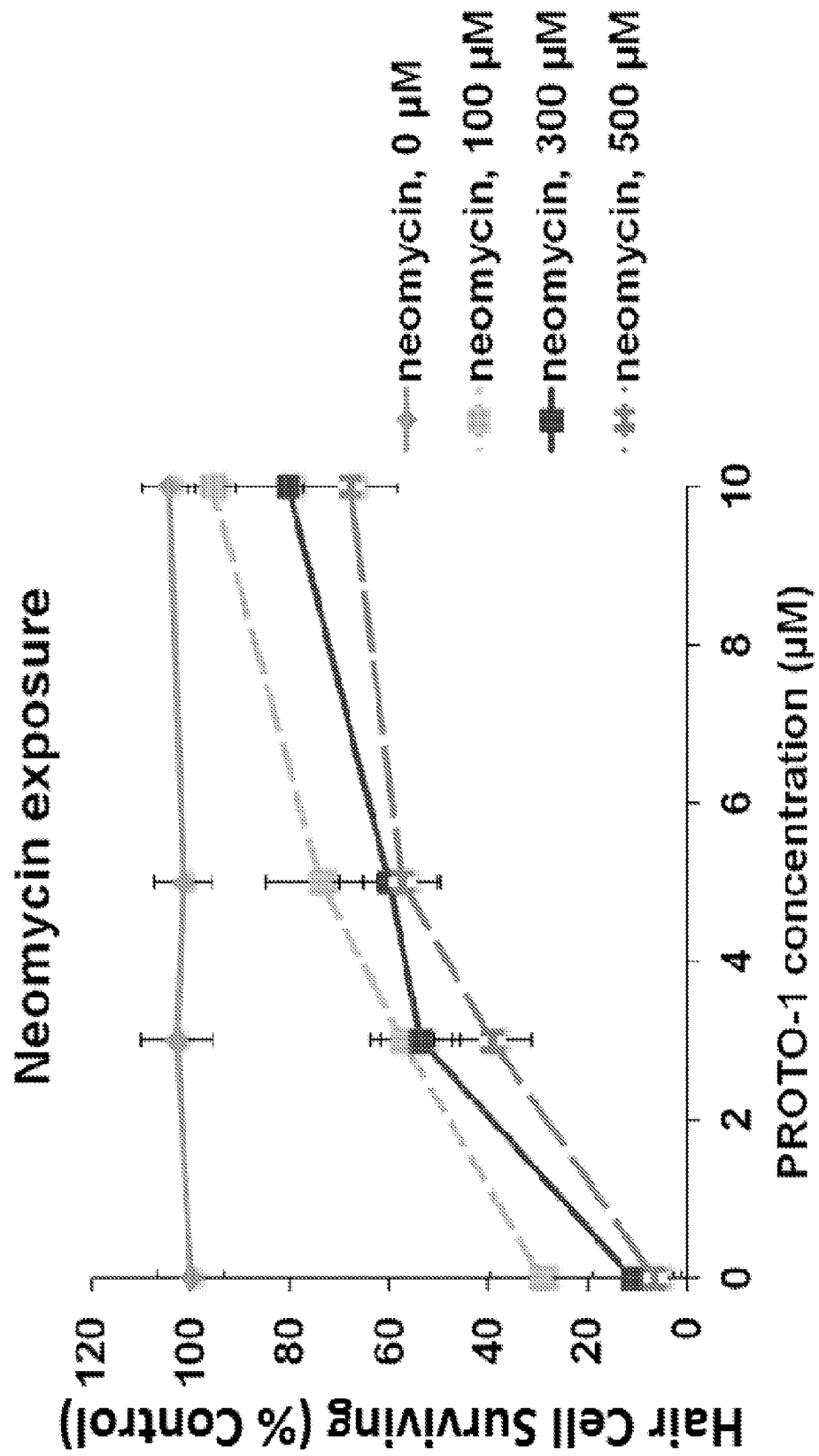
FIG. 1 shows hair cell survival in the zebrafish assay following treatment with neomycin and PROTO-1.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the ═O radical.
"Thioxo" refers to the ═S radical.
"Imino" refers to the ═N—H radical.
"Oximo" refers to the ═N—OH radical.
"Hydrazino" refers to the ═N—$NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to six carbon atoms (e.g., $C_2$-$C_6$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —OC(O)— N($R^a$)$_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a$)$_2$ (where t is 1 or 2) where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl. Depending on the structure, an alkyl group is optionally a monoradical or a diradical (i.e. an alkylene group).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to six carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —OC(O)— N($R^a$)$_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a$)$_2$ (where t is 1 or 2) where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butyryl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)— N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group is optionally through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)— N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocycloalkyl, heterocycloalkylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyl may be saturated, (i.e., containing single C—C bonds only) or partially unsaturated. Examples of monocyclic cycloalkyls include, e.g., cyclopropyl, cyclobutyl, cyclopentyl, cyclohexyl, cycloheptyl, and cyclooctyl. An unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "cycloalkyl" is meant to include cycloalkyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Cycloalkylalkyl" refers to a radical of the formula —$R^c$-cycloalkyl where $R^c$ is an alkylene chain as defined above. The alkylene chain and the cycloalkyl radical is optionally substituted as defined above.

"Cycloalkylalkoxy" refers to a radical bonded through an oxygen atom of the formula —O—$R^c$-cycloalkyl where $R^c$ is an alkylene chain as defined above. The alkylene chain and the cycloalkyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$OR^a$ (where t is 1 or 2) and —$R^b$—S(O)$_1$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocycloalkyl" or "N-attached heterocycloalkyl" refers to a heterocycloalkyl radical as defined above containing at least one nitrogen and where the point of attachment of the heterocycloalkyl radical to the rest of the molecule is through a nitrogen atom in the heterocycloalkyl radical. An N-heterocycloalkyl radical is optionally substituted as described above for heterocycloalkyl radicals. Examples of such N-heterocycloalkyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocycloalkyl" or "C-attached heterocycloalkyl" refers to a heterocycloalkyl radical as defined above containing at least one heteroatom and where the point of attachment of the heterocycloalkyl radical to the rest of the molecule is through a carbon atom in the heterocycloalkyl radical. A C-heterocycloalkyl radical is optionally substituted as described above for heterocycloalkyl radicals. Examples of such C-heterocycloalkyl radicals include, but are not limited to, 2-morpholinyl, 2- or 3- or 4-piperidinyl, 2-piperazinyl, 2- or 3-pyrrolidinyl, and the like.

"Heterocycloalkylalkyl" refers to a radical of the formula —$R^c$-heterocycloalkyl where $R^c$ is an alkylene chain as defined above. If the heterocycloalkyl is a nitrogen-containing heterocycloalkyl, the heterocycloalkyl is optionally attached to the alkyl radical at the nitrogen atom. The alkylene chain of the heterocycloalkylalkyl radical is optionally substituted as defined above for an alkylene chain. The heterocycloalkyl part of the heterocycloalkylalkyl radical is optionally substituted as defined above for a heterocycloalkyl group.

"Heterocycloalkylalkoxy" refers to a radical bonded through an oxygen atom of the formula —O—$R^c$-heterocycloalkyl where $R^c$ is an alkylene chain as defined above. If the heterocycloalkyl is a nitrogen-containing heterocycloalkyl, the heterocycloalkyl is optionally attached to the alkyl radical at the nitrogen atom. The alkylene chain of the heterocycloalkylalkoxy radical is optionally substituted as defined above for an alkylene chain. The heterocycloalkyl part of the heterocycloalkylalkoxy radical is optionally substituted as defined above for a heterocycloalkyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

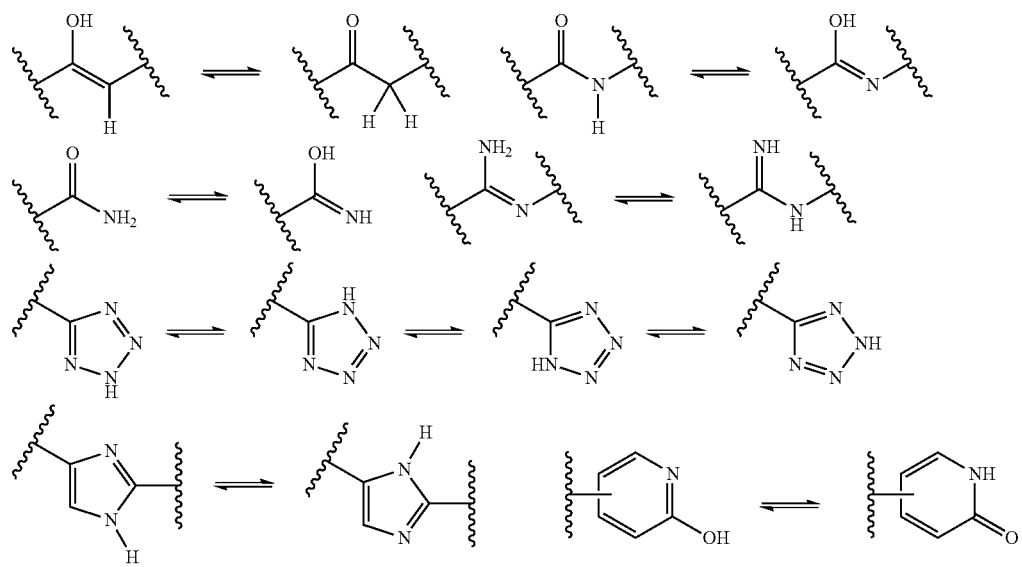

"Optional" or "optionally" means that a subsequently described event or circumstance may or may not occur and that the description includes instances when the event or circumstance occurs and instances in which it does not.

"Optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2$H, —$CO_2$-alkyl, nitro, haloalkyl, fluoroalkyl, and amino, including mono- and di-substituted amino groups (e.g. —$NH_2$, —NHR, —N(R)$_2$), and the protected derivatives thereof. By way of example, an optional substituents may be $L^s R^s$, wherein each $L^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —($C_1$-$C_6$alkyl)-, or —($C_2$-$C_6$alkenyl)-; and each $R^s$ is independently selected from among H, ($C_1$-$C_6$alkyl), ($C_3$-$C_8$cycloalkyl), aryl, heteroaryl, heterocycloalkyl, and $C_1$-$C_6$heteroalkyl. The protecting groups that may form the protective derivatives of the above substituents are found in sources such as Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). Acid addition salts of basic compounds may be prepared by contacting the free base forms with a sufficient amount of the desired acid to produce the salt according to known methods and techniques.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable counterion" refers to an ion that accompanies an ionic species in order to maintain electric neutrality that is not biologically or otherwise undesirable.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Compounds

The compounds, and compositions comprising these compounds, described herein are useful for preventing, treating, and/or protecting against sensory hair cell death.

In one embodiment is a compound of Formula (I):

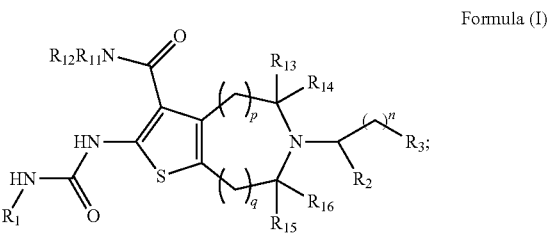

Formula (I)

wherein:

$R_1$ is $C_6$-$C_{10}$aryl or $C_3$-$C_9$heteroaryl, wherein $C_6$-$C_{10}$aryl and $C_3$-$C_9$heteroaryl are optionally substituted with one or more $R_4$;

$R_2$ is H, $C_1$-$C_4$alkyl, or $C_2$-$C_4$alkenyl;

$R_3$ is $C_2$-$C_6$alkyl, $C_2$-$C_6$alkenyl, $C_1$-$C_4$haloalkyl, optionally substituted $C_3$-$C_6$cycloalkyl, optionally substituted $C_2$-$C_7$heterocycloalkyl, optionally substituted $C_6$-$C_{10}$aryl, —$OR_6$, —$NR_5R_6$, —$C(O)R_7$, —$CO_2R_6$, —$C(O)NR_5R_6$, —$N(R_5)C(O)R_7$, —$N(R_5)CO_2R_7$, —$NHS(O)_2R_7$, —$S(O)_2NR_5R_6$,

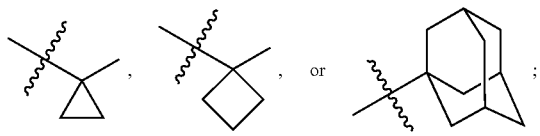

or $R_2$ and $R_3$ together form an optionally substituted $C_2$-$C_7$heterocycloalkyl ring;

each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, $C_6$-$C_{10}$aryl, and $C_3$-$C_9$heteroaryl;

$R_5$ is H, or $C_1$-$C_6$alkyl;

$R_6$ is H, $C_1$-$C_6$alkyl, optionally substituted $C_3$-$C_6$cycloalkyl, optionally substituted $C_2$-$C_7$heterocycloalkyl, optionally substituted $C_6$-$C_{10}$aryl, optionally substituted $C_3$-$C_9$heteroaryl, optionally substituted $C_1$-$C_6$alkyl$C_6$-$C_{10}$aryl, or optionally substituted $C_1$-$C_6$alkyl$C_3$-$C_9$heteroaryl;

$R_7$ is $C_1$-$C_6$alkyl, optionally substituted $C_3$-$C_6$cycloalkyl, optionally substituted $C_2$-$C_7$heterocycloalkyl, optionally substituted $C_6$-$C_{10}$aryl, $C_3$-$C_9$heteroaryl, optionally substituted $C_1$-$C_6$alkyl$C_6$-$C_{10}$aryl, or optionally substituted $C_1$-$C_6$alkyl$C_3$-$C_9$heteroaryl;

$R_8$ is H, or $C_1$-$C_6$alkyl;

$R_9$ is H, $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

$R_{10}$ is $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

$R_{11}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

or $R_{11}$ and $R_{12}$ together with the nitrogen to which they are attached form an optionally substituted $C_2$-$C_7$heterocycloalkyl ring;

$R_{13}$, $R_{14}$, $R_{15}$, and $R_{16}$ are each independently H, or $C_1$-$C_4$alkyl;

n is an integer selected from 0-4;

p is an integer selected from 0-3; and q is an integer selected from 0-3;

or a pharmaceutically acceptable salt, pharmaceutically acceptable solvate or hydrate, pharmaceutically acceptable salt hydrate, or pharmaceutically acceptable prodrug thereof.

In another embodiment is a compound of Formula (I) having the structure of Formula (Ia):

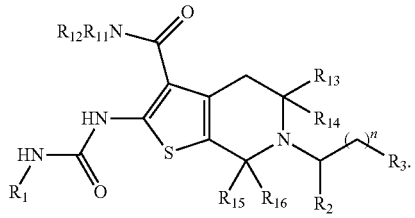

Formula (Ia)

In a further embodiment is a compound of Formula (Ia) wherein $R_1$ is $C_6$-$C_{10}$aryl. In a further embodiment is a compound of Formula (Ia) wherein $R_1$ is phenyl. In a further embodiment is a compound of Formula (Ia) wherein $R_1$ is phenyl substituted with one or more $R_4$, and $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, $C_1$-$C_6$alkyl, and $C_1$-$C_6$haloalkyl. In yet a further embodiment is a compound of Formula (Ia) wherein $R_1$ is phenyl substituted with one or more $R_4$, and $R_4$ is independently selected from F, Cl, Br, I, —CN, —CF$_3$, —OR$_9$, —OCF$_3$, —C(O)R$_{10}$, —CO$_2$R$_9$, and $C_1$-$C_6$alkyl. In another embodiment is a compound of Formula (Ia) wherein $R_1$ is 4-fluorophenyl, 4-chlorophenyl, 3,4-dichlorophenyl, 4-bromophenyl, 4-iodophenyl, 3-cyanophenyl, 4-trifluoromethylphenyl, 4-trifluoromethoxyphenyl, 4-phenoxyphenyl, or 4-benzoylphenyl.

In another embodiment is a compound of Formula (I) or Formula (Ia) wherein $R_{11}$ and $R_{12}$ are each H. In another embodiment is a compound of Formula (I) or Formula (Ia) wherein $R_2$ is H. In another embodiment is a compound of Formula (I) or Formula (Ia) wherein $R_2$ is methyl. In another embodiment is a compound of Formula (I) or Formula (Ia) wherein $R_3$ is $C_2$-$C_4$alkyl, $C_3$-$C_6$cycloalkyl, $C_2$-$C_7$heterocycloalkyl, —OR$_6$, —CO$_2$R$_6$, —C(O)NR$_5$R$_6$, —N(H)C(O)R$_7$, —N(H)CO$_2$R$_7$,

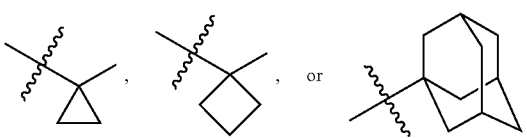

In a further embodiment is a compound of Formula (I) or Formula (Ia) wherein $R_6$ is H, $C_1$-$C_6$alkyl, or $C_1$-$C_6$alkylC$_6$-$C_{10}$aryl, and $R_7$ is $C_1$-$C_6$alkyl, $C_6$-$C_{10}$aryl, $C_1$-$C_6$alkylC$_6$-$C_{10}$aryl, or $C_1$-$C_6$alkylC$_3$-$C_9$heteroaryl.

In another embodiment is a compound of Formula (I) or Formula (Ia) wherein $R_2$ and $R_3$ together form an optionally substituted $C_2$-$C_7$heterocycloalkyl ring. In a further embodiment is a compound of Formula (I) or Formula (Ia) wherein $R_2$ and $R_3$ together form an optionally substituted oxetane, pyrrolidine, piperidine, or tetrahydropyran ring.

In another embodiment is a compound of Formula (II):

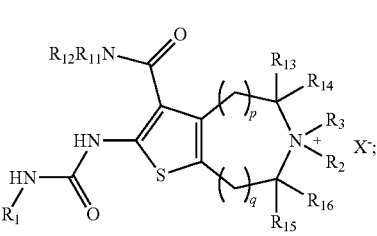

Formula (II)

wherein:

X$^-$ is a pharmaceutically acceptable counterion;

$R_1$ is $C_6$-$C_{10}$aryl or $C_3$-$C_9$heteroaryl, wherein $C_6$-$C_{10}$aryl and $C_3$-$C_9$heteroaryl are optionally substituted with one or more $R_4$;

$R_2$ is $C_1$-$C_6$alkyl, $C_1$-$C_6$alkyl-OR$_5$, or $C_1$-$C_6$alkylC$_3$-$C_6$cycloalkyl; $R_3$ is $C_1$-$C_6$alkyl, $C_1$-$C_6$haloalkyl, $C_1$-$C_6$alkyl-OR$_5$, optionally substituted $C_1$-$C_6$alkylC$_3$-$C_6$cycloalkyl, optionally substituted $C_2$-$C_7$heterocycloalkyl, $C_1$-$C_6$alkyl-CO$_2$R$_6$, $C_1$-$C_6$alkyl-C(O)NR$_5$R$_6$,

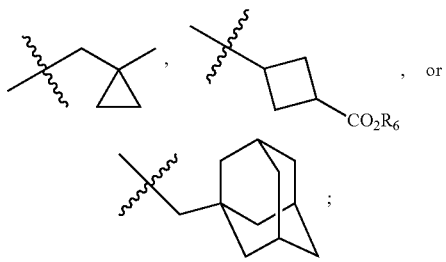

or $R_2$ and $R_3$ together with the nitrogen to which they are attached form an optionally substituted $C_2$-$C_7$heterocycloalkyl ring;

each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, —C(O)NR$_8$R$_9$, —N(R$_8$)C(O)R$_{10}$, —N(R$_8$)CO$_2$R$_{10}$, —NHS(O)$_2$R$_{10}$, —S(O)$_2$NR$_8$R$_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, $C_6$-$C_{10}$aryl, and $C_3$-$C_9$heteroaryl;

each $R_5$ is independently H, or $C_1$-$C_6$alkyl;

$R_6$ is H, or $C_1$-$C_6$alkyl;

$R_8$ is H, or $C_1$-$C_6$alkyl;

$R_9$ is H, $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkylC$_6$-$C_{10}$aryl, or $C_1$-$C_6$alkylC$_3$-$C_9$heteroaryl;

$R_{10}$ is $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkylC$_6$-$C_{10}$aryl, or $C_1$-$C_6$alkylC$_3$-$C_9$heteroaryl;

$R_{11}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkylC$_3$-$C_6$cycloalkyl, $C_1$-$C_6$alkylC$_6$-$C_{10}$aryl, or $C_1$-$C_6$alkylC$_3$-$C_9$heteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkylC$_3$-$C_6$cycloalkyl, $C_1$-$C_6$alkylC$_6$-$C_{10}$aryl, or $C_1$-$C_6$alkylC$_3$-$C_9$heteroaryl;

or $R_{11}$ and $R_{12}$ together with the nitrogen to which they are attached form an optionally substituted $C_2$-$C_7$heterocycloalkyl ring;

$R_{13}$, $R_{14}$, $R_{15}$, and $R_{16}$ are each independently H, or $C_1$-$C_4$alkyl;

p is an integer selected from 0-3; and q is an integer selected from 0-3;

or a pharmaceutically acceptable salt, pharmaceutically acceptable solvate or hydrate, pharmaceutically acceptable salt hydrate, or pharmaceutically acceptable prodrug thereof.

In another embodiment is a compound of Formula (II) having the structure of Formula (IIa):

Formula (IIa)

![Formula IIa structure]

In a further embodiment is a compound of Formula (IIa) wherein $R_1$ is $C_6$-$C_{10}$aryl. In a further embodiment is a compound of Formula (IIa) wherein $R_1$ is phenyl. In a further embodiment is a compound of Formula (IIa) wherein $R_1$ is phenyl substituted with one or more $R_4$, and $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, $C_1$-$C_6$alkyl, and $C_1$-$C_6$haloalkyl. In yet a further embodiment is a compound of Formula (IIa) wherein $R_1$ is phenyl substituted with one or more $R_4$, and $R_4$ is independently selected from F, Cl, Br, I, —CN, —CF$_3$, —OR$_9$, —OCF$_3$, —C(O)R$_{10}$, —CO$_2$R$_9$, and $C_1$-$C_6$alkyl. In another embodiment is a compound of Formula (IIa) wherein $R_1$ is 4-chlorophenyl.

In another embodiment is a compound of Formula (II) or Formula (IIa) wherein $R_{11}$ and $R_{12}$ are each H. In another embodiment is a compound of Formula (II) or Formula (IIa) wherein $R_3$ is $C_1$-$C_6$alkyl-CO$_2$R$_6$, and $R_6$ is $C_1$-$C_6$alkyl. In another embodiment is a compound of Formula (II) or Formula (IIa) wherein $R_3$ is $C_1$-$C_6$alkylC$_3$-$C_6$cycloalkyl. In another embodiment is a compound of Formula (II) or Formula (IIa) wherein $R_2$ is methyl or ethyl. In another embodiment is a compound of Formula (II) or Formula (IIa) wherein $R_2$ and $R_3$ together form an optionally substituted $C_2$-$C_7$heterocycloalkyl ring.

In another embodiment is a compound of Formula (III):

Formula (III)

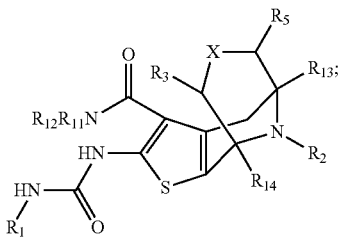

wherein:

X is a single bond, double bond, —CH$_2$—, or —O—;

$R_1$ is $C_6$-$C_{10}$aryl or $C_3$-$C_9$heteroaryl, wherein $C_6$-$C_{10}$aryl and $C_3$-$C_9$heteroaryl are optionally substituted with one or more $R_4$;

$R_2$ is H, $C_1$-$C_6$alkyl, $C_1$-$C_6$alkyl-OR$_6$, $C_1$-$C_6$alkylC$_3$-$C_6$cycloalkyl, $C_1$-$C_6$alkylC$_2$-$C_7$heterocycloalkyl, $C_1$-$C_6$alkyl-CO$_2$R$_6$, optionally substituted $C_1$-$C_6$alkylC$_6$-$C_{10}$aryl, or optionally substituted $C_1$-$C_6$alkylC$_3$-$C_9$heteroaryl;

$R_3$ are $R_5$ are each independently H, or $C_1$-$C_6$alkyl; or $R_3$ and $R_5$ together form an optionally substituted $C_3$-$C_6$cycloalkyl ring, optionally substituted $C_2$-$C_7$heterocycloalkyl ring, optionally substituted $C_6$-$C_{10}$aryl ring, or an optionally substituted $C_3$-$C_9$heteroaryl ring;

each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, —C(O)NR$_8$R$_9$, —N(R$_8$)C(O)R$_{10}$, —N(R$_8$)CO$_2$R$_{10}$, —NHS(O)$_2$R$_{10}$, —S(O)$_2$NR$_8$R$_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, $C_6$-$C_{10}$aryl, and $C_3$-$C_9$heteroaryl;

$R_6$ is H, or $C_1$-$C_6$alkyl;

$R_8$ is H, or $C_1$-$C_6$alkyl;

$R_9$ is H, $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkylC$_6$-$C_{10}$aryl, or $C_1$-$C_6$alkylC$_3$-$C_9$heteroaryl;

$R_{10}$ is $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkylC$_6$-$C_{10}$aryl, or $C_1$-$C_6$alkylC$_3$-$C_9$heteroaryl;

$R_{11}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkylC$_3$-$C_6$cycloalkyl, $C_1$-$C_6$alkylC$_6$-$C_{10}$aryl, or $C_1$-$C_6$alkylC$_3$-$C_9$heteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkylC$_3$-$C_6$cycloalkyl, $C_1$-$C_6$alkylC$_6$-$C_{10}$aryl, or $C_1$-$C_6$alkylC$_3$-$C_9$heteroaryl;

or $R_{11}$ and $R_{12}$ together with the nitrogen to which they are attached form an optionally substituted $C_2$-$C_7$heterocycloalkyl ring; and $R_{13}$ are $R_{14}$ are each independently H, or $C_1$-$C_6$alkyl;

or a pharmaceutically acceptable salt, pharmaceutically acceptable solvate or hydrate, pharmaceutically acceptable salt hydrate, or pharmaceutically acceptable prodrug thereof.

In another embodiment is a compound of Formula (III) wherein $R_1$ is $C_6$-$C_{10}$aryl. In a further embodiment is a compound of Formula (III) wherein $R_1$ is phenyl. In a further embodiment is a compound of Formula (III) wherein $R_1$ is phenyl substituted with one or more $R_4$, and $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, $C_1$-$C_6$alkyl, and $C_1$-$C_6$haloalkyl. In yet a further embodiment is a compound of Formula (III) wherein $R_1$ is phenyl substituted with one or more $R_4$, and $R_4$ is independently selected from F, Cl, Br, I, —CN, —CF$_3$, —OR$_9$, —OCF$_3$, —C(O)R$_{10}$, —CO$_2$R$_9$, and $C_1$-$C_6$alkyl. In another embodiment is a compound of Formula (III) wherein $R_1$ is 4-chlorophenyl.

In another embodiment is a compound of Formula (III) wherein $R_{11}$ and $R_{12}$ are each H. In another embodiment is a compound of Formula (III) wherein $R_2$ is H. In another embodiment is a compound of Formula (III) wherein $R_2$ is $C_1$-$C_6$alkyl. In another embodiment is a compound of Formula (III) wherein $R_{13}$ and $R_{14}$ are each H. In another embodiment is a compound of Formula (III) wherein $R_{13}$ and $R_{14}$ are each CH$_3$. In another embodiment is a compound of Formula (III) wherein $R_3$ and $R_5$ are each H.

In another embodiment is a compound of Formula (IV):

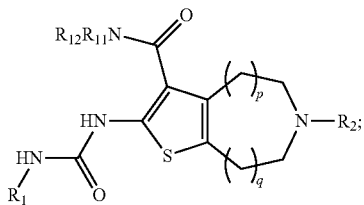

Formula (IV)

wherein:

$R_1$ is $C_6$-$C_{10}$aryl or $C_3$-$C_9$heteroaryl, wherein $C_6$-$C_{10}$aryl and $C_3$-$C_9$heteroaryl are optionally substituted with one or more $R_4$;

$R_2$ is H, —$CH_3$, —$CH_2CH_3$, or —$CH(CH_3)_2$;

each $R_4$ is independently selected from F, Br, I, —CN, —$NO_2$, —$OR_9$, —$OCF_3$, —$NR_8R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_2$-$C_6$alkyl, $C_3$-$C_6$cycloalkyl, $C_1$-$C_6$heteroalkyl, $C_2$-$C_7$heterocycloalkyl, $C_6$-$C_{10}$aryl, and $C_3$-$C_9$heteroaryl;

$R_8$ is H, or $C_1$-$C_6$alkyl;

$R_9$ is H, $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

$R_{10}$ is $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

$R_{11}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

or $R_{11}$ and $R_{12}$ together with the nitrogen to which they are attached form an optionally substituted $C_2$-$C_7$heterocycloalkyl ring;

p is an integer selected from 0-3; and q is an integer selected from 0-3;

or a pharmaceutically acceptable salt, pharmaceutically acceptable solvate or hydrate, pharmaceutically acceptable salt hydrate, or pharmaceutically acceptable prodrug thereof.

In another embodiment is a compound of Formula (IV) having the structure of Formula (IVa):

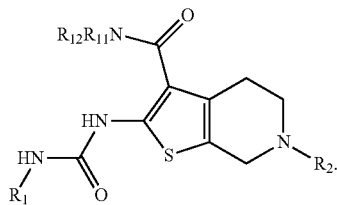

Formula (IVa)

In a further embodiment is a compound of Formula (IVa) wherein $R_1$ is $C_6$-$C_{10}$aryl. In a further embodiment is a compound of Formula (IVa) wherein $R_1$ is phenyl. In a further embodiment is a compound of Formula (IVa) wherein $R_1$ is phenyl substituted with one or more $R_4$, and $R_4$ is independently selected from F, Br, I, —CN, —$OR_9$, —$OCF_3$, —$NR_8R_9$, —$C(O)R_{10}$, —$CO_2R_9$, and $C_2$-$C_6$alkyl. In yet a further embodiment is a compound of Formula (IVa) wherein $R_1$ is phenyl substituted with one or more $R_4$, and $R_4$ is independently selected from F, Br, I, —CN, —$CF_3$, —$OR_9$, —$OCF_3$, —$C(O)R_{10}$, —$CO_2R_9$, and $C_2$-$C_6$alkyl.

In another embodiment is a compound of Formula (IV) or Formula (IVa) wherein $R_{11}$ and $R_{12}$ are each H. In another embodiment is a compound of Formula (IV) or Formula (IVa) wherein $R_2$ is H. In another embodiment is a compound of Formula (IV) or Formula (IVa) wherein $R_2$ is —$CH_3$. In another embodiment is a compound of Formula (IV) or Formula (IVa) wherein $R_2$ is —$CH_2CH_3$. In another embodiment is a compound of Formula (IV) or Formula (IVa) wherein $R_2$ is —$CH(CH_3)_2$.

In another embodiment is a compound of Formula (V):

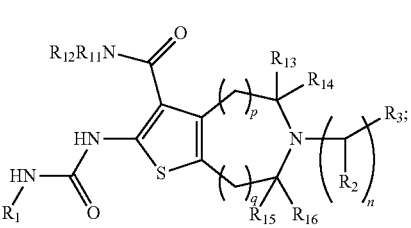

Formula (V)

wherein:

$R_1$ is $C_6$-$C_{10}$aryl or $C_3$-$C_9$heteroaryl, wherein $C_6$-$C_{10}$aryl and $C_3$-$C_9$heteroaryl are optionally substituted with one or more $R_4$;

each $R_2$ is independently H, or $C_1$-$C_4$alkyl;

$R_3$ is H, $C_1$-$C_6$alkyl, $C_1$-$C_6$haloalkyl, optionally substituted $C_3$-$C_6$cycloalkyl, optionally substituted $C_2$-$C_7$heterocycloalkyl, optionally substituted $C_6$-$C_{10}$aryl, optionally substituted $C_3$-$C_9$heteroaryl, —$OR_6$, —$NR_5R_6$, —$C(O)R_7$, —$CO_2R_6$, —$C(O)NR_5R_6$, —$N(R_8)C(O)R_7$, —$N(R_8)CO_2R_7$, —$NHS(O)_2R_7$, —$S(O)_2NR_5R_6$,

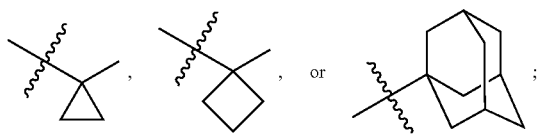

or $R_2$ and $R_3$ together form an optionally substituted $C_2$-$C_7$heterocycloalkyl ring;

each $R_4$ is independently selected from F, Cl, Br, I, —CN, —$NO_2$, —$CF_3$, —$OR_9$, —$OCF_3$, —$NR_8R_9$, —$C(O)R_{10}$, —$CO_2R_9$, —$C(O)NR_8R_9$, —$N(R_8)C(O)R_{10}$, —$N(R_8)CO_2R_{10}$, —$NHS(O)_2R_{10}$, —$S(O)_2NR_8R_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, $C_6$-$C_{10}$aryl, and $C_3$-$C_9$heteroaryl;

$R_5$ is H, or $C_1$-$C_6$alkyl;

$R_6$ is H, $C_1$-$C_6$alkyl, optionally substituted $C_3$-$C_6$cycloalkyl, optionally substituted $C_2$-$C_7$heterocycloalkyl, optionally substituted $C_6$-$C_{10}$aryl, optionally substituted $C_3$-$C_9$heteroaryl, optionally substituted $C_1$-$C_6$alkyl$C_6$-$C_{10}$aryl, or optionally substituted $C_1$-$C_6$alkyl$C_3$-$C_9$heteroaryl;

$R_7$ is $C_1$-$C_6$alkyl, optionally substituted $C_3$-$C_6$cycloalkyl, optionally substituted $C_2$-$C_7$heterocycloalkyl, optionally substituted $C_6$-$C_{10}$aryl, $C_3$-$C_9$heteroaryl, optionally substituted $C_1$-$C_6$alkyl$C_6$-$C_{10}$aryl, or optionally substituted $C_1$-$C_6$alkyl$C_3$-$C_9$heteroaryl;

$R_8$ is H, or $C_1$-$C_6$alkyl;
$R_9$ is H, $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;
$R_{10}$ is $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;
$R_{11}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;
$R_{12}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;
or $R_{11}$ and $R_{12}$ together with the nitrogen to which they are attached form an optionally substituted $C_2$-$C_7$heterocycloalkyl ring;
$R_{13}$, $R_{14}$, $R_{15}$, and $R_{16}$ are each independently H, or $C_1$-$C_4$alkyl, wherein at least one of $R_{13}$, $R_{14}$, $R_{15}$, and $R_{16}$ is not H; or $R_3$ and $R_{13}$ together form an optionally substituted $C_2$-$C_7$heterocycloalkyl ring; or $R_3$ and $R_{15}$ together form an optionally substituted $C_2$-$C_7$heterocycloalkyl ring; and
n is an integer selected from 0-5;
p is an integer selected from 0-3; and
q is an integer selected from 0-3;
or a pharmaceutically acceptable salt, pharmaceutically acceptable solvate or hydrate, pharmaceutically acceptable salt hydrate, or pharmaceutically acceptable prodrug thereof.

In another embodiment is a compound of Formula (V) having the structure of Formula (Va):

Formula (Va)

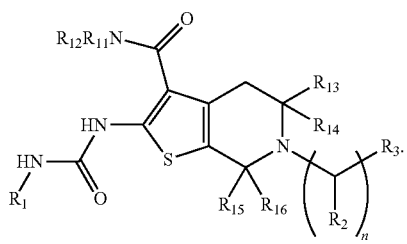

In a further embodiment is a compound of Formula (Va) wherein $R_1$ is $C_6$-$C_{10}$aryl. In a further embodiment is a compound of Formula (Va) wherein $R_1$ is phenyl. In a further embodiment is a compound of Formula (Va) wherein $R_1$ is phenyl substituted with one or more $R_4$, and $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, $C_1$-$C_6$alkyl, and $C_1$-$C_6$haloalkyl. In yet a further embodiment is a compound of Formula (Va) wherein $R_1$ is phenyl substituted with one or more $R_4$, and $R_4$ is independently selected from F, Cl, Br, I, —CN, —CF$_3$, —OR$_9$, —OCF$_3$, —C(O)R$_{10}$, —CO$_2$R$_9$, and $C_1$-$C_6$alkyl. In another embodiment is a compound of Formula (Va) wherein $R_1$ is 4-fluorophenyl, 4-chlorophenyl, 3,4-dichlorophenyl, 4-bromophenyl, 4-iodophenyl, 3-cyanophenyl, 4-trifluoromethylphenyl, 4-trifluoromethoxyphenyl, 4-phenoxyphenyl, or 4-benzoylphenyl.

In another embodiment is a compound of Formula (V) or Formula (Va) wherein $R_{11}$ and $R_{12}$ are each H. In another embodiment is a compound of Formula (V) or Formula (Va) wherein n is 0. In another embodiment is a compound of Formula (V) or Formula (Va) wherein $R_3$ is H. In another embodiment is a compound of Formula (V) or Formula (Va) wherein $R_3$ is methyl. In another embodiment is a compound of Formula (V) or Formula (Va) wherein $R_3$ is $C_1$-$C_6$alkyl, $C_3$-$C_6$cycloalkyl, $C_2$-$C_7$heterocycloalkyl, —OR$_6$, —CO$_2$R$_6$, —C(O)NR$_5$R$_6$, —N(H)C(O)R$_7$, —N(H)CO$_2$R$_7$,

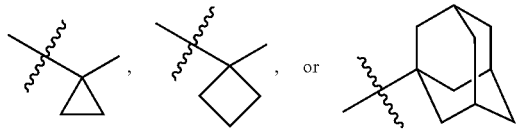

In another embodiment is a compound of Formula (V) or Formula (Va) wherein $R_6$ is H, $C_1$-$C_6$alkyl, or $C_1$-$C_6$alkyl$C_6$-$C_{10}$aryl, and $R_7$ is $C_1$-$C_6$alkyl, $C_6$-$C_{10}$aryl, $C_1$-$C_6$alkyl$C_6$-$C_{10}$aryl, or $C_1$-$C_6$alkyl$C_3$-$C_9$heteroaryl.

In another embodiment is a compound of Formula (VI):

Formula (VI)

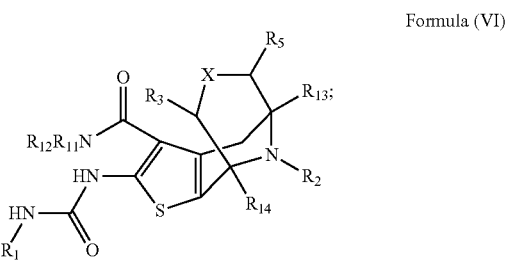

wherein:
X is a single bond, double bond, —CH$_2$—, or —O—;
$R_1$ is $C_6$-$C_{10}$aryl or $C_3$-$C_9$heteroaryl, wherein $C_6$-$C_{10}$aryl and $C_3$-$C_9$heteroaryl are optionally substituted with one or more $R_4$;
$R_{2a}$ is $C_1$-$C_6$alkyl, $C_1$-$C_6$alkyl-OR$_5$, or $C_1$-$C_6$alkyl$C_3$-$C_6$cycloalkyl;
$R_2$ is $C_1$-$C_6$alkyl, $C_1$-$C_6$alkyl-OR$_6$, $C_1$-$C_6$alkyl$C_3$-$C_6$cycloalkyl, or $C_1$-$C_6$alkyl-CO$_2$R;
$R_3$ are $R_5$ are each independently H, or $C_1$-$C_6$alkyl; or
$R_3$ and $R_5$ together form an optionally substituted $C_3$-$C_6$cycloalkyl ring, optionally substituted $C_2$-$C_7$heterocycloalkyl ring, optionally substituted $C_6$-$C_{10}$aryl ring, or an optionally substituted $C_3$-$C_9$heteroaryl ring;
each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, —C(O)NR$_8$R$_9$, —N(R$_8$)C(O)R$_{10}$, —N(R$_8$)CO$_2$R$_{10}$, —NHS(O)$_2$R$_{10}$, —S(O)$_2$NR$_8$R$_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, $C_6$-$C_{10}$aryl, and $C_3$-$C_9$heteroaryl;
$R_6$ is H, or $C_1$-$C_6$alkyl;
$R_8$ is H, or $C_1$-$C_6$alkyl;
$R_9$ is H, $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;
$R_{10}$ is $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;
$R_{11}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

or $R_{11}$ and $R_{12}$ together with the nitrogen to which they are attached form an optionally substituted $C_2$-$C_7$heterocycloalkyl ring; and $R_{13}$ are $R_{14}$ are each independently H, or $C_1$-$C_6$alkyl;

or a pharmaceutically acceptable salt, pharmaceutically acceptable solvate or hydrate, pharmaceutically acceptable salt hydrate, or pharmaceutically acceptable prodrug thereof.

In another embodiment is a compound of Formula (VI) wherein $R_1$ is $C_6$-$C_{10}$aryl. In a further embodiment is a compound of Formula (VI) wherein $R_1$ is phenyl. In a further embodiment is a compound of Formula (VI) wherein $R_1$ is phenyl substituted with one or more $R_4$, and $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, $C_1$-$C_6$alkyl, and $C_1$-$C_6$haloalkyl. In yet a further embodiment is a compound of Formula (VI) wherein $R_1$ is phenyl substituted with one or more $R_4$, and $R_4$ is independently selected from F, Cl, Br, I, —CN, —CF$_3$, —OR$_9$, —OCF$_3$, —C(O)R$_{10}$, —CO$_2$R$_9$, and $C_1$-$C_6$alkyl. In another embodiment is a compound of Formula (VI) wherein $R_1$ is 4-chlorophenyl.

In another embodiment is a compound of Formula (VI) wherein $R_{11}$ and $R_{12}$ are each H. In another embodiment is a compound of Formula (VI) wherein $R_2$ is $C_1$-$C_6$alkyl-CO$_2$R$_6$. In another embodiment is a compound of Formula (VI) wherein $R_{2a}$ is $C_1$-$C_6$alkyl. In another embodiment is a compound of Formula (VI) wherein $R_{13}$ and $R_{14}$ are each H. In another embodiment is a compound of Formula (VI) wherein $R_{13}$ and $R_{14}$ are each CH$_3$. In another embodiment is a compound of Formula (VI) wherein $R_3$ and $R_5$ are each H.

In another embodiment is a compound of Formula (VII):

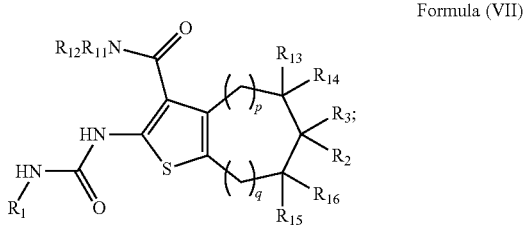

Formula (VII)

wherein:
$R_1$ is $C_6$-$C_{10}$aryl or $C_3$-$C_9$heteroaryl, wherein $C_6$-$C_{10}$aryl and $C_3$-$C_9$heteroaryl are optionally substituted with one or more $R_4$;

$R_2$ is H, $C_1$-$C_6$alkyl, $C_1$-$C_6$alkyl-NR$_5$R$_6$, $C_1$-$C_6$alkyl-OR$_5$, or $C_1$-$C_6$alkyl$C_3$-$C_6$cycloalkyl;

$R_3$ is —NR$_5$R$_6$, $C_1$-$C_6$alkyl-NR$_5$R$_6$, $C_1$-$C_6$haloalkyl, $C_1$-$C_6$alkyl-OR$_5$, optionally substituted $C_1$-$C_6$alkyl$C_3$-$C_6$cycloalkyl, optionally substituted $C_2$-$C_7$heterocycloalkyl, $C_1$-$C_6$alkyl-CO$_2$R$_6$, $C_1$-$C_6$alkyl-C(O)NR$_5$R$_6$,

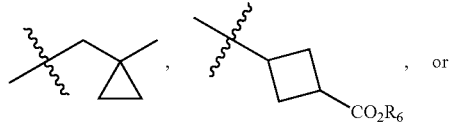

, or

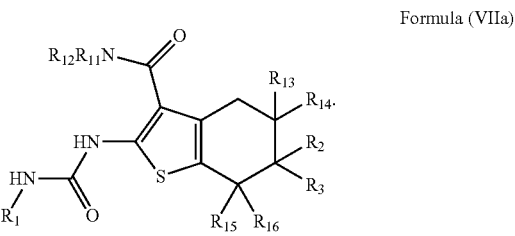

or $R_2$ and $R_3$ together with the carbon atom to which they are attached form an optionally substituted $C_2$-$C_7$heterocycloalkyl ring;

each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, —C(O)NR$_8$R$_9$, —N(R$_8$)C(O)R$_{10}$, —N(R$_8$)CO$_2$R$_{10}$, —NHS(O)$_2$R$_{10}$, —S(O)$_2$NR$_8$R$_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, $C_6$-$C_{10}$aryl, and $C_3$-$C_9$heteroaryl;

each $R_5$ is independently H, or $C_1$-$C_6$alkyl;

$R_6$ is H, or $C_1$-$C_6$alkyl;

$R_8$ is H, or $C_1$-$C_6$alkyl;

$R_9$ is H, $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

$R_{10}$ is $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

$R_{11}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

or $R_{11}$ and $R_{12}$ together with the nitrogen to which they are attached form an optionally substituted $C_2$-$C_7$heterocycloalkyl ring;

$R_{13}$, $R_{14}$, $R_{15}$, and $R_{16}$ are each independently H, or $C_1$-$C_4$alkyl;

p is an integer selected from 0-3; and
q is an integer selected from 0-3;

or a pharmaceutically acceptable salt, pharmaceutically acceptable solvate or hydrate, pharmaceutically acceptable salt hydrate, or pharmaceutically acceptable prodrug thereof.

In another embodiment is a compound of Formula (VII) having the structure of Formula (VIIa):

Formula (VIIa)

In a further embodiment is a compound of Formula (VIIa) wherein $R_1$ is $C_6$-$C_{10}$aryl. In a further embodiment is a compound of Formula (VIIa) wherein $R_1$ is phenyl. In a further embodiment is a compound of Formula (VIIa) wherein $R_1$ is phenyl substituted with one or more $R_4$, and $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, $C_1$-$C_6$alkyl, and $C_1$-$C_6$haloalkyl. In yet a further embodiment is a compound of Formula (VIIa) wherein $R_1$ is phenyl substituted with one or more $R_4$, and $R_4$ is independently selected from F, Cl, Br, I, —CN, —CF$_3$, —OR$_9$, —OCF$_3$, —C(O)R$_{10}$, —CO$_2$R$_9$, and C$_1$-C$_6$alkyl. In another embodiment is a compound of Formula (VIIa) wherein $R_1$ is 4-chlorophenyl.

In another embodiment is a compound of Formula (VII) or Formula (VIIa) wherein $R_{11}$ and $R_{12}$ are each H. In another embodiment is a compound of Formula (VII) or Formula (VIIa) wherein $R_2$ and $R_3$ together with the carbon atom to which they are attached form an optionally substituted C$_2$-C$_7$heterocycloalkyl ring. In another embodiment is a compound of Formula (VII) or Formula (VIIa) wherein $R_2$ is H, and $R_3$ is —NR$_5$R$_6$. In another embodiment is a compound of Formula (VII) or Formula (VIIa) wherein $R_2$ is H, and $R_3$ is optionally substituted C$_2$-C$_7$heterocycloalkyl.

In some embodiments is a compound of Formula (I)-(VII) having the structure:

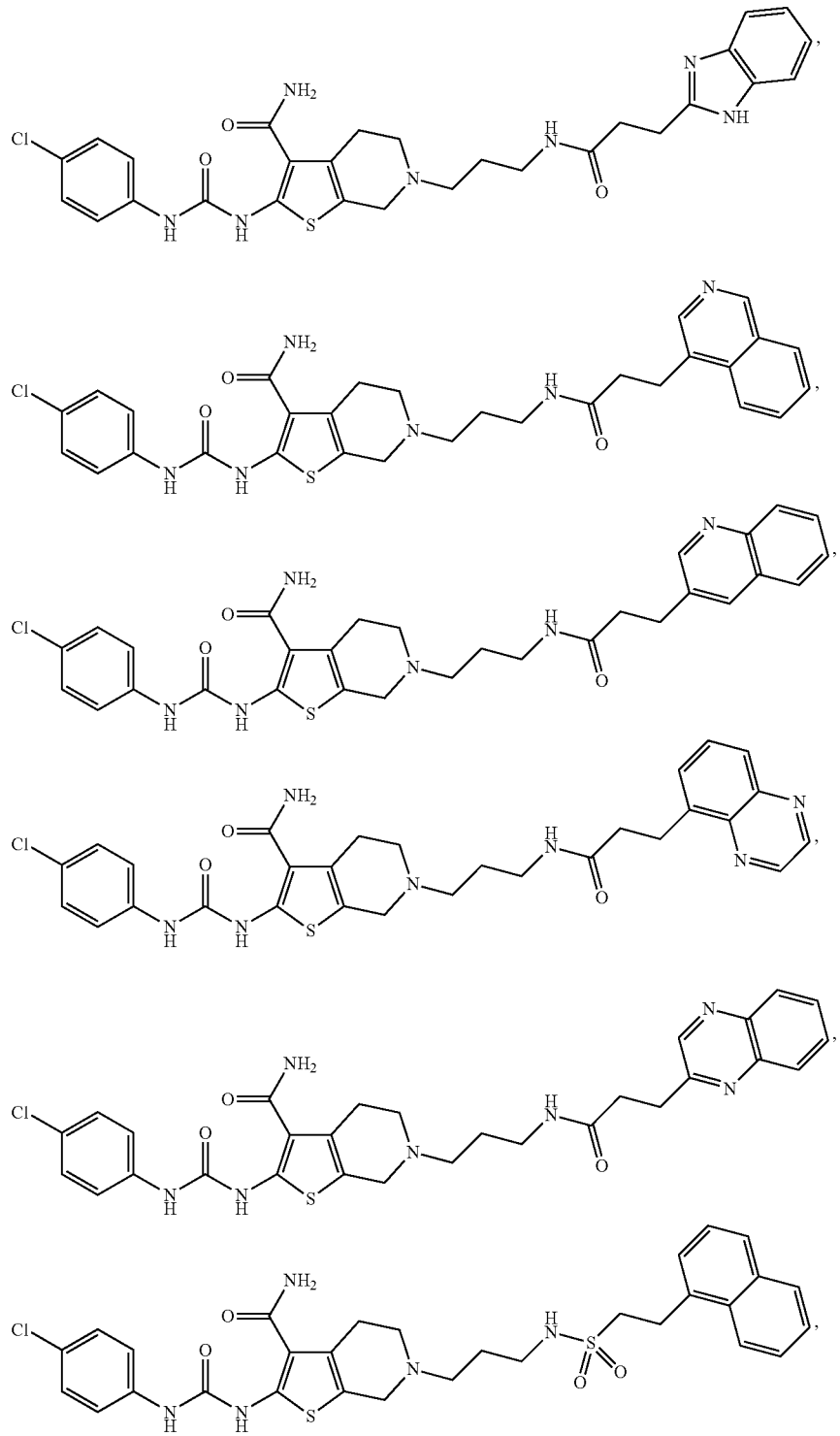

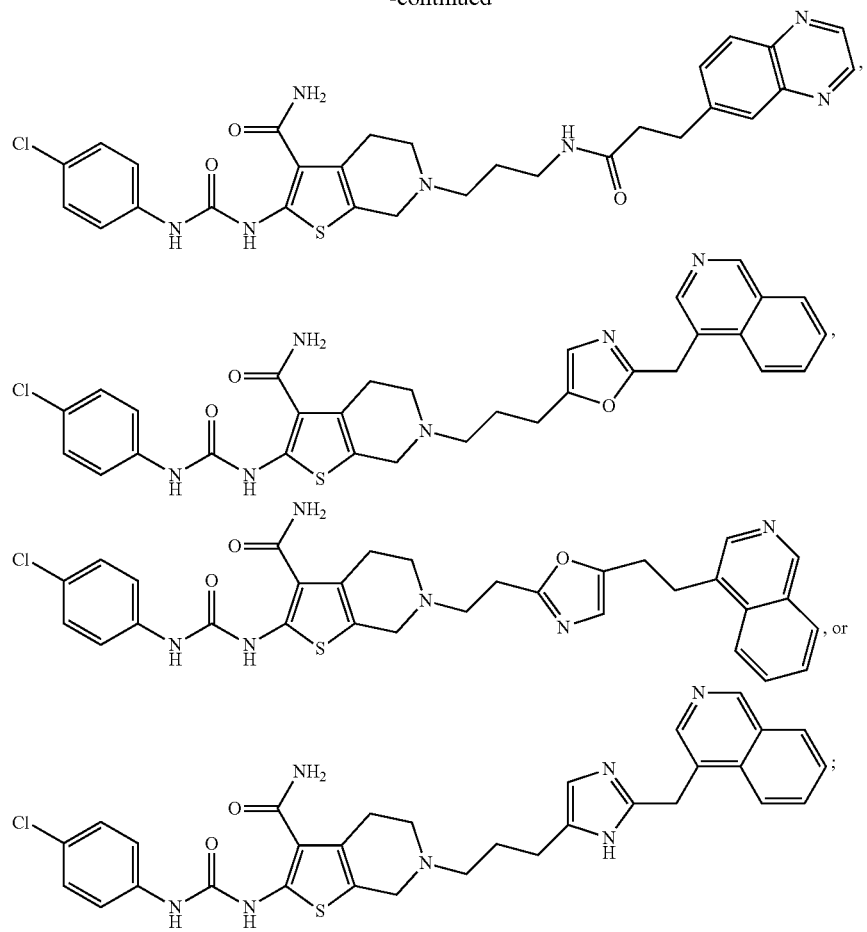

or a pharmaceutically acceptable salt, pharmaceutically acceptable solvate or hydrate, pharmaceutically acceptable salt hydrate, or pharmaceutically acceptable prodrug thereof.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein.

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups are optionally removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and are optionally subsequently removed by metal or pi-acid catalysts. For example, an allyl-blocked carboxylic acid are optionally deprotected with a Pd⁰-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

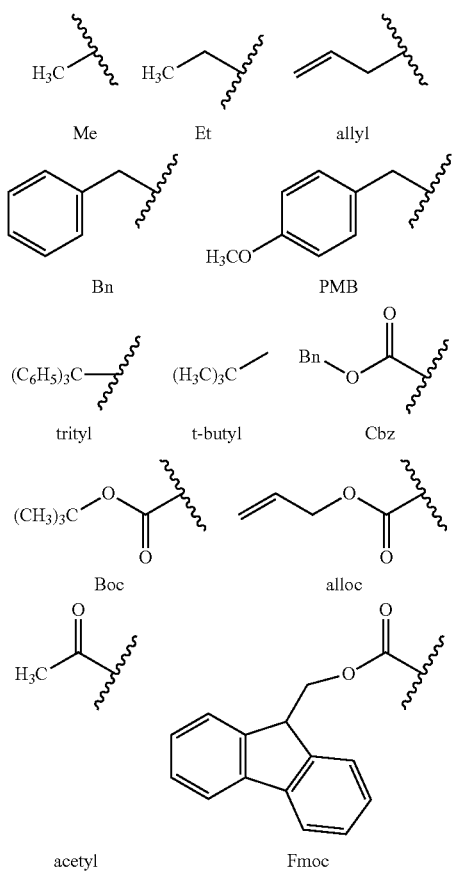

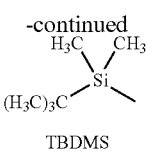

TBDMS

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Pharmaceutical Compositions and Methods of Administration

Pharmaceutical compositions may be formulated in a conventional manner using one or more physiologically acceptable carriers including excipients and auxiliaries which facilitate processing of the active compounds into preparations which are optionally used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (I)-(VII) described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount depends on the severity of the disease, the age and relative health of the subject, the potency of the compound used and other factors. The compounds of Formula (I)-(VII) are optionally used singly or in combination with one or more therapeutic agents as components of mixtures (as in combination therapy).

The pharmaceutical formulations described herein are optionally administered to a subject by multiple administration routes, including but not limited to, oral, parenteral (e.g., intravenous, subcutaneous, intramuscular), intranasal, buccal, topical, rectal, or transdermal administration routes. Moreover, the pharmaceutical compositions described herein, which include a compound of Formula (I)-(VII) described herein, are optionally formulated into any suitable dosage form, including but not limited to, aqueous oral dispersions, liquids, gels, syrups, elixirs, slurries, suspensions, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

One may administer the compounds and/or compositions in a local rather than systemic manner, for example, via injection of the compound directly into an organ or tissue, often in a depot preparation or sustained release formulation. Such long acting formulations may be administered by implantation (for example subcutaneously or intramuscularly) or by intramuscular injection. Furthermore, one may administer the drug in a targeted drug delivery system, for example, in a liposome coated with organ-specific antibody. The liposomes will be targeted to and taken up selectively by the organ. In addition, the drug may be provided in the form of a rapid release formulation, in the form of an extended release formulation, or in the form of an intermediate release formulation.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I)-(VII) described herein, as an active ingredient in free-acid or free-base form, or in a pharmaceutically acceptable salt form. In addition, the methods and pharmaceutical compositions described herein include the use of crystalline forms (also known as polymorphs), as well as active metabolites of these compounds having the same type of activity. In some situations, compounds may exist as tautomers. All tautomers are included within the scope of the compounds presented herein. Additionally, many of the compounds described herein exist in unsolvated as well as solvated forms with pharmaceutically acceptable solvents such as water, ethanol, and the like. The solvated forms of the compounds presented herein are also considered to be disclosed herein.

In certain embodiments, compositions provided herein may also include one or more preservatives to inhibit microbial activity. Suitable preservatives include quaternary ammonium compounds such as benzalkonium chloride, cetyltrimethylammonium bromide and cetylpyridinium chloride.

Pharmaceutical preparations for oral use are optionally obtained by mixing one or more solid excipient with one or more of the compounds of Formula (I)-(VII) described herein, optionally grinding the resulting mixture, and processing the mixture of granules, after adding suitable auxiliaries, if desired, to obtain tablets, pills, or capsules. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that are used orally include push-fit capsules made of gelatin, as well as soft, sealed capsules made of gelatin and a plasticizer, such as glycerol or sorbitol. The push-fit capsules optionally contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the compounds described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound of Formula (I)-(VII) described herein, with one or more pharmaceutical excipients to form a bulk blend composition. When referring to these bulk blend compositions as homogeneous, it is meant that the particles of the compound of Formula (I)-(VII) described herein, are dispersed evenly throughout the composition so that the composition may be subdivided into equally effective unit dosage forms, such as tablets, pills, and capsules. The individual unit dosages may also include film coatings, which disintegrate upon oral ingestion or upon contact with diluent. These formulations are optionally manufactured by conventional pharmacological techniques.

The pharmaceutical solid dosage forms described herein include a compound of Formula (I)-(VII) described herein, and optionally one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethylcellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of Formula (I)-(VII) from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that are optionally filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. In some embodiments, formulators determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol optionally is selected to have a molecular weight of about 300 to about 6000, or about 3350 to about 4000, or about 5400 to about 7000, vinyl pyrrolidone/vinyl acetate copolymer (S630), sodium carboxymethylcellulose, methylcellulose, hydroxypropylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

There is considerable overlap between additives used in the solid dosage forms described herein. Thus, the above-listed additives should be taken as merely exemplary, and not limiting, of the types of additives that can be included in solid dosage forms of the pharmaceutical compositions described herein.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of the compounds of Formula (I) described herein from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of Formula (I) described herein and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Microencapsulated compounds described herein may be formulated by methods that include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

The pharmaceutical solid oral dosage forms including formulations described herein, which include a compound described herein, can be further formulated to provide a controlled release of the compound of Formula (I). Controlled release refers to the release of the compounds described herein from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In other embodiments, the formulations described herein, which include a compound of Formula (I) described herein, are delivered using a pulsatile dosage form. A pulsatile dosage form is capable of providing one or more immediate release pulses at predetermined time points after a controlled lag time or at specific sites. Pulsatile dosage forms may be administered using a variety of pulsatile formulations including, but are not limited to, those described in U.S. Pat. Nos. 5,011,692; 5,017,381; 5,229,135; 5,840,329; 4,871,549; 5,260,068; 5,260,069; 5,508,040; 5,567,441 and 5,837,284.

Many other types of controlled release systems are suitable for use with the formulations described herein. Examples of such delivery systems include, e.g., polymer-based systems, such as polylactic and polyglycolic acid, polyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., Pharmaceutical Dosage Forms, 2 Ed., Vol. 1, pp. 209-214 (1990); Singh et al., Encyclopedia of Pharmaceutical Technology, 2nd Ed., pp. 751-753 (2002); U.S. Pat. Nos. 4,327,725; 4,624,848; 4,968,509; 5,461,140; 5,456,923; 5,516,527; 5,622,721; 5,686,105; 5,700,410; 5,977,175; 6,465,014; and 6,932,983.

In some embodiments, pharmaceutical formulations are provided that include particles of the compounds described herein, e.g. compounds of Formula (I), and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002).

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

The pharmaceutical compositions described herein may include sweetening agents such as, but not limited to, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally recognized in the field. For other parenteral injections, appropriate formulations may include aqueous or non-aqueous solutions, preferably with physiologically compatible buffers or excipients. Such excipients are generally recognized in the field.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

Generally, an agent, such as a compound of Formula (I), is administered in an amount effective for amelioration of, or prevention of the development of symptoms of, the disease or disorder (i.e., a therapeutically effective amount). Thus, a therapeutically effective amount can be an amount that is capable of at least partially preventing or reversing a disease or disorder. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based in in vivo animal studies.

An agent can be administered prior to, concurrently with and subsequent to the appearance of symptoms of a disease or disorder. In some embodiments, an agent is administered to a subject with a family history of the disease or disorder, or who has a phenotype that may indicate a predisposition to a disease or disorder, or who has a genotype which predisposes the subject to the disease or disorder.

Methods of Dosing and Treatment Regimens

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multidose containers, with an added preservative.

The daily dosages appropriate for the compounds described herein are from about 0.01 mg/kg to about 20 mg/kg. In one embodiment, the daily dosages are from about 0.1 mg/kg to about 10 mg/kg. An indicated daily dosage in the larger mammal, including, but not limited to, humans, is in the range from about 0.5 mg to about 1000 mg, conveniently administered in a single dose or in divided doses, including, but not limited to, up to four times a day or in extended release form. Suitable unit dosage forms for oral administration include from about 1 to about 500 mg active ingredient. In one embodiment, the unit dosage is about 1 mg, about 5 mg, about, 10 mg, about 20 mg, about 50 mg, about 100 mg, about 200 mg, about 250 mg, about 400 mg, or about 500 mg. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The compounds of Formula (I)-(VII) described herein, and compositions thereof, may also be used in combination with other therapeutic agents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In certain instances, it may be appropriate to administer at least one compound described herein in combination with another therapeutic agent. By way of example only, if one of the side effects experienced by a patient upon receiving one of the compounds herein, such as a compound of Formula (I), is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

In some embodiments, a compound of Formula (I)-(VII) is administered in combination with an aminoglycoside antibiotic. In some embodiments, a compound of Formula (I)-(VII)

is administered in combination with an aminoglycoside antibiotic selected from streptomycin, neomycin, framycetin, paromomycin, paromomycin sulfate, ribostamycin, kanamycin, amikacin, arbekacin, bekanamycin, dibekacin, tobramycin, spectinomycin, hygromycin B, gentamicin, netilmicin, sisomicin, isepamicin, verdamicin, and astromicin. In some embodiments, a compound of Formula (I)-(VII) is administered in combination with streptomycin. In some embodiments, a compound of Formula (I)-(VII) is administered in combination with amikacin. In some embodiments, a compound of Formula (I)-(VII) is administered in combination with neomycin. In some embodiments, a compound of Formula (I)-(VII) is administered in combination with kanamycin. In some embodiments, a compound of Formula (I)-(VII) is administered in combination with gentamicin. In some embodiments, a compound of Formula (I)-(VII) is administered in combination with tobramycin.

In some embodiments, a compound of Formula (I)-(VII) is administered in combination with a chemotherapeutic agent. In some embodiments, a compound of Formula (I)-(VII) is administered in combination with a chemotherapeutic agent selected from cisplatin and carboplatin. In some embodiments, a compound of Formula (I)-(VII) is administered in combination with cisplatin. In some embodiments, a compound of Formula (I)-(VII) is administered in combination with carboplatin.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the physician after evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula (I)-(VII) described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over about 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from 1 day to about 3 months. The length of treatment can vary for each subject, and the length can be determined using the known criteria. For example, the compound or a formulation containing the compound can be administered for at least 2 weeks, preferably about 1 month to about 5 years.

EXAMPLES

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Example 1

Preparation of 2-[3-(4-chlorophenyl)ureido]-6-(cyclopropylmethyl)-4,5,6,7-tetrahydrothieno[2,3-c]pyridine-3-carboxamide hydrochloride (A6)

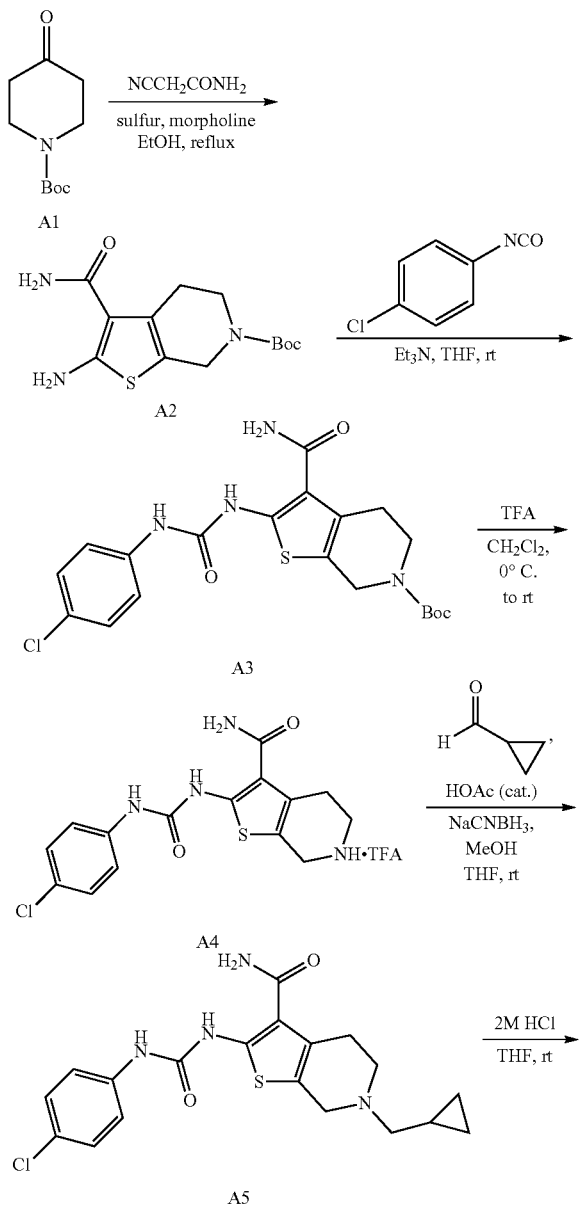

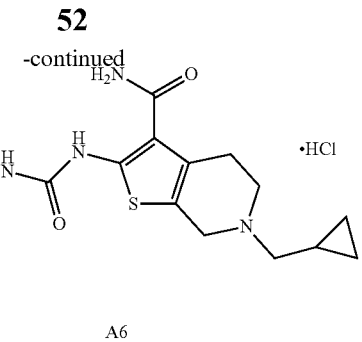

Step 1: tert-Butyl 2-amino-3-carbamoyl-4,5-dihydrothieno[2,3-c]pyridine-6(7H)-carboxylate (A2)

A suspension of cyanoacetamide (4.65 g, 55.3 mmol), tert-butyl 4-oxopiperidine-1-carboxylate (A1, 10.0 g, 50.3 mmol), sulfur (1.92 g, 59.9 mmol), and morpholine (8.71 mL, 100 mmol) in ethanol (50 mL) was heated to reflux for 4 h and then cooled to room temperature. The reaction mixture was concentrated under reduced pressure. The resulting residue was triturated with a 1:1 mixture of methylene chloride and ethyl acetate to afford compound A2 as a light orange solid (14.2 g, 95%): $^1$H NMR (300 MHz, DMSO-$d_6$) δ 6.98 (bs, 2H), 6.60 (bs, 2H), 4.27 (bs, 2H), 3.55-3.48 (m, 2H), 2.71-2.67 (m, 2H), 1.42 (s, 9H). MS (M+H) 298.

Step 2: tert-Butyl 3-carbamoyl-2-[3-(4-chlorophenyl)ureido]-4,5-dihydrothieno[2,3-c]pyridine-6(7H)-carboxylate (A3)

A solution of 4-chlorophenyl isocyanate (11.1 g, 72.3 mmol), compound A2 (19.5 g, 65.6 mmol), and triethylamine (12.0 mL, 86.1 mmol) in anhydrous tetrahydrofuran (150 mL) was stirred at room temperature for 16 h. After this time, the reaction mixture was concentrated under reduced pressure. The resulting residue was triturated with a mixture of 1:1 methylene chloride and ethyl acetate to afford compound A3 as an off-white solid (25.3 g, 86%): $^1$H NMR (300 MHz, DMSO-$d_6$) δ 10.85 (s, 1H), 10.20 (s, 1H), 7.52-7.45 (m, 3H), 7.34 (d, J=9.0 Hz, 2H), 6.94 (bs, 1H), 4.43 (s, 2H), 3.57-3.53 (m, 2H), 2.79-2.75 (m, 2H), 1.43 (s, 9H). MS (M+Na) 473.

Step 3: 2-[3-(4-Chlorophenyl)ureido]-4,5,6,7-tetrahydrothieno[2,3-c]pyridine-3-carboxamide trifluoroacetate (A4)

To a solution of compound A3 (16.0 g, 35.5 mmol) in methylene chloride (100 mL) was added trifluoroacetic acid (30.0 mL, 392 mmol) dropwise over 5 min at 0° C. After the addition complete, the reaction mixture was warmed to room temperature and stirred for 4 h. The reaction mixture was concentrated under reduced pressure and the resulting residue was triturated with ethyl acetate (75 mL) to afford compound A4 as an off-white solid (16.5 g, quantitative yield): $^1$H NMR (500 MHz, DMSO-$d_6$) δ 10.97 (s, 1H), 10.24 (s, 1H), 9.17 (bs, 2H), 7.60-7.12 (m, 6H), 4.25 (s, 2H), 3.37-3.34 (m, 2H), 3.01-2.98 (m, 2H). MS (M+H) 351.

Step 4: 2-[3-(4-Chlorophenyl)ureido]-6-(cyclopropylmethyl)-4,5,6,7-tetrahydrothieno[2,3-c]pyridine-3-carboxamide (A5)

To a slurry of compound A4 (300 mg, 0.645 mmol) in methanol (4 mL) and tetrahydrofuran (2 mL) two drops of glacial acetic acid and cyclopropanecarbaldehyde (94.0 mg, 1.34 mmol) were added. After stirring at room temperature for 5 min, sodium cyanoborohydride (122 mg, 1.94 mmol) was added and the reaction mixture was stirred for an additional 3 h. After this time, the reaction was quenched with water (25 mL) and saturated aqueous sodium bicarbonate (50 mL). The resulting mixture was extracted with ethyl acetate (100 mL). The extracts were dried over anhydrous sodium sulfate, filtered, and concentrated under reduced pressure. The resulting residue was triturated with methylene chloride to afford compound A5 as a white solid (245 mg, 94%): $^1$H NMR (500 MHz, DMSO-$d_6$) δ 10.95 (s, 1H), 10.16 (s, 1H), 7.54-7.40 (m, 3H), 7.33 (d, J=9.0 Hz, 2H), 6.83 (bs, 1H), 3.54 (s, 2H), 2.84-2.78 (m, 2H), 2.78-2.69 (m, 2H), 2.36 (s, 2H), 0.95-0.87 (m, 1H), 0.53-0.45 (m, 2H), 0.17-0.09 (m, 2H). MS (M+H) 405.

Step 5: 2-[3-(4-Chlorophenyl)ureido]-6-(cyclopropylmethyl)-4,5,6,7-tetrahydrothieno[2,3-c]pyridine-3-carboxamide hydrochloride (A6)

To a solution of compound A5 (121 mg, 0.299 mmol) in tetrahydrofuran (5 mL) was added hydrochloride (2 M in diethyl ether, 0.200 mL, 0.400 mmol). After stirring at room temperature for 15 min, the reaction mixture was concentrated under reduced pressure and the resulting residue was triturated with methylene chloride to afford compound A6 as a yellow solid (94 mg, 71%): $^1$H NMR (500 MHz, DMSO-$d_6$) δ 10.97 (s, 1H), 10.28 (bs, 1H), 10.26 (s, 1H), 7.55-7.48 (m, 3H), 7.35 (d, J=9.0 Hz, 2H), 7.14 (bs, 1H), 4.61-4.57 (m, 1H), 4.31-4.28 (m, 1H), 3.72-3.70 (m, 1H), 3.39-3.36 (m, 1H), 3.22-3.19 (m, 1H), 3.11-3.08 (m, 3H), 1.19-1.11 (m, 1H), 0.70-0.63 (m, 2H), 0.45-0.39 (m, 2H). MS (M+H) 405.

Example 2

Preparation of 2-[3-(4-Chlorophenyl)ureido]-6-isopropyl-4,5,6,7-tetrahydrothieno[2,3-c]pyridine-3-carboxamide hydrochloride

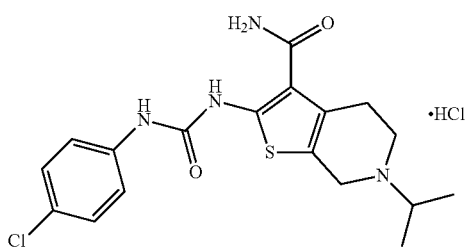 [SMILES: CC(C)N1CCc2c(sc(NC(=O)Nc3ccc(Cl)cc3)c2C(N)=O)C1 ; Cl]

The title compound was prepared using a similar procedure as described in Example 1. MS (M+H) 393. $^1$H NMR (500 MHz, DMSO-$d_6$) δ 11.03 (s, 1H), 10.28 (s, 1H), 10.25 (bs, 1H), 7.55-7.02 (m, 6H), 4.43-4.39 (m, 1H), 4.36-4.28 (m, 1H), 3.71-3.61 (m, 2H), 3.30-3.04 (m, 3H), 1.36-1.32 (m, 6H).

Example 3

Preparation of 2-[3-(4-Chlorophenyl)ureido]-6-(3-methoxypropyl)-4,5,6,7-tetrahydrothieno[2,3-c]pyridine-3-carboxamide hydrochloride

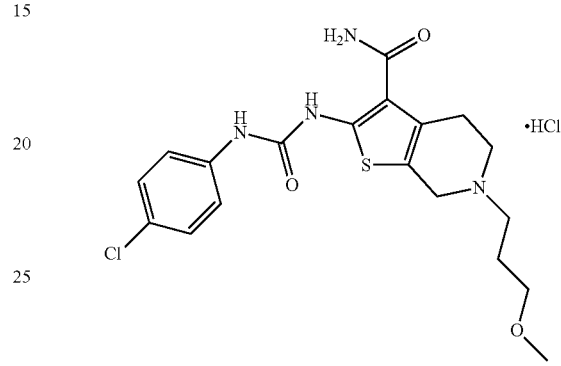

The title compound was prepared using a similar procedure as described in Example 1. MS (M+H) 423. $^1$H NMR (500 MHz, DMSO-$d_6$) δ 10.95 (s, 1H), 10.30 (bs, 1H), 10.26 (s, 1H), 7.70-7.00 (m, 6H), 4.57-4.53 (m, 1H), 4.26-4.22 (m, 1H), 3.71-3.62 (m, 1H), 3.48-3.40 (m, 2H), 3.28-3.20 (m, 6H), 3.13-3.06 (m, 2H), 2.04-1.96 (m, 2H).

Example 4

Preparation of tert-Butyl 3-{3-carbamoyl-2-[3-(4-chlorophenyl)ureido]-4,5-dihydrothieno[2,3-c]pyridin-6(7H)-yl}pyrrolidine-1-carboxylate

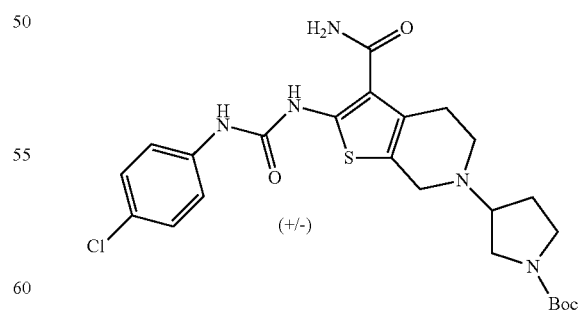

The title compound was prepared using a similar procedure as described in Example 1. MS (M+H) 520. $^1$H NMR (500 MHz, DMSO-$d_6$) δ 10.94 (s, 1H), 10.16 (s, 1H), 7.71-7.20 (m, 5H), 6.82 (bs, 1H), 3.62-3.56 (m, 2H), 3.53-3.49 (m, 1H),

Example 5

Preparation of 2-[3-(4-Chlorophenyl)ureido]-6-(tetrahydro-2H-pyran-4-yl)-4,5,6,7-tetrahydrothieno[2,3-c]pyridine-3-carboxamide hydrochloride

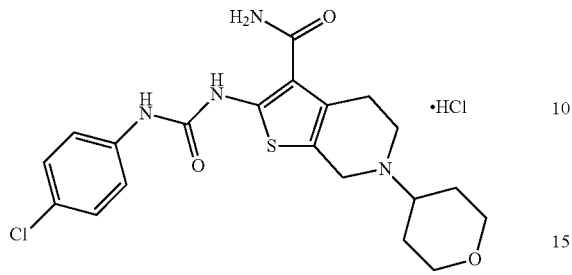

The title compound was prepared using a similar procedure as described in Example 1. MS (M+H) 435. $^1$H NMR (500 MHz, DMSO-d$_6$) δ 11.00 (s, 1H), 10.41 (bs, 1H), 10.27 (s, 1H), 7.72-7.30 (m, 5H), 7.11 (bs, 1H), 4.51-4.47 (m, 1H), 4.39-4.33 (m, 1H), 4.04-3.96 (m, 2H), 3.81-3.75 (m, 1H), 3.59-3.51 (m, 1H), 3.40-3.35 (m, 2H), 3.32-3.28 (m, 1H), 3.17-3.09 (m, 2H), 2.12-2.09 (m, 1H), 2.07-1.98 (m, 1H), 1.83-1.72 (m, 2H).

Example 6

Preparation of 2-[3-(4-Chlorophenyl)ureido]-6-(oxetan-3-yl)-4,5,6,7-tetrahydrothieno[2,3-c]pyridine-3-carboxamide hydrochloride

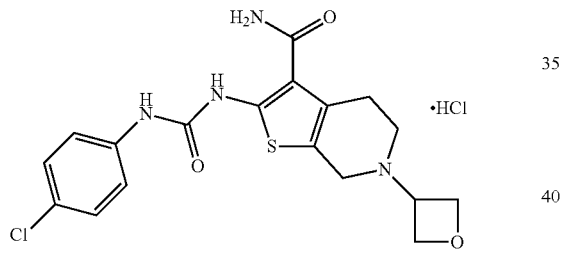

The title compound was prepared using a similar procedure as described in Example 1. MS (M+H) 407. $^1$H NMR (500 MHz, DMSO-d$_6$) δ 11.61 (bs, 1H), 10.93 (s, 1H), 10.26 (s, 1H), 7.73-6.97 (m, 6H), 4.93-4.70 (m, 3H), 4.69-4.49 (m, 2H), 4.19-4.06 (m, 1H), 3.78-3.48 (m, 2H), 3.40-3.21 (m, 1H), 3.19-3.02 (m, 2H).

Example 7

Preparation of (+/−)-2-[3-(4-Chlorophenyl)ureido]-6-(pyrrolidin-3-yl)-4,5,6,7-tetrahydrothieno[2,3-c]pyridine-3-carboxamide dihydrochloride

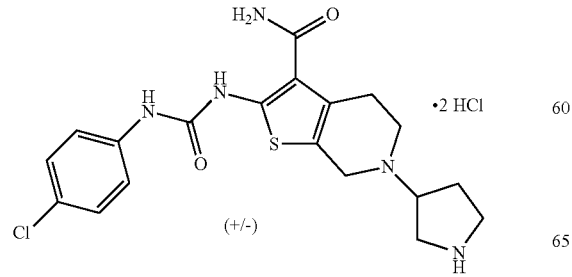

The title compound was prepared using a similar procedure as described in Example 1. MS (M+H) 420. $^1$H NMR (500 MHz, DMSO-d$_6$) δ 11.85 (bs, 1H), 10.96 (s, 1H), 10.26 (s, 1H), 9.48 (bs, 2H), 7.73-7.00 (m, 6H), 4.70-4.50 (m, 1H), 4.42-4.28 (m, 1H), 4.22-4.00 (m, 1H), 3.86-3.40 (m, 5H), 3.31-3.00 (m, 4H), 2.45-2.27 (m, 1H).

Example 8

Preparation of 2-[3-(4-Chlorophenyl)ureido]-6-(1-methylpiperidin-4-yl)-4,5,6,7-tetrahydrothieno[2,3-c]pyridine-3-carboxamide dihydrochloride

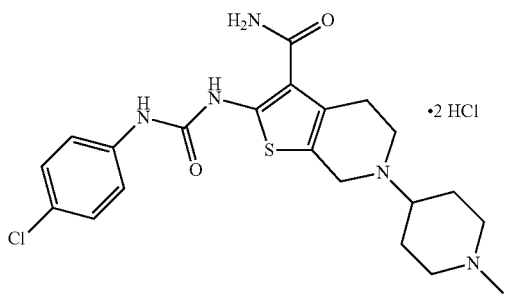 [SMILES: CN1CCC(N2CCc3c(sc(NC(=O)Nc4ccc(Cl)cc4)c3C(N)=O)C2)CC1 ; "·2 HCl"]

The title compound was prepared using a similar procedure as described in Example 1. MS (M+H) 448. $^1$H NMR (500 MHz, DMSO-d$_6$) δ 11.15 (bs, 1H), 10.99 (s, 1H), 10.49 (bs, 1H), 10.28 (s, 1H), 7.79-6.98 (m, 6H), 4.58-4.49 (m, 1H), 4.42-4.34 (m, 1H), 3.78-3.48 (m, 4H), 3.21-3.10 (m, 2H), 3.18-2.94 (m, 2H), 2.83-2.72 (m, 4H), 2.48-2.30 (m, 2H), 2.19-2.05 (m, 2H).

Example 9

Preparation of (+/−)-2-[3-(4-Chlorophenyl)ureido]-6-(1-methylpyrrolidin-3-yl)-4,5,6,7-tetrahydrothieno[2,3-c]pyridine-3-carboxamide dihydrochloride

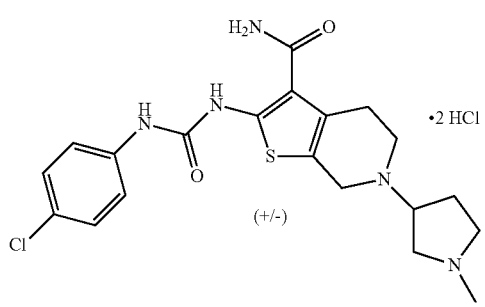 [SMILES: CN1CCC(N2CCc3c(sc(NC(=O)Nc4ccc(Cl)cc4)c3C(N)=O)C2)C1 ; "·2 HCl"]

The title compound was prepared using a similar procedure as described in Example 1. MS (M+H) 434. $^1$H NMR (500 MHz, DMSO-d$_6$) δ 11.14 (bs, 1H), 10.97 (s, 1H), 10.77 (bs, 1H), 10.25 (s, 1H), 7.74-6.83 (m, 6H), 4.85-3.89 (m, 4H), 3.82-3.50 (m, 3H), 3.21-3.00 (m, 2H), 2.96-2.82 (m, 4H), 2.62-2.50 (m, 3H).

Example 10

Preparation of tert-Butyl 2-{3-carbamoyl-2-[3-(4-chlorophenyl)ureido]-4,5-dihydrothieno[2,3-c]pyridin-6(7H)-yl}ethylcarbamate

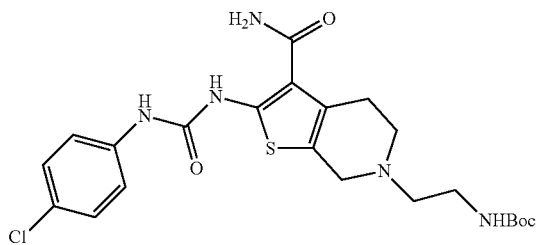 [SMILES: CC(C)(C)OC(=O)NCCN1CCc2c(sc(NC(=O)Nc3ccc(Cl)cc3)c2C(N)=O)C1]

The title compound was prepared using a similar procedure as described in Example 1. MS (M+H) 494. $^1$H NMR (300 MHz, DMSO-d$_6$) δ 10.97 (s, 1H), 10.19 (s, 1H), 7.67-7.26 (m, 5H), 6.85 (bs, 1H), 6.79-6.68 (m, 1H), 3.57-3.48 (m, 2H), 3.18-3.03 (m, 2H), 2.83-2.63 (m, 4H), 2.60-2.50 (m, 2H), 1.38 (s, 9H).

Example 11

Preparation of 6-(2-Aminoethyl)-2-[3-(4-chlorophenyl)ureido]-4,5,6,7-tetrahydrothieno[2,3-c]pyridine-3-carboxamide dihydrochloride

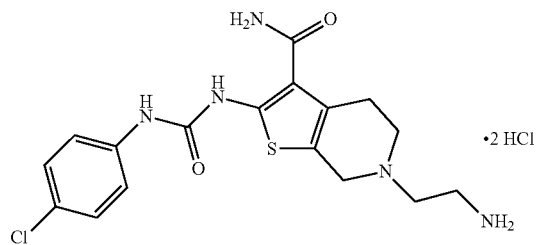 [SMILES: NCCN1CCc2c(sc(NC(=O)Nc3ccc(Cl)cc3)c2C(N)=O)C1 ; "·2 HCl"]

The title compound was prepared using a similar procedure as described in Example 1. MS (M+H) 394. $^1$H NMR (500 MHz, DMSO-d$_6$) δ 11.37 (bs, 1H), 10.96 (s, 1H), 10.27 (s, 1H), 8.34 (bs, 3H), 7.70-6.94 (m, 6H), 4.72-4.56 (m, 1H), 4.38-4.23 (m, 1H), 3.80-3.69 (m, 1H), 3.59-3.39 (m, 5H), 3.23-3.10 (m, 2H).

Example 12

Preparation of 2-[3-(4-Chlorophenyl)ureido]-6-(cyclobutylmethyl)-4,5,6,7-tetrahydrothieno[2,3-c]pyridine-3-carboxamide hydrochloride

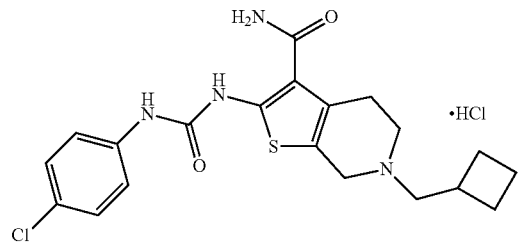 [SMILES: NC(=O)c1c(NC(=O)Nc2ccc(Cl)cc2)sc2c1CCN(CC1CCC1)C2 ; Cl]

The title compound was prepared using a similar procedure as described in Example 1. MS (M+H) 419. $^1$H NMR (500 MHz, DMSO-d$_6$) δ 10.95 (s, 1H), 10.34 (bs, 1H), 10.26 (s, 1H), 7.77-6.94 (m, 6H), 4.47-4.38 (m, 1H), 4.23-4.11 (m, 1H), 3.65-3.54 (m, 1H), 3.31-3.21 (m, 3H), 3.13-3.04 (m, 2H), 2.87-2.78 (m, 1H), 2.19-2.07 (m, 2H), 1.95-1.78 (m, 4H).

Example 13

Preparation of 4-{3-Carbamoyl-2-[3-(4-chlorophenyl)ureido]-4,5-dihydrothieno[2,3-c]pyridin-6(7H)-yl}butanoic acid hydrochloride

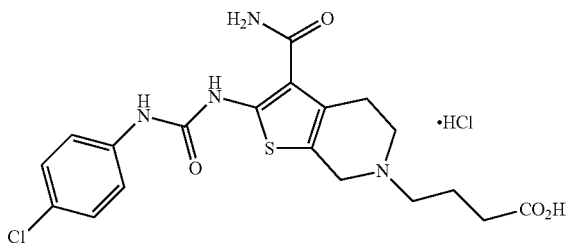 [SMILES: NC(=O)c1c(NC(=O)Nc2ccc(Cl)cc2)sc2c1CCN(CCCC(=O)O)C2 ; Cl]

The title compound was prepared using a similar procedure as described in Example 1. MS (M+H) 437. $^1$H NMR (500 MHz, DMSO-d$_6$) δ 12.24 (bs, 1H), 10.95 (s, 1H), 10.25 (s, 1H), 7.77-6.90 (m, 6H), 4.40-4.08 (m, 2H), 3.48-3.35 (m, 2H), 3.18-2.98 (m, 4H), 2.38-2.33 (m, 2H), 1.97-1.88 (m, 2H).

Example 14

Preparation of tert-Butyl 4-{3-carbamoyl-2-[3-(4-chlorophenyl)ureido]-4,5-dihydrothieno[2,3-c]pyridin-6(7H)-yl}butanoate

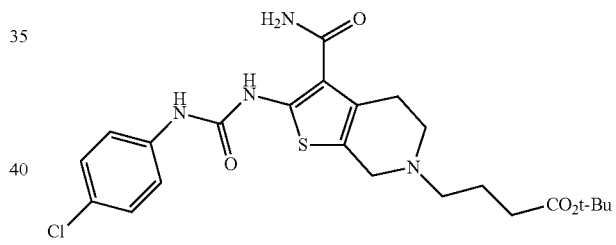

The title compound was prepared using a similar procedure as described in Example 1. MS (M+H) 493. $^1$H NMR (300 MHz, DMSO-d$_6$) δ 10.96 (s, 1H), 10.18 (s, 1H), 7.63-6.70 (m, 6H), 3.52-3.41 (m, 2H), 2.85-2.72 (m, 2H), 2.71-2.61 (m, 2H), 2.50-2.40 (m, 2H), 2.29-2.19 (m, 2H), 1.81-1.67 (m, 2H), 1.39 (s, 9H).

Example 15

Preparation of 6-(2-Acetamidoethyl)-2-[3-(4-chlorophenyl)ureido]-4,5,6,7-tetrahydrothieno[2,3-c]pyridine-3-carboxamide trifluoroacetate

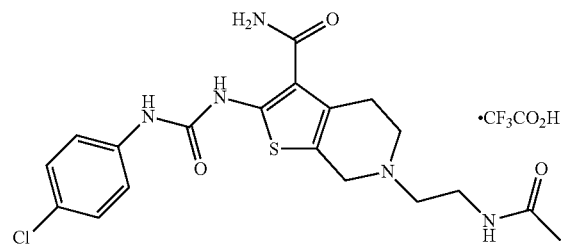 [SMILES: CC(=O)NCCN1CCc2c(sc(NC(=O)Nc3ccc(Cl)cc3)c2C(N)=O)C1 ; "·CF3CO2H"]

The title compound was prepared using a similar procedure as described in Example 1. MS (M+H) 436. ¹H NMR (500 MHz, DMSO-d₆) δ 10.97 (s, 1H), 10.25 (s, 1H), 9.88 (bs, 1H), 8.12 (bs, 1H), 7.70-7.02 (m, 6H), 4.63-4.58 (m, 1H), 4.31-4.26 (m, 1H), 3.77-3.73 (m, 1H), 3.62-3.41 (m, 4H), 3.38-3.22 (m, 1H), 3.16-3.07 (m, 2H), 1.86 (s, 3H).

Example 16

Preparation of 2-[3-(4-Chlorophenyl)ureido]-6-(cyclohexylmethyl)-4,5,6,7-tetrahydrothieno[23-c]pyridine-3-carboxamide hydrochloride

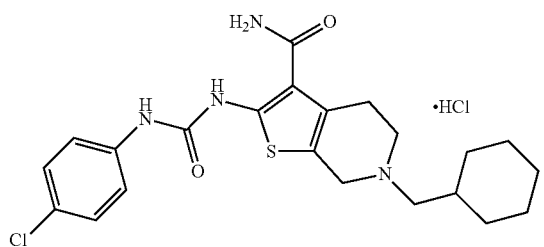 [SMILES: NC(=O)c1c(NC(=O)Nc2ccc(Cl)cc2)sc2c1CCN(CC1CCCCC1)C2 ; Cl]

The title compound was prepared using a similar procedure as described in Example 1. MS (M+H) 447. ¹H NMR (500 MHz, DMSO-d₆) δ 10.94 (s, 1H), 10.27 (s, 1H), 10.15 (bs, 1H), 7.70-7.00 (m, 6H), 4.58-4.53 (m, 1H), 4.25-4.22 (m, 1H), 3.66-3.59 (m, 1H), 3.43-3.31 (m, 1H), 3.12-3.00 (m, 4H), 1.90-1.60 (m, 6H), 1.33-1.11 (m, 3H), 1.02-0.92 (m, 2H).

Example 17

Preparation of 2-[3-(4-Chlorophenyl)ureido]-6-(cyclopentylmethyl)-4,5,6,7-tetrahydrothieno[2,3-c]pyridine-3-carboxamide hydrochloride

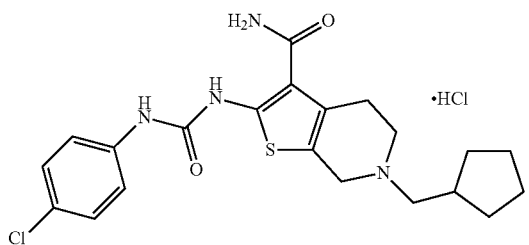 [SMILES: NC(=O)c1c(NC(=O)Nc2ccc(Cl)cc2)sc2c1CCN(CC1CCCC1)C2 ; Cl]

The title compound was prepared using a similar procedure as described in Example 1. MS (M+H) 433. ¹H NMR (500 MHz, DMSO-d₆) δ 10.95 (s, 1H), 10.27 (s, 1H), 10.14 (bs, 1H), 7.73-6.98 (m, 6H), 4.57-4.53 (m, 1H), 4.30-4.22 (m, 1H), 3.70-3.61 (m, 1H), 3.33-3.07 (m, 5H), 2.38-2.27 (m, 1H), 1.91-1.83 (m, 2H), 1.68-1.52 (m, 4H), 1.32-1.20 (m, 2H).

Example 18

Preparation of tert-Butyl 6-{3-carbamoyl-2-[3-(4-chlorophenyl)ureido]-4,5-dihydrothieno[2,3-c]pyridin-6(7H)-yl}hexanoate

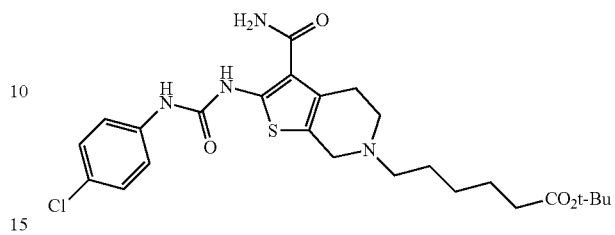

The title compound was prepared using a similar procedure as described in Example 1. MS (M+H) 521. ¹H NMR (500 MHz, DMSO-d₆) δ 10.95 (s, 1H), 10.19 (s, 1H), 7.70-7.30 (m, 5H), 6.89 (bs, 1H), 3.68-3.40 (m, 3H), 2.93-2.70 (m, 3H), 2.52-2.48 (m, 2H), 2.23-2.17 (m, 2H), 1.66-1.49 (m, 4H), 1.40 (s, 9H), 1.35-1.28 (m, 2H).

Example 19

Preparation of tert-Butyl 5-{3-carbamoyl-2-[3-(4-chlorophenyl)ureido]-4,5-dihydrothieno[2,3-c]pyridin-6(7H)-yl}pentanoate

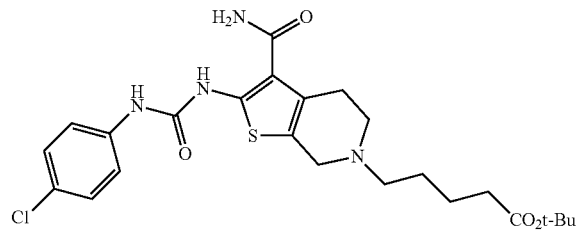 [SMILES: CC(C)(C)OC(=O)CCCCN1CCc2c(sc(NC(=O)Nc3ccc(Cl)cc3)c2C(N)=O)C1]

The title compound was prepared using a similar procedure as described in Example 1. MS (M+H) 507. ¹H NMR (500 MHz, DMSO-d₆) δ 10.94 (s, 1H), 10.17 (s, 1H), 7.61-7.29 (m, 5H), 6.84 (bs, 1H), 3.50-3.40 (m, 2H), 2.82-2.74 (m, 2H), 2.68-2.59 (m, 2H), 2.47-2.40 (m, 2H), 2.25-2.19 (m, 2H), 1.57-1.48 (m, 4H), 1.40 (s, 9H).

Example 20

Preparation of Methyl 4-{3-carbamoyl-2-[3-(4-chlorophenyl)ureido]-4,5-dihydrothieno[2,3-c]pyridin-6(7H)-yl}butanoate hydrochloride

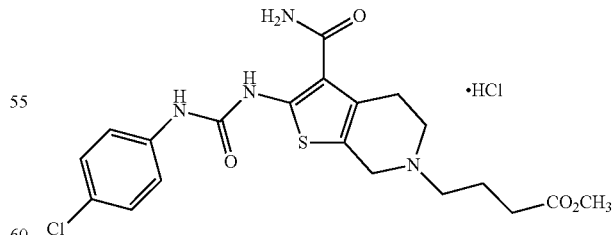

The title compound was prepared using a similar procedure as described in Example 1. MS (M+H) 451. ¹H NMR (500 MHz, DMSO-d₆) δ 10.96 (s, 1H), 10.26 (bs, 2H), 7.72-6.90 (m, 6H), 4.59-4.53 (m, 1H), 4.27-4.18 (m, 1H), 3.74-3.63 (m, 1H), 3.62 (s, 3H), 3.30-3.18 (m, 3H), 3.12-3.02 (m, 2H), 2.48-2.41 (m, 2H), 2.00-1.92 (m, 2H).

Example 21

Preparation of Ethyl 4-{3-carbamoyl-2-[3-(4-chlorophenyl)ureido]-4,5-dihydrothieno[2,3-c]pyridin-6(7H)-yl}butanoate hydrochloride

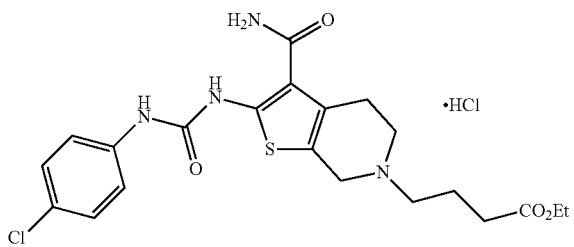 [SMILES: CCOC(=O)CCCN1CCc2c(sc(NC(=O)Nc3ccc(Cl)cc3)c2C(N)=O)C1 ; Cl]

The title compound was prepared using a similar procedure as described in Example 1. MS (M+H) 465. $^1$H NMR (500 MHz, DMSO-d$_6$) δ 10.96 (s, 1H), 10.26 (s, 1H), 10.24 (bs, 1H), 7.72-7.00 (m, 6H), 4.60-4.54 (m, 1H), 4.27-4.20 (m, 1H), 4.11-4.05 (m, 2H), 3.71-3.64 (m, 1H), 3.31-3.18 (m, 3H), 3.11-3.02 (m, 2H), 2.48-2.41 (m, 2H), 2.01-1.92 (m, 2H), 1.20 (t, J=7.0 Hz, 3H).

Example 22

Preparation of tert-Butyl 3-{3-carbamoyl-2-[3-(4-chlorophenyl)ureido]-4,5-dihydrothieno[2,3-c]pyridin-6(7H)-yl}cyclobutanecarboxylate

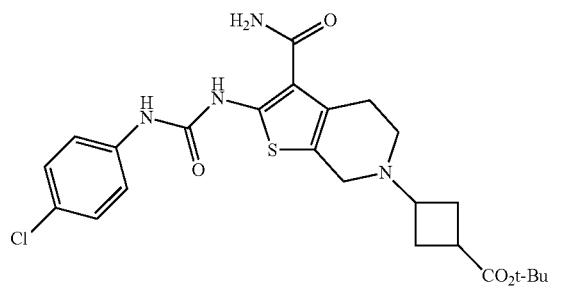 [SMILES: CC(C)(C)OC(=O)C1CC(N2CCc3c(sc(NC(=O)Nc4ccc(Cl)cc4)c3C(N)=O)C2)C1]

The title compound was prepared using a similar procedure as described in Example 1. MS (M+H) 505. $^1$H NMR (500 MHz, DMSO-d$_6$) δ 10.94 (s, 1H), 10.16 (s, 1H), 7.72-7.19 (m, 5H), 6.82 (bs, 1H), 3.63-3.40 (m, 4H), 2.93-2.70 (m, 4H), 2.37-2.22 (m, 2H), 2.03-1.87 (m, 2H), 1.40 (s, 9H).

Example 23

Preparation of 2-[3-(4-Chlorophenyl)ureido]-6-[4-(dimethylamino)-4-oxobutyl]-4,5,6,7-tetrahydrothieno[2,3-c]pyridine-3-carboxamide hydrochloride

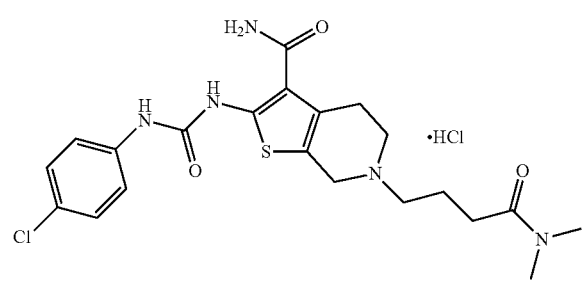 [SMILES: CN(C)C(=O)CCCN1CCc2c(sc(NC(=O)Nc3ccc(Cl)cc3)c2C(N)=O)C1 ; Cl]

The title compound was prepared using a similar procedure as described in Example 1. MS (M+H) 464. $^1$H NMR (500 MHz, DMSO-d$_6$) δ 10.95 (s, 1H), 10.53 (bs, 1H), 10.27 (s, 1H), 7.71-7.00 (m, 6H), 4.58-4.52 (m, 1H), 4.26-4.18 (m, 1H), 3.69-3.63 (m, 1H), 3.34-3.30 (m, 1H), 3.28-3.05 (m, 4H), 2.96 (s, 3H), 2.84 (s, 3H), 2.49-2.42 (m, 2H), 2.00-1.91 (m, 2H).

Example 24

Preparation of 2-[3-(4-Chlorophenyl)ureido]-6-[(1-methylcyclobutyl)methyl]-4,5,6,7-tetrahydrothieno[2,3-c]pyridine-3-carboxamide trifluoroacetate

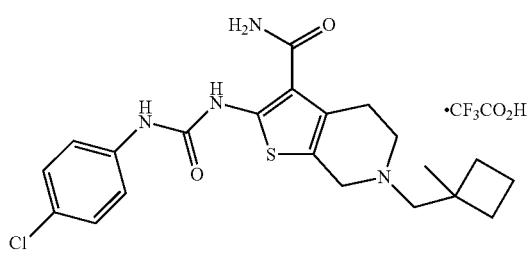 [SMILES: CC1(CN2CCc3c(sc(NC(=O)Nc4ccc(Cl)cc4)c3C(N)=O)C2)CCC1 ; "·CF3CO2H"]

The title compound was prepared using a similar procedure as described in Example 1. MS (M+H) 433. $^1$H NMR (500 MHz, DMSO-d$_6$) δ 10.96 (s, 1H), 10.25 (s, 1H), 9.71 (bs, 1H), 7.70-6.99 (m, 6H), 4.44-4.39 (m, 1H), 4.29-4.22 (m, 1H), 3.61-3.48 (m, 1H), 3.43-3.32 (m, 1H), 3.31-3.23 (m, 2H), 3.14-3.07 (m, 2H), 2.08-1.97 (m, 3H), 1.87-1.71 (m, 3H), 1.33 (s, 3H).

Example 25

Preparation of 2-[3-(4-Chlorophenyl)ureido]-6-[4-(isopropylamino)-4-oxobutyl]-4,5,6,7-tetrahydrothieno[2,3-c]pyridine-3-carboxamide hydrochloride

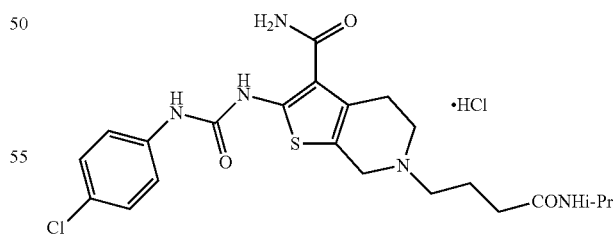

The title compound was prepared using a similar procedure as described in Example 1. MS (M+H) 478. $^1$H NMR (500 MHz, DMSO-d$_6$) δ 10.95 (s, 1H), 10.52 (bs, 1H), 10.27 (s, 1H), 7.88-7.86 (m, 1H), 7.71-7.00 (m, 6H), 4.58-4.52 (m, 1H), 4.27-4.23 (m, 1H), 3.86-3.82 (m, 1H), 3.71-3.66 (m, 1H), 3.39-3.30 (m, 1H), 3.26-3.07 (m, 4H), 2.21-2.17 (m, 2H), 1.99-1.91 (m, 2H), 1.05 (d, J=6.5 Hz, 6H).

Example 26

Preparation of 2-[3-(4-Chlorophenyl)ureido]-6-isobutyl-4,5,6,7-tetrahydrothieno[2,3-c]pyridine-3-carboxamide hydrochloride

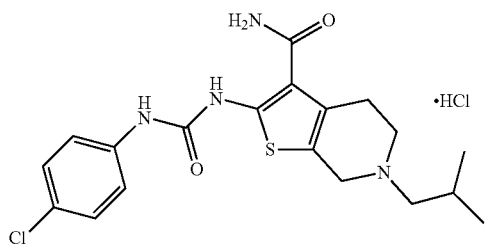 [SMILES: CC(C)CN1CCc2c(sc(NC(=O)Nc3ccc(Cl)cc3)c2C(N)=O)C1 ; Cl]

The title compound was prepared using a similar procedure as described in Example 1. MS (M+H) 407. $^1$H NMR (500 MHz, DMSO-$d_6$) δ 10.95 (s, 1H), 10.27 (s, 1H), 9.98 (bs, 1H), 7.90-6.80 (m, 6H), 4.55-3.63 (m, 3H), 3.20-3.00 (m, 4H), 2.63-2.15 (m, 2H), 1.00 (bs, 6H).

Example 27

Preparation of 2-[3-(4-Chlorophenyl)ureido]-6-neopentyl-4,5,6,7-tetrahydrothieno[2,3-c]pyridine-3-carboxamide hydrochloride

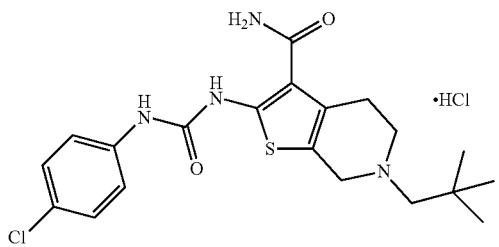 [SMILES: CC(C)(C)CN1CCc2c(sc(NC(=O)Nc3ccc(Cl)cc3)c2C(N)=O)C1 ; Cl]

The title compound was prepared using a similar procedure as described in Example 1. MS (M+H) 421. $^1$H NMR (500 MHz, DMSO-$d_6$) δ 10.92 (s, 1H), 10.27 (s, 1H), 9.85 (bs, 1H), 7.80-6.90 (m, 6H), 4.56-4.29 (m, 2H), 3.57-3.42 (m, 2H), 3.24-2.97 (m, 4H), 1.10 (s, 9H).

Example 28

Preparation of 2-[3-(4-Chlorophenyl)ureido]-5-ethyl-5,6-dihydro-4H-thieno[2,3-c]pyrrole-3-carboxamide hydrochloride

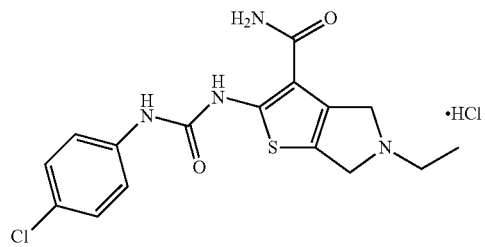 [SMILES: CCN1Cc2sc(NC(=O)Nc3ccc(Cl)cc3)c(C(N)=O)c2C1 ; Cl]

The title compound was prepared using a similar procedure as described in Example 1. MS (M+H) 365. $^1$H NMR (500 MHz, DMSO-$d_6$) δ 11.99 (s, 1H), 11.27 (s, 1H), 10.39 (s, 1H), 7.70-6.80 (m, 6H), 4.88-4.38 (m, 4H), 3.40-3.38 (m, 2H), 1.31 (t, J=7.1 Hz, 3H).

Example 29

Preparation of tert-Butyl 4-[3-(3-carbamoyl-6-ethyl-4,5,6,7-tetrahydrothieno[2,3-c]pyridin-2-yl)ureido]benzoate

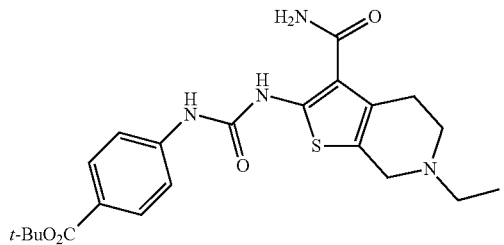

The title compound was prepared using a similar procedure as described in Example 1. MS (M+H) 445. $^1$H NMR (500 MHz, DMSO-$d_6$) δ 11.01 (s, 1H), 10.42 (s, 1H), 7.90-6.80 (m, 6H), 3.70-3.40 (m, 2H), 2.95-2.60 (m, 6H), 1.53 (s, 9H), 1.13 (bs, 3H).

Example 30

Preparation of tert-Butyl 2-{4-[3-(3-carbamoyl-6-ethyl-4,5,6,7-tetrahydrothieno[2,3-c]pyridin-2-yl)ureido]phenyl}acetate

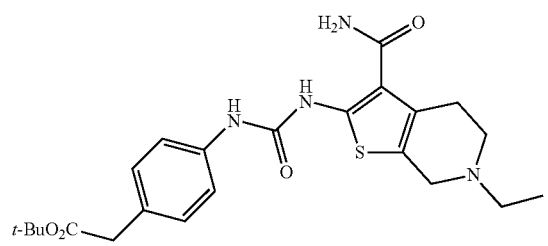

The title compound was prepared using a similar procedure as described in Example 1. S (M+H) 459. $^1$H NMR (500 MMHz, DMSO-$d_6$) δ 10.89 (s, 1H), 10.06 (s, 1H), 7.70-6.80 (m, 6H), 2.47 (s, 2H), 3.35-2.60 (m, 8H), 1.39 (s, 9H), 1.25 (bs, 3H).

Example 31

Preparation of Methyl 4-[3-(3-carbamoyl-6-ethyl-4,5,6,7-tetrahydrothieno[2,3-c]pyridin-2-yl)ureido]benzoate trifluoroacetate

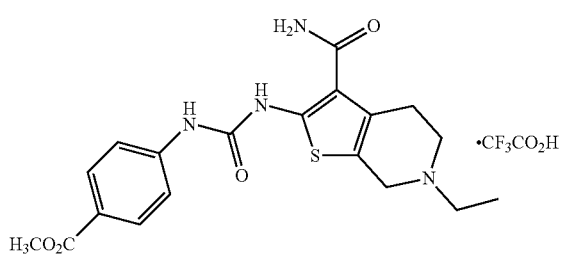 [SMILES: CCN1CCc2c(sc(NC(=O)Nc3ccc(C(=O)OC)cc3)c2C(N)=O)C1 ; "·CF3CO2H"]

The title compound was prepared using a similar procedure as described in Example 1. MS (M+H) 403. ¹H NMR (300 MHz, DMSO-d₆) δ 11.04 (s, 1H), 10.56 (s, 1H), 10.10 (bs, 1H), 7.93-6.90 (m, 6H), 4.59-4.18 (m, 2H), 3.82 (s, 3H), 3.75-3.10 (m, 6H), 1.30 (t, J=7.2 Hz, 3H).

Example 32

Preparation of 4-[3-(3-Carbamoyl-6-ethyl-4,5,6,7-tetrahydrothieno[2,3-c]pyridin-2-yl)ureido]benzoic acid trifluoroacetate

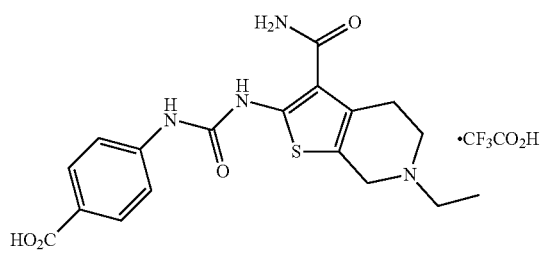 [SMILES: CCN1CCc2c(sc(NC(=O)Nc3ccc(C(=O)O)cc3)c2C(N)=O)C1 ; "·CF3CO2H"]

The title compound was prepared using a similar procedure as described in Example 1. MS (M+H) 389. ¹H NMR (300 MHz, DMSO-d₆) δ 12.70 (bs, 1H), 11.02 (s, 1H), 10.51 (s, 1H), 9.97 (bs, 1H), 7.90-6.90 (m, 6H), 4.60-4.18 (m, 2H), 3.72-3.10 (m, 6H), 1.30 (t, J=7.2 Hz, 3H).

Example 33

Preparation of 2-{4-[3-(3-Carbamoyl-6-ethyl-4,5,6,7-tetrahydrothieno[2,3-c]pyridin-2-yl)ureido]phenyl}acetic acid trifluoroacetate

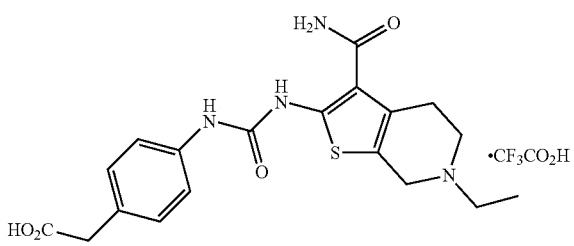 [SMILES: CCN1CCc2c(sc(NC(=O)Nc3ccc(CC(=O)O)cc3)c2C(N)=O)C1 ; "·CF3CO2H"]

The title compound was prepared using a similar procedure as described in Example 1. MS (M+H) 403. ¹H NMR (500 MHz, DMSO-d₆) δ 12.26 (bs, 1H), 10.89 (s, 1H), 10.09 (s, 1H), 9.93 (bs, 1H), 7.80-6.90 (m, 6H), 4.56-3.67 (m, 3H), 3.50 (s, 2H), 3.32-3.08 (m, 5H), 1.29 (t, J=7.2 Hz, 3H). ¹H NMR (300 MHz, DMSO-d₆) δ 11.00 (s, 1H), 10.38 (s, 1H), 10.06 (bs, 1H), 8.15 (s, 1H), 7.88-6.90 (m, 8H), 4.58-4.22 (m, 2H), 3.66-3.04 (m, 6H), 2.19-2.14 (m, 1H), 1.03-0.98 (m, 6H).

Example 34

Preparation of 6-Isobutyl-2-[3-(naphthalen-2-yl)ureido]-4,5,6,7-tetrahydrothieno[2,3-c]pyridine-3-carboxamide hydrochloride

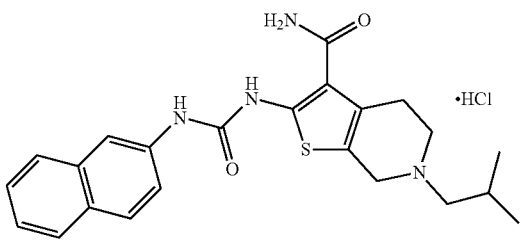 [SMILES: CC(C)CN1CCc2c(sc(NC(=O)Nc3ccc4ccccc4c3)c2C(N)=O)C1 ; Cl]

The title compound was prepared using a similar procedure as described in Example 1. MS (M+H) 423. ¹H NMR (300 MHz, DMSO-d₆) δ 11.00 (s, 1H), 10.38 (s, 1H), 10.06 (bs, 1H), 8.15 (s, 1H), 7.88-6.90 (m, 8H), 4.58-4.22 (m, 2H), 3.66-3.04 (m, 6H), 2.19-2.14 (m, 1H), 1.03-0.98 (m, 6H).

Example 35

Preparation of 6-(Cyclobutylmethyl)-2-[3-(naphthalen-2-yl)ureido]-4,5,6,7-tetrahydrothieno[2,3-c]pyridine-3-carboxamide hydrochloride

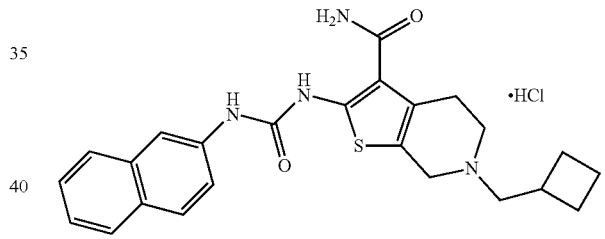

The title compound was prepared using a similar procedure as described in Example 1. MS (M+H) 435. ¹H NMR (300 MHz, DMSO-d₆) δ 11.00 (s, 1H), 10.43 (bs, 1H), 10.37 (s, 1H), 8.14 (s, 1H), 7.90-7.00 (m, 8H), 4.56-4.15 (m, 2H), 3.70-2.75 (m, 7H), 2.20-1.85 (m, 6H).

Example 36

Preparation of 2-[3-(Naphthalen-2-yl)ureido]-6-neopentyl-4,5,6,7-tetrahydrothieno[2,3-c]pyridine-3-carboxamide hydrochloride

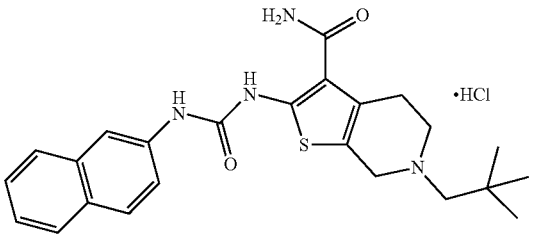 [SMILES: CC(C)(C)CN1CCc2c(sc(NC(=O)Nc3ccc4ccccc4c3)c2C(N)=O)C1 ; Cl]

The title compound was prepared using a similar procedure as described in Example 1. MS (M+H) 437. $^1$H NMR (500 MHz, DMSO-d$_6$) δ 10.96 (s, 1H), 10.36 (s, 1H), 9.95 (bs, 1H), 8.13 (s, 1H), 7.90-6.90 (m, 8H), 4.60-4.25 (m, 2H), 3.60-2.95 (m, 6H), 1.11 (s, 9H).

Example 37

Preparation of 6-(4-Hydroxybutyl)-2-[3-(naphthalen-2-yl)ureido]-4,5,6,7-tetrahydrothieno[2,3-c]pyridine-3-carboxamide hydrochloride

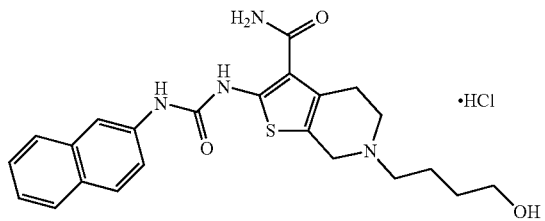 [SMILES: NC(=O)c1c(NC(=O)Nc2ccc3ccccc3c2)sc2c1CCN(CCCCO)C2 ; Cl]

The title compound was prepared using a similar procedure as described in Example 1. MS (M+H) 439. $^1$H NMR (300 MHz, DMSO-d$_6$) δ 11.10 (bs, 1H), 10.99 (s, 1H), 10.40 (s, 1H), 8.15 (s, 1H), 7.90-6.90 (m, 8H), 4.70-4.20 (m, 3H), 3.65-3.00 (m, 8H), 1.85-1.46 (m, 4H).

Example 38

Preparation of Methyl 3-{3-carbamoyl-2-[3-(4-chlorophenyl)ureido]-4,5-dihydrothieno[2,3-c]pyridin-6(7H)-yl}-2,2-dimethylpropanoate hydrochloride

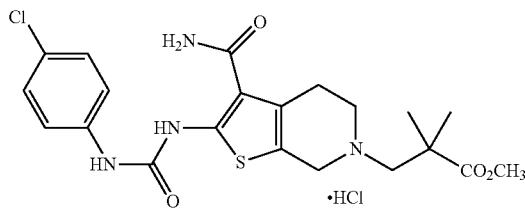 [SMILES: COC(=O)C(C)(C)CN1CCc2c(sc(NC(=O)Nc3ccc(Cl)cc3)c2C(N)=O)C1 ; Cl]

The title compound was prepared using a similar procedure as described in Example 1. MS (M+H) 465. $^1$H NMR (300 MHz, DMSO-d$_6$) δ 10.95 (s, 1H), 10.32 (bs, 2H), 7.85-6.90 (m, 6H), 4.52-4.30 (m, 2H), 3.70 (s, 3H), 3.50-3.05 (m, 6H), 1.32 (s, 6H).

Example 39

Preparation of 2-[3-(4-Chloronaphthalen-1-yl)ureido]-6-isobutyl-4,5,6,7-tetrahydrothieno[2,3-c]pyridine-3-carboxamide hydrochloride

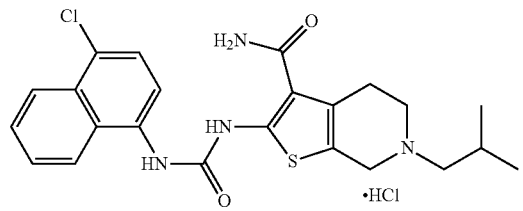 [SMILES: CC(C)CN1CCc2c(sc(NC(=O)Nc3ccc(Cl)c4ccccc34)c2C(N)=O)C1 ; Cl]

The title compound was prepared using a similar procedure as described in Example 1. MS (M+H) 457. $^1$H NMR (300 MHz, DMSO-d$_6$) δ 11.01 (s, 1H), 10.14 (s, 1H), 10.03 (bs, 1H), 8.27 (dd, J=7.2 and 2.1 Hz, 1H), 8.22 (dd, J=7.2 and 2.1 Hz, 1H), 7.87 (d, J=8.1 Hz, 1H), 7.78-6.90 (m, 5H), 4.58-4.52 (m, 1H), 4.24 (dd, J=15.0 and 6.3 Hz, 1H), 3.68-3.57 (m, 1H), 3.14-3.00 (m, 5H), 2.21-2.09 (m, 1H), 1.01 (d, J=6.3 Hz, 3H), 0.99 (d, J=6.3 Hz, 3H).

Example 40

Preparation of 2-[3-(4-Chloronaphthalen-1-yl)ureido]-6-(cyclobutylmethyl)-4,5,6,7-tetrahydrothieno[2,3-c]pyridine-3-carboxamide hydrochloride

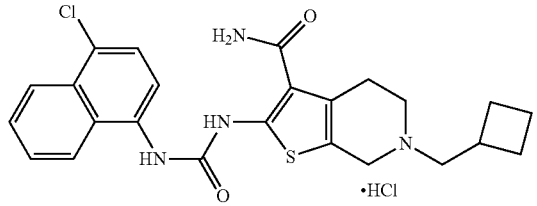 [SMILES: NC(=O)c1c(NC(=O)Nc2ccc(Cl)c3ccccc23)sc2c1CCN(CC1CCC1)C2 ; Cl]

The title compound was prepared using a similar procedure as described in Example 1. MS (M+H) 469. $^1$H NMR (500 MHz, DMSO-d$_6$) δ 11.00 (s, 1H), 10.35 (bs, 1H), 10.11 (s, 1H), 8.27 (d, J=8.0 Hz, 1H), 8.21 (d, J=8.0 Hz, 1H), 7.75 (d, J=6.5 Hz, 1H), 7.72-6.95 (m, 5H), 4.44-4.40 (m, 1H), 4.20-4.17 (m, 1H), 3.41-3.10 (m, 4H), 3.08 (bs, 2H), 2.82-2.79 (m, 1H), 2.16-2.06 (m, 2H), 1.93-1.78 (m, 4H).

Example 41

Preparation of 2-[3-(4-Chloronaphthalen-1-yl)ureido]-6-neopentyl-4,5,6,7-tetrahydrothieno[2,3-c]pyridine-3-carboxamide hydrochloride

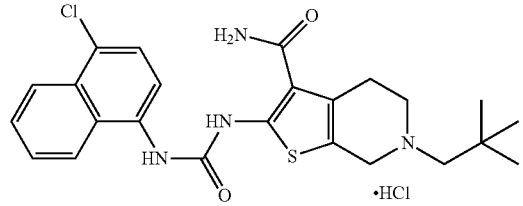 [SMILES: CC(C)(C)CN1CCc2c(sc(NC(=O)Nc3ccc(Cl)c4ccccc34)c2C(N)=O)C1 ; Cl]

The title compound was prepared using a similar procedure as described in Example 1. MS (M+H) 471. $^1$H NMR (300 MHz, DMSO-d$_6$) δ 10.98 (s, 1H), 10.15 (s, 1H), 9.98 (bs, 1H), 8.30-8.19 (m, 2H), 7.87 (d, J=8.4 Hz, 1H), 7.78-7.00 (m, 5H), 4.57-4.51 (m, 1H), 4.33-4.26 (m, 1H), 3.61-3.39 (m, 2H), 3.29-2.96 (m, 4H), 1.10 (s, 9H).

Example 42

Preparation of 2-[3-(4-Chlorophenyl)ureido]-6-(dimethylamino)-4,5,6,7-tetrahydrobenzo[b]thiophene-3-carboxamide hydrochloride

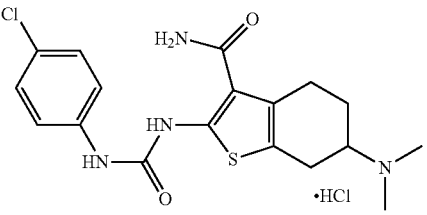 [SMILES: CN(C)C1CCc2c(sc(NC(=O)Nc3ccc(Cl)cc3)c2C(N)=O)C1 ; Cl]

The title compound was prepared using a similar procedure as described in Example 1. MS (M+H) 393. $^1$H NMR (500 MHz, DMSO-d$_6$) δ 11.01 (s, 1H), 10.75 (bs, 1H), 10.18 (s, 1H), 7.70-6.70 (m, 6H), 3.45 (bs, 1H), 3.18-2.70 (m, 10H), 2.30-1.80 (m, 2H).

Example 43

Preparation of 6-(Azetidin-1-yl)-2-[3-(4-chlorophenyl)ureido]-4,5,6,7-tetrahydrobenzo[b]thiophene-3-carboxamide hydrochloride

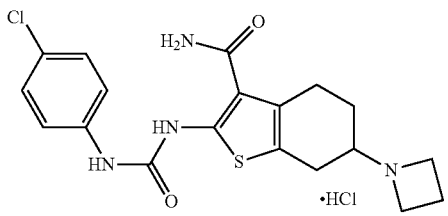 [SMILES: NC(=O)c1c(NC(=O)Nc2ccc(Cl)cc2)sc2c1CCC(N1CCC1)C2 ; Cl]

The title compound was prepared using a similar procedure as described in Example 1. MS (M+H) 405. $^1$H NMR (300 MHz, CD$_3$OD) δ 7.48-7.26 (m, 4H), 4.20-3.55 (m, 5H), 3.15-1.75 (m, 8H).

Example 44

Preparation of 2-[3-(4-chlorophenyl)ureido]-6-[2-(piperidin-1-yl)ethyl]-4,5,6,7-tetrahydrothieno[2,3-c]pyridine-3-carboxamide ditrifluoroacetate (B2)

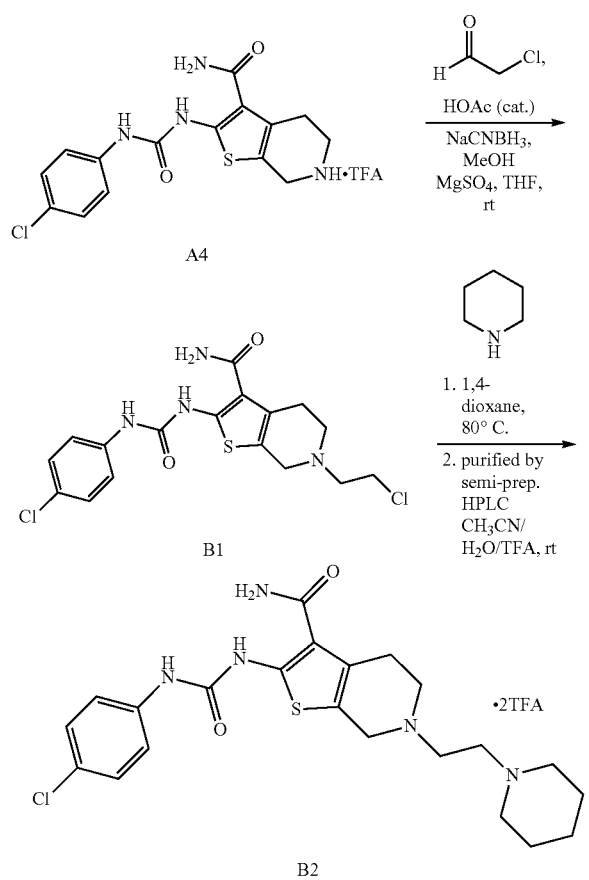

Step 1: 6-(2-Chloroethyl)-2-[3-(4-chlorophenyl)ureido]-4,5,6,7-tetrahydrothieno[2,3-c]pyridine-3-carboxamide (B1)

To a slurry of compound A4 (200 mg, 0.431 mmol) and magnesium sulfate (2 g) in methanol (4 mL) and tetrahydrofuran (2 mL) was added two drops of glacial acetic acid and 2-chloroacetaldehyde (45% in water, 0.340 mL, 1.95 mmol). After stirring at room temperature for 5 min, sodium cyanoborohydride (271 mg, 4.31 mmol) was added and the reaction mixture was stirred for an additional 16 h at room temperature. After this time, the reaction was diluted with saturated aqueous sodium bicarbonate (100 mL), sonicated, and filtered. The filter cake was washed with water (50 mL) and triturated with methylene chloride to afford compound B1 as a white solid (176 mg, 99%): $^1$H NMR (300 MHz, DMSO-d$_6$) δ 10.94 (s, 1H), 10.19 (s, 1H), 7.57-7.29 (m, 5H), 6.87 (bs, 1H), 3.76 (t, J=6.6 Hz, 2H), 3.57 (s, 2H), 2.87-2.71 (m, 6H). MS (M+H) 413.

Step 2: 2-[3-(4-Chlorophenyl)ureido]-6-[2-(piperidin-1-yl)ethyl]-4,5,6,7-tetrahydrothieno[2,3-c]pyridine-3-carboxamide ditrifluoroacetate (B2)

A solution of compound B1 (130 mg, 0.315 mmol) and piperidine (800 mg, 9.40 mmol) in 1,4-dioxane (2.5 mL) was heated to 80° C. for 16 h. After this time, the reaction mixture was cooled to room temperature and concentrated under reduced pressure. The resulting residue was purified by flash column chromatography on silica gel eluting with methylene chloride to methanol/methylene chloride (1:9). Further purification by reverse-phase semi-preparative HPLC, eluting with 0.05% TFA in acetonitrile/water (gradient from 10% to 100%, Phenomenex Luna column) afforded compound B2 as a yellow solid (67 mg, 46%): $^1$H NMR (500 MHz, DMSO-d$_6$) δ 10.98 (s, 1H), 10.20 (s, 1H), 7.52-7.29 (m, 5H), 6.89 (bs, 1H), 6.51 (bs, 1H), 3.51 (m, 4H), 3.32-3.11 (m, 6H), 3.00-2.73 (m, 4H), 1.80-1.69 (m, 4H), 1.58-1.48 (m, 2H). MS (M+H) 462.

Example 45

Preparation of 2-[3-(4-Chlorophenyl)ureido]-6-[2-(4-methylpiperazin-1-yl)ethyl]-4,5,6,7-tetrahydrothieno[2,3-c]pyridine-3-carboxamide hydrochloride

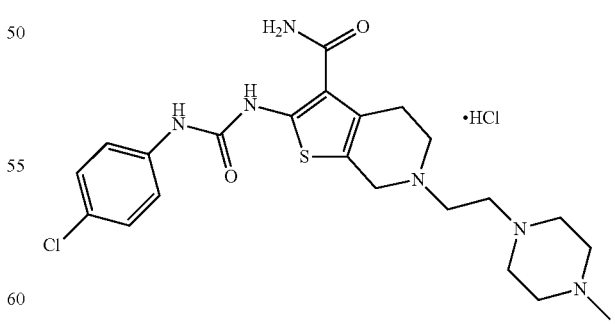

The title compound was prepared using a similar procedure as described in Example 44. MS (M+H) 477. $^1$H NMR (500 MHz, DMSO-d$_6$) δ 10.95 (s, 1H), 10.49 (bs, 1H), 10.27 (s, 1H), 7.70-6.97 (m, 6H), 4.42 (s, 2H), 3.53-3.32 (m, 8H), 3.19-3.02 (m, 6H), 2.92-2.87 (m, 2H), 2.76 (s, 3H).

Example 46

Preparation of 2-[3-(4-Chlorophenyl)ureido]-6-(2-morpholinoethyl)-4,5,6,7-tetrahydrothieno[2,3-c]pyridine-3-carboxamide trifluoroacetate

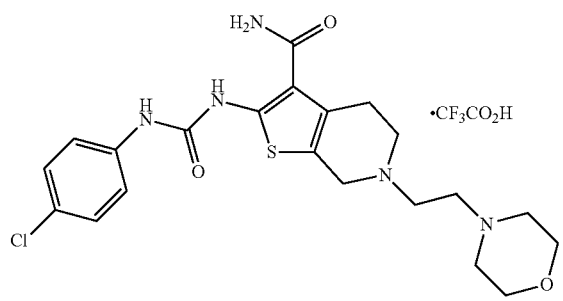 [SMILES: NC(=O)c1c(NC(=O)Nc2ccc(Cl)cc2)sc2c1CCN(CCN1CCOCC1)C2 ; "·CF3CO2H"]

The title compound was prepared using a similar procedure as described in Example 44. MS (M+H) 464. $^1$H NMR (500 MHz, DMSO-d$_6$) δ 11.28 (bs, 0.5H), 10.66 (bs, 0.5H), 9.75 (bs, 0.5H), 8.85 (bs, 0.5H), 8.01 (bs, 1H), 7.72-7.28 (m, 6H), 4.12-3.45 (m, 18H).

Example 47

Preparation of (+/−)-2-[3-(4-chlorophenyl)ureido]-6-(1-cyclobutylethyl)-4,5,6,7-tetrahydrothieno[2,3-c]pyridine-3-carboxamide hydrochloride [(+/−)-C2]

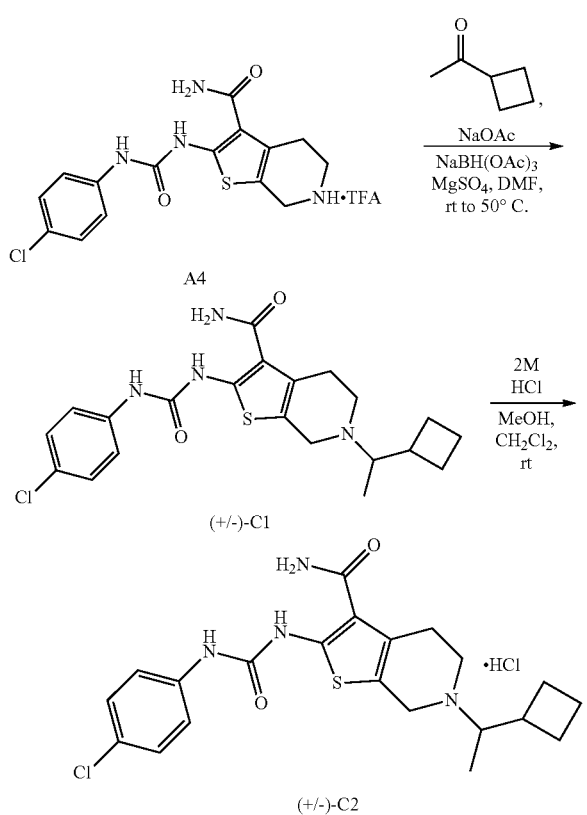

Step 1: (+/−)-2-[3-(4-Chlorophenyl)ureido]-6-(1-cyclobutylethyl)-4,5,6,7-tetrahydrothieno[2,3-c]pyridine-3-carboxamide [(+/−)-C1]

To a slurry of compound A4 (400 mg, 0.860 mmol), sodium acetate (212 mg, 2.58 mmol), and magnesium sulfate (1 g) in anhydrous N,N-dimethylformamide (5 mL) was added 1-cyclobutylethanone (253 mg, 2.57 mmol). After stirring at room temperature for 5 min, sodium triacetoxyborohydride (911 mg, 4.30 mmol) was added. The reaction mixture was then heated at 50° C. for 20 h. After this time, the reaction mixture was cooled to room temperature and diluted with saturated aqueous sodium bicarbonate (10 mL), methanol (5 mL), methylene chloride (20 mL), and water (10 mL). The layers were separated and the aqueous layer back extracted with 20% methanol/methylene chloride (2×30 mL). The combined organic layers were dried over anhydrous sodium sulfate, filtered, and concentrated under reduced pressure. The resulting residue was purified by flash column chromatography on silica gel eluting with 2% to 6% methanol/methylene chloride to afford compound (+/−)-C1 as a white solid (199 mg, 53%): MS (M+H) 433.

Step 2: (+/−)-2-[3-(4-Chlorophenyl)ureido]-6-(1-cyclobutylethyl)-4,5,6,7-tetrahydrothieno[2,3-c]pyridine-3-carboxamide hydrochloride [(+/−)-C2]

To a solution of compound (+/−)-C1 (36 mg, 0.083 mmol) in methanol (5 mL) and methylene chloride (5 mL) was added hydrochloride (2 M in diethyl ether, 0.800 mL, 1.60 mmol). After stirring at room temperature for 15 min, the reaction mixture was concentrated under reduced pressure and the residue was triturated with a mixture of methanol (0.5 mL), ethyl acetate (5 mL), and hexanes (5 mL) to afford compound (+/−)-C2 as a light yellow solid (33 mg, 85%): $^1$H NMR (300 MHz, DMSO-d$_6$) δ 11.04 (bs, 1H), 10.30 (s, 1H), 10.10 (bs, 1H), 7.80-7.00 (m, 6H), 4.34-4.27 (m, 2H), 3.70-3.55 (m, 2H), 3.30-3.00 (m, 3H), 2.80-2.60 (m, 1H), 2.20-1.60 (m, 6H), 1.22 (d, J=5.5 z, 3H). MS (M+H) 433.

Example 48

Preparation of (+/−)-2-[3-(4-Chlorophenyl)ureido]-6-(3-methylbutan-2-yl)-4,5,6,7-tetrahydrothieno[2,3-c]pyridine-3-carboxamide hydrochloride

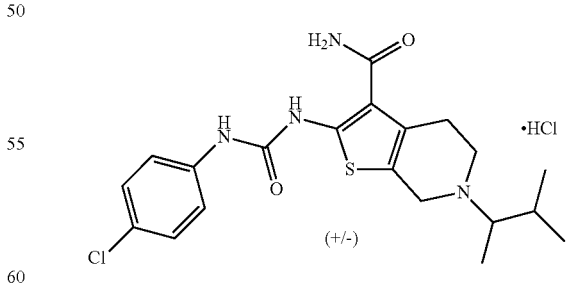

The title compound was prepared using a similar procedure as described in Example 47. MS (M+H) 421. $^1$H NMR (300 MHz, DMSO-d$_6$) δ 11.01 (s, 1H), 10.31 (s, 1H), 9.99 and 9.91 (2 s, 1H), 7.80-6.90 (m, 6H), 4.50-3.60 (m, 3H), 3.25-3.05 (m, 4H), 2.36-2.27 (m, 1H), 1.29-1.22 (m, 3H), 0.99-0.94 (m, 6H).

Example 49

Preparation of 6-[(3r,5r,7r)-Adamantan-1-ylmethyl]-2-[3-(4-chlorophenyl)ureido]-4,5,6,7-tetrahydrothieno[2,3-c]pyridine-3-carboxamide hydrochloride

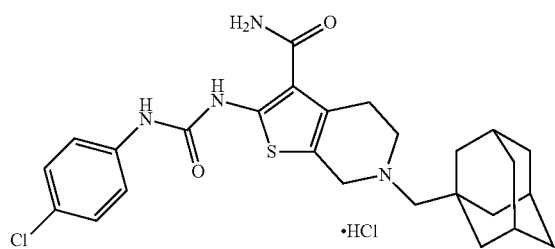 [SMILES: NC(=O)c1c(NC(=O)Nc2ccc(Cl)cc2)sc2c1CCN(CC13CC4CC(CC(C4)C1)C3)C2 ; Cl]

The title compound was prepared using a similar procedure as described in Example 47. MS (M+H) 499. $^1$H NMR (500 MHz, DMSO-$d_6$) δ 10.86 (s, 1H), 10.54 (bs, 1H), 10.35 (s, 1H), 7.80-7.00 (m, 6H), 4.51-4.21 (m, 2H), 3.45-2.75 (m, 6H), 2.00-1.65 (m, 15H).

Example 50

Preparation of 6-(3-amino-3-oxopropyl)-2-[3-(4-chlorophenyl)ureido]-4,5,6,7-tetrahydrothieno[2,3-c]pyridine-3-carboxamide hydrochloride (D2)

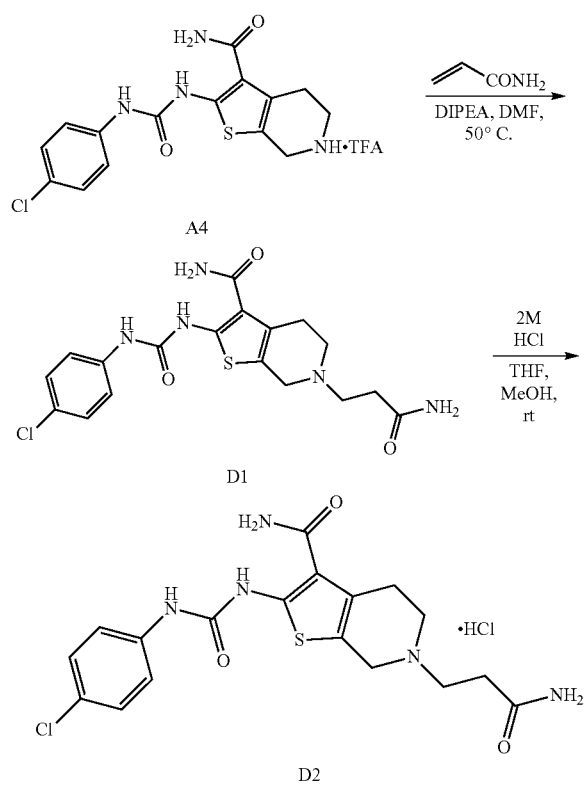

Step 1: 6-(3-Amino-3-oxopropyl)-2-[3-(4-chlorophenyl)ureido]-4,5,6,7-tetrahydrothieno[2,3-c]pyridine-3-carboxamide (D1)

A solution of compound A4 (200 mg, 0.431 mmol), acrylamide (156 mg, 2.19 mmol), and diisopropylethylamine (0.400 mL, 2.25 mmol) in N,N-dimethylformamide (2.5 mL) was heated at 50° C. for 8 h. After this time, the reaction mixture was cooled to room temperature and concentrated under reduced pressure. The resulting residue was purified by flash column chromatography on silica gel eluting with 0% to 10% methanol/methylene chloride to afford compound D1 as a yellow solid (180 mg, 99%): $^1$H NMR (300 MHz, DMSO-$d_6$) δ 10.95 (s, 1H), 10.19 (s, 1H), 7.59-7.29 (m, 6H), 6.90-6.73 (m, 2H), 3.48 (s, 2H), 2.83-2.65 (m, 6H), 2.33-2.25 (m, 2H). MS (M+H) 422.

Step 2: 6-(3-Amino-3-oxopropyl)-2-[3-(4-chlorophenyl)ureido]-4,5,6,7-tetrahydrothieno[2,3-c]pyridine-3-carboxamide hydrochloride (D2)

To a solution of compound D1 (90.0 mg, 0.210 mmol) in tetrahydrofuran (2.5 mL) and methanol (2.5 mL) was added hydrochloride (2 M in diethyl ether, 0.140 mL, 0.280 mmol). After stirring at room temperature for 30 min, the reaction mixture was concentrated under reduced pressure and the resulting residue was triturated with methylene chloride to afford compound D2 as a yellow solid (95 mg, 99%): $^1$H NMR (500 MHz, DMSO-$d_6$) δ 10.94 (s, 1H), 10.55 (bs, 1H), 10.27 (s, 1H), 7.62 (bs, 1H), 7.55-7.30 (m, 5H), 7.19-7.02 (m, 2H), 4.52-4.48 (m, 1H), 4.28-4.25 (m, 1H), 3.68-3.60 (m, 1H), 3.49-3.42 (m, 3H), 3.13-3.08 (m, 2H), 2.74-2.67 (m, 2H). MS (M+H) 422.

Example 51

Preparation of tert-Butyl 3-{3-Carbamoyl-2-[3-(4-chlorophenyl)ureido]-4,5-dihydrothieno[2,3-c]pyridin-6(7H)-yl}propanoate

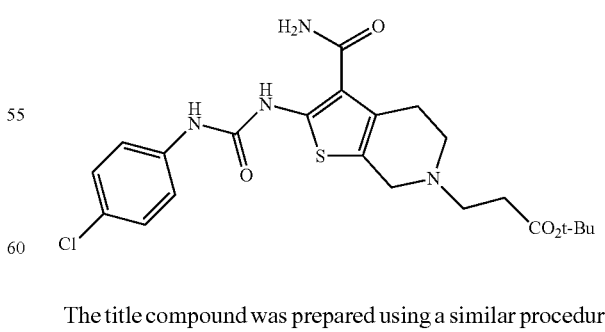

The title compound was prepared using a similar procedure as described in Example 50. MS (M+H) 479. $^1$H NMR (500 MHz, DMSO-$d_6$) δ 10.96 (s, 1H), 10.16 (s, 1H), 7.62-7.28 (m, 5H), 6.83 (bs, 1H), 3.49 (s, 2H), 2.80-2.63 (m, 6H), 2.47-2.41 (m, 2H), 1.40 (s, 9H).

Example 52

Preparation of 3-{3-Carbamoyl-2-[3-(4-chlorophenyl)ureido]-4,5-dihydrothieno[2,3-c]pyridin-6(7H)-yl}propanoic acid trifluoroacetate

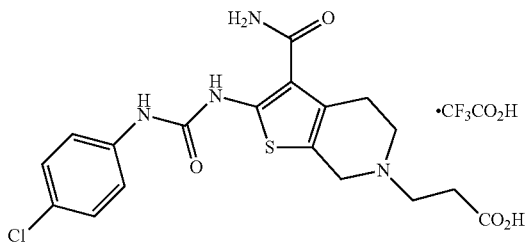 [SMILES: NC(=O)c1c(NC(=O)Nc2ccc(Cl)cc2)sc2c1CCN(CCC(=O)O)C2 ; "·CF3CO2H"]

The title compound was prepared using a similar procedure as described in Example 50. MS (M+H) 423. $^1$H NMR (500 MHz, DMSO-$d_6$) δ 12.73 (bs, 1H), 10.95 (s, 1H), 10.25 (s, 1H), 10.02 (bs, 1H), 7.70-6.94 (m, 6H), 4.64-4.22 (m, 2H), 3.76-3.48 (m, 4H), 3.13-3.06 (m, 2H), 2.87-2.79 (m, 2H).

Example 53

Preparation of 2-[3-(4-Chlorophenyl)ureido]-6-[3-(dimethylamino)-3-oxopropyl]-4,5,6,7-tetrahydrothieno[2,3-c]pyridine-3-carboxamide hydrochloride

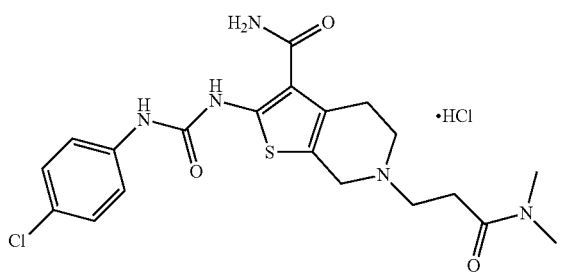 [SMILES: CN(C)C(=O)CCN1CCc2c(sc(NC(=O)Nc3ccc(Cl)cc3)c2C(N)=O)C1 ; Cl]

The title compound was prepared using a similar procedure as described in Example 50. MS (M+H) 450. $^1$H NMR (500 MHz, DMSO-$d_6$) δ 10.94 (s, 1H), 10.26 (s, 1H), 10.17 (bs, 1H), 7.72-7.00 (m, 6H), 4.60-4.54 (m, 1H), 4.32-4.26 (m, 1H), 3.77-3.67 (m, 1H), 3.51-3.35 (m, 3H), 3.12-3.02 (m, 2H), 2.99 (s, 3H), 2.93-2.87 (m, 2H), 2.86 (s, 3H).

Example 54

Preparation of Isopropyl 3-{3-carbamoyl-2-[3-(4-chlorophenyl)ureido]-4,5-dihydrothieno[2,3-c]pyridin-6(7H)-yl}propanoate hydrochloride

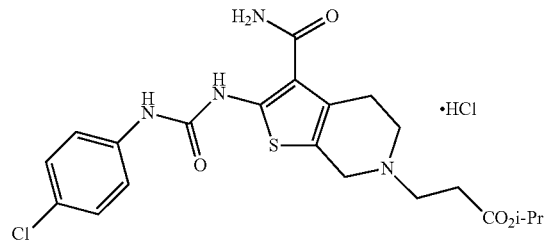

The title compound was prepared using a similar procedure as described in Example 50. MS (M+H) 465. $^1$H NMR (500 MHz, DMSO-$d_6$) δ 10.95 (s, 1H), 10.46 (bs, 1H), 10.26 (s, 1H), 7.71-6.97 (m, 6H), 5.00-4.91 (m, 1H), 4.57-4.51 (m, 1H), 4.30-4.25 (m, 1H), 3.75-3.67 (m, 1H), 3.56-3.38 (m, 3H), 3.15-3.02 (m, 2H), 2.98-2.87 (m, 2H), 1.22 (d, J=6.0 Hz, 6H).

Example 55

Preparation of Methyl 3-{3-carbamoyl-2-[3-(4-chlorophenyl)ureido]-4,5-dihydrothieno[2,3-c]pyridin-6(7H)-yl}propanoate

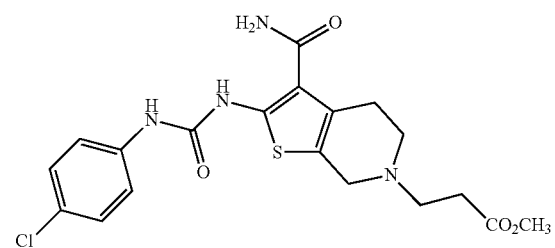 [SMILES: COC(=O)CCN1CCc2c(sc(NC(=O)Nc3ccc(Cl)cc3)c2C(N)=O)C1]

The title compound was prepared using a similar procedure as described in Example 50. MS (M+H) 437. $^1$H NMR (300 MHz, DMSO-$d_6$) δ 10.94 (s, 1H), 10.19 (s, 1H), 7.68-7.28 (m, 5H), 6.85 (bs, 1H), 3.60 (s, 3H), 3.53-3.47 (m, 2H), 2.80-2.66 (m, 6H), 2.61-2.53 (m, 2H).

Example 56

Preparation of Ethyl 3-{3-carbamoyl-2-[3-(4-chlorophenyl)ureido]-4,5-dihydrothieno[2,3-c]pyridin-6(7H)-yl}propanoate hydrochloride

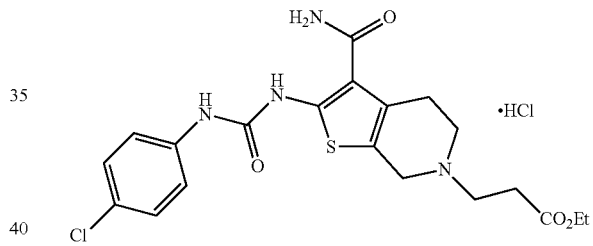

The title compound was prepared using a similar procedure as described in Example 50. MS (M+H) 451. $^1$H NMR (500 MHz, DMSO-$d_6$) δ 10.95 (s, 1H), 10.49 (bs, 1H), 10.26 (s, 1H), 7.72-6.99 (m, 6H), 4.57-4.52 (m, 1H), 4.30-4.25 (m, 1H), 4.13 (q, J=7.5 Hz, 2H), 3.76-3.66 (m, 1H), 3.57-3.37 (m, 3H), 3.12-3.08 (m, 2H), 2.98-2.89 (m, 2H), 1.22 (t, J=7.0 Hz, 3H).

Example 57

Preparation of 2-[3-(4-Chlorophenyl)ureido]-6-[3-(isopropylamino)-3-oxopropyl]-4,5,6,7-tetrahydrothieno[2,3-c]pyridine-3-carboxamide hydrochloride

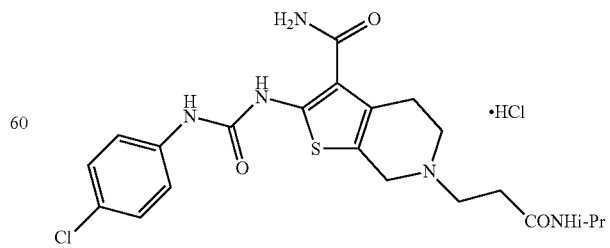

The title compound was prepared using a similar procedure as described in Example 50. MS (M+H) 464. $^1$H NMR (500

MHz, DMSO-$d_6$) δ 10.94 (s, 1H), 10.31 (bs, 1H), 10.26 (s, 1H), 8.07-8.03 (m, 1H), 7.69-7.00 (m, 6H), 4.53-4.47 (m, 1H), 4.30-4.25 (m, 1H), 3.88-3.82 (m, 1H), 3.68-3.63 (m, 1H), 3.51-3.35 (m, 3H), 3.12-3.08 (m, 2H), 2.67-2.63 (m, 2H), 1.07 (d, J=6.5 Hz, 6H).

Example 58

Preparation of tert-butyl 2-{3-carbamoyl-2-[3-(4-chlorophenyl)ureido]-4,5-dihydrothieno[2,3-c]pyridin-6(7H)-yl}acetate (E1)

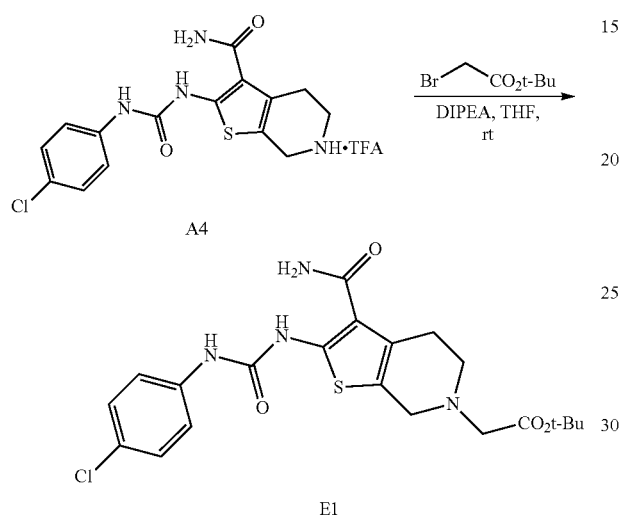

A solution of compound A4 (300 mg, 0.646 mmol), diisopropylethylamine (0.350 mL, 1.97 mmol), and tert-butyl 2-bromoacetate (0.140 mL, 0.950 mmol) in tetrahydrofuran (4 mL) was stirred at room temperature for 8 h. After this time, the reaction mixture was diluted with methylene chloride (10 mL), sonicated, and filtered to afford compound E1 as a light yellow solid (191 mg, 64%): $^1$H NMR (500 MHz, DMSO-$d_6$) δ 10.93 (s, 1H), 10.18 (s, 1H), 7.59-7.29 (m, 5H), 6.89 (bs, 1H), 3.61 (s, 2H), 3.30 (s, 2H), 2.82-2.76 (m, 4H), 1.43 (s, 9H). MS (M+H) 465.

Example 59

Preparation of (+/−)-tert-Butyl 2-{3-carbamoyl-2-[3-(4-chlorophenyl)ureido]-4,5-dihydrothieno[2,3-c]pyridin-6(7H)-yl}propanoate

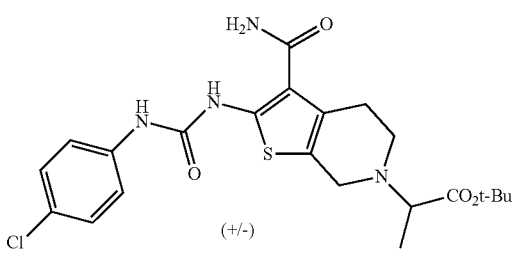 [SMILES: CC(C(=O)OC(C)(C)C)N1CCc2c(sc(NC(=O)Nc3ccc(Cl)cc3)c2C(N)=O)C1]

The title compound was prepared using a similar procedure as described in Example 58. MS (M+H) 479. $^1$H NMR (500 MHz, DMSO-$d_6$) δ 10.92 (s, 1H), 10.16 (s, 1H), 7.58-7.28 (m, 5H), 6.83 (bs, 1H), 3.75-3.67 (m, 2H), 3.44-3.36 (m, 1H), 2.91-2.87 (m, 1H), 2.81-2.73 (m, 3H), 1.43 (s, 9H), 1.28-1.17 (m, 3H).

Example 60

Preparation of 2-[3-(4-Chlorophenyl)ureido]-6-(2-hydroxyethyl)-4,5,6,7-tetrahydrothieno[2,3-c]pyridine-3-carboxamide hydrochloride

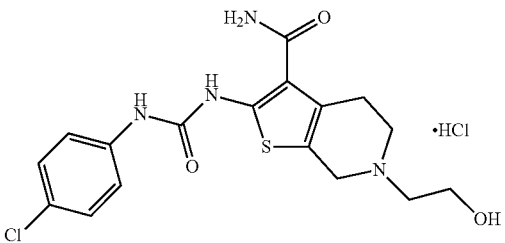 [SMILES: NC(=O)c1c(NC(=O)Nc2ccc(Cl)cc2)sc2c1CCN(CCO)C2 ; Cl]

The title compound was prepared using a similar procedure as described in Example 58. MS (M+H) 395. $^1$H NMR (500 MHz, DMSO-$d_6$) δ 10.95 (s, 1H), 10.68 (bs, 1H), 10.29 (s, 1H), 7.70-6.99 (m, 6H), 5.46-5.35 (m, 1H), 4.53-4.47 (m, 1H), 4.36-4.28 (m, 1H), 3.88-3.83 (m, 2H), 3.72-3.65 (m, 1H), 3.63-3.59 (m, 1H), 3.47-3.36 (m, 1H), 3.13-3.08 (m, 2H), 1.76-1.74 (m, 1H).

Example 61

Preparation of 2-{3-Carbamoyl-2-[3-(4-chlorophenyl)ureido]-4,5-dihydrothieno[2,3-c]pyridin-6(7H)-yl}acetic acid hydrochloride

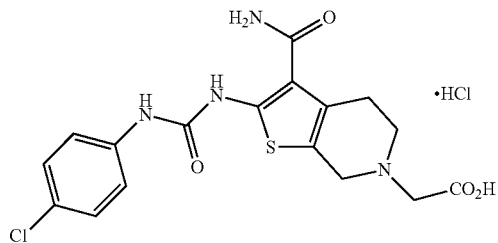 [SMILES: NC(=O)c1c(NC(=O)Nc2ccc(Cl)cc2)sc2c1CCN(CC(=O)O)C2 ; Cl]

The title compound was prepared using a similar procedure as described in Example 58. MS (M+H) 409. $^1$H NMR (500 MHz, DMSO-$d_6$) δ 10.93 (s, 1H), 10.22 (s, 1H), 7.70-6.90 (m, 6H), 4.24-4.09 (m, 2H), 3.99-3.80 (m, 2H), 3.55-3.39 (m, 2H), 3.02-2.96 (m, 2H).

Example 62

Preparation of (+/−)-2-{3-Carbamoyl-2-[3-(4-chlorophenyl)ureido]-4,5-dihydrothieno[2,3-c]pyridin-6(7H)-yl}propanoic acid hydrochloride

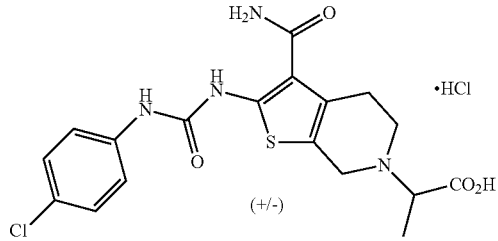 [SMILES: CC(C(=O)O)N1CCc2c(sc(NC(=O)Nc3ccc(Cl)cc3)c2C(N)=O)C1 ; Cl]

The title compound was prepared using a similar procedure as described in Example 58. MS (M+H) 423. $^1$H NMR (500

MHz, DMSO-d$_6$) δ 10.97 (s, 1H), 10.26 (s, 1H), 7.70-6.90 (m, 6H), 4.51-4.17 (m, 3H), 3.20-3.00 (m, 4H), 1.60-1.52 (m, 3H).

Example 63

Preparation of 2-[3-(4-Chlorophenyl)ureido]-6-[(1-methylcyclopropyl)methyl]-4,5,6,7-tetrahydrothieno[2,3-c]pyridine-3-carboxamide hydrochloride

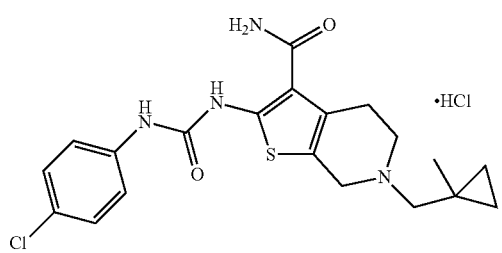 [SMILES: CC1(CN2CCc3c(sc(NC(=O)Nc4ccc(Cl)cc4)c3C(N)=O)C2)CC1 ; Cl]

The title compound was prepared using a similar procedure as described in Example 58. MS (M+H) 419. $^1$H NMR (500 MHz, DMSO-d$_6$) δ 10.97 (s, 1H), 10.27 (s, 1H), 10.10 (bs, 1H), 7.71-6.99 (m, 6H), 4.58-4.53 (m, 1H), 4.32-4.25 (m, 1H), 3.72-3.68 (m, 1H), 3.32-3.28 (m, 2H), 3.19-2.99 (m, 3H), 1.20 (s, 3H), 0.68-0.47 (m, 4H).

Example 64

Preparation of 2-[3-(4-chloro-3-methylphenyl)ureido]-6-ethyl-4,5,6,7-tetrahydrothieno[2,3-c]pyridine-3-carboxamide hydrochloride (F6)

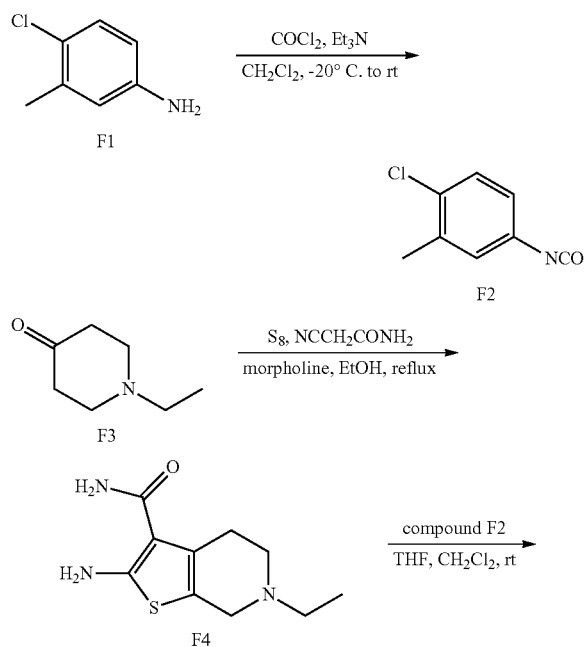

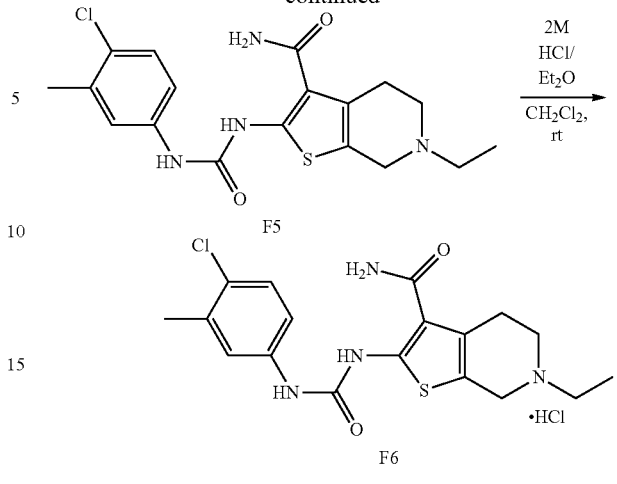

Step 1: 1-Chloro-4-isocyanato-2-methylbenzene (F2)

To the stirred mixture of 4-chloro-3-methylaniline (F1, 1.01 g, 7.13 mmol) and triethylamine (866 mg, 8.56 mmol) in methylene chloride (20 mL) at −20° C. under nitrogen was added phosgene solution (0.15 weight/weight in toluene, 6.15 g, 9.13 mmol) dropwise over 5 min. After addition, the reaction mixture was warmed up to room temperature over 2 h, and then stirred at room temperature for another 2 h. After this time, the reaction mixture was cooled to 0° C., and slowly quenched with saturated aqueous sodium bicarbonate (30 mL). The mixture was extracted with ethyl acetate (100 mL). The organic extract was washed with 2 M hydrochloric acid (50 mL), brine (30 mL), dried over anhydrous sodium sulfate, and filtered. The filtrate was concentrated under reduced pressure. The resulting residue was triturated with methylene chloride (40 mL) and filtered. The filtrate was concentrated under reduced pressure to provide compound F2 as a light brown liquid (1.08 g, 90%): $^1$H NMR (300 MHz, CDCl$_3$) δ 7.27 (d, J=8.4 Hz, 1H), 6.97 (d, J=2.4 Hz, 1H), 6.88-6.84 (m, 1H), 2.34 (s, 3H).

Step 2: 2-Amino-6-ethyl-4,5,6,7-tetrahydrothieno[2,3-c]pyridine-3-carboxamide (F4)

A stirred mixture of compound F3 (22.7 g, 178 mmol), 2-cyanoacetamide (16.5 g, 197 mmol), sulphur (6.87 g, 215 mmol) and morpholine (31.5 g, 362 mmol) in ethanol (350 mL) was heated to reflux under nitrogen for 5 h. After this time, the reaction mixture was cooled to room temperature and concentrated under reduced pressure. The residue was mixed with saturated aqueous sodium bicarbonate (200 mL), water (200 mL). The aqueous mixture was extracted with methylene chloride (5×200 mL). The combined organic extracts were dried over anhydrous sodium sulfate, filtered, and concentrated under reduced pressure. The resulting residue was triturated with cold methanol (30 mL) and filtered. The filter cake was washed with cold methanol (2×10 mL) and then dried under reduced pressure to provide compound F4 as a yellow solid (21.7 g, 54%): $^1$H NMR (300 MHz, DMSO-d$_6$) δ 6.98 (s, 2H), 6.52 (bs, 2H), 3.29 (s, 2H), 2.66 (d, J=4.8 Hz, 2H), 2.60 (d, J=4.8 Hz, 2H), 2.46 (q, J=7.2 Hz, 2H), 1.04 (t, J=7.2 Hz, 3H). MS (M+H) 226.

Step 3: 2-[3-(4-Chloro-3-methylphenyl)ureido]-6-ethyl-4,5,6,7-tetrahydrothieno[2,3-c]pyridine-3-carboxamide (F5)

To a stirred solution of compound F4 (450 mg, 2.00 mmol) in anhydrous tetrahydrofuran (10 mL) at room temperature under nitrogen was added a solution of compound F2 (402 mg, 2.40 mmol) in anhydrous methylene chloride (6 mL) dropwise over 3 min. Then the reaction mixture was stirred overnight at room temperature. The reaction mixture was filtered. The filter cake was washed with methylene chloride (5 mL) and then dried under reduced pressure to provide compound F5 as a white solid (301 mg, 38%): $^1$H NMR (300 MHz, DMSO-$d_6$) δ 10.94 (s, 1H), 10.12 (s, 1H), 7.48-6.75 (m, 5H), 3.45 (s, 2H), 2.77 (d, J=4.8 Hz, 2H), 2.65 (d, J=4.8 Hz, 2H), 2.55-2.45 (m, 2H), 2.30 (s, 3H), 1.07 (t, J=6.6 Hz, 3H).

Step 4: 2-[3-(4-Chloro-3-methylphenyl)ureido]-6-ethyl-4,5,6,7-tetrahydrothieno[2,3-c]pyridine-3-carboxamide hydrochloride (F6)

To a stirred mixture of compound F5 (157 mg, 0.400 mmol) in methylene chloride (50 mL) at room temperature was added hydrochloride (2 M in diethyl ether, 0.300 mL, 0.600 mmol). After addition, the mixture was concentrated under reduced pressure. The resulting solid was triturated with methylene chloride and filtered to afford compound F6 as yellow solid: $^1$H NMR (500 MHz, DMSO-$d_6$) δ 10.94 (s, 1H), 10.84 (bs, 1H), 10.22 (s, 1H), 7.75-6.90 (m, 5H), 4.49 (d, J=14.5 Hz, 1H), 4.22-4.16 (m, 1H), 3.65-3.62 (m, 1H), 3.38-3.05 (m, 5H), 2.30 (s, 3H), 1.32 (t, J=7.2 Hz, 3H). MS (M+H) 393.

Example 65

Preparation of 2-[3-(2-Chlorophenyl)ureido]-6-ethyl-4,5,6,7-tetrahydrothieno[2,3-c]pyridine-3-carboxamide hydrochloride

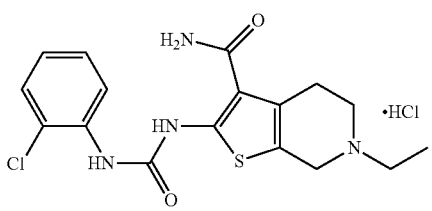 [SMILES: CCN1CCc2c(sc(NC(=O)Nc3ccccc3Cl)c2C(N)=O)C1 ; Cl]

The title compound was prepared using a similar procedure as described in Example 64. MS (M+H) 379. $^1$H NMR (300 MHz, DMSO-$d_6$) δ 10.83 (s, 1H), 10.60 (bs, 1H), 9.69 (s, 1H), 7.87 (d, J=6.9 Hz, 1H), 7.69-7.06 (m, 5H), 4.53-4.48 (m, 1H), 4.23-4.15 (m, 1H), 3.67-3.62 (m, 1H), 3.36-3.10 (m, 3H), 3.06 (bs, 2H), 1.31 (t, J=7.1 Hz, 3H).

Example 66

Preparation of 6-Ethyl-2-[3-(4-fluorophenyl)ureido]-4,5,6,7-tetrahydrothieno[2,3-c]pyridine-3-carboxamide hydrochloride

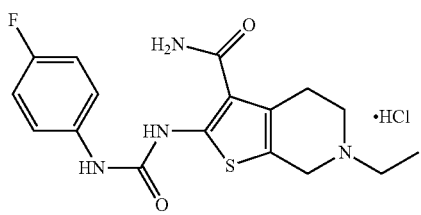 [SMILES: CCN1CCc2c(sc(NC(=O)Nc3ccc(F)cc3)c2C(N)=O)C1 ; Cl]

The title compound was prepared using a similar procedure as described in Example 64. MS (M+H) 363. $^1$H NMR (300 MHz, DMSO-$d_6$) δ 10.93 (s, 1H), 10.69 (bs, 1H), 10.19 (s, 1H), 7.80-6.89 (m, 6H), 4.54-4.48 (m, 1H), 4.23-4.15 (m, 1H), 3.67-3.62 (m, 1H), 3.33-3.00 (m, 5H), 1.31 (t, J=7.2 Hz, 3H).

Example 67

Preparation of 2-[3-(4-Cyanophenyl)ureido]-6-ethyl-4,5,6,7-tetrahydrothieno[2,3-c]pyridine-3-carboxamide hydrochloride

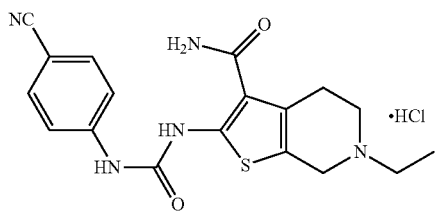 [SMILES: CCN1CCc2c(sc(NC(=O)Nc3ccc(C#N)cc3)c2C(N)=O)C1 ; Cl]

The title compound was prepared using a similar procedure as described in Example 64. MS (M+H) 370. $^1$H NMR (300 MHz, DMSO-$d_6$) δ 11.08 (s, 1H), 10.77 (bs, 1H), 10.68 (s, 1H), 8.00-6.95 (m, 6H), 4.55-4.49 (m, 1H), 4.22-4.15 (m, 1H), 3.70-3.56 (m, 1H), 3.40-3.04 (m, 5H), 1.32 (t, J=6.8 Hz, 3H).

Example 68

Preparation of 2-(3-Cyclohexylureido)-6-ethyl-4,5,6,7-tetrahydrothieno[2,3-c]pyridine-3-carboxamide hydrochloride

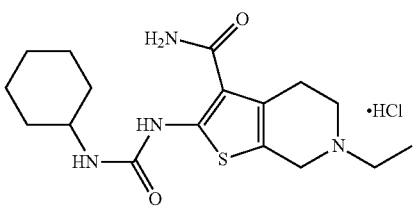 [SMILES: CCN1CCc2c(sc(NC(=O)NC3CCCCC3)c2C(N)=O)C1 ; Cl]

The title compound was prepared using a similar procedure as described in Example 64. MS (M+H) 351. $^1$H NMR (300 MHz, DMSO-$d_6$) δ 10.48-10.33 (m, 2H), 7.71-6.85 (m, 3H), 4.50-4.44 (m, 1H), 4.19-4.15 (m, 1H), 3.70-3.61 (m, 1H), 3.50-2.95 (m, 6H), 1.80-1.05 (m, 13H).

Example 69

Preparation of 6-Ethyl-2-[3-(pyridin-3-yl)ureido]-4,5,6,7-tetrahydrothieno[2,3-c]pyridine-3-carboxamide dihydrochloride

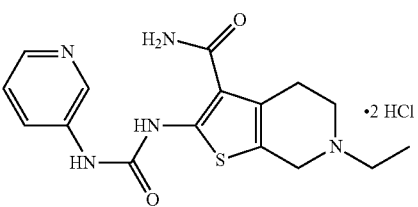 [SMILES: CCN1CCc2c(sc(NC(=O)Nc3cccnc3)c2C(N)=O)C1 ; "·2 HCl"]

The title compound was prepared using a similar procedure as described in Example 64. MS (M+H) 346. $^1$H NMR (300 MHz, DMSO-$d_6$) δ 11.26 (s, 1H), 11.04 (s, 1H), 10.95 (bs, 1H), 8.98 (s, 1H), 8.48 (d, J=5.4 Hz, 1H), 8.27 (d, J=8.4 Hz, 1H), 7.82 (dd, J=8.4 and 5.4 Hz, 1H), 7.81-7.00 (m, 2H), 4.55-4.17 (m, 3H), 3.71-3.60 (m, 1H), 3.39-3.05 (m, 4H), 1.32 (t, J=7.2 Hz, 3H).

Example 70

Preparation of 2-[3-(3,4-Difluorophenyl)ureido]-6-ethyl-4,5,6,7-tetrahydrothieno[2,3-c]pyridine-3-carboxamide hydrochloride

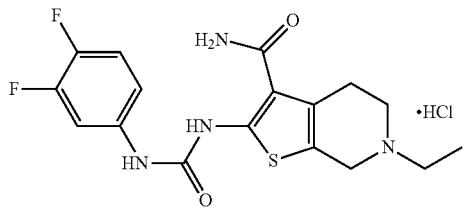 [SMILES: CCN1CCc2c(sc(NC(=O)Nc3ccc(F)c(F)c3)c2C(N)=O)C1 ; Cl]

The title compound was prepared using a similar procedure as described in Example 64. MS (M+H) 381. $^1$H NMR (300 MHz, DMSO-d$_6$) δ 11.01 (s, 1H), 10.76 (bs, 1H), 10.41 (s, 1H), 7.85-6.88 (m, 5H), 4.54-4.46 (m, 1H), 4.29-4.14 (m, 1H), 3.69-3.61 (m, 1H), 3.39-3.00 (m, 5H), 1.32 (t, J=7.1 Hz, 3H).

Example 71

Preparation of 6-Ethyl-2-[3-(3-fluorophenyl)ureido]-4,5,6,7-tetrahydrothieno[2,3-c]pyridine-3-carboxamide hydrochloride

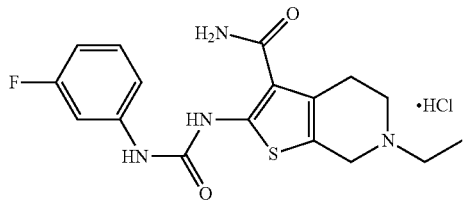 [SMILES: CCN1CCc2c(sc(NC(=O)Nc3cccc(F)c3)c2C(N)=O)C1 ; Cl]

The title compound was prepared using a similar procedure as described in Example 64. MS (M+H) 363. $^1$H NMR (300 MHz, DMSO-d$_6$) δ 10.98 (s, 1H), 10.41 (bs, 1H), 10.39 (s, 1H), 7.80-6.75 (m, 6H), 4.56-4.47 (m, 1H), 4.25-4.16 (m, 1H), 3.68-3.62 (m, 1H), 3.49-3.00 (m, 5H), 1.31 (t, J=7.2 Hz, 3H).

Example 72

Preparation of 6-Ethyl-2-[3-(4-(trifluoromethyl)phenyl)ureido]-4,5,6,7-tetrahydrothieno[2,3-c]pyridine-3-carboxamide hydrochloride

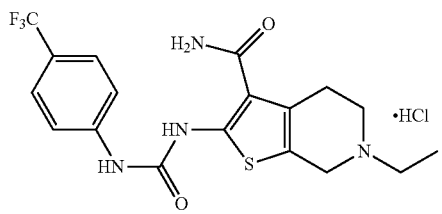 [SMILES: CCN1CCc2c(sc(NC(=O)Nc3ccc(C(F)(F)F)cc3)c2C(N)=O)C1 ; Cl]

The title compound was prepared using a similar procedure as described in Example 64. MS (M+H) 413. $^1$H NMR (300 MHz, DMSO-d$_6$) δ 11.04 (s, 1H), 10.85 (bs, 1H), 10.60 (s, 1H), 8.15-6.90 (m, 6H), 4.60-4.46 (m, 1H), 4.26-4.15 (m, 1H), 3.67-3.60 (m, 1H), 3.49-3.00 (m, 5H), 1.32 (t, J=7.2 Hz, 3H).

Example 73

Preparation of 2-[3-(3-Cyanophenyl)ureido]-6-ethyl-4,5,6,7-tetrahydrothieno[2,3-c]pyridine-3-carboxamide hydrochloride

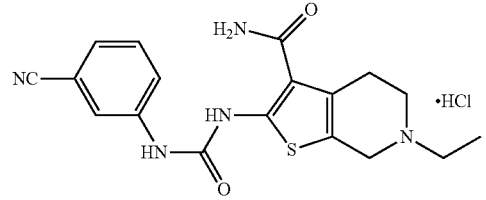 [SMILES: CCN1CCc2c(sc(NC(=O)Nc3cccc(C#N)c3)c2C(N)=O)C1 ; Cl]

The title compound was prepared using a similar procedure as described in Example 64. MS (M+H) 370. $^1$H NMR (300 MHz, DMSO-d$_6$) δ 11.06 (s, 1H), 10.78 (bs, 1H), 10.56 (s, 1H), 7.99 (s, 1H), 7.88-6.85 (m, 5H), 4.55-4.46 (m, 1H), 4.25-4.15 (m, 1H), 3.68-3.62 (m, 1H), 3.32-3.00 (m, 5H), 1.32 (t, J=7.2 Hz, 3H).

Example 74

Preparation of 2-[3-(2,3-Dichlorophenyl)ureido]-6-ethyl-4,5,6,7-tetrahydrothieno[2,3-c]pyridine-3-carboxamide hydrochloride

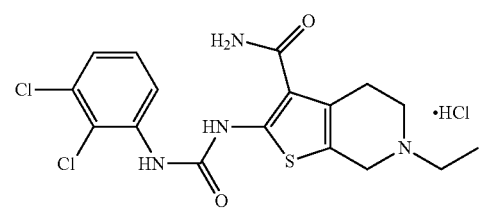 [SMILES: CCN1CCc2c(sc(NC(=O)Nc3cccc(Cl)c3Cl)c2C(N)=O)C1 ; Cl]

The title compound was prepared using a similar procedure as described in Example 64. MS (M+H) 413. $^1$H NMR (300 MHz, DMSO-d$_6$) δ 10.88 (s, 1H), 10.59 (bs, 1H), 9.84 (s, 1H), 7.88 (dd, J=7.8 and 1.8 Hz, 1H), 7.75-7.15 (m, 4H), 4.54-4.48 (m, 1H), 4.24-4.15 (m, 1H), 3.68-3.62 (m, 1H), 3.34-3.13 (m, 3H), 3.06 (bs, 2H), 1.31 (t, J=7.2 Hz, 3H).

Example 75

Preparation of 2-[3-(3-Chlorobenzyl)ureido]-6-ethyl-4,5,6,7-tetrahydrothieno[2,3-c]pyridine-3-carboxamide hydrochloride

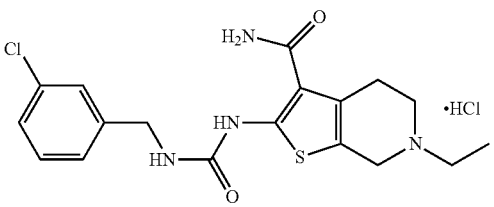 [SMILES: CCN1CCc2c(sc(NC(=O)NCc3cccc(Cl)c3)c2C(N)=O)C1 ; Cl]

The title compound was prepared using a similar procedure as described in Example 64. MS (M+H) 393. ¹H NMR (300 MHz, DMSO-d₆) δ 10.70 (s, 1H), 10.57 (bs, 1H), 8.30 (t, J=5.2 Hz, 1H), 7.70-6.91 (m, 6H), 4.51-4.42 (m, 1H), 4.30 (d, J=5.2 Hz, 2H), 4.19-4.11 (m, 1H), 3.66-3.60 (m, 1H), 3.32-3.11 (m, 3H), 3.06 (bs, 2H), 1.30 (t, J=6.8 Hz, 3H).

Example 76

Preparation of 2-[3-(4-Chlorobenzyl)ureido]-6-ethyl-4,5,6,7-tetrahydrothieno[2,3-c]pyridine-3-carboxamide hydrochloride

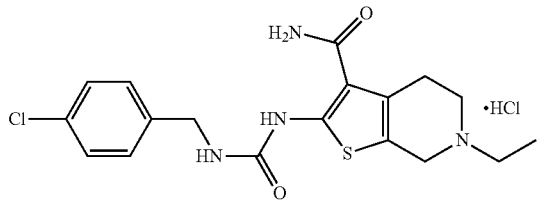 [SMILES: CCN1CCc2c(sc(NC(=O)NCc3ccc(Cl)cc3)c2C(N)=O)C1 ; Cl]

The title compound was prepared using a similar procedure as described in Example 64. MS (M+H) 393. ¹H NMR (300 MHz, DMSO-d₆) δ 10.68 (s, 1H), 10.62 (bs, 1H), 8.29 (t, J=5.4 Hz, 1H), 7.69-6.90 (m, 6H), 4.49-4.42 (m, 1H), 4.28 (d, J=5.4 Hz, 2H), 4.17-4.10 (m, 1H), 3.68-3.60 (m, 1H), 3.31-3.00 (m, 5H), 1.30 (t, J=7.1 Hz, 3H).

Example 77

Preparation of 2-[3-(5-Chloropyridin-3-yl)ureido]-6-ethyl-4,5,6,7-tetrahydrothieno[2,3-c]pyridine-3-carboxamide dihydrochloride

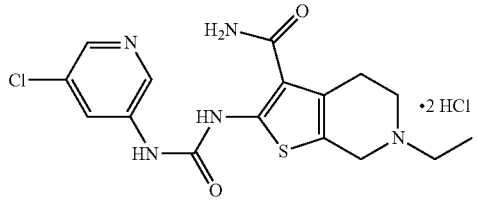 [SMILES: CCN1CCc2c(sc(NC(=O)Nc3cncc(Cl)c3)c2C(N)=O)C1 ; "·2 HCl"]

The title compound was prepared using a similar procedure as described in Example 64. MS (M+H) 380. ¹H NMR (300 MHz, DMSO-d₆) δ 11.15 (s, 1H), 10.74 (bs, 1H), 10.68 (s, 1H), 8.51 (d, J=2.1 Hz, 1H), 8.29 (d, J=2.1 Hz, 1H), 8.16 (t, J=2.1 Hz, 1H), 7.60 (bs, 1H), 7.20 (bs, 1H), 4.56-4.50 (m, 1H), 4.23-4.15 (m, 1H), 3.80-3.61 (m, 2H), 3.35-3.00 (m, 4H), 1.32 (t, J=7.2 Hz, 3H).

Example 78

Preparation of 6-Ethyl-2-[3-(quinolin-3-yl)ureido]-4,5,6,7-tetrahydrothieno[2,3-c]pyridine-3-carboxamide dihydrochloride

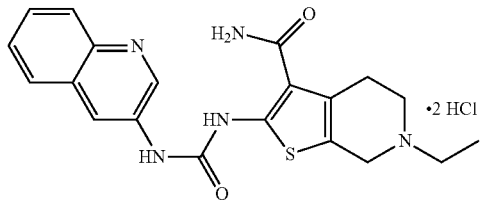 [SMILES: CCN1CCc2c(sc(NC(=O)Nc3cnc4ccccc4c3)c2C(N)=O)C1 ; "·2 HCl"]

The title compound was prepared using a similar procedure as described in Example 64. MS (M+H) 396. ¹H NMR (300 MHz, DMSO-d₆) δ 11.23 (s, 1H), 10.89 (s, 1H), 10.78 (bs, 1H), 8.99 (s, 1H), 8.73 (s, 1H), 8.52-7.10 (m, 6H), 4.55-4.50 (m, 1H), 4.26-3.90 (m, 2H), 3.69-3.63 (m, 1H), 3.35-3.08 (m, 4H), 1.33 (t, J=7.2 Hz, 3H).

Example 79

Preparation of 6-Ethyl-2-[3-(quinolin-6-yl)ureido]-4,5,6,7-tetrahydrothieno[2,3-c]pyridine-3-carboxamide dihydrochloride

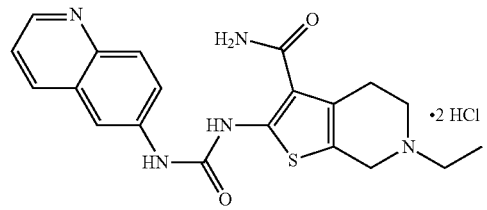 [SMILES: CCN1CCc2c(sc(NC(=O)Nc3ccc4ncccc4c3)c2C(N)=O)C1 ; "·2 HCl"]

The title compound was prepared using a similar procedure as described in Example 64. MS (M+H) 396. ¹H NMR (300 MHz, DMSO-d₆) δ 11.13 (bs 2H), 10.93 (s, 1H), 9.08 (d, J=4.5 Hz, 1H), 9.02 (d, J=8.4 Hz, 1H), 8.56 (s, 1H), 8.35 (d, J=9.3 Hz, 1H), 8.04-7.91 (m, 2H), 7.55 (bs, 1H), 7.20 (bs, 1H), 4.55-4.48 (m, 1H), 4.32-3.00 (m, 7H), 1.35 (t, J=7.1 Hz, 1H).

Example 80

Preparation of 2-[3-(Benzo[c][1,2,5]thiadiazol-4-yl)ureido]-6-ethyl-4,5,6,7-tetrahydrothieno[2,3-c]pyridine-3-carboxamide hydrochloride

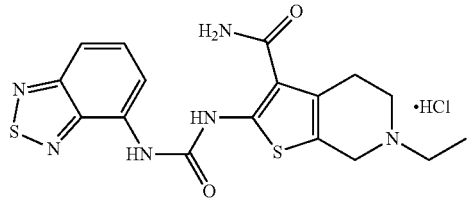 [SMILES: CCN1CCc2c(sc(NC(=O)Nc3cccc4nsnc34)c2C(N)=O)C1 ; Cl]

The title compound was prepared using a similar procedure as described in Example 64. MS (M+H) 403. ¹H NMR (300 MHz, DMSO-d₆) δ 10.95 (s, 1H), 10.81 (s, 1H), 10.51 (bs, 1H), 8.24 (dd, J=5.7 and 2.7 Hz, 1H), 7.73-7.25 (m, 4H), 4.57-4.50 (m, 1H), 4.25-4.15 (m, 1H), 3.69-3.62 (m, 1H), 3.34-3.10 (m, 3H), 3.06 (bs, 2H), 1.32 (t, J=7.1 Hz, 3H).

Example 81

Preparation of 6-Ethyl-2-[3-(isoquinolin-4-yl)ureido]-4,5,6,7-tetrahydrothieno[2,3-c]pyridine-3-carboxamide dihydrochloride

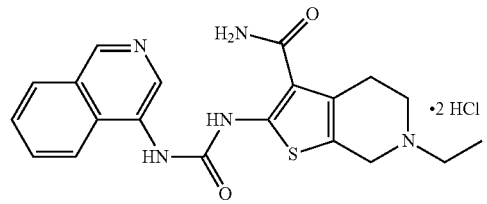 [SMILES: CCN1CCc2c(sc(NC(=O)Nc3cncc4ccccc34)c2C(N)=O)C1 ; "·2 HCl"]

The title compound was prepared using a similar procedure as described in Example 64. MS (M+H) 396. ¹H NMR (300

MHz, DMSO-d$_6$) δ 11.19 (s, 1H), 10.80 (bs, 1H), 10.70 (s, 1H), 9.50 (s, 1H), 9.13 (s, 1H), 8.56 (d, J=7.5 Hz, 1H), 8.47 (d, J=7.5 Hz, 1H), 8.19 (t, J=7.5 Hz, 1H), 8.00 (t, J=7.5 Hz, 1H), 7.64 (bs, 1H), 7.28 (bs, 1H), 4.57-4.50 (m, 1H), 4.26-4.14 (m, 1H), 4.10-3.00 (m, 6H), 1.33 (t, J=7.2 Hz, 3H).

Example 82

Preparation of 6-Ethyl-2-[3-(1-methyl-1H-indol-3-yl)ureido]-4,5,6,7-tetrahydrothieno[2,3-c]pyridine-3-carboxamide hydrochloride

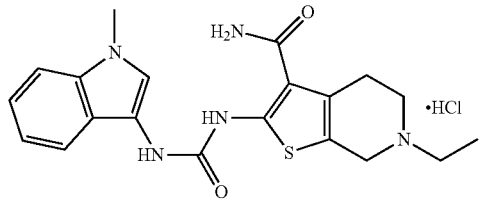 [SMILES: CCN1CCc2c(sc(NC(=O)Nc3cn(C)c4ccccc34)c2C(N)=O)C1 ; Cl]

The title compound was prepared using a similar procedure as described in Example 64. MS (M+H) 398. $^1$H NMR (300 MHz, DMSO-d$_6$) δ 10.90 (bs, 1H), 10.42 (bs, 1H), 10.02 (bs, 1H), 7.71-6.95 (m, 7H), 4.54-4.49 (m, 1H), 4.23-4.13 (m, 1H), 3.76 (s, 3H), 3.69-3.63 (m, 1H), 3.45-3.12 (m, 3H), 3.09 (bs, 2H), 1.31 (t, J=7.2 Hz, 3H).

Example 83

Preparation of 2-[3-(3-Chloro-4-methylphenyl)ureido]-6-ethyl-4,5,6,7-tetrahydrothieno[2,3-c]pyridine-3-carboxamide hydrochloride

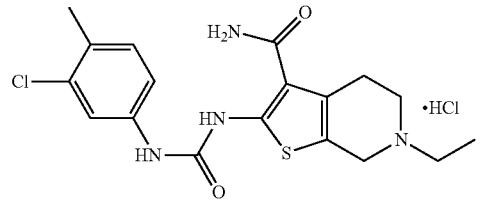 [SMILES: CCN1CCc2c(sc(NC(=O)Nc3ccc(C)c(Cl)c3)c2C(N)=O)C1 ; Cl]

The title compound was prepared using a similar procedure as described in Example 64. MS (M+H) 393. $^1$H NMR (300 MHz, DMSO-d$_6$) δ 10.96 (s, 1H), 10.73 (bs, 1H), 10.25 (s, 1H), 7.67 (s, 1H), 7.65-6.90 (m, 4H), 4.52-4.48 (m, 1H), 4.22-4.16 (m, 1H), 3.66-3.62 (m, 1H), 3.30-3.06 (m, 5H), 2.27 (s, 3H), 1.33 (t, J=7.1 Hz, 3H).

Example 84

Preparation of 6-Ethyl-2-[3-(1-methyl-1H-indol-4-yl)ureido]-4,5,6,7-tetrahydrothieno[2,3-c]pyridine-3-carboxamide hydrochloride

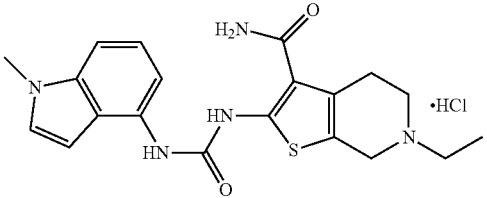 [SMILES: CCN1CCc2c(sc(NC(=O)Nc3cccc4c3ccn4C)c2C(N)=O)C1 ; Cl]

The title compound was prepared using a similar procedure as described in Example 64. MS (M+H) 398. $^1$H NMR (300 MHz, DMSO-d$_6$) δ 10.78 (s, 1H), 10.69 (s, 1H), 9.83 (s, 1H), 7.61 (d, J=6.3 Hz, 1H), 7.60-7.10 (m, 5H), 6.68 (d, J=3.0 Hz, 1H), 4.54-4.48 (m, 1H), 4.24-4.15 (m, 1H), 3.77 (s, 3H), 3.70-3.62 (m, 1H), 3.29-3.10 (m, 3H), 3.08 (bs, 2H), 1.32 (t, J=7.2 Hz, 3H).

Example 85

Preparation of 2-[3-(2,2-Difluorobenzo[d][1,3]dioxol-5-yl)ureido]-6-ethyl-4,5,6,7-tetrahydrothieno[2,3-c]pyridine-3-carboxamide hydrochloride

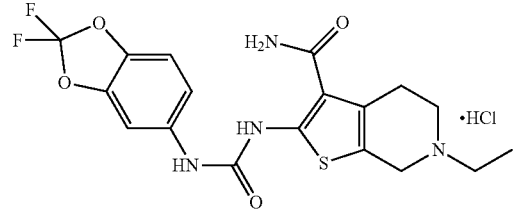 [SMILES: CCN1CCc2c(sc(NC(=O)Nc3ccc4c(c3)OC(F)(F)O4)c2C(N)=O)C1 ; Cl]

The title compound was prepared using a similar procedure as described in Example 64. MS (M+H) 425. $^1$H NMR (300 MHz, DMSO-d$_6$) δ 11.00 (s, 1H), 10.61 (bs, 1H), 10.38 (s, 1H), 7.65 (d, J=2.1 Hz, 1H), 7.64-6.95 (m, 4H), 4.55-4.48 (m, 1H), 4.24-4.15 (m, 1H), 3.68-3.63 (m, 1H), 3.35-3.15 (m, 3H), 3.10 (bs, 2H), 1.31 (t, J=7.2 Hz, 3H).

Example 86

Preparation of 2-[3-(4-Chlorophenyl)ureido]-4-methyl-5-(morpholinomethyl)thiophene-3-carboxamide hydrochloride

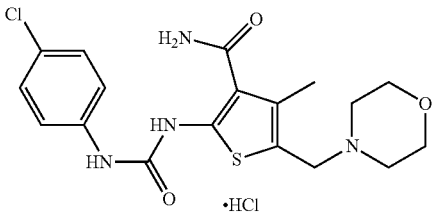 [SMILES: Cc1c(CN2CCOCC2)sc(NC(=O)Nc2ccc(Cl)cc2)c1C(N)=O ; Cl]

The title compound was prepared using a similar procedure as described in Example 64. MS (M+H) 407. $^1$H NMR (300 MHz, DMSO-d$_6$) δ 10.65 (s, 1H), 10.43 (bs, 1H), 10.25 (s, 1H), 7.64 (bs, 1H), 7.50 (d, J=8.7 Hz, 2H), 7.35 (d, J=8.7 Hz, 2H), 7.34 (bs, 1H), 4.46 (s, 2H), 4.00-3.94 (m, 2H), 3.73 (t, J=11.7 Hz, 2H), 3.36-3.22 (m, 2H), 3.16-3.05 (m, 2H), 2.36 (s, 3H).

Example 87

Preparation of 1-(4-Chlorophenyl)-3-(3-cyano-6-ethyl-4,5,6,7-tetrahydrothieno[2,3-c]pyridin-2-yl)urea

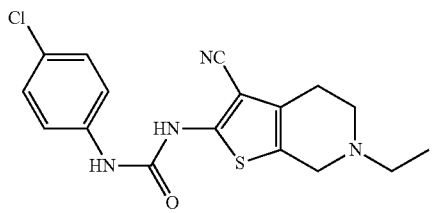 [SMILES: CCN1CCc2c(sc(NC(=O)Nc3ccc(Cl)cc3)c2C#N)C1]

The title compound was prepared using a similar procedure as described in Example 64. MS (M+H) 361. $^1$H NMR (500 MHz, DMSO-d$_6$) δ 10.19 (s, 1H), 9.32 (s, 1H), 7.48 (d, J=9.0 Hz, 2H), 7.36 (d, J=9.0 Hz, 2H), 3.49-3.43 (m, 2H), 2.77-2.69 (m, 2H), 2.59-2.53 (m, 4H), 1.07 (t, J=7.0 Hz, 3H).

Example 88

Preparation of 2-[3-(4-Benzoylphenyl)ureido]-6-ethyl-4,5,6,7-tetrahydrothieno[2,3-c]pyridine-3-carboxamide

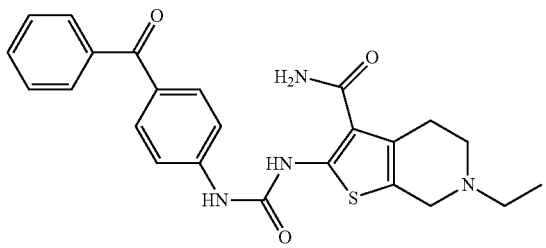 [SMILES: CCN1CCc2c(sc(NC(=O)Nc3ccc(C(=O)c4ccccc4)cc3)c2C(N)=O)C1]

The title compound was prepared using a similar procedure as described in Example 64. MS (M+H) 449. $^1$H NMR (500 MHz, DMSO-$d_6$) δ 11.05 (s, 1H), 10.50 (s, 1H), 7.79-7.63 (m, 7H), 7.58-7.35 (m, 3H), 6.86 (bs, 1H), 3.47 (s, 2H), 2.81-2.77 (m, 2H), 2.68-2.61 (m, 2H), 2.57-2.53 (m, 2H), 1.08 (t, J=7.0 Hz, 3H).

Example 89

Preparation of 2-[3-(4-Chlorophenyl)ureido]-6-(2,2,2-trifluoroethyl)-4,5,6,7-tetrahydrothieno[2,3-c]pyridine-3-carboxamide

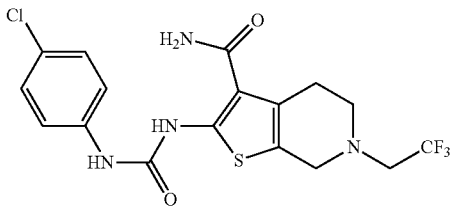 [SMILES: NC(=O)c1c(NC(=O)Nc2ccc(Cl)cc2)sc2c1CCN(CC(F)(F)F)C2]

The title compound was prepared using a similar procedure as described in Example 64. MS (M+H) 433. $^1$H NMR (500 MHz, DMSO-$d_6$) δ 10.90 (s, 1H), 10.17 (s, 1H), 7.71-7.29 (m, 5H), 6.87 (bs, 1H), 3.75 (s, 2H), 3.40-3.33 (m, 2H), 2.92-2.88 (m, 2H), 2.82-2.78 (m, 2H).

Example 90

Preparation of 2-[3-(4-Chlorophenyl)ureido]-5,5,7,7-tetramethyl-4,5,6,7-tetrahydrothieno[2,3-c]pyridine-3-carboxamide hydrochloride

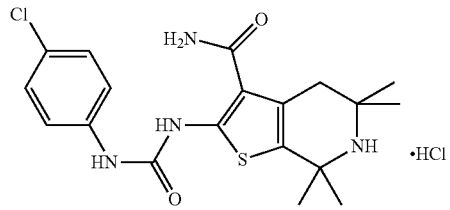 [SMILES: CC1(C)Cc2c(sc(NC(=O)Nc3ccc(Cl)cc3)c2C(N)=O)C(C)(C)N1 ; Cl]

The title compound was prepared using a similar procedure as described in Example 64. MS (M+H) 407. $^1$H NMR (300 MHz, DMSO-$d_6$) δ 10.80 (s, 1H), 10.27 (s, 1H), 9.38 (bs, 2H), 7.80-6.90 (m, 6H), 2.92 (s, 2H), 1.73 (s, 6H), 1.44 (s, 6H).

Example 91

Preparation of 2-[3-(4-Chlorophenyl)ureido]-6-oxo-4,5,6,7-tetrahydrobenzo[b]thiophene-3-carboxamide

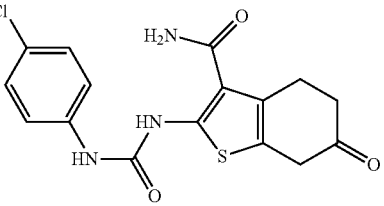

The title compound was prepared using a similar procedure as described in Example 64. MS (M+H) 364. $^1$H NMR (300 MHz, DMSO-$d_6$) δ 10.68 (s, 1H), 10.17 (s, 1H), 7.80-6.80 (m, 6H), 3.51 (s, 2H), 3.10-3.06 (m, 2H), 2.60-2.55 (m, 2H).

Example 92

Preparation of 2-[3-(4-Chlorophenyl)ureido]-5,7-dihydro-4H-thieno[2,3-c]pyran-3-carboxamide

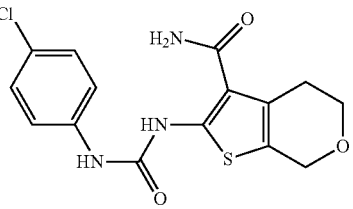

The title compound was prepared using a similar procedure as described in Example 64. MS (M+H) 374. $^1$H NMR (300 MHz, DMSO-$d_6$) δ 10.95 (s, 1H), 10.21 (s, 1H), 7.70-6.70 (m, 6H), 4.62 (s, 2H), 3.85-3.81 (m, 2H), 2.79 (bs, 2H).

Example 93

Preparation of 6-ethyl-2-[3-(6-fluoronaphthalen-2-yl)ureido]-4,5,6,7-tetrahydrothieno[2,3-c]pyridine-3-carboxamide hydrochloride (G3)

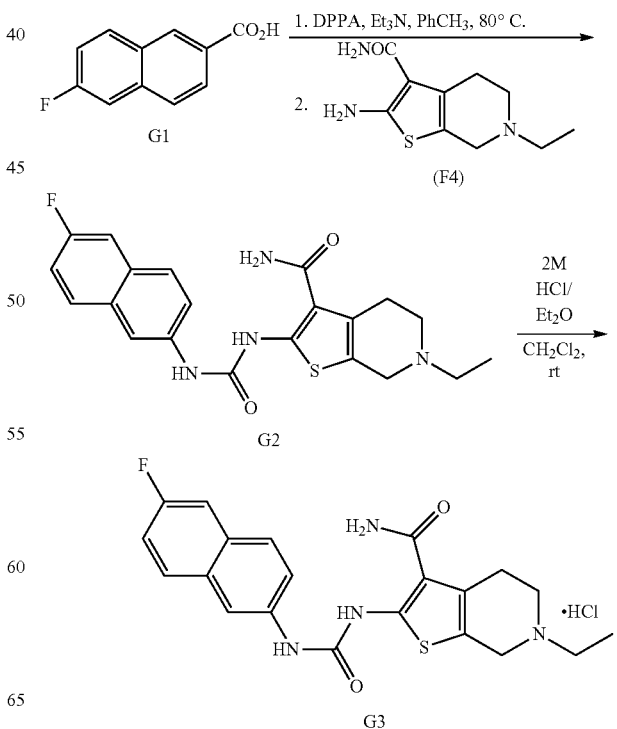

Step 1: 6-Ethyl-2-[3-(6-fluoronaphthalen-2-yl)ureido]-4,5,6,7-tetrahydrothieno[2,3-c]pyridine-3-carboxamide (G2)

To a stirred mixture of 6-fluoro-2-naphthoic acid (G1, 0.951 g, 5.00 mmol), triethylamine (0.759 g, 7.50 mmol) in anhydrous toluene (40 mL) was added diphenyl phosphorazidate (1.51 g, 5.50 mmol). After addition, the reaction mixture was heated at 80° C. for 2 h and then cooled to room temperature. The resulting solution was added to another stirred solution of compound F4 (1.13 g, 5.00 mmol) in anhydrous tetrahydrofuran (50 mL). After addition, the resulting mixture was heated at 80° C. for another 2 h. After this time, the reaction mixture was cooled to room temperature, quenched with saturated aqueous sodium bicarbonate (60 mL), and extracted with ethyl acetate (3×100 mL). The combined organic extracts were dried over anhydrous sodium sulfate, filtered, and concentrated under reduced pressure. The resulting residue was purified by flash column chromatography on silica gel eluting with methanol/methylene chloride (15:85) to afford compound G2 as an off-white solid (451 mg, 22%): $^1$H NMR (300 MHz, DMSO-$d_6$) δ 11.01 (s, 1H), 10.27 (s, 1H), 8.19 (d, J=1.8 Hz, 1H), 7.91 (dd, J=10.8 and 5.7 Hz, 1H), 7.84 (d, J=9.0 Hz, 1H), 7.64-6.70 (m, 5H), 3.47 (s, 2H), 2.78 (d, J=5.1 Hz, 2H), 2.66 (d, J=5.1 Hz, 2H), 2.55-2.49 (m, 2H), 1.08 (t, J=7.0 Hz, 3H). MS (M+H) 413.

Step 2: 6-Ethyl-2-[3-(6-fluoronaphthalen-2-yl)ureido]-4,5,6,7-tetrahydrothieno[2,3-c]pyridine-3-carboxamide hydrochloride (G3)

To a mixture of compound G2 (124 mg, 0.300 mmol) in methylene chloride (8 mL) at room temperature was added hydrochloride (2 M in diethyl ether, 1.00 mL, 2.00 mmol). The resulting mixture was sonicated for 20 min, and then concentrated under reduced pressure. The residue was triturated with methylene chloride to afford compound G3 as an off-white solid (105 mg, 78%): $^1$H NMR (300 MHz, DMSO-$d_6$) δ 11.02 (s, 1H), 10.56 (bs, 1H), 10.38 (s, 1H), 8.19 (d, J=1.8 Hz, 1H), 7.92 (dd, J=9.0 and 5.7 Hz, 1H), 7.84 (d, J=9.0 Hz, 1H), 7.85-6.90 (m, 5H), 4.16 (bs, 2H), 3.75-2.80 (m, 6H), 1.28 (t, J=7.0 Hz, 3H). MS (M+H) 413.

Example 94

Preparation of 2-[3-(5-Chlorothiophen-2-yl)ureido]-6-ethyl-4,5,6,7-tetrahydrothieno[2,3-c]pyridine-3-carboxamide hydrochloride

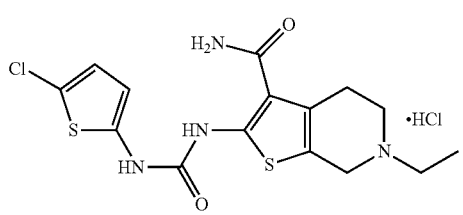 [SMILES: CCN1CCc2c(sc(NC(=O)Nc3ccc(Cl)s3)c2C(N)=O)C1 ; Cl]

The title compound was prepared using a similar procedure as described in Example 93. MS (M+H) 385. $^1$H NMR (300 MHz, DMSO-$d_6$) δ 11.40 (s, 1H), 11.13 (s, 1H), 10.72 (bs, 1H), 7.48 (bs, 2H), 6.85 (d, J=3.9 Hz, 1H), 6.37 (d, J=3.9 Hz, 1H), 4.55-4.47 (m, 1H), 4.24-4.16 (m, 1H), 3.67-3.61 (m, 1H), 3.33-3.04 (m, 5H), 1.31 (t, J=7.1 Hz, 3H).

Example 95

Preparation of 1-(4-chlorophenyl)-3-[6-ethyl-3-(morpholine-4-carbonyl)-4,5,6,7-tetrahydrothieno[2,3-c]pyridin-2-yl]urea hydrochloride (H7)

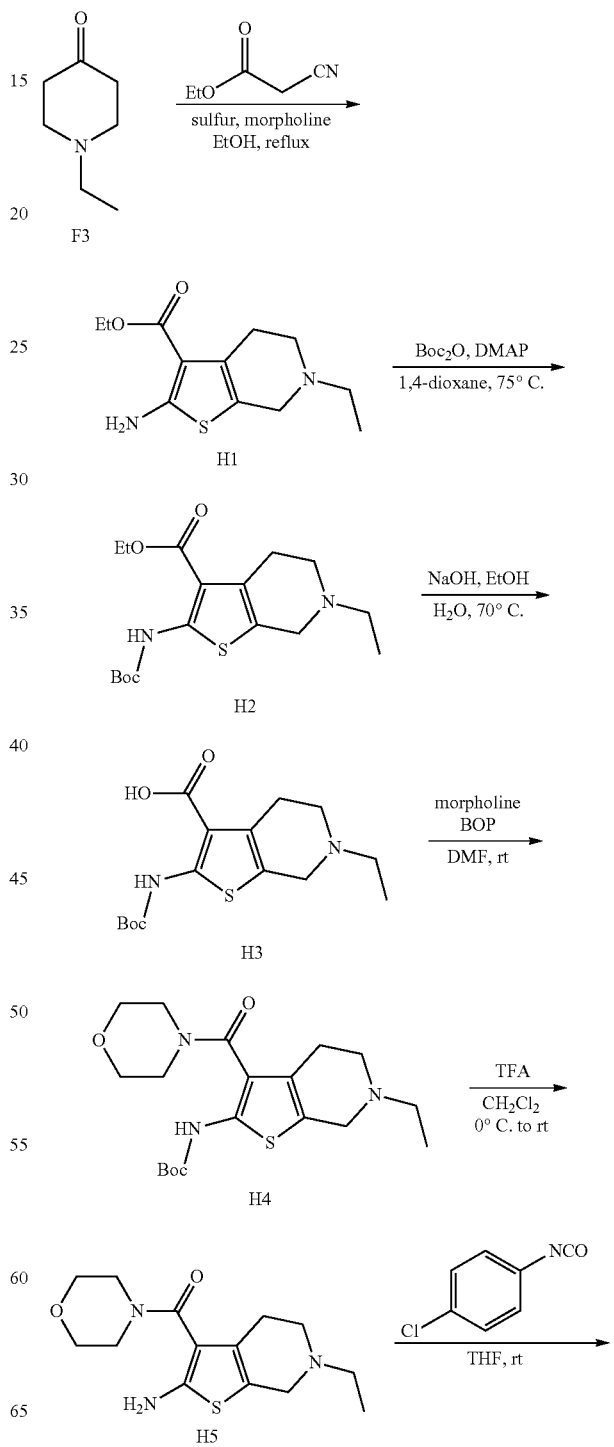

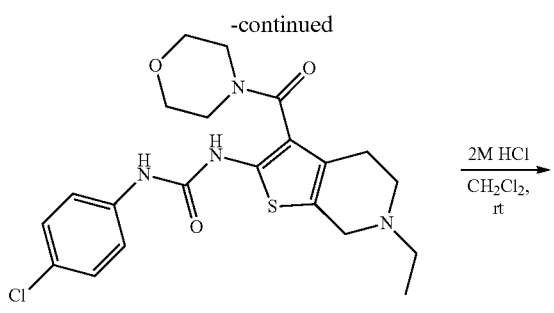

Step 1: Ethyl 2-amino-6-ethyl-4,5,6,7-tetrahydrothieno[2,3-c]pyridine-3-carboxylate (H1)

A solution of ethyl 2-cyanoacetate (4.87 g, 43.1 mmol), 1-ethylpiperidin-4-one (F3, 5.00 g, 39.3 mmol), sulfur (1.50 g, 46.8 mmol), and morpholine (6.80 mL, 78.1 mmol) in ethanol (30 mL) was heated to reflux for 6 h and then the reaction mixture was cooled to room temperature, concentrated under reduced pressure. The resulting residue was purified by flash column chromatography on silica gel eluting with methylene chloride to methanol to methylene chloride (1:19). Further purification by flash column chromatography on silica gel was required eluting from methylene chloride to ethyl acetate to afford compound H1 as a light orange solid (9.77 g, 98%): $^1$H NMR (300 MHz, CDCl$_3$) δ 5.95 (bs, 2H), 4.26 (q, J=7.2 Hz, 2H), 3.42-3.41 (m, 2H), 2.88-2.80 (m, 2H), 2.77-2.69 (m, 2H), 2.57 (q, J=7.2 Hz, 2H), 1.33 (t, J=7.2 Hz, 3H), 1.16 (t, J=7.2 Hz, 3H).

Step 2: Ethyl 2-(tert-butoxycarbonylamino)-6-ethyl-4,5,6,7-tetrahydrothieno[2,3-c]pyridine-3-carboxylate (H2)

A solution of compound H1 (2.00 g, 7.86 mmol), di-tert-butyl dicarbonate (3.50 g, 16.0 mmol), and 4-dimethylaminopyridine (97.0 mg, 0.790 mmol) in anhydrous 1,4-dioxane (25 mL) was stirred at 75° C. for 3 h. After this time, the reaction mixture was cooled to room temperature and concentrated under reduced pressure. The resulting residue was dissolved in chloroform (200 mL) and washed with water (200 mL). The aqueous layer was back extracted with chloroform (3×100 mL). The combined organics were dried over anhydrous sodium sulfate, filtered, and concentrated under reduced pressure to afford compound H2 as an orange viscous oil (3.43 g, >100%) that was used in the next step without further purification.

Step 3: 2-(tert-Butoxycarbonylamino)-6-ethyl-4,5,6,7-tetrahydrothieno[2,3-c]pyridine-3-carboxylic acid (H3)

To a solution of compound H2 (3.43 g, crude) in ethanol (25 mL) and water (12 mL) was added sodium hydroxide (1.28 g, 32.0 mmol). The reaction mixture was heated to 70° C. for 1 h. After this time, the reaction mixture was cooled to room temperature and diluted with water (25 mL) and ethyl acetate (75 mL). The layers were separated. The aqueous layer was neutralized with 0.5 M citric acid to pH 7. The aqueous layer was then chilled to 0° C. for 16 h. After this time, the resulting solids were collected by suction filtration to afford compound H3 as a light orange solid (1.60 g, 62% over two steps): $^1$H NMR (500 MHz, DMSO-d$_6$) δ 11.11 (bs, 1H), 3.70-3.60 (m, 2H), 2.88-2.76 (m, 4H), 2.66 (q, J=7.0 Hz, 2H), 1.48 (s, 9H), 1.11 (t, J=7.0 Hz, 3H). MS (M−H) 325.

Step 4: tert-Butyl 6-ethyl-3-(morpholine-4-carbonyl)-4,5,6,7-tetrahydrothieno[2,3-c]pyridin-2-ylcarbamate (H4)

To a solution of compound H3 (250 mg, 0.766 mmol), diisopropylethylamine (0.300 mL, 1.69 mmol), and morpholine (100 mg, 1.15 mmol) in N,N-dimethylformamide (3 mL) was added (benzotriazol-1-yloxy)tris(dimethylamino)phosphonium hexafluorophosphate (BOP) (678 mg, 1.53 mmol). After stirring at room temperature for 16 h, the reaction mixture was diluted with ethyl acetate (50 mL) and water (75 mL). The layers were separated and the aqueous layer was back extracted with methylene chloride (75 mL) and ethyl acetate (100 mL). The combined organics were dried over anhydrous sodium sulfate, filtered, and concentrated under reduced pressure. The resulting residue was purified by flash column chromatography on silica gel eluting with methylene chloride to ethyl acetate to afford compound H4 as a yellow solid (285 mg, 94%): $^1$H NMR (500 MHz, CDCl$_3$) δ 8.09 (bs, 1H), 3.78-3.45 (m, 10H), 2.86-2.78 (m, 2H), 2.74-2.69 (m, 2H), 2.67-2.62 (m, 2H), 1.50 (s, 9H), 1.19 (t, J=7.0 Hz, 3H). MS (M+H) 396.

Step 5: (2-Amino-6-ethyl-4,5,6,7-tetrahydrothieno[2,3-c]pyridin-3-yl)(morpholino)methanone (H5)

To a solution of compound H4 (285 mg, 0.721 mmol) in anhydrous methylene chloride (5 mL) was added trifluoroacetic acid (3 mL) at 0° C. The reaction mixture was gradually warmed to room temperature over 2 h and stirred at room temperature for another 14 h. After this time, the reaction mixture was concentrated under reduced pressure. The resulting residue was dissolved in methylene chloride (50 mL), washed with saturated aqueous sodium bicarbonate (50 mL), dried over anhydrous sodium sulfate, filtered, and concentrated under reduced pressure to afford compound H5 as a glassy brown solid (145 mg, 68%): $^1$H NMR (500 MHz, CDCl$_3$) δ 4.38 (bs, 2H), 3.71-3.63 (m, 4H), 3.65-3.53 (m, 4H), 3.45 (s, 2H), 2.73-2.69 (m, 2H), 2.62-2.56 (m, 4H), 1.16 (t, J=7.0 Hz, 3H). MS (M+H) 296.

Step 6: 1-(4-Chlorophenyl)-3-[6-ethyl-3-(morpholine-4-carbonyl)-4,5,6,7-tetrahydrothieno[2,3-c]pyridin-2-yl]urea (H6)

A solution of compound H5 (125 mg, 0.423 mmol) and 4-chlorophenyl isocyanate (84.0 mg, 0.547 mmol) in anhydrous tetrahydrofuran (3.5 mL) was stirred at room temperature for 16 h. After this time, the reaction mixture was concentrated under reduced pressure. The resulting residue was purified by flash column chromatography on silica gel eluting with methylene chloride to methanol/methylene chloride (1:19) to afford compound H6 as a glassy brown solid (150 mg, 79%): $^1$H NMR (500 MHz, CDCl$_3$) δ 8.70 (bs, 1H), 7.83 (bs, 1H), 7.21-7.16 (m, 4H), 3.80-3.52 (m, 10H), 2.75-2.53 (m, 6H), 1.18 (t, J=7.0 Hz, 3H). MS (M+H) 449.

Step 7: 1-(4-Chlorophenyl)-3-[6-ethyl-3-(morpholine-4-carbonyl)-4,5,6,7-tetrahydrothieno[2,3-c]pyridin-2-yl]urea hydrochloride (H7)

To a solution of compound H6 (150 mg, 0.334 mmol) in anhydrous methylene chloride (3.5 mL) was added hydrochloride (2 M in diethyl ether, 0.220 mL, 0.440 mmol). After stirring at room temperature for 20 min, the reaction mixture was diluted with ethyl acetate (20 mL), sonicated, and the solids collected by suction filtration to afford compound H7 as a yellow solid (136 mg, 84%): $^1$H NMR (500 MHz, DMSO-$d_6$) δ 10.21 (bs, 1H), 10.03 (bs, 1H), 9.61 (bs, 1H), 7.49 (d, J=9.0 Hz, 2H), 7.35 (d, J=9.0 Hz, 2H), 4.58-4.51 (m, 1H), 4.26-4.17 (m, 1H), 3.81-3.70 (m, 3H), 3.62-3.47 (m, 6H), 3.32-3.20 (m, 3H), 2.91-2.83 (m, 1H), 2.78-2.69 (m, 1H), 1.30 (t, J=7.0 Hz, 3H). MS (M+H) 449.

Example 96

Preparation of 2-[3-(4-Chlorophenyl)ureido]-6-ethyl-N-(2,2,2-trifluoroethyl)-4,5,6,7-tetrahydrothieno[2,3-c]pyridine-3-carboxamide hydrochloride

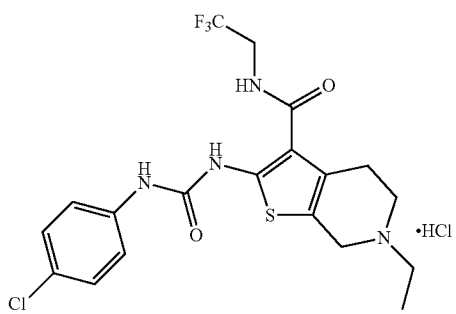 [SMILES: CCN1CCc2c(sc(NC(=O)Nc3ccc(Cl)cc3)c2C(=O)NCC(F)(F)F)C1 ; Cl]

The title compound was prepared using a similar procedure as described in Example 95. MS (M+H) 461. $^1$H NMR (300 MHz, CD$_3$OD) δ 7.53-7.29 (m, 4H), 4.70-3.80 (m, 5H), 3.50-3.39 (m, 3H), 3.28-3.15 (m, 2H), 1.46 (t, J=7.1 Hz, 3H).

Example 97

Preparation of 2-[3-(4-Chlorophenyl)ureido]-N-(cyclopropylmethyl)-6-ethyl-4,5,6,7-tetrahydrothieno[2,3-c]pyridine-3-carboxamide hydrochloride

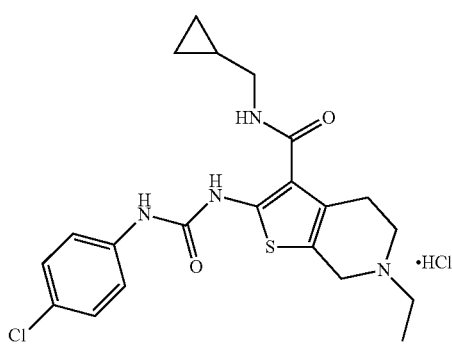 [SMILES: CCN1CCc2c(sc(NC(=O)Nc3ccc(Cl)cc3)c2C(=O)NCC2CC2)C1 ; Cl]

The title compound was prepared using a similar procedure as described in Example 95. MS (M+H) 433. $^1$H NMR (300 MHz, CD$_3$OD) δ 7.50-7.29 (m, 4H), 4.60-3.80 (m, 3H), 3.55-3.34 (m, 3H), 3.26-3.15 (m, 4H), 1.46 (t, J=7.1 Hz, 3H), 1.20-1.10 (m, 1H), 0.65-0.25 (m, 4H).

Example 98

Preparation of 2-[3-(4-Chlorophenyl)ureido]-6-ethyl-N-(pyridin-3-ylmethyl)-4,5,6,7-tetrahydrothieno[2,3-c]pyridine-3-carboxamide dihydrochloride

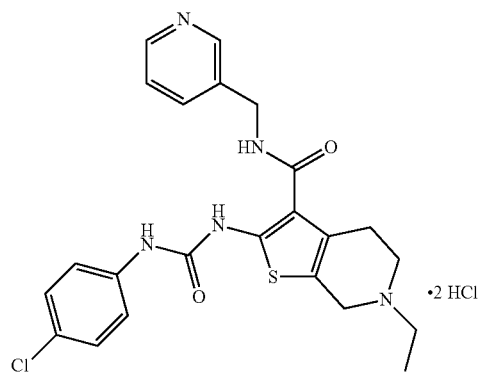 [SMILES: CCN1CCc2c(sc(NC(=O)Nc3ccc(Cl)cc3)c2C(=O)NCc2cccnc2)C1 ; "·2 HCl"]

The title compound was prepared using a similar procedure as described in Example 95. MS (M+H) 470. $^1$H NMR (300 MHz, CD$_3$OD) δ 8.96 (s, 1H), 8.80-8.69 (m, 2H), 8.10-8.06 (m, 1H), 7.53-7.29 (m, 4H), 4.80 (s, 2H), 4.70-3.80 (m, 3H), 3.45-3.32 (m, 5H), 1.47 (t, J=7.2 Hz, 3H).

Example 99

Preparation of 2-[3-(4-Chlorophenyl)ureido]-N-[2-(dimethylamino)ethyl]-6-ethyl-4,5,6,7-tetrahydrothieno[2,3-c]pyridine-3-carboxamide dihydrochloride

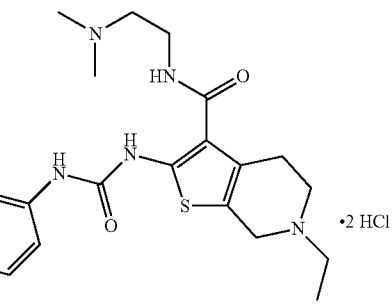

The title compound was prepared using a similar procedure as described in Example 95. MS (M+H) 450. $^1$H NMR (500 MHz, DMSO-$d_6$) δ 10.76 (bs, 1H), 10.69 (s, 1H), 10.45 (s, 1H), 10.32 (bs, 1H), 7.95 (t, J=5.0 Hz, 1H), 7.53-7.34 (m, 4H), 4.53-3.63 (m, 5H), 3.29-3.10 (m, 7H), 2.83 (s, 6H), 1.32 (t, J=7.1 Hz, 3H).

Example 100

Preparation of 2-[3-(4-Chlorophenyl)ureido]-6-ethyl-N-(2-morpholinoethyl)-4,5,6,7-tetrahydrothieno[2,3-c]pyridine-3-carboxamide dihydrochloride

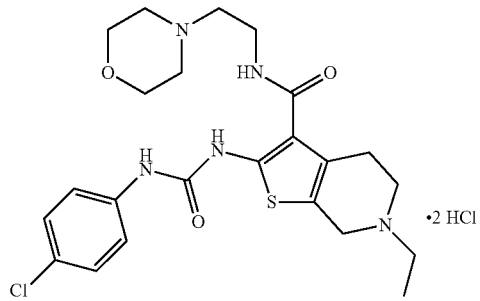 [SMILES: CCN1CCc2c(sc(NC(=O)Nc3ccc(Cl)cc3)c2C(=O)NCCN2CCOCC2)C1 ; "·2 HCl"]

The title compound was prepared using a similar procedure as described in Example 95. MS (M+H) 492. $^1$H NMR (300 MHz, DMSO-d$_6$) δ 11.23 (bs, 1H), 10.96 (bs, 1H), 10.67 (s, 1H), 10.48 (s, 1H), 8.06 (t, J=5.1 Hz, 1H), 7.54-7.33 (m, 4H), 4.53-3.83 (m, 6H), 3.75-3.50 (m, 10H), 3.40-3.10 (m, 4H), 1.33 (t, J=7.2 Hz, 3H).

Example 101

Preparation of 2-[3-(4-Chlorophenyl)ureido]-6-ethyl-N-(2-hydroxyethyl)-4,5,6,7-tetrahydrothieno[2,3-c]pyridine-3-carboxamide hydrochloride

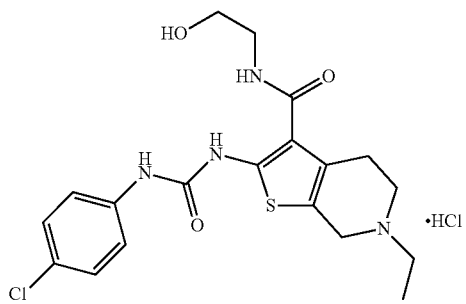 [SMILES: CCN1CCc2c(sc(NC(=O)Nc3ccc(Cl)cc3)c2C(=O)NCCO)C1 ; Cl]

The title compound was prepared using a similar procedure as described in Example 95. MS (M+H) 423. $^1$H NMR (300 MHz, CD$_3$OD) δ 7.49-7.28 (m, 4H), 4.65-4.25 (m, 2H), 3.90-3.38 (m, 8H), 3.25-3.15 (m, 2H), 1.44 (t, J=7.4 Hz, 3H).

Example 102

Preparation of 2-[3-(4-Chlorophenyl)ureido]-6-ethyl-N-(oxetan-3-yl)-4,5,6,7-tetrahydrothieno[2,3-c]pyridine-3-carboxamide

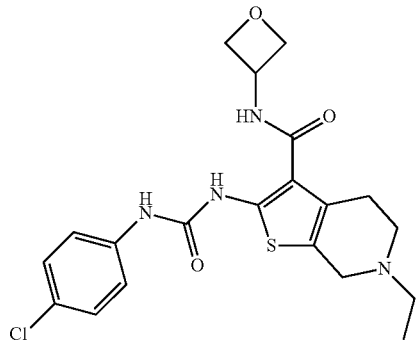 [SMILES: CCN1CCc2c(sc(NC(=O)Nc3ccc(Cl)cc3)c2C(=O)NC2COC2)C1]

The title compound was prepared using a similar procedure as described in Example 95. MS (M+H) 435. $^1$H NMR (300 MHz, CD$_3$OD) δ 7.53-7.30 (m, 4H), 4.46-3.60 (m, 7H), 2.93-2.62 (m, 6H), 1.21 (t, J=7.2 Hz, 3H).

Example 103

Preparation of 1-(4-chlorophenyl)-3-[6-ethyl-3-(3-methyl-1,2,4-oxadiazol-5-yl)-4,5,6,7-tetrahydrothieno[2,3-c]pyridin-2-yl]urea hydrochloride (I5)

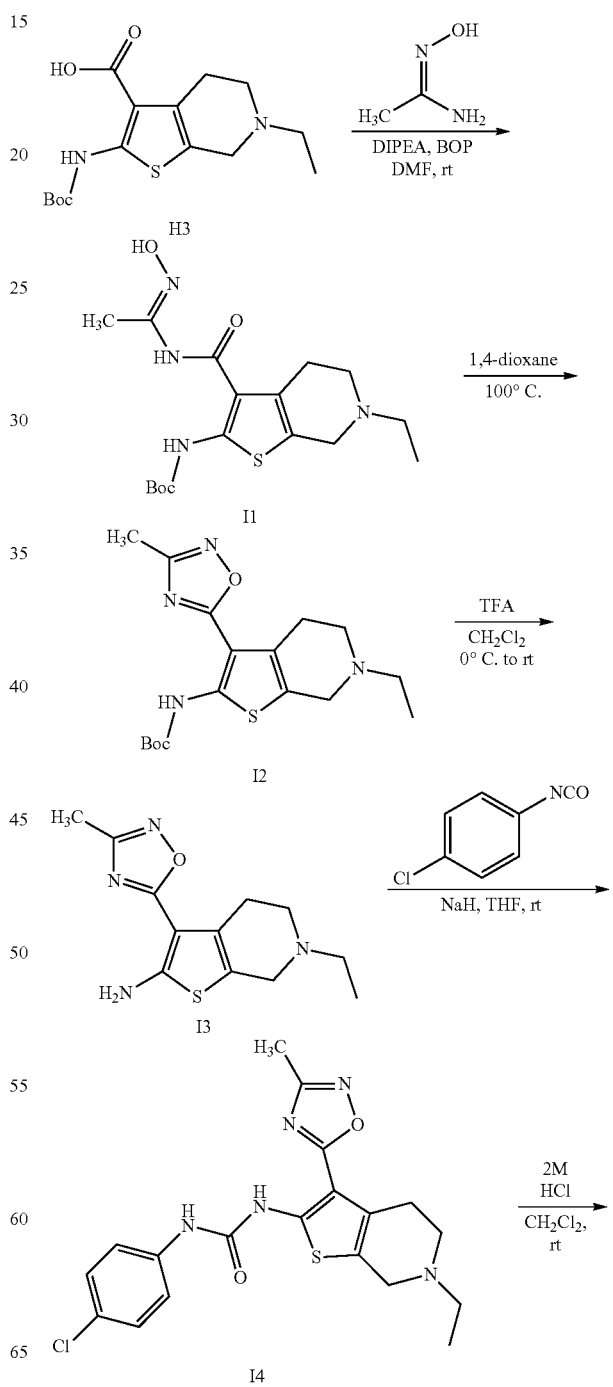

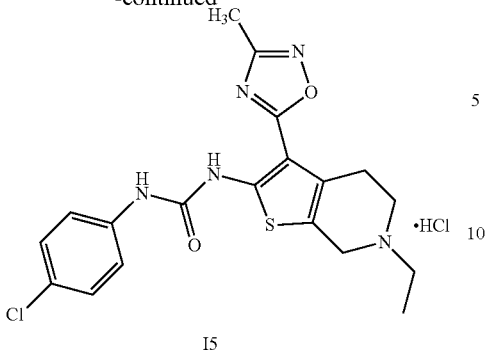

I5

Step 1: tert-Butyl 6-ethyl-3-[1-(hydroxyimino)ethylcarbamoyl]-4,5,6,7-tetrahydrothieno[2,3-c]pyridin-2-ylcarbamate (I1)

To a solution of compound H3 (300 mg, 0.919 mmol), diisopropylethylamine (0.320 mL, 1.80 mmol), and N'-hydroxyacetimidamide (102 mg, 1.38 mmol) in N,N-dimethylformamide (3.5 mL) was added (benzotriazol-1-yloxy)tris(dimethylamino)phosphonium hexafluorophosphate (BOP) (813 mg, 1.84 mmol). After stirring at room temperature for 16 h, the reaction mixture was diluted with ethyl acetate (50 mL) and water (75 mL). The layers were separated and the aqueous layer was back extracted with methylene chloride (75 mL) and ethyl acetate (100 mL). The combined organics were dried over anhydrous sodium sulfate, filtered, and concentrated under reduced pressure. The resulting residue was purified by flash column chromatography on silica gel eluting with methylene chloride to ethyl acetate and then to methanol/methylene chloride (1:19) to afford compound I1 as a yellow solid (340 mg, 97%): $^1$H NMR (500 MHz, CDCl$_3$) δ 10.33 (bs, 1H), 4.77 (bs, 2H), 3.55 (s, 2H), 2.95-2.92 (m, 2H), 2.81-2.76 (m, 2H), 2.62 (q, J=7.0 Hz, 2H), 2.04 (s, 3H), 1.51 (s, 9H), 1.19 (t, J=7.0 Hz, 3H). MS (M+H) 383.

Step 2: tert-Butyl 6-ethyl-3-(3-methyl-1,2,4-oxadiazol-5-yl)-4,5,6,7-tetrahydrothieno[2,3-c]pyridin-2-ylcarbamate (I2)

A solution of compound I1 (340 mg, 0.889 mmol) in anhydrous 1,4-dioxane (5 mL) was heated to reflux for 14 h. After this time, the reaction mixture was cooled to room temperature and concentrated under reduced pressure. The resulting residue was purified by flash column chromatography on silica gel eluting with methylene chloride to methanol/methylene chloride (1:19) to afford compound I2 as a yellow solid (118 mg, 36%): $^1$H NMR (500 MHz, CDCl$_3$) δ 10.40 (bs, 1H), 3.59 (s, 2H), 3.04-3.01 (m, 2H), 2.84-2.81 (m, 2H), 2.64 (q, J=7.0 Hz, 2H), 2.46 (s, 3H), 1.57 (s, 9H), 1.19 (t, J=7.0 Hz, 3H). MS (M+H) 365.

Step 3: 6-Ethyl-3-(3-methyl-1,2,4-oxadiazol-5-yl)-4,5,6,7-tetrahydrothieno[2,3-c]pyridin-2-amine (I3)

To a solution of compound I2 (87.0 mg, 0.240 mmol) in anhydrous methylene chloride (3 mL) was added trifluoroacetic acid (3 mL) at 0° C. The reaction mixture was warmed to room temperature and stirred for 24 h. After this time, the reaction mixture was concentrated under reduced pressure. The resulting residue was dissolved in methylene chloride (50 mL), washed with saturated aqueous sodium bicarbonate (50 mL), dried over anhydrous sodium sulfate, filtered, and concentrated under reduced pressure. The resulting residue was purified by flash column chromatography on silica gel eluting with methylene chloride to methanol/methylene chloride (1:19) to afford compound I3 as a yellow solid (38 mg, 60%): $^1$H NMR (500 MHz, CDCl$_3$) δ 6.17 (bs, 2H), 3.48 (s, 2H), 2.99-2.96 (m, 2H), 2.82-2.79 (m, 2H), 2.62 (q, J=7.0 Hz, 2H), 2.39 (s, 3H), 1.18 (t, J=7.0 Hz, 3H). MS (M+H) 265.

Step 4: 1-(4-Chlorophenyl)-3-[6-ethyl-3-(3-methyl-1,2,4-oxadiazol-5-yl)-4,5,6,7-tetrahydrothieno[2,3-c]pyridin-2-yl]urea (I4)

To a solution of compound I3 (38.0 mg, 0.140 mmol) in anhydrous tetrahydrofuran (2 mL) was added sodium hydride (60% dispersed in oil, 10.0 mg, 0.250 mmol) in one portion under nitrogen. After stirring at room temperature for 5 min, 4-chlorophenyl isocyanate (22.0 mg, 0.140 mmol) was added. The reaction mixture was stirred at room temperature for 10 min. After this time, the reaction was quenched with slow addition of methanol (5 mL) and the resulting mixture was concentrated under reduced pressure. The resulting residue was purified by flash column chromatography on silica gel eluting with methylene chloride to methanol/methylene chloride (1:19) to afford compound I4 as an off-white solid (25 mg, 43%): $^1$H NMR (500 MHz, DMSO-d$_6$) δ 10.44 (bs, 1H), 10.35 (bs, 1H), 7.47 (d, J=9.0 Hz, 2H), 7.32 (d, J=9.0 Hz, 2H), 3.52-3.49 (m, 2H), 2.88-2.84 (m, 2H), 2.75-2.68 (m, 2H), 2.59-2.52 (m, 2H), 2.47 (s, 3H), 1.09 (t, J=7.0 Hz, 3H). MS (M+H) 418.

Step 5: 1-(4-Chlorophenyl)-3-[6-ethyl-3-(3-methyl-1,2,4-oxadiazol-5-yl)-4,5,6,7-tetrahydrothieno[2,3-c]pyridin-2-yl]urea hydrochloride (I5)

To a solution of compound I4 (25 mg, 0.060 mmol) in anhydrous methylene chloride (5 mL) was added hydrochloride (2 M in diethyl ether, 0.10 mL, 0.20 mmol). After stirring at room temperature for 15 min, the reaction mixture was concentrated under reduced pressure and the resulting residue was triturated with methylene chloride to afford compound I5 as a white solid (22 mg, 81%): $^1$H NMR (500 MHz, DMSO-d$_6$) δ 10.62 (bs, 1H), 10.53 (bs, 1H), 10.40 (bs, 1H), 7.57 (d, J=9.0 Hz, 2H), 7.41 (d, J=9.0 Hz, 2H), 4.62-4.51 (m, 1H), 4.30-4.19 (m, 1H), 3.81-3.70 (m, 1H), 3.31-3.13 (m, 5H), 2.50 (s, 3H), 1.32 (t, J=7.0 Hz, 3H). MS (M+H) 418.

Example 104

Preparation of 1-(4-chlorophenyl)-3-[6-ethyl-3-(1,3,4-oxadiazol-2-yl)-4,5,6,7-tetrahydrothieno[2,3-c]pyridin-2-yl]urea hydrochloride (I5)

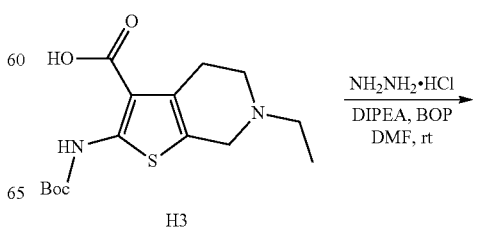

H3

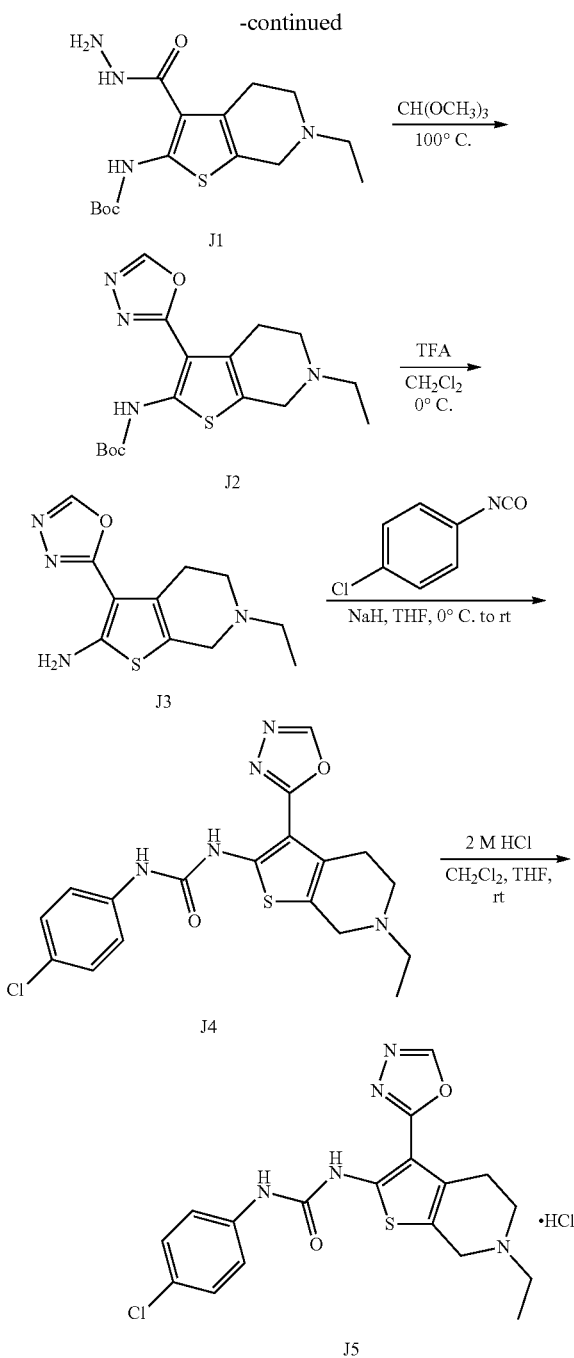

Step 1: tert-Butyl 6-ethyl-3-(hydrazinecarbonyl)-4,5, 6,7-tetrahydrothieno[2,3-c]pyridin-2-ylcarbamate (J1)

To a solution of compound H3 (500 mg, 1.53 mmol), diisopropylethylamine (1.34 mL, 7.53 mmol), and hydrazine hydrochloride (210 mg, 3.07 mmol) in N,N-dimethylformamide (4 mL) was added (benzotriazol-1-yloxy)tris(dimethylamino)phosphonium hexafluorophosphate (BOP) (1.37 g, 3.10 mmol). After stirring at room temperature for 16 h, the reaction mixture was diluted with ethyl acetate (50 mL) and water (75 mL). The layers were separated and the aqueous layer was back extracted with methylene chloride (75 mL) and ethyl acetate (100 mL). The combined organics were dried over anhydrous sodium sulfate, filtered, and concentrated under reduced pressure. The resulting residue was purified by flash column chromatography on silica gel eluting with methylene chloride to methanol/methylene chloride (1:9) to afford compound J1 as a yellow solid (418 mg, 80%): $^1$H NMR (300 MHz, CDCl$_3$) δ 10.75 (bs, 1H), 6.93 (bs, 1H), 4.02 (bs, 2H), 3.56 (s, 2H), 2.82-2.78 (m, 4H), 2.62 (q, J=7.2 Hz, 2H), 1.52 (s, 9H), 1.18 (t, J=7.2 Hz, 3H). MS (M+H) 341.

Step 2: tert-Butyl 6-ethyl-3-(1,3,4-oxadiazol-2-yl)-4, 5,6,7-tetrahydrothieno[2,3-c]pyridin-2-ylcarbamate (J2)

A mixture of compound J1 (640 mg, 1.88 mmol) and trimethyl orthoformate (15.0 mL, 137 mmol) were heated to 120° C. for 30 h. After this time, the reaction mixture was cooled to room temperature and concentrated under reduced pressure. The resulting residue was purified by flash column chromatography on silica gel eluting with methylene chloride to methanol/methylene chloride (1:19) to afford compound J2 as a yellow solid (414 mg, 63%): $^1$H NMR (300 MHz, CDCl$_3$) δ 10.23 (bs, 1H), 8.36 (s, 1H), 3.49 (s, 2H), 2.99-2.92 (m, 2H), 2.87-2.78 (m, 2H), 2.64 (q, J=7.2 Hz, 2H), 1.55 (s, 9H), 1.20 (t, J=7.2 Hz, 3H). MS (M+H) 351.

Step 3: 6-Ethyl-3-(1,3,4-oxadiazol-2-yl)-4,5,6,7-tetrahydrothieno[2,3-c]pyridin-2-amine (J3)

To a solution of compound J2 (410 mg, 1.17 mmol) in anhydrous methylene chloride (3 mL) was added trifluoroacetic acid (3 mL) at 0° C. After stirring at 0° C. for 3 h, the reaction mixture was concentrated under reduced pressure. The resulting residue was dissolved in methylene chloride (75 mL), washed with saturated aqueous sodium bicarbonate (75 mL), dried over anhydrous sodium sulfate, filtered, and concentrated under reduced pressure. The resulting residue was purified by flash column chromatography on silica gel eluting with methylene chloride to methanol/methylene chloride (1:9) to afford compound J3 as a yellow solid (138 mg, 47%): $^1$H NMR (500 MHz, CDCl$_3$) δ 8.28 (s, 1H), 6.06 (bs, 2H), 3.49 (s, 2H), 2.93-2.88 (m, 2H), 2.81-2.77 (m, 2H), 2.61 (q, J=7.0 Hz, 2H), 1.18 (t, J=7.0 Hz, 3H). MS (M+H) 251.

Step 4: 1-(4-Chlorophenyl)-3-[6-ethyl-3-(1,3,4-oxadiazol-2-yl)-4,5,6,7-tetrahydrothieno[2,3-c]pyridin-2-yl]urea (J4)

To a solution of compound J3 (133 mg, 0.531 mmol) in anhydrous tetrahydrofuran (3 mL) was added sodium hydride (60% dispersed in oil, 22.0 mg, 0.550 mmol) in one portion at 0° C. under nitrogen. After stirring at 0° C. for 5 min, 4-chlorophenyl isocyanate (90.0 mg, 0.590 mmol) was added. The reaction mixture was warmed to room temperature and stirred at room temperature for 45 min. After this time, the reaction was quenched with slow addition of methanol (5 mL) and the resulting mixture was concentrated under reduced pressure. The resulting residue was purified by flash column chromatography on silica gel eluting with methylene chloride to methanol/methylene chloride (1:9) to afford compound J4 as a yellow solid (175 mg, 82%): $^1$H NMR (500 MHz, CDCl$_3$) δ 10.62 (bs, 1H), 8.38 (s, 1H), 7.46 (d, J=8.5 Hz, 2H), 7.31 (d, J=8.5 Hz, 2H), 7.17 (bs, 1H), 3.60 (s, 2H), 2.97-2.95 (m, 2H), 2.83-2.81 (m, 2H), 2.65 (q, J=7.5 Hz, 2H), 1.19 (t, J=7.5 Hz, 3H). MS (M+H) 404.

Step 5: 1-(4-Chlorophenyl)-3-[6-ethyl-3-(1,3,4-oxa-diazol-2-yl)-4,5,6,7-tetrahydrothieno[2,3-c]pyridin-2-yl]urea hydrochloride (J5)

To a solution of compound J4 (175 mg, 0.433 mmol) in anhydrous methylene chloride (3 mL) and anhydrous tetrahydrofuran (3 mL) was added hydrochloride (2 M in diethyl ether, 0.300 mL, 0.600 mmol). After stirring at room temperature for 15 min, the reaction mixture was concentrated under reduced pressure and the resulting residue was triturated with methylene chloride to afford compound J5 as a yellow solid (133 mg, 70%): $^1$H NMR (500 MHz, DMSO-$d_6$) δ 10.63 (s, 1H), 10.46 (bs, 1H), 10.42 (s, 1H), 9.37 (s, 1H), 7.55 (d, J=9.0 Hz, 2H), 7.39 (d, J=8.5 Hz, 2H), 4.63-4.56 (m, 1H), 4.29-4.21 (m, 1H), 3.81-3.72 (m, 1H), 3.42-3.36 (m, 1H), 3.26-3.12 (m, 4H), 1.32 (t, J=7.0 Hz, 3H). MS (M+H) 404.

Example 105

Preparation of 2-[1-(4-chlorophenyl)cyclopropanecarboxamido]-6-ethyl-4,5,6,7-tetrahydrothieno[2,3-c]pyridine-3-carboxamide (K2)

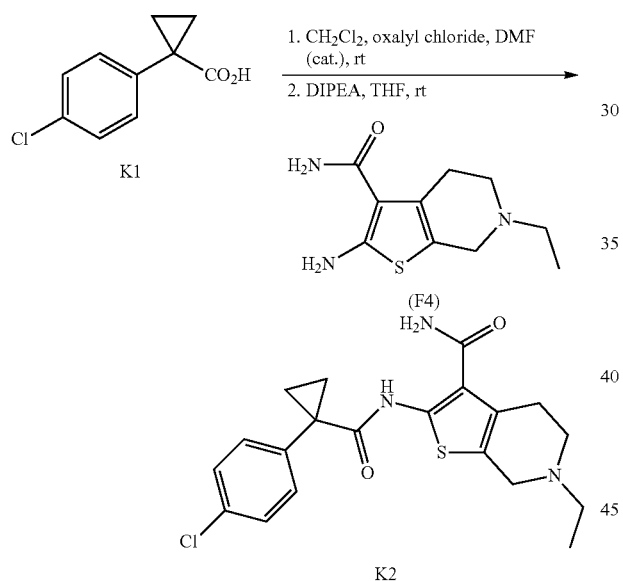

To a solution of 1-(4-chlorophenyl)cyclopropanecarboxylic acid (K1, 131 mg, 0.666 mmol) in anhydrous methylene chloride (3 mL) was added oxalyl chloride (0.100 mL, 1.17 mmol) followed by 2 drops of N,N-dimethylformamide at room temperature under nitrogen. After stirring at room temperature for 1 h, the reaction mixture was concentrated under reduced pressure. The resulting residue was dissolved in anhydrous tetrahydrofuran (3 mL). To the resulting solution was added diisopropylethylamine (0.200 mL, 1.12 mmol) followed by a suspension of compound F4 (150 mg, 0.666 mmol) in anhydrous tetrahydrofuran (3 mL). After stirring at room temperature for 3 h, the reaction mixture was concentrated under reduced pressure and the resulting residue was purified by flash column chromatography on silica gel eluting with methylene chloride to methanol/methylene chloride (1:19). Further purification by trituration with acetonitrile gave compound K2 as a light yellow solid (87 mg, 32%): $^1$H NMR (500 MHz, CDCl$_3$) δ 11.79 (bs, 1H), 7.47-7.42 (s, 4H), 5.56 (bs, 2H), 3.57 (s, 2H), 2.82-2.77 (m, 4H), 2.62 (q, J=7.0 Hz, 2H), 1.78-1.74 (m, 2H), 1.20-1.12 (m, 5H). MS (M+H) 404.

Example 106

Preparation of 2-[3-(4-chlorophenyl)-3-methylureido]-6-ethyl-4,5,6,7-tetrahydrothieno[2,3-c]pyridine-3-carboxamide hydrochloride (L5)

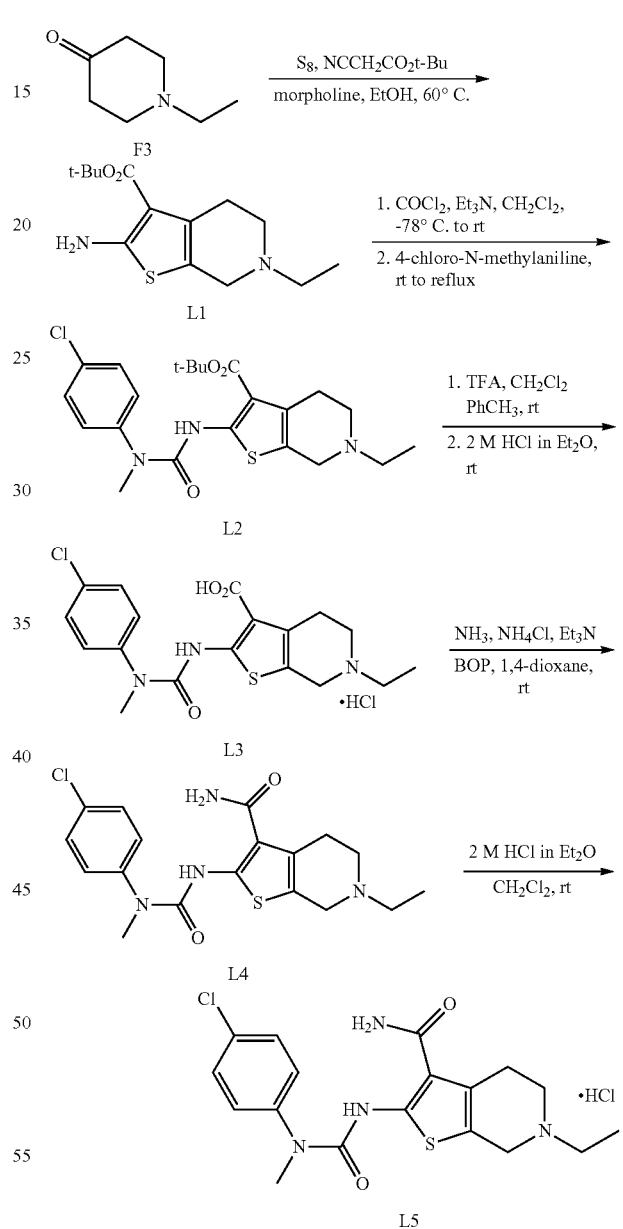

Step 1: tert-Butyl 2-amino-6-ethyl-4,5,6,7-tetrahydrothieno[2,3-c]pyridine-3-carboxylate (L1)

A mixture of 1-ethylpiperidin-4-one (F3, 5.09 g, 40.0 mmol), tert-butyl 2-cyanoacetate (5.65 g, 40.0 mmol), sulphur (1.54 g, 48.0 mmol), and morpholine (6.97 g, 80.0 mmol) in ethanol (200 mL) was stirred at 60° C. for 3 h under nitrogen. After this time, the reaction mixture was cooled to room temperature and concentrated under reduced pressure. The resulting residue was added saturated aqueous sodium bicarbonate (100 mL). The resulting aqueous mixture was extracted with methylene chloride (3×200 mL). The combined organic extracts were dried over anhydrous sodium sulfate, filtered, and concentrated under reduced pressure. The resulting residue was purified by flash column chromatography on silica gel eluting with methanol/methylene chloride (1:9) to afford compound L1 as a yellow solid (8.65 g, 76%): $^1$H NMR (300 MHz, DMSO-$d_6$) δ 7.18 (s, 2H), 3.26 (s, 2H), 2.62-2.50 (m, 4H), 2.44 (q, J=7.0 Hz, 2H), 1.47 (s, 9H), 1.03 (t, J=7.0 Hz, 3H). MS (M+H) 283.

Step 2: tert-Butyl 2-[3-(4-chlorophenyl)-3-methylureido]-6-ethyl-4,5,6,7-tetrahydrothieno[2,3-c]pyridine-3-carboxylate (L2)

To methylene chloride (5 mL) at −78° C. under nitrogen was added a solution of phosgene (0.15 weight/weight in toluene, 4.61 g, 7.00 mmol). The reaction mixture was stirred for 5 min and was added a solution of compound L1 (1.41 g, 5.00 mmol) and triethylamine (2.13 g, 21.0 mmol) in methylene chloride (20 mL) dropwise over 20 min. After addition, the reaction mixture was slowly warmed to room temperature over 2 h. Then to the reaction mixture was added 4-chloro-N-methylaniline (1.28 g, 9.04 mmol). After addition, the reaction mixture was stirred overnight at room temperature, followed by refluxing for another 2 h. After cooled to room temperature, the reaction mixture was quenched with saturated aqueous sodium bicarbonate (60 mL) and extracted with methylene chloride (3×100 mL). The combined organic extracts were dried over anhydrous sodium sulfate, filtered, and concentrated under reduced pressure. The resulting residue was purified by flash column chromatography on silica gel eluting with ethyl acetate to afford partial purified products which was further purified by flash column chromatography on silica gel eluting with methanol/methylene chloride (1:19) to afford compound L2 as a yellow gum (309 mg, 14%): $^1$H NMR (300 MHz, DMSO-$d_6$) δ 10.51 (s, 1H), 7.57 (d, J=8.8 Hz, 2H), 7.48 (d, J=8.8 Hz, 2H), 3.40 (s, 2H), 3.25 (s, 3H), 2.66-2.59 (m, 4H), 2.46 (q, J=7.0 Hz, 2H), 1.39 (s, 9H), 1.04 (t, J=7.0 Hz, 3H). MS (M+H) 450.

Step 3: 2-[3-(4-Chlorophenyl)-3-methylureido]-6-ethyl-4,5,6,7-tetrahydrothieno[2,3-c]pyridine-3-carboxylic acid hydrochloride (L3)

To a stirred mixture of compound L2 (303 mg, 0.673 mmol) in methylene chloride (6 mL) and toluene (2 mL) at room temperature was added trifluoroacetic acid (9.21 g, 80.8 mmol) dropwise over 2 min. After addition, the reaction mixture was stirred for another 2.5 h and concentrated under reduced pressure. The resulting residue was mixed with hydrochloride (2 M in diethyl ether, 6.00 mL, 12.0 mmol) and then concentrated, this procedure was repeated two times, to afford compound L3 as a brown gum (290 mg, >99%): MS (M+H) 394. This product was used in next step without further purification.

Step 4: 2-[3-(4-Chlorophenyl)-3-methylureido]-6-ethyl-4,5,6,7-tetrahydrothieno[2,3-c]pyridine-3-carboxamide (L4)

To a stirred mixture of compound L3 (290 mg, 0.736 mmol) in N,N-dimethylformamide (5 mL) was added ammonia solution (0.5 M in 1,4-dioxane, 20.0 mL, 10.0 mmol), ammonium chloride (535 mg, 10.0 mmol), triethylamine (1.01 g, 10.0 mmol), and (benzotriazol-1-yloxy)tris(dimethylamino)phosphonium hexafluorophosphate (BOP) (1.31 g, 2.95 mmol). After addition, the reaction mixture was stirred overnight at room temperature and concentrated under reduced pressure. The resulting residue was mixed with saturated aqueous sodium bicarbonate (40 mL) and the resulting aqueous mixture was extracted with methylene chloride (3×100 mL). The combined organic extracts were dried over anhydrous sodium sulfate, filtered, and concentrated under reduced pressure. The resulting residue was purified by flash column chromatography on silica gel eluting with methanol/methylene chloride (1:9) to afford compound L4 as a pale yellow solid (125 mg, 47% over two steps): $^1$H NMR (300 MHz, DMSO-$d_6$) δ 11.42 (s, 1H), 7.54 (d, J=8.7 Hz, 2H), 7.45 (d, J=8.7 Hz, 2H), 7.43 (bs, 1H), 6.60 (bs, 1H), 3.43 (s, 2H), 3.23 (s, 3H), 2.70 (d, J=4.8 Hz, 2H), 2.61 (d, J=4.8 Hz, 2H), 2.48 (q, J=7.0 Hz, 2H), 1.06 (t, J=7.0 Hz, 3H). MS (M+H) 393.

Step 5: 2-[3-(4-Chlorophenyl)-3-methylureido]-6-ethyl-4,5,6,7-tetrahydrothieno[2,3-c]pyridine-3-carboxamide hydrochloride (L5)

To a mixture of compound L4 (47.0 mg, 0.120 mmol) in methylene chloride (10 mL) at room temperature was added hydrochloride (2 M in diethyl ether, 1.00 mL, 2.00 mmol). The resulting mixture was sonicated for 10 min, and then concentrated under reduced pressure. The resulting residue was dissolved in a mixture of methanol (2 mL) and water (2 mL) and then lyophilized to afford compound L5 as a yellow solid (50 mg, 97%): $^1$H NMR (300 MHz, DMSO-$d_6$) δ 11.47 (s, 1H), 10.48 (bs, 1H), 7.56 (d, J=8.7 Hz, 2H), 7.46 (d, J=8.7 Hz, 2H), 7.19 (bs, 2H), 4.53-4.47 (m, 1H), 4.21-4.12 (m, 1H), 3.65-3.60 (m, 1H), 3.32-2.92 (m, 8H), 1.29 (t, J=7.2 Hz, 3H). MS (M+H) 393.

Example 107

Preparation of 6-ethyl-2-ureido-4,5,6,7-tetrahydrothieno[2,3-c]pyridine-3-carboxamide hydrochloride (M2)

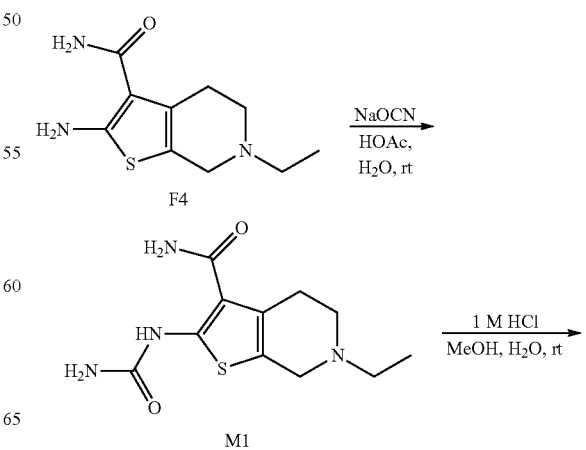

107

-continued

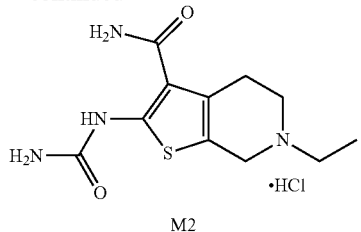

M2

Step 1: 6-Ethyl-2-ureido-4,5,6,7-tetrahydrothieno[2,3-c]pyridine-3-carboxamide (M1)

To a stirred mixture of compound F4 (451 mg, 2.00 mmol) in acetic acid (6 mL) at room temperature was added a solution of sodium cyanate (169 mg, 2.60 mmol) in water (2.5 mL) dropwise over 2 min. After addition, the reaction mixture was stirred for another 2 h and then concentrated under reduced pressure. The resulting residue was mixed with saturated aqueous sodium bicarbonate (50 mL) and extracted with methylene chloride (3×150 mL). The combined organic extracts were dried over anhydrous sodium sulfate, filtered, and concentrated under reduced pressure. The resulting residue was purified by flash column chromatography on silica gel eluting with methanol/methylene chloride (15:85) to afford compound M1 as a yellow solid (125 mg, 23%): $^1$H NMR (300 MHz, DMSO-$d_6$) δ 10.45 (s, 1H), 7.31 (bs, 1H), 6.77 (bs, 3H), 3.41 (s, 2H), 2.73 (d, J=4.8 Hz, 2H), 2.63 (d, J=4.8 Hz, 2H), 2.50-2.45 (m, 2H), 1.06 (t, J=7.0 Hz, 3H). MS (M+H) 269.

Step 2: 6-Ethyl-2-ureido-4,5,6,7-tetrahydrothieno[2,3-c]pyridine-3-carboxamide hydrochloride (M2)

To a mixture of compound M1 (108 mg, 0.400 mmol) in water (6 mL) and methanol (2 mL) at room temperature was added 1 M hydrochloric acid (0.600 mL, 0.600 mmol). After addition, the mixture was sonicated to form clear solution and then lyophilized to afford compound M2 as a grey solid (107 mg, 88%): $^1$H NMR (300 MHz, DMSO-$d_6$) δ 10.57 (bs, 1H), 10.46 (s, 1H), 7.65-6.60 (m, 4H), 4.48-4.43 (m, 1H), 4.19-4.10 (m, 1H), 3.37-3.14 (m, 4H), 3.05 (bs, 2H), 1.30 (t, J=7.2 Hz, 3H). MS (M+H) 269.

Example 108

Preparation of 6-ethyl-2-formamido-4,5,6,7-tetrahydrothieno[2,3-c]pyridine-3-carboxamide hydrochloride (N2)

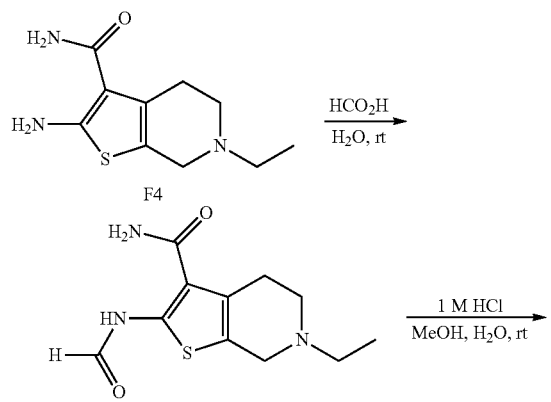

108

-continued

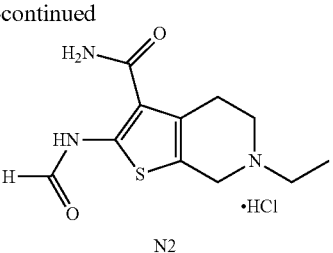

N2

Step 1: 6-Ethyl-2-formamido-4,5,6,7-tetrahydrothieno[2,3-c]pyridine-3-carboxamide (N1)

A mixture of compound F4 (225 mg, 1.00 mmol) in formic acid (5 mL) and water (1 mL) was stirred overnight at room temperature. After that time, the reaction mixture was concentrated under reduced pressure. The residue was mixed with saturated aqueous sodium bicarbonate (50 mL) and extracted with methylene chloride (3×150 mL). The combined organic extracts were dried over anhydrous sodium sulfate, filtered, and concentrated under reduced pressure. The resulting residue was purified by flash column chromatography on silica gel eluting with methanol/methylene chloride (15:85) to afford compound N1 as an off-white solid (208 mg, 82%): $^1$H NMR (300 MHz, DMSO-$d_6$) δ 11.44 (s, 1H), 8.40 (s, 1H), 7.52 (bs, 1H), 7.03 (bs, 1H), 3.48 (s, 2H), 2.76 (d, J=4.8 Hz, 2H), 2.65 (d, J=4.8 Hz, 2H), 2.54-2.47 (m, 2H), 1.07 (t, J=7.0 Hz, 3H). MS (M+H) 254.

Step 2: 6-Ethyl-2-formamido-4,5,6,7-tetrahydrothieno[2,3-c]pyridine-3-carboxamide hydrochloride (N2)

To a mixture of compound N1 (152 mg, 0.600 mmol) in water (6 mL) and methanol (2 mL) at room temperature was added 1 M hydrochloric acid (1.00 mL, 1.00 mmol). After addition, the mixture was sonicated to form clear solution and then lyophilized to afford compound N2 as a white solid (165 mg, 95%): $^1$H NMR (300 MHz, DMSO-$d_6$) δ 11.49 (s, 1H), 10.94 (bs, 1H), 8.44 (s, 1H), 7.61 (bs, 1H), 7.37 (bs, 1H), 4.55-4.49 (m, 1H), 4.25-4.17 (m, 1H), 3.29-3.07 (m, 6H), 1.31 (t, J=7.2 Hz, 3H). MS (M+H) 254.

Example 109

Preparation of 2-({2-[(4-chlorophenyl)amino]-3,4-dioxocyclobut-1-en-1-yl}amino)-6-ethyl-4,5,6,7-tetrahydrothieno[2,3-c]pyridine-3-carboxamide hydrochloride (O6)

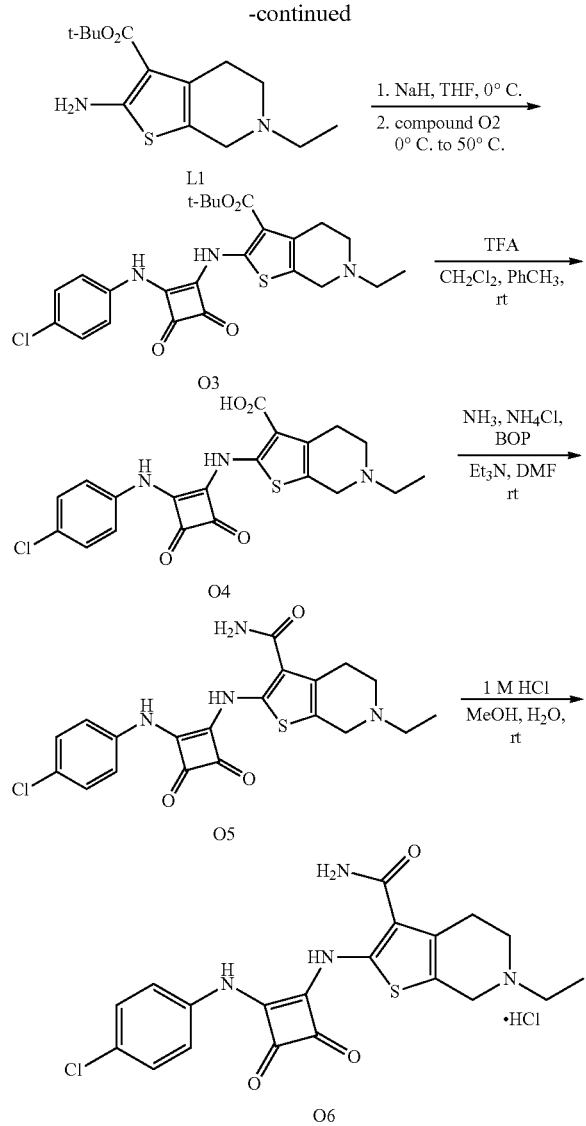

(1.13 g, 4.00 mmol) in anhydrous tetrahydrofuran (15 mL) dropwise over 10 min. After addition, the reaction mixture was stirred for another 15 min. Then to the reaction mixture was added a solution of compound O2 (0.951 g, 4.00 mmol) in anhydrous tetrahydrofuran (20 mL) over 5 min. After addition, the reaction mixture was stirred at 0° C. for 0.5 h and then heated to 50° C. for another 2 h. After cooled to room temperature, the reaction mixture was quenched with saturated aqueous sodium bicarbonate (100 mL). The aqueous mixture was extracted with methylene chloride (2×200 mL). The combined organic extracts were dried over anhydrous sodium sulfate, filtered, and concentrated under reduced pressure. The resulting residue was purified by flash column chromatography on silica gel eluting with methanol/ethyl acetate (1:19) to afford compound O3 as a yellow solid (445 mg, 23%): $^1$H NMR (500 MHz, DMSO-$d_6$) δ 10.42 (bs, 2H), 7.43-7.38 (m, 4H), 3.54 (s, 2H), 2.89-2.60 (m, 4H), 2.57-2.54 (m, 2H), 1.48 (s, 9H), 1.09 (t, J=7.0 Hz, 3H). MS (M–H) 486.

Step 3: 2-({2-[(4-Chlorophenyl)amino]-3,4-dioxocyclobut-1-en-1-yl}amino)-6-ethyl-4,5,6,7-tetrahydrothieno[2,3-c]pyridine-3-carboxylic acid (O4)

To a stirred mixture of compound O3 (293 mg, 0.600 mmol) in methylene chloride (12 mL) and toluene (3 mL) at room temperature under nitrogen was added trifluoroacetic acid (6.91 g, 60.6 mmol) dropwise over 2 min. After addition, the reaction mixture was stirred for another 2 h. The reaction mixture was diluted with toluene (20 mL) and concentrated under reduced pressure. The resulting residue was purified by flash column chromatography on silica gel eluting with ammonium hydroxide/methanol/methylene chloride (1:14:85) to afford compound O4 as yellow solid (120 mg, 46%): MS (M–H) 430.

Step 4: 2-({2-[(4-Chlorophenyl)amino]-3,4-dioxocyclobut-1-en-1-yl}amino)-6-ethyl-4,5,6,7-tetrahydrothieno[2,3-c]pyridine-3-carboxamide (O5)

To a stirred mixture of compound O4 (110 mg, 0.255 mmol) in anhydrous N,N-dimethylformamide (4 mL) at room temperature under nitrogen was added sequentially ammonium chloride (535 mg, 10.0 mmol), triethylamine (1.02 g, 10.0 mmol), ammonia solution (0.5 M in 1,4-dioxane, 6.00 mL, 3.00 mmol), and (benzotriazol-1-yloxy)tris(dimethylamino)phosphonium hexafuorophosphate (BOP) (339 mg, 0.766 mmol). After addition, the reaction mixture was stirred for 4 h and then diluted with water (6 mL). The resulting aqueous mixture was lyophilized. The resulting residue was diluted with saturated aqueous sodium bicarbonate (10 mL) and then extracted with methylene chloride (3×30 mL). The combined organic extracts were dried over anhydrous sodium sulfate, filtered, and concentrated under reduced pressure. The resulting residue was purified two times by flash column chromatography on silica gel eluting with methanol/methylene chloride (15:85) to afford compound O5 as a yellow solid (34 mg, 31%): MS (M+H) 431.

Step 5: 2-({2-[(4-Chlorophenyl)amino]-3,4-dioxocyclobut-1-en-1-yl}amino)-6-ethyl-4,5,6,7-tetrahydrothieno[2,3-c]pyridine-3-carboxamide hydrochloride (O6)

To mixture of compound O5 (28 mg, 0.065 mmol) in methanol (3 mL) was added 1 M hydrochloric acid (0.10 mL, 0.10 mmol). The mixture was sonicated for 3 min, diluted with water (6 mL), and lyophilized to afford compound O6 as Step 1: 3-[(4-Chlorophenyl)amino]-4-methoxycyclobut-3-ene-1,2-dione (O2)

To a stirred mixture of 3,4-dimethoxycyclobut-3-ene-1,2-dione (O1, 1.00 g, 7.04 mmol) in methanol (7 mL) at 0° C. under nitrogen was added a solution of 4-chloroaniline (0.898 g, 7.04 mmol) in methanol (8 mL) dropwise over 0.5 h. After addition, the reaction mixture was slowly warmed to room temperature and stirred at room temperature for another 2 days. The reaction mixture was filtered. The filter cake was washed with cold methanol (5 mL) and dried under reduced pressure to afford compound O2 as a yellow solid (1.48 g, 89%): $^1$H NMR (300 MHz, DMSO-$d_6$) δ 10.84 (s, 1H), 7.44-7.35 (m, 4H), 4.38 (s, 3H). MS (M+H) 238.

Step 2: tert-Butyl 2-({2-[(4-chlorophenyl)amino]-3,4-dioxocyclobut-1-en-1-yl}amino)-6-ethyl-4,5,6,7-tetrahydrothieno[2,3-c]pyridine-3-carboxylate (O3)

To a stirred mixture of sodium hydride (60% in mineral oil, 240 mg, 6.00 mmol) in anhydrous tetrahydrofuran (5 mL) at 0° C. under nitrogen was added the solution of compound L1 a brown solid (25 mg, 83%): ¹H NMR (300 MHz, DMSO-d₆) δ 10.85 (s, 1H), 10.77 (s, 1H), 10.34 (bs, 1H), 7.70-7.41 (m, 6H), 4.62-4.56 (m, 1H), 4.29-4.20 (m, 1H), 3.71-3.62 (m, 1H), 3.52-3.12 (m, 3H), 3.03 (bs, 2H), 1.30 (t, J=7.0 Hz, 3H). MS (M+H) 431.

Example 110

Preparation of Ethyl 2-({2-[(4-chlorophenyl)amino]-3,4-dioxocyclobut-1-en-1-yl}amino)-6-ethyl-4,5,6,7-tetrahydrothieno[2,3-c]pyridine-3-carboxylate hydrochloride

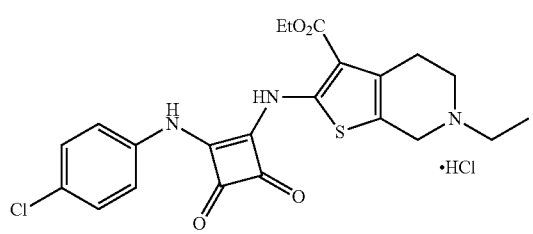 [SMILES: CCOC(=O)c1c(Nc2c(Nc3ccc(Cl)cc3)c(=O)c2=O)sc2c1CCN(CC)C2 ; Cl]

The title compound was prepared using a similar procedure as described in Example 109. MS (M+H) 458. ¹H NMR (300 MHz, DMSO-d₆) δ 11.18 (s, 1H), 10.95 (s, 1H), 10.37 (bs, 1H), 7.49 (d, J=5.1 Hz, 2H), 7.44 (d, J=5.1 Hz, 2H), 4.61-4.57 (m, 1H), 4.29-4.20 (m, 3H), 3.71-3.68 (m, 1H), 3.40-3.21 (min, 3H), 3.18-3.03 (m, 2H), 1.33-1.22 (m, 6H).

Example 111

Preparation of (+/−)-2-[3-(4-chlorophenyl)ureido]-1'-methyl-5,7-dihydro-4H-spiro(benzo[b]thiophene-6,2'-pyrrolidine)-3-carboxamide hydrochloride [(+/−)-P8]

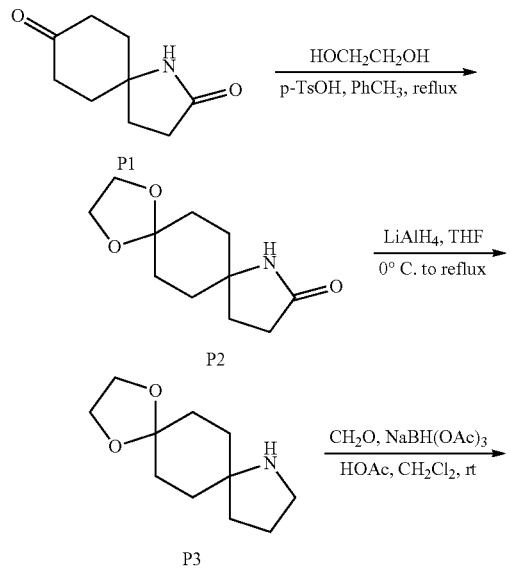

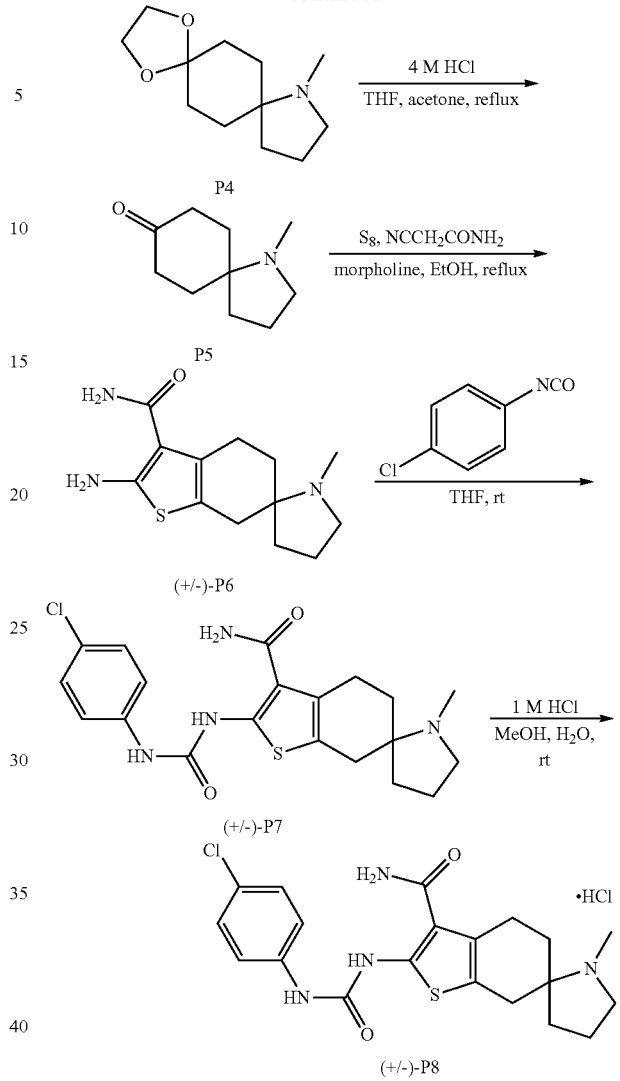

Step 1: 1,4-Dioxa-9-azadispiro[4.2.4.2]tetradecan-10-one (P2)

A stirred mixture of 1-azaspiro[4.5]decane-2,8-dione (P1, 2.00 g, 12.0 mmol), ethylene glycol (2.96 g, 47.7 mmol), and 4-methylbenzenesulfonic acid (100 mg, 0.735 mmol) in toluene (100 mL) was refluxed for 20 h with Dean-Stark apparatus to remove water. After this time, the reaction mixture was cooled to room temperature and concentrated under reduced pressure. The resulting residue was mixed with saturated aqueous sodium bicarbonate (100 mL) and the resulting aqueous mixture was extracted with 5% methanol/ethyl acetate (4×150 mL). The combined organic extracts were dried over anhydrous sodium sulfate, filtered, and concentrated under reduced pressure to afford compound P2 as an off-white solid (2.41 g, 95%): ¹H NMR (300 MHz, DMSO-d₆) δ 5.82 (bs, 1H), 3.95 (s, 4H), 2.41 (t, J=8.0 Hz, 2H), 1.99 (t, J=8.0 Hz, 2H), 1.80-1.65 (m, 8H). MS (M+H) 212.

Step 2: 1,4-Dioxa-9-azadispiro[4.2.4.2]tetradecane (P3)

To a stirred mixture of compound P2 (2.40 g, 11.4 mmol) in anhydrous tetrahydrofuran (50 mL) at 0° C. under nitrogen was added lithium aluminium hydride solution (1.0 M in tetrahydrofuran, 18.2 mL, 18.2 mmol) dropwise over 10 min. After addition, the reaction mixture was stirred at 0° C. for another 20 min, followed with 4 h refluxing. The reaction mixture was cooled to 0° C. and to the reaction mixture was added another portion of lithium aluminium hydride (1.0 M in tetrahydrofuran, 9.00 mL, 9.00 mmol) dropwise over 5 min. After addition, the reaction mixture was refluxed for another 4 h. After cooled to 0° C., the reaction was quenched by slow addition of sodium sulfate decahydrate. To the mixture was added triethylamine (3 mL). The resulting mixture was stirred for 0.5 h and filtered through a short silica gel plug. The solid cake was washed with 5% diethylamine/tetrahydrofuran (3×100 mL) and filtered. The combined filtrate was concentrated under reduced pressure. The resulting residue was purified by flash column chromatography on silica gel eluting with ammonium hydroxide/methanol/methylene chloride (1:14:85) to afford compound P3 as a colourless oil (1.39 g, 62%): MS (M+H) 198.

Step 3: 1,4-Dioxa-N-methyl-9-azadispiro[4.2.4.2] tetradecane (P4)

The formaldehyde aqueous solution (37% w/w in water, 10 mL) was extracted with methylene chloride (100 mL). The organic extract was dried over anhydrous sodium sulfate and filtered. The resulting stock solution was used for the following reaction without characterization.

To a stirred solution of compound P3 (1.39 g, 7.05 mmol) in methylene chloride (50 mL) under nitrogen was added formaldehyde stock solution (30.0 mL) in one portion, followed with acetic acid (420 mg, 6.99 mmol). After addition, the reaction mixture was stirred for another 10 min. Then to the reaction mixture was added sodium triacetoxyborohydride (4.48 g, 21.1 mmol) in one portion. After stirred for 40 min, to the reaction mixture was added another portion of formaldehyde stock solution (10.0 mL) and sodium triacetoxyborohydride (2.98 g, 14.1 mmol). After addition, the reaction mixture was stirred for another 20 min. After this time, the reaction was quenched by slow addition of saturated aqueous sodium bicarbonate (80 mL). The resulting aqueous mixture was extracted with methylene chloride (3×200 mL). The combined organic extracts were dried over anhydrous sodium sulfate, filtered, and concentrated under reduced pressure to afford compound P4 as colourless oil (1.42 g, 95%): MS (M+H) 212.

Step 4: 1-Methyl-1-azaspiro[4.5]decan-8-one (P5)

To a stirred mixture of compound P4 (1.42 g, 6.72 mmol) in tetrahydrofuran (10 mL) and acetone (2 mL) under nitrogen was added 4 M hydrochloric acid (10.0 mL, 40.0 mmol). After addition, the reaction mixture was heated to reflux for 4 h. After cooled to room temperature, the reaction was quenched by slow addition of saturated aqueous sodium bicarbonate (80 mL). The resulting aqueous mixture was extracted with 5% methanol in methylene chloride (4×100 mL). The combined organic extracts were dried over anhydrous sodium sulfate, filtered, and concentrated under reduced pressure. The resulting residue was purified by flash column chromatography on silica gel eluting with methanol/methylene chloride (15:85) to provide compound P5 as a colourless oil (1.01 g, 90%): $^1$H NMR (300 MHz, CDCl$_3$) δ 2.83 (t, J=6.9 Hz, 2H), 2.46-2.39 (m, 4H), 2.30 (s, 3H), 2.00-1.82 (m, 6H), 1.78-1.60 (m, 2H). MS (M+H) 168.

Step 5: (+/−)-2-Amino-1'-methyl-5,7-dihydro-4H-spiro(benzo[b]thiophene-6,2'-pyrrolidine)-3-carboxamide [(+/−)-P6]

A stirred mixture of compound P5 (1.00 g, 5.98 mmol), 2-cyanoacetamide (603 mg, 7.17 mmol), sulphur (230 mg, 7.17 mmol), and morpholine (1.04 g, 11.9 mmol) in ethanol (50 mL) was heated to reflux for 3 h under nitrogen. After cooled to room temperature, the reaction mixture was concentrated under reduced pressure. The resulting residue was purified by flash column chromatography on silica gel eluting with methanol/methylene chloride (15:85) to provide compound (+/−)-P6 as a yellow solid (1.01 g, 90%): MS (M+H) 266.

Step 6: (+/−)-2-[3-(4-Chlorophenyl)ureido]-1'-methyl-5,7-dihydro-4H-spiro(benzo[b]thiophene-6,2'-pyrrolidine)-3-carboxamide [(+/−)-P7]

To a stirred mixture of compound (+/−)-P6 (305 mg, 1.15 mmol) in tetrahydrofuran (25 mL) at room temperature under nitrogen was added 4-chlorophenyl isocyanate (212 mg, 1.38 mmol) in one portion. After addition, the reaction mixture was stirred overnight under nitrogen. After that time, the reaction mixture was concentrated under reduced pressure. The resulting residue was purified by flash column chromatography on silica gel eluting with ammonium hydroxide/methanol/methylene chloride (1:14:85) to provide compound (+/−)-P7 as a white solid (324 mg, 67%): $^1$H NMR (300 MHz, DMSO-d$_6$) δ 10.91 (s, 1H), 10.13 (s, 1H), 7.50 (d, J=9.0 Hz, 2H), 7.45 (bs, 1H), 7.33 (d, J=9.0 Hz, 2H), 6.91 (bs, 1H), 2.81-2.62 (m, 5H), 2.27-2.21 (m, 4H), 1.70-1.45 (m, 6H). MS (M+H) 419.

Step 7: (+/−)-2-[3-(4-Chlorophenyl)ureido]-1'-methyl-5,7-dihydro-4H-spiro(benzo[b]thiophene-6,2'-pyrrolidine)-3-carboxamide hydrochloride [(+/−)-P8]

To a mixture of compound (+/−)-P7 (100 mg, 0.240 mmol) in methanol (15 mL) was added 1 M hydrochloric acid (0.500 mL, 0.500 mmol) dropwise. After addition, the reaction mixture was stirred for 10 min, diluted with water (20 mL), and lyophilized to afford compound (+/−)-P8 as a white solid (104 mg, 95%): $^1$H NMR (300 MHz, DMSO-d$_6$) δ 10.88 and 10.82 (2 s, 1H), 10.68 and 10.58 (2 s, 1H), 10.21 (s, 1H), 7.75-6.85 (m, 6H), 3.60-3.52 (m, 1H), 3.30-2.68 (m, 8H), 2.20-1.73 (m, 6H). MS (M+H) 419.

Example 112

Preparation of 6-[3-(4-chlorophenyl)ureido]-2-ethyl-1,2,3,4-tetrahydroisoquinoline-5-carboxamide hydrochloride (Q10)

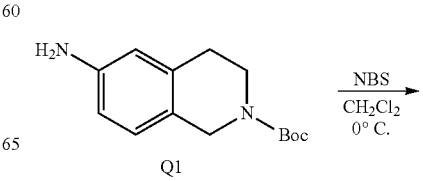

-continued

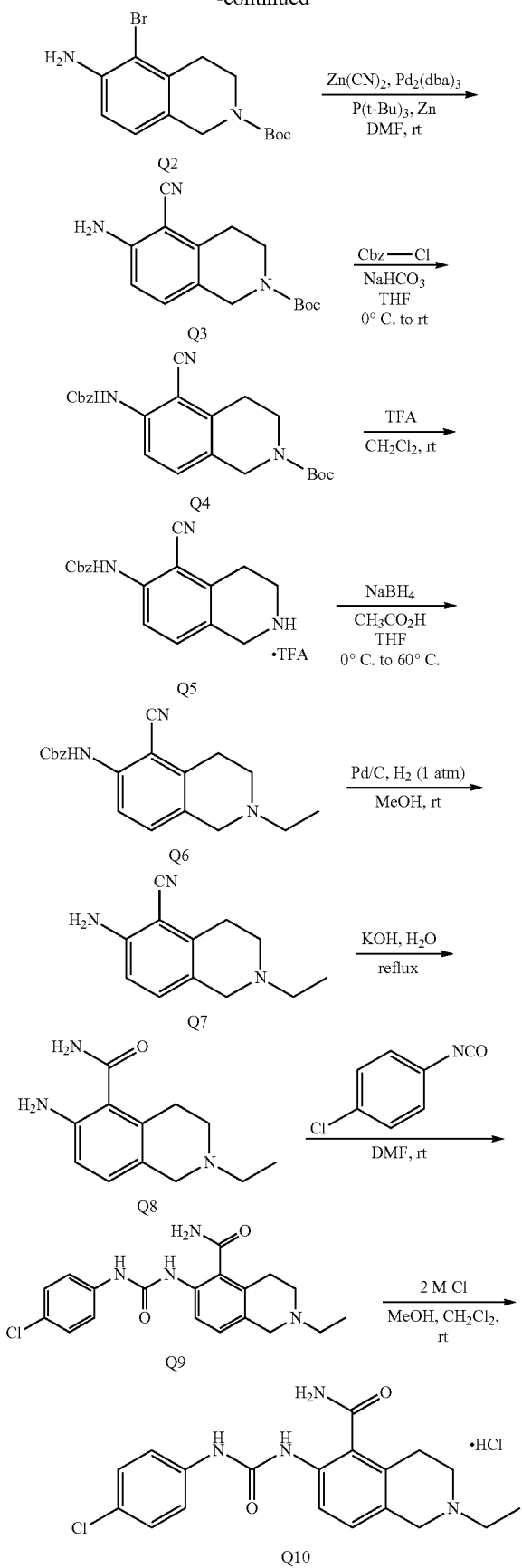

Step 1: tert-Butyl 6-amino-5-bromo-3,4-dihydroiso-quinoline-2(1H)-carboxylate (Q2)

To a solution of tert-butyl 6-amino-3,4-dihydroisoquino-line-2(1H)-carboxylate (Q1, 683 mg, 2.75 mmol) in methylene chloride (40 mL) was added N-bromosuccinimide (NBS) (490 mg, 2.75 mmol) at 0° C. The reaction mixture was stirred for 30 min and then diluted with methylene chloride (200 mL). The resulting solution was washed with water (50 mL), saturated aqueous sodium bicarbonate (50 mL), and brine (50 mL), dried over anhydrous sodium sulfate, filtered, and concentrated under reduced pressure. The resulting residue was purified by flash column chromatography on silica gel eluting with 12% to 30% ethyl acetate/hexanes to afford compound Q2 as a white solid (743 mg, 83%): $^1$H NMR (500 MHz, CDCl$_3$) δ 6.86 (d, J=8.2 Hz, 1H), 6.65 (d, J=8.2 Hz, 1H), 4.47 (s, 2H), 4.07 (s, 2H), 3.63 (t, J=5.8 Hz, 2H), 2.82 (t, J=5.8 Hz, 2H), 1.48 (s, 9H).

Step 2: tert-Butyl 6-amino-5-cyano-3,4-dihydroiso-quinoline-2(1H)-carboxylate (Q3)

To a degased mixture of compound Q2 (656 mg, 2.01 mmol), zinc dust (131 mg, 2.01 mmol), zinc cyanide (472 mg, 4.02 mmol) in anhydrous N, N-dimethylformamide (8 mL) was added tris(dibenzylideneacetone)dipalladium(0) (920 mg, 1.01 mmol) followed by tri-tert-butylphosphine (409 mg, 2.02 mmol) at room temperature. After addition, the reaction mixture was stirred for 3 days under nitrogen and then diluted with ethyl acetate (200 mL), water (50 mL), and saturated aqueous sodium bicarbonate (10 mL). The resulting mixture was filtered and the filter cake was washed with ethyl acetate (50 mL). The combined filtrate layers were separated. The organic layer was washed with water (3×30 mL) and brine (50 mL), dried over anhydrous sodium sulfate, filtered, and concentrated under reduced pressure. The resulting residue was purified by flash column chromatography on silica gel eluting with 20% to 30% ethyl acetate/hexanes to afford compound Q3 as a yellow form (435 mg, 79%): $^1$H NMR (500 MHz, CDCl$_3$) δ 7.05 (d, J=8.4 Hz, 1H), 6.59 (d, J=8.4 Hz, 1H), 4.43 (s, 2H), 4.35 (s, 2H), 3.65 (t, J=5.8 Hz, 2H), 2.90 (t, J=5.8 Hz, 2H), 1.49 (s, 9H). MS (M+H—C$_4$H$_8$) 218.

Step 3: tert-Butyl 6-{[(benzyloxy)carbonyl]amino}-5-cyano-3,4-dihydroisoquinoline-2(1H)-carboxylate (Q4)

To a stirred mixture of compound Q3 (569 mg, 2.08 mmol), sodium bicarbonate (489 mg, 5.82 mmol) in anhydrous tetrahydrofuran (15 mL) was added benzyl chloroformate (848 mg, 4.97 mmol) at 0° C. under nitrogen. After addition, the reaction mixture was warmed to room temperature and stirred for 26 h. After this time, the reaction was quenched with saturated aqueous sodium bicarbonate (80 mL). The resulting mixture was extracted with methylene chloride (3×50 mL). The combined extracts were dried over anhydrous sodium sulfate, filtered, and concentrated under reduced pressure. The resulting residue was purified by flash column chromatography on silica gel eluting with 20% ethyl acetate/hexanes to afford compound Q4 as a light yellow form (606 mg, 72%): $^1$H NMR (300 MHz, CDCl$_3$) δ 8.06 (d, J=8.6 Hz, 1H), 7.44-7.28 (m, 6H), 7.16 (s, 1H), 5.23 (s, 2H), 4.53 (s, 2H), 3.68 (t, J=5.8 Hz, 2H), 2.96 (t, J=5.8 Hz, 2H), 1.49 (s, 9H). MS (M+H—C$_4$H$_8$) 352.

Step 4: Benzyl (5-cyano-1,2,3,4-tetrahydroisoquino-lin-6-yl)carbamate trifluoroacetate (Q5)

To a stirred solution of compound Q4 (468 mg, 1.15 mmol) in methylene chloride (3 mL) was added trifluoroacetic acid (1.5 mL) at room temperature. After stirring for 1 h, the reaction mixture was concentrated under reduced pressure.

The resulting residue was dried under high vacuum to afford compound Q5 as a light brown form (656 mg, >99%): MS (M+H) 308. This product was used in the next step without further purification.

Step 5: Benzyl (5-cyano-2-ethyl-1,2,3,4-tetrahydroisoquinolin-6-yl)carbamate (Q6)

To a stirred mixture of compound Q5 (127 mg, 0.292 mmol) and acetic acid (0.56 mL) in anhydrous tetrahydrofuran (1 mL) was added sodium borohydride (55.0 mg, 1.45 mmol) at 0° C. under nitrogen. After addition, the reaction mixture was heated to 60° C. for 4 h and cooled to room temperature. The reaction mixture was concentrated and the residue was mixed with saturated aqueous sodium bicarbonate (50 mL). The resulting mixture was extracted with methylene chloride (3×30 mL). The combined extracts were dried over anhydrous sodium sulfate, filtered, and concentrated under reduced pressure. The resulting residue was purified by flash column chromatography on silica gel eluting with 4% to 10% methanol/methylene chloride to afford compound Q6 as a light yellow solid (62 mg, 63% over two steps): MS (M+H) 336.

Step 6: 6-Amino-2-ethyl-1,2,3,4-tetrahydroisoquinoline-5-carbonitrile (Q7)

A mixture of compound Q6 (60.0 mg, 0.179 mmol) and 10% palladium on carbon (50% wet, 10 mg) in methanol (15 mL) was stirred under hydrogen (1 atm) at room temperature for 6 h. After this time, the reaction mixture was filtered through a short pad of Celite and washed with methanol (50 mL). The combined filtrate was concentrated under reduced pressure to afford compound Q7 as an off-white solid (33 mg, 92%): $^1$H NMR (300 MHz, CDCl$_3$) δ 6.98 (d, J=8.4 Hz, 1H), 6.53 (d, J=8.4 Hz, 1H), 4.30 (bs, 2H), 3.48 (s, 2H), 2.97 (t, J=5.8 Hz, 2H), 2.73 (t, J=5.8 Hz, 2H), 2.57 (q, J=7.2 Hz, 2H), 1.18 (t, J=7.2 Hz, 3H). MS (M+H) 202.

Step 7: 6-Amino-2-ethyl-1,2,3,4-tetrahydroisoquinoline-5-carboxamide (Q8)

A solution of compound Q7 (163 mg, 0.810 mmol) and potassium hydroxide (909 mg, 16.2 mmol) in water (20 mL) was heated to reflux for 18 h. After this time, the reaction mixture was cooled to room temperature, diluted with water (10 mL), neutralized with 2 N hydrochloric acid to pH 8, and concentrated under reduced pressure. The resulting residue was triturated with methanol (3×30 mL) and filtered. The combined filtrate was concentrated under reduced pressure. The resulting residue was purified by flash column chromatography on silica gel eluting with 50% to 60% methanol/methylene chloride to afford compound Q8 as an off-white solid (219 mg, >99%): MS (M+H) 220. This product was used in the next step without further purification.

Step 8: 6-[3-(4-Chlorophenyl)ureido]-2-ethyl-1,2,3,4-tetrahydroisoquinoline-5-carboxamide (Q9)

A solution of compound Q8 (263 mg, 0.960 mmol) and 4-chlorophenyl isocyanate (147 mg, 0.960 mmol) in anhydrous N,N-dimethylformamide (5 mL) was stirred under nitrogen at room temperature for 19 h. After this time, the reaction mixture was concentrated under reduced pressure. The resulting residue was triturated with a mixture of methanol (5 mL), methylene chloride (10 mL), concentrated ammonium hydroxide aqueous solution (1 mL), and hexanes (20 mL) to afford compound Q9 as a white solid (143 mg, 40% over two steps): MS (M+H) 373.

Step 9: 6-[3-(4-Chlorophenyl)ureido]-2-ethyl-1,2,3,4-tetrahydroisoquinoline-5-carboxamide hydrochloride (Q10)

A mixture of compound Q9 (66.0 mg, 0.177 mmol) and hydrochloride (2 M in diethyl ether, 0.097 mL, 0.194 mmol) in methanol (2 mL) and methylene chloride (4 mL) was stirred at room temperature for 5 min. After this time, the reaction mixture was concentrated under reduced pressure. The resulting residue was triturated with a mixture of methanol (0.5 mL), methylene chloride (5 mL), ethyl acetate (3 mL), and hexanes (3 mL) to afford compound Q10 as a white solid (57 mg, 79%): $^1$H NMR (500 MHz, DMSO-d$_6$) δ 10.50 (bs, 1H), 9.64 (s, 1H), 8.07 (s, 2H), 7.81 (d, J=8.6 Hz, 1H), 7.80 (s, 1H), 7.48-7.30 (m, 4H), 7.18 (d, J=8.6 Hz, 1H), 4.51-4.19 (m, 2H), 3.67-3.65 (m, 1H), 3.29-3.07 (m, 5H), 1.33 (t, J=7.2 Hz, 3H). MS (M+H) 373.

Example 113

Preparation of 2-[3-(4-chlorophenyl)-1-ethylureido]-6-ethyl-4,5,6,7-tetrahydrothieno[2,3-c]pyridine-3-carboxamide hydrochloride (R3)

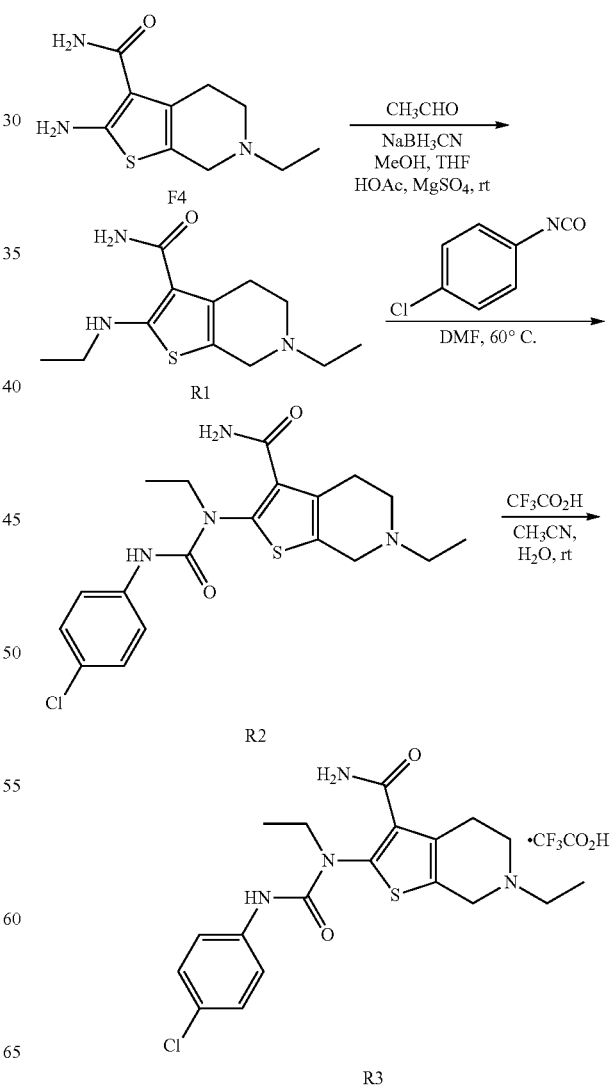

Step 1: 6-Ethyl-2-(ethylamino)-4,5,6,7-tetrahydrothieno[2,3-c]pyridine-3-carboxamide (R1)

To a stirred mixture of compound F4 (200 mg, 0.888 mmol), acetaldehyde (5 M in tetrahydrofuran, 0.360 mL, 1.80 mmol), acetic acid (two drops), anhydrous magnesium sulfate (200 mg) in anhydrous methanol (6 mL) and anhydrous tetrahydrofuran (3 mL) was added sodium cyanoborohydride (167 mg, 2.66 mmol) at room temperature under nitrogen. The reaction mixture was stirred for 23 h and then filtered. The filtrate was concentrated. The resulting residue was purified by flash column chromatography on silica gel eluting with 10% to 20% methanol/methylene chloride to afford compound R1 as a colourless syrup (181 mg, 80%): MS (M+H) 254.

Step 2: 2-[3-(4-Chlorophenyl)-1-ethylureido]-6-ethyl-4,5,6,7-tetrahydrothieno[2,3-c]pyridine-3-carboxamide (R2)

A solution of compound R1 (181 mg, 0.714 mmol) and 4-chlorophenyl isocyanate (110 mg, 0.714 mmol) in anhydrous N,N-dimethylformamide (5 mL) was heated to 60° C. for 18 h, cooled to room temperature, and concentrated under reduced pressure. The resulting residue was purified by flash column chromatography on silica gel eluting with 4% to 20% methanol/methylene chloride to afford compound R2 as a light yellow solid (72 mg, 25%): MS (M+H) 407.

Step 3: 2-[3-(4-Chlorophenyl)-1-ethylureido]-6-ethyl-4,5,6,7-tetrahydrothieno[2,3-c]pyridine-3-carboxamide trifluoroacetate (R3)

To a solution of compound R2 (72.0 mg, 0.177 mmol) in acetonitrile (2 mL) and water (1 mL) was added trifluoroacetic acid (22.0 mg, 0.193 mmol). The resulting solution was lyophilized to afford compound R3 as a white solid (56 mg, 61%): $^1$H NMR (500 MHz, DMSO-$d_6$) δ 9.95 (bs, 1H), 8.67 (s, 1H), 7.73 (s, 1H), 7.46 (s, 1H), 7.43-7.30 (m, 4H), 4.65-4.27 (m, 2H), 3.73-2.94 (m, 8H), 1.30 (t, J=7.2 Hz, 3H), 1.10 (t, J=7.1 Hz, 3H). MS (M+H) 407.

Example 114

Preparation of 2-[3-(4-chlorophenyl)ureido)-7-ethyl-5,6,7,8-tetrahydro-4H-thieno[2,3-c]azepine-3-carboxamide hydrochloride (S9)

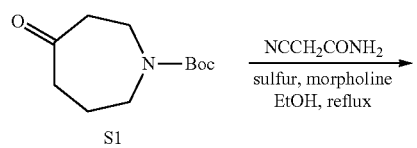

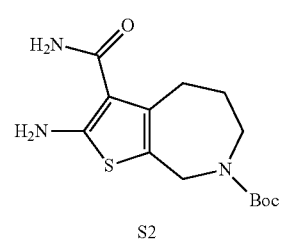

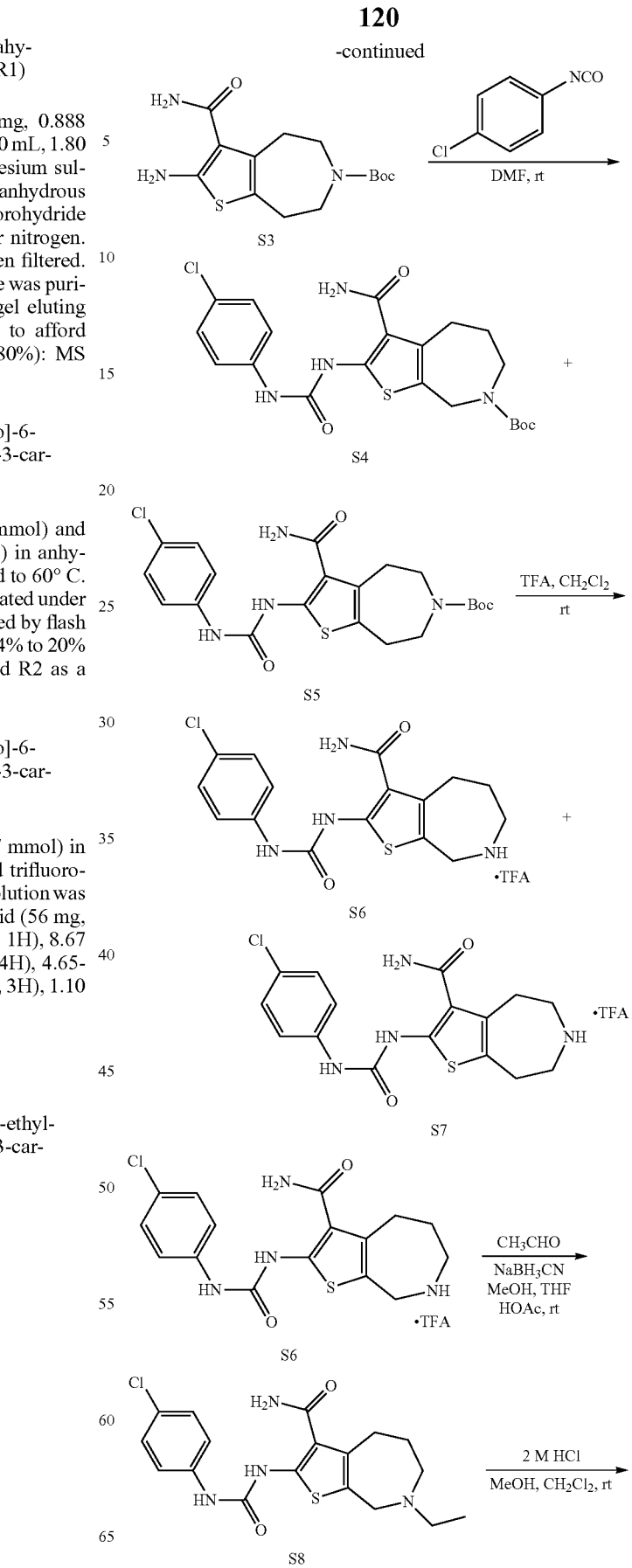

-continued

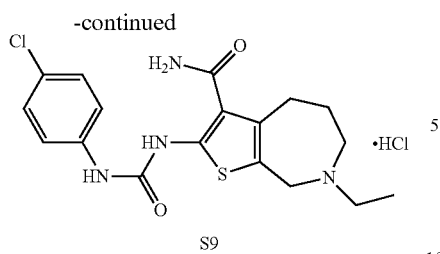

S9

Step 1: tert-Butyl 2-amino-3-carbamoyl-5,6-dihydro-4H-thieno[2,3-c]azepine-7(8H)-carboxylate (S2) and tert-butyl 2-amino-3-carbamoyl-7,8-dihydro-4H-thieno[2,3-d]azepine-6(5H)-carboxylate (S3)

A mixture of compound S1 (1.00 g, 4.69 mmol), 2-cyanoacetamide (394 mg, 4.69 mmol), sulphur (150 mg, 4.69 mmol), and morpholine (410 mg, 4.71 mmol) in ethanol (10 mL) was heated to reflux for 4 h under nitrogen. After cooled to room temperature, the reaction mixture was concentrated under reduced pressure. The resulting residue was purified by flash column chromatography on silica gel eluting with 4% methanol/methylene chloride to provide an inseparable mixture of isomers S2 and compound S3 as a yellow solid (564 mg, 39%): MS (M+H) 312.

Step 2: tert-Butyl 3-carbamoyl-2-[3-(4-chlorophenyl)ureido]-5,6-dihydro-4H-thieno[2,3-c]azepine-7(8H)-carboxylate (S4) and tert-butyl 3-carbamoyl-2-[3-(4-chlorophenyl)ureido]-7,8-dihydro-4H-thieno[2,3-d]azepine-6(5H)-carboxylate (S5)

To a stirred mixture of compound S2 and S3 (300 mg, 0.963 mmol) in N,N-dimethylformamide (2 mL) at room temperature under nitrogen was added 4-chlorophenyl isocyanate (148 mg, 0.964 mmol). After addition, the reaction mixture was stirred for 21 h. After this time, the reaction mixture was concentrated under reduced pressure. The resulting residue was purified by flash column chromatography on silica gel eluting with 50% ethyl acetate/methylene chloride to provide an inseparable mixture of isomers S4 and S5 as a white solid (375 mg, 84%): MS (M+Na) 487.

Step 3: 2-[3-(4-Chlorophenyl)ureido]-5,6,7,8-tetrahydro-4H-thieno[2,3-c]azepine-3-carboxamide trifluoroacetae (S6) and 2-[3-(4-chlorophenyl)ureido]-5,6,7,8-tetrahydro-4H-thieno[2,3-d]azepine-3-carboxamide trifluoroacetae (S7)

To a mixture of compound S4 and S5 (374 mg, 0.804 mmol) in methylene chloride (4 mL) was added trifluoroacetic acid (2 mL). After addition, the reaction mixture was stirred for 1 h and then concentrated under reduced pressure. The resulting residue was purified by reverse phase semi-preparative HPLC, eluting with 0.05% TFA in acetonitrile/water (gradient from 10% to 100%, Phenomenex Luna column) to afford compound S6 as a white solid (188 mg, 49%) and compound S7 as a white solid (106 mg, 28%). Compound S6: $^1$H NMR (500 MHz, DMSO-$d_6$) δ 10.06 (s, 1H), 10.05 (s, 1H), 8.77 (s, 2H), 7.70-7.30 (m, 6H), 4.32 (s, 2H), 3.37 (bs, 2H), 2.96-2.94 (m, 2H), 1.87 (bs, 2H). MS (M+H) 365. Compound S7: $^1$H NMR (500 MHz, DMSO-$d_6$) δ 10.02 (s, 1H), 9.94 (s, 1H), 8.85 (s, 2H), 7.70-7.30 (m, 6H), 3.22 (bs, 4H), 3.08-2.98 (m, 4H). MS (M+H) 365.

Step 4: 2-[3-(4-Chlorophenyl)ureido]-7-ethyl-5,6,7,8-tetrahydro-4H-thieno[2,3-c]azepine-3-carboxamide (S8)

To a stirred mixture of compound S6 (185 mg, 0.386 mmol), acetaldehyde (5 M solution in tetrahydrofuran, 0.160 mL, 0.800 mmol), and acetic acid (2 drops) in anhydrous methanol (6 mL) and anhydrous tetrahydrofuran (3 mL) at room temperature under nitrogen was added sodium cyanoborohydride (73.0 mg, 1.16 mmol). After addition, the reaction mixture was stirred for 17 h. After this time, the reaction mixture was diluted with methylene chloride (100 mL), washed with saturated aqueous sodium bicarbonate (30 mL), dried over anhydrous sodium sulfate, filtered, and concentrated under reduced pressure. The resulting residue was purified by flash column chromatography on silica gel eluting with 20% to 60% methanol/methylene chloride to provide compound S8 as a light yellow solid (92 mg, 61%): MS (M+H) 393.

Step 5: 2-[3-(4-Chlorophenyl)ureido]-7-ethyl-5,6,7,8-tetrahydro-4H-thieno[2,3-c]azepine-3-carboxamide hydrochloride (S9)

To a stirred mixture of compound S8 (41.0 mg, 0.104 mmol) in methanol (3 mL) and methylene chloride (3 mL) at room temperature was added hydrochloride (2 M in diethyl ether, 0.100 mL, 0.200 mmol). After addition, the reaction mixture was stirred for 5 min and concentrated under reduced pressure. The resulting residue was dissolved in acetonitrile (1 mL) and water (1 mL) and lyophilized to provide compound S9 as an off-white solid (45 mg, 100%): $^1$H NMR (500 MHz, DMSO-$d_6$) δ 10.12 (s, 1H), 10.11 (s, 1H), 10.04 (bs, 1H), 7.70-7.30 (m, 6H), 4.56-4.40 (m, 2H), 3.59-3.36 (m, 2H), 3.09-2.94 (m, 4H), 2.01-1.84 (m, 2H), 1.25 (t, J=7.2 Hz, 3H). MS (M+H) 393.

Example 115

Preparation of 2-[3-(4-Chlorophenyl)ureido]-6-ethyl-5,6,7,8-tetrahydro-4H-thieno[2,3-d]azepine-3-carboxamide hydrochloride

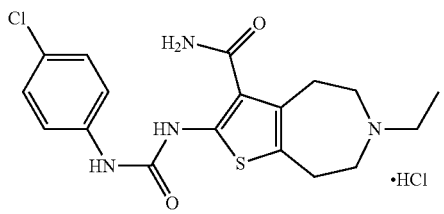 [SMILES: CCN1CCc2sc(NC(=O)Nc3ccc(Cl)cc3)c(C(N)=O)c2CC1 ; Cl]

The title compound was prepared using a similar procedure as described in Example 114. MS (M+H) 393. $^1$H NMR (500 MHz, DMSO-$d_6$) δ 10.27 (bs, 1H), 10.05 (s, 1H), 10.02 (s, 1H), 7.70-7.25 (m, 6H), 3.60-3.56 (m, 2H), 3.25-3.06 (m, 8H), 1.27 (t, J=7.2 Hz, 3H).

Example 116

Preparation of 2-[3-(4-Chlorophenyl)ureido]-5-ethyl-4,5,6,7-tetrahydrothieno[3,2-c]pyridine-3-carboxamide hydrochloride

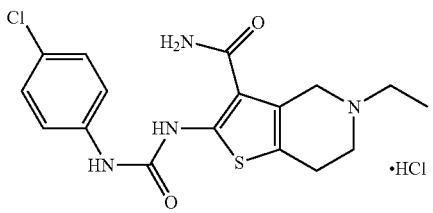 [SMILES: CCN1CCc2sc(NC(=O)Nc3ccc(Cl)cc3)c(C(N)=O)c2C1 ; Cl]

The title compound was prepared using a similar procedure as described in Example 114. MS (M+H) 379. ¹H NMR (500 MHz, DMSO-d₆) δ 10.58 (s, 1H), 10.18 (s, 1H), 9.85 (bs, 1H), 7.65-7.15 (m, 6H), 4.52-3.68 (m, 3H), 3.29-3.00 (m, 5H), 1.30 (t, J=7.2 Hz, 3H).

Example 117

Preparation of (+/−)-2-[3-(4-chlorophenyl)ureido]-4a,5,6,7,8,10-hexahydro-4H-thieno[3,2-b]quinolizine-3-carboxamide hydrochloride [(+/−)-T8]

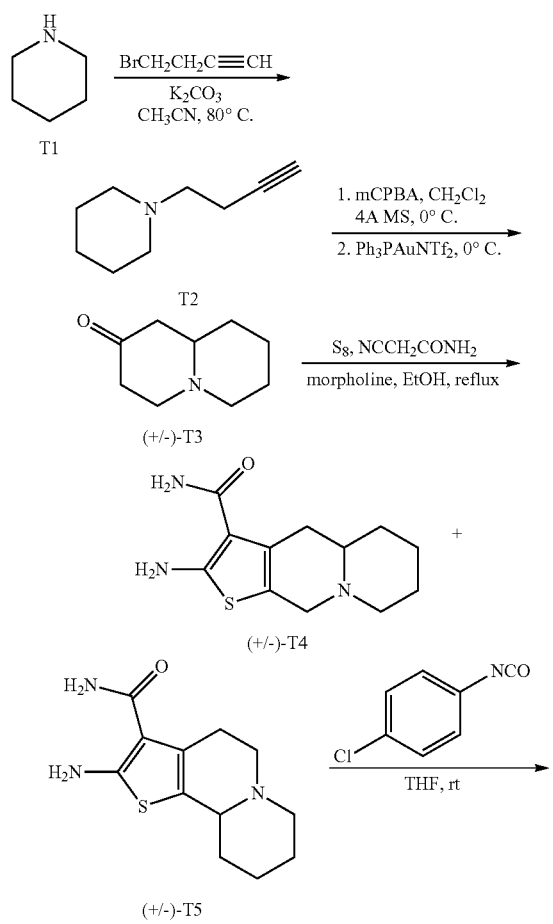

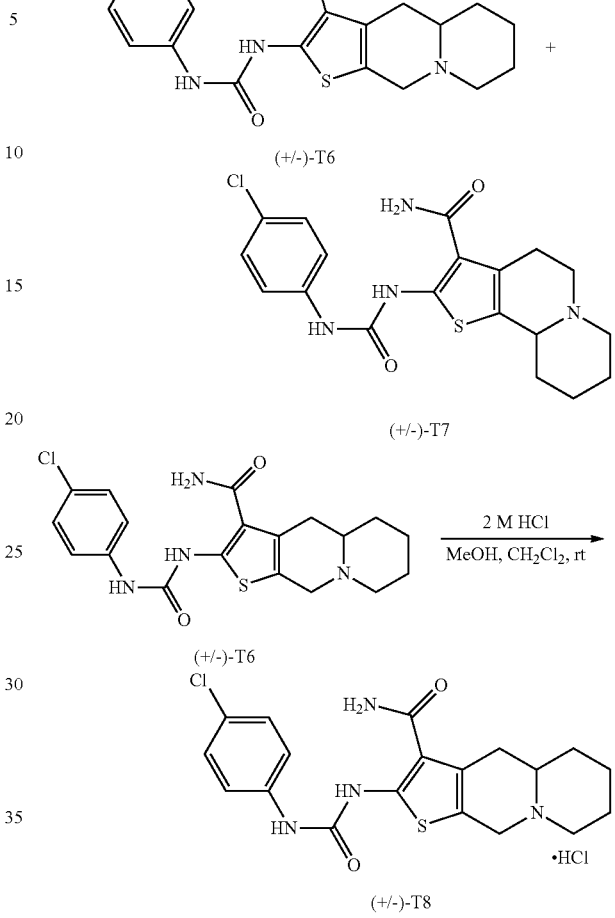

Step 1: 1-(But-3-yn-1-yl)piperidine (T2)

A mixture of piperidine (T1, 2.90 g, 34.0 mmol), potassium carbonate (3.00 g, 21.7 mmol), and 4-bromobut-1-yne (5.00 g, 37.6 mmol) in anhydrous acetonitrile (60 mL) was heated to 80° C. under nitrogen for 20 h. After this time, the reaction mixture was cooled to room temperature and diluted with water (50 mL). The resulting mixture was extracted with ethyl acetate (3×50 mL). The combined extracts were dried over anhydrous sodium sulfate, filtered, and concentrated under reduced pressure to afford compound T2 as light brown oil (1.89 g, 40%): MS (M+H) 138.

Step 2: (+/−)-Hexahydro-1H-quinolizin-2(6H)-one [(+/−)-T3]

To a stirred mixture of compound T2 (1.89 g, 13.8 mmol) and 4 Å molecular sieves (15.5 g) in anhydrous methylene chloride (50 mL) at 0° C. under nitrogen was added 3-chloroperbenzoic acid (mCPBA) (77%, 3.10 g, 13.8 mmol). After addition, the reaction mixture was stirred at 0° C. for 1.5 h. After this time, to the reaction mixture was added triphenylphosphinegold(I) bis(trifluoromethanesulfonyl)imidate (510 mg, 0.690 mmol) and stirred at 0° C. under nitrogen for another 4.5 h. The reaction mixture was diluted with methylene chloride (100 mL), washed with 5% aqueous sodium carbonate (2×150 mL), dried over anhydrous sodium sulfate, filtered, and concentrated under reduced pressure. The resulting residue was purified by flash column chromatography on silica gel eluting with ammonium hydroxide/methanol/ethyl acetate (0.1:1:10) to afford compound (+/−)-T3 as a brown oil (930 mg, 44%): MS (M+H) 154.

Step 3: (+/−)-2-Amino-4a,5,6,7,8,10-hexahydro-4H-thieno[3,2-b]quinolizine-3-carboxamide [(+/−)-T4] and (+/−)-2-amino-5,5a,6,7,8,9-hexahydro-4H-thieno[3,2-c]quinolizine-3-carboxamide [(+/−)-T5]

A mixture of compound (+/−)-T3 (500 mg, 3.26 mmol), 2-cyanoacetamide (274 mg, 3.26 mmol), sulphur (105 mg, 3.27 mmol), and morpholine (280 mg, 3.21 mmol) in ethanol (5 mL) was heated to reflux for 3.5 h under nitrogen. After this time, the reaction mixture was cooled to room temperature and concentrated under reduced pressure. The resulting residue was purified by flash column chromatography on silica gel eluting with 4% to 6% methanol/methylene chloride to provide an inseparable isomers (+/−)-T4 and (+/−)-T5 as a brown solid (450 mg, 55%): MS (M+H) 252.

Step 4: (+/−)-2-[3-(4-Chlorophenyl)ureido]-4a,5,6,7,8,10-hexahydro-4H-thieno[3,2-b]quinolizine-3-carboxamide [(+/−)-T6] and (+/−)-2-[3-(4-chlorophenyl)ureido]-5,5a,6,7,8,9-hexahydro-4H-thieno[3,2-c]quinolizine-3-carboxamide [(+/−)-T7]

To a stirred mixture of compound (+/−)-T4 and (+/−)-T5 (450 mg, 1.79 mmol) in anhydrous N,N-dimethylformamide (9 mL) at room temperature under nitrogen was added 4-chlorophenyl isocyanate (275 mg, 1.79 mmol). After addition, the reaction mixture was stirred for 21 h. After this time, the reaction mixture was concentrated under reduced pressure. The resulting residue was purified by flash column chromatography on silica gel eluting with 4% to 10% methanol/methylene chloride to provide compound (+/−)-T6 as a yellow solid (110 mg, 15%) and compound (+/−)-T7 as a yellow solid (304 mg, 42%). Compound (+/−)-T6: $^1$H NMR (500 MHz, DMSO-$d_6$) δ 10.89 (s, 1H), 10.15 (s, 1H), 7.51-6.45 (m, 6H), 3.10-2.80 (m, 2H), 2.60-2.55 (m, 1H), 2.45-2.15 (m, 2H), 1.95-1.25 (m, 8H). MS (M+H) 405. Compound (+/−)-T7: $^1$H NMR (500 MHz, DMSO-$d_6$) δ 10.97 (s, 1H), 10.16 (s, 1H), 7.55-6.60 (m, 6H), 3.75-3.65 (m, 1H), 3.15-2.60 (m, 4H), 2.20-1.20 (m, 8H). MS (M+H) 405.

Step 5: (+/−)-2-[3-(4-Chlorophenyl)ureido]-4a,5,6,7,8,10-hexahydro-4H-thieno[3,2-b]quinolizine-3-carboxamide hydrochloride [(+/−)-T8]

To a mixture of compound (+/−)-T6 (40 mg, 0.099 mmol) in methanol (2 mL) and methylene chloride (2 mL) was added hydrochloride (2 M in diethyl ether, 0.099 mL, 0.198 mmol) at room temperature. After addition, the reaction mixture was stirred for 2 min and concentrated under reduced pressure. The resulting residue was triturated with a mixture of methanol (0.5 mL), methylene chloride (2 mL), ethyl acetate (5 mL), and hexanes (5 mL) to afford compound (+/−)-T8 as a yellow solid (24 mg, 55%): $^1$H NMR (300 MHz, DMSO-$d_6$) δ 11.02 (s, 1H), 10.28 (bs, 2H), 7.80-7.00 (m, 6H), 4.50-4.40 (m, 1H), 3.70-3.45 (m, 2H), 3.32-2.95 (m, 4H), 2.30-1.55 (m, 6H). MS (M+H) 405.

Example 118

Preparation of (+/−)-2-[3-(4-Chlorophenyl)ureido]-5,7,8,9,10,10a-hexahydro-4H-thieno[2,3-a]quinolizine-3-carboxamide hydrochloride

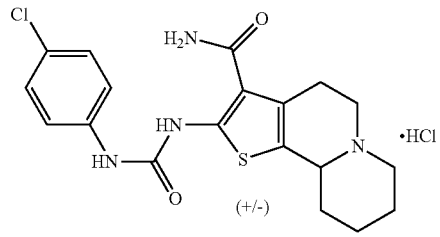 [SMILES: NC(=O)c1c(NC(=O)Nc2ccc(Cl)cc2)sc2c1CCN1CCCCC21 ; Cl]

The title compound was prepared using a similar procedure as described in Example 117. MS (M+H) 405. $^1$H NMR (300 MHz, DMSO-$d_6$) δ 11.04 (s, 1H), 10.52 (bs, 1H), 10.29 (s, 1H), 7.90-6.90 (m, 6H), 4.50-4.15 (m, 2H), 3.55-3.34 (m, 2H), 3.20-2.88 (m, 3H), 2.10-1.47 (m, 6H).

Example 119

Preparation of 2-[3-(4-chlorophenyl)ureido]-6-(2-hydroxy-2-methylpropyl)-4,5,6,7-tetrahydrothieno[2,3-c]pyridine-3-carboxamide (U1)

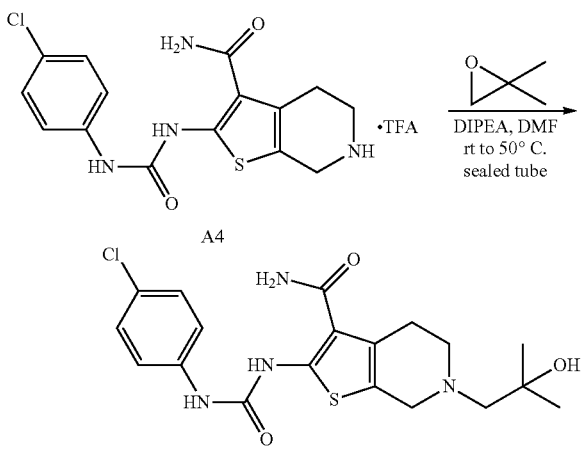

2-[3-(4-Chlorophenyl)ureido]-6-(2-hydroxy-2-methylpropyl)-4,5,6,7-tetrahydrothieno[2,3-c]pyridine-3-carboxamide (U1)

A solution of compound A4 (200 mg, 0.430 mmol), 2,2-dimethyloxirane (155 mg, 2.15 mmol), and diisopropylethylamine (167 mg, 1.29 mmol) in anhydrous N,N-dimethylformamide (1.5 mL) was stirred at room temperature for 2 h and heated to 50° C. in a sealed tube for another 21 h. After this time, the reaction mixture was cooled to room temperature and concentrated under reduced pressure. The resulting residue was purified by flash column chromatography on silica gel eluting with 2% to 6% methanol/methylene chloride to afford compound U1 as a yellow solid (36 mg, 20%): $^1$H NMR (300 MHz, DMSO-$d_6$) δ 10.97 (s, 1H), 10.19 (s, 1H), 7.70-6.70 (m, 6H), 4.19 (s, 1H), 3.62 (s, 2H), 2.78 (bs, 4H), 2.38 (s, 2H), 1.12 (s, 6H). MS (M+H) 423.

Example 120

Preparation of 2-[3-(4-chlorophenyl)ureido]-5,5,6,7,7-pentamethyl-4,5,6,7-tetrahydrothieno[2,3-c]pyridine-3-carboxamide hydrochloride (V3)

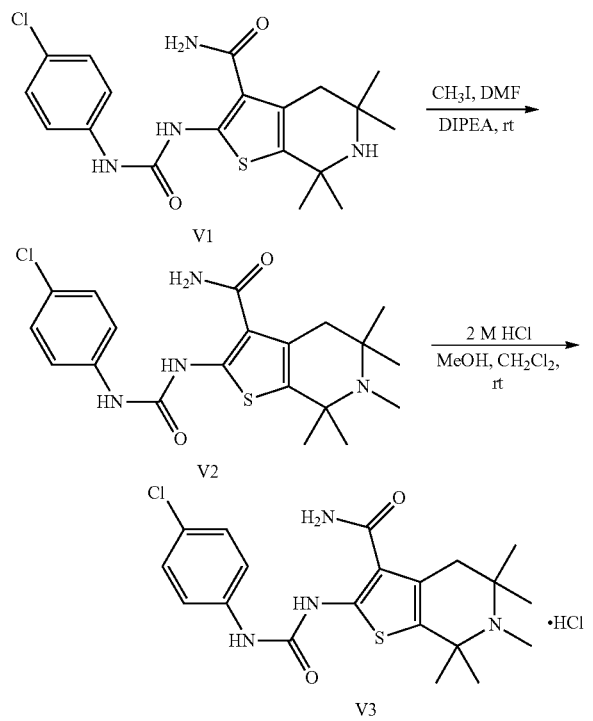

Step 1: 2-[3-(4-Chlorophenyl)ureido]-5,5,6,7,7-pentamethyl-4,5,6,7-tetrahydrothieno[2,3-c]pyridine-3-carboxamide (V2)

A solution of compound V1 (100 mg, 0.246 mmol), iodomethane (173 mg, 1.22 mmol), and diisopropylethylamine (64.0 mg, 0.494 mmol) in anhydrous N,N-dimethylformamide (3 mL) was stirred at room temperature under nitrogen for 90 h. After this time, the reaction mixture was concentrated under reduced pressure. The resulting residue was purified by flash column chromatography on silica gel eluting with 4% to 12% methanol/methylene chloride to afford compound V2 as an off-white solid (63 mg, 61%): $^1$H NMR (300 MHz, DMSO-$d_6$) δ 10.80 (s, 1H), 10.17 (s, 1H), 7.53-6.70 (m, 6H), 2.62 (s, 2H), 2.30 (s, 3H), 1.35 (s, 6H), 1.04 (s, 6H). MS (M+Na) 443.

Step 2: 2-[3-(4-Chlorophenyl)ureido]-5,5,6,7,7-pentamethyl-4,5,6,7-tetrahydrothieno[2,3-c]pyridine-3-carboxamide hydrochloride (V3)

To a stirred solution of compound V2 (63 mg, 0.15 mmol) in methanol (2 mL) and methylene chloride (2 mL) was added hydrochloride (2 M in diethyl ether, 0.075 mL, 0.15 mmol). After addition, the reaction mixture was stirred at room temperature for 2 min and concentrated under reduced pressure. The resulting residue was triturated with a mixture of methanol (0.5 mL), methylene chloride (2 mL), ethyl acetate (5 mL), and hexanes (5 mL) to afford compound V3 as a white solid (54 mg, 79%): $^1$H NMR (300 MHz, DMSO-$d_6$) δ 10.89 (s, 1H), 10.28 (s, 1H), 10.03 (bs, 1H), 7.90-7.00 (m, 6H), 3.27 (s, 1H), 2.92 (s, 1H), 2.85 (s, 3H), 1.78 (s, 3H), 1.63 (s, 3H), 1.53 (s, 3H), 1.27 (s, 3H). MS (M+Na) 443.

Example 121

Preparation of 2-[3-(4-chlorophenyl)ureido]-6-(methoxyimino)-4,5,6,7-tetrahydrobenzo[b]thiophene-3-carboxamide (W2, isomer A) and W3 (isomer B)

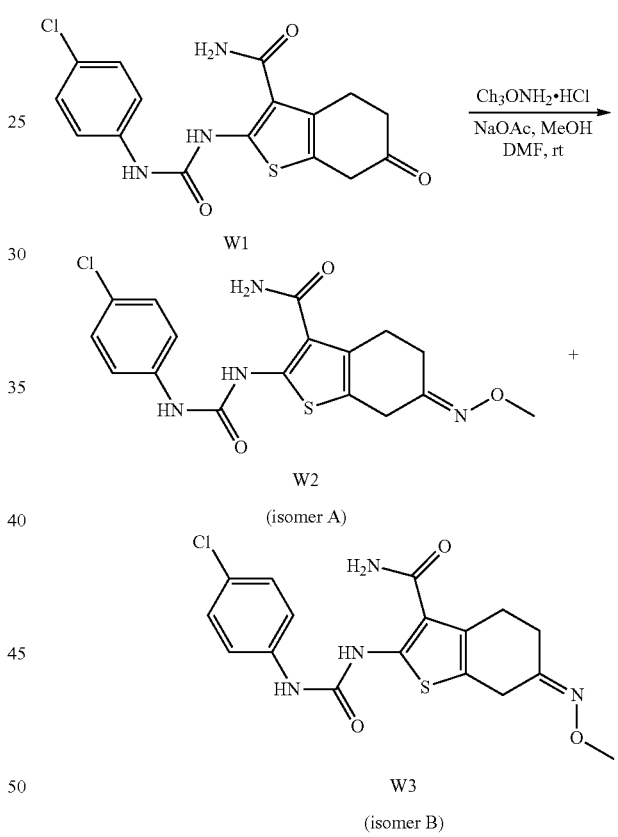

To a stirred solution of compound W1 (100 mg, 0.275 mmol) in anhydrous N,N-dimethylformamide (4 mL) and methanol (10 mL) was added methoxyamine hydrochloride (46.0 mg, 0.551 mmol) followed by sodium acetate (56.0 mg, 0.683 mmol). After addition, the reaction mixture was stirred at room temperature for 20 h. After this time, the reaction mixture was concentrated under reduced pressure. The resulting residue was purified by flash column chromatography on silica gel eluting with 30% to 50% ethyl acetate/methylene chloride to afford isomer A W2 as a light yellow solid (22 mg, 20%) and isomer B W3 as a light yellow solid (35 mg, 32%). Isomer A (W2): $^1$H NMR (300 MHz, DMSO-$d_6$) δ 10.71 (s, 1H), 10.17 (s, 1H), 7.65-6.80 (m, 6H), 3.78 (s, 3H), 3.42 (s, 2H), 2.90-2.65 (m, 4H). MS (M+Na) 415. Isomer B (W3): $^1$H NMR (300 MHz, DMSO-d$_6$) δ 10.71 (s, 1H), 10.17 (s, 1H), 7.70-6.80 (m, 6H), 3.79 (s, 3H), 3.61 (s, 2H), 2.88-2.85 (m, 2H), 2.49-2.45 (m, 2H). MS (M+Na) 415.

Example 122

Preparation of (+/−)-2-[3-(4-chlorophenyl)ureido]-5,6,7,8-tetrahydro-4H-5,8-epiminocyclohepta[b]thiophene-3-carboxamide hydrochloride [(+/−)-X8 and (+/−)-X9, mixture of atropisomers]

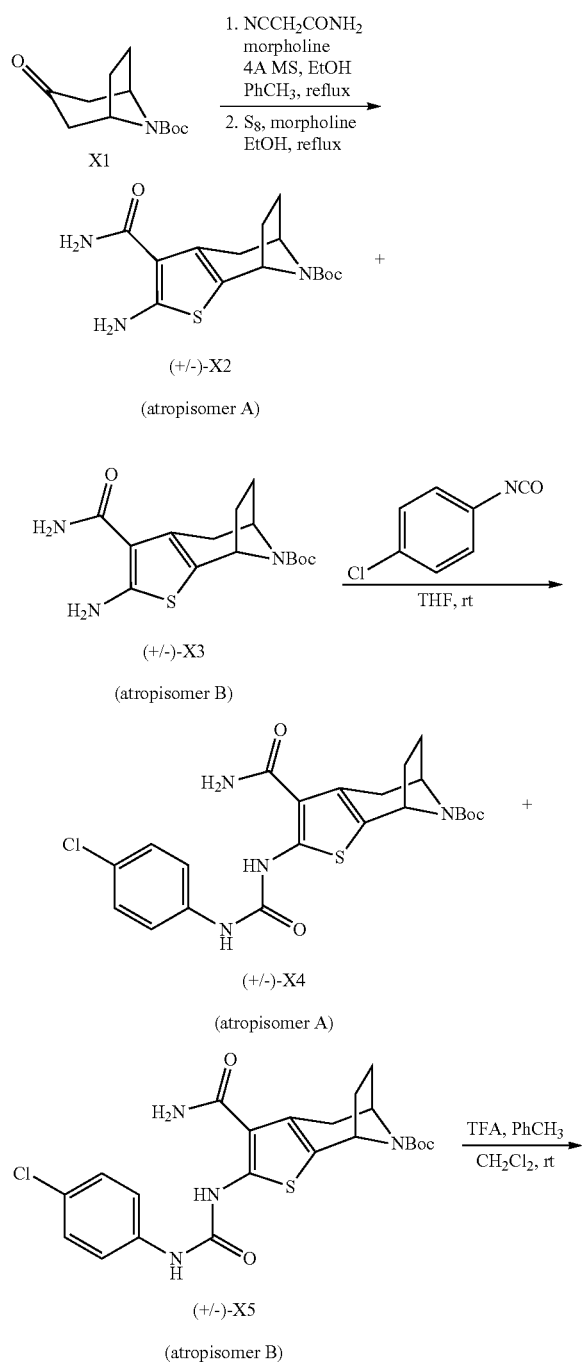

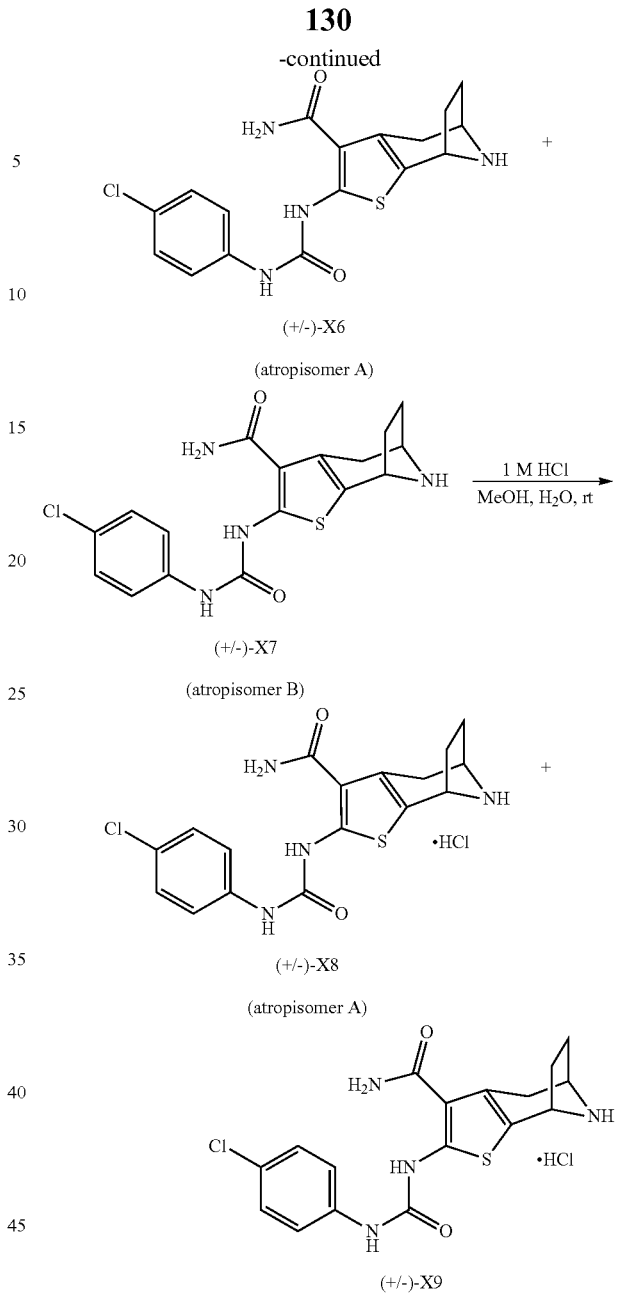

Step 1: 2-[3-(4-Chlorophenyl)ureido]-5,6,7,8-tetrahydro-4H-thieno[2,3-c]azepine-3-carboxamide A stirred mixture of tert-butyl 3-oxo-8-azabicyclo[3.2.1]octane-8-carboxylate (X1, 2.48 g, 11.0 mmol), 2-cyanoacetamide (1.02 g, 12.1 mmol), morpholine (1.92 g, 22.0 mmol), and 4 Å molecular sieves (4.00 g) in ethanol (100 mL) and toluene (60 mL) was heated to reflux under nitrogen overnight. After this time, the reaction mixture was cooled to room temperature and filtered. The filter cake was washed with ethanol (30 mL) and filtered. The filtrate was concentrated. The resulting residue was purified by a silica gel plug eluting with methanol/methylene chloride (1:9) to provide a partially purified product which was used in the subsequent step without further purification (1.10 g): MS (M+H-Boc) 192.

A stirred mixture of the product described above (1.10 g), sulfur (145 mg, 4.52 mmol), and morpholine (656 mg, 7.53 mmol) in ethanol (40 mL) was heated to reflux overnight under nitrogen. After this time, the reaction mixture was cooled to room temperature and concentrated under reduced pressure. The resulting residue was mixed with saturated aqueous sodium bicarbonate (30 mL). The resulting aqueous mixture was extracted with methylene chloride (3×50 mL). The combined organic extracts were dried over anhydrous sodium sulfate, filtered, and concentrated under reduced pressure. The resulting residue was purified by flash column chromatography on silica gel eluting with ethyl acetate/hexanes (8:2) to provide an inseparable atropisomers (+/−)-X2 and (+/−)-X3 as a yellow solid (391 mg, 11%): $^1$H NMR (300 MHz, DMSO-$d_6$) δ 7.02 (bs, 0.25H), 6.70-6.40 (m, 3.75H), 5.05 (d, J=5.4 Hz, 0.86H), 4.62 (d, J=5.4 Hz, 0.14H), 4.32 (bs, 1H), 3.08-2.94 (m, 1H), 2.30-1.81 (m, 4H), 1.61-1.50 (m, 1H), 1.36 and 1.30 (2 s, 9H). MS (M+H) 324.

Step 2: (+/−)-tert-Butyl 3-carbamoyl-2-[3-(4-chlorophenyl)ureido]-5,6,7,8-tetrahydro-4H-5,8-epiminocyclohepta[b]thiophene-9-carboxylate [(+/−)-X4, atropisomer A; and (+/−)-X5, atropisomer B]

A stirred mixture of atropisomers (+/−)-X2 and (+/−)-X3 (387 mg, 1.20 mmol) in methylene chloride (8 mL) at room temperature under nitrogen was added 4-chlorophenyl isocyanate (221 mg, 1.44 mmol). After addition, the reaction mixture was stirred overnight and concentrated under reduced pressure. The resulting residue was purified by flash column chromatography on silica gel eluting with ethyl acetate/hexanes (9:1) to provide atropisomer A (+/−)-X4 as a pale yellow solid (396 mg, 69%) and atropisomer B (+/−)-X5 as a yellow solid (112 mg, 20%). Atropisomer A [(+/−)-X4]: $^1$H NMR (300 MHz, DMSO-$d_6$) δ 10.59-10.51 (m, 1H), 10.06 (s, 1H), 7.51-6.80 (m, 6H), 5.03 (d, J=5.1 Hz, 1H), 4.38 (bs, 1H), 3.19-3.10 (m, 1H), 2.29-1.90 (m, 4H), 1.65-1.60 (m, 1H), 1.36 and 1.28 (2 bs, 9H). MS (M−H) 475. Atropisomer B [(+/−)-X5]: $^1$H NMR (300 MHz, DMSO-$d_6$) δ 11.09-11.01 (m, 1H), 10.20 (s, 1H), 7.62-6.70 (m, 6H), 4.82 (d, J=5.1 Hz, 1H), 4.38 (bs, 1H), 2.15-1.52 (m, 6H), 1.23 (bs, 9H). MS (M−H) 475.

Step 3: (+/−)-2-[3-(4-Chlorophenyl)ureido]-5,6,7,8-tetrahydro-4H-5,8-epiminocyclohepta[b]thiophene-3-carboxamide [(+/−)-X6 and (+/−)-X7, mixture of atropisomers)

To a stirred mixture of atropisomers (+/−)-X4 and (+/−)-X5 (3.5:1) (500 mg, 1.05 mmol) in methylene chloride (20 mL) and toluene (3 mL) at room temperature under nitrogen was added trifluoroacetic acid (4.60 g, 40.3 mmol). After addition, the reaction mixture was stirred for 4 h and concentrated under reduced pressure. The resulting residue was mixed with saturated aqueous sodium bicarbonate (30 mL). The resulting aqueous mixture was extracted with 5% methanol/methylene chloride (4×60 mL). The combined organic extracts were dried over anhydrous sodium sulfate, filtered, and concentrated under reduced pressure. The resulting residue was purified by flash column chromatography on silica gel eluting with ammonium hydroxide/methanol/methylene chloride (1:14:85) to provide an inseparable atropisomers (+/−)-X6 and (+/−)-X7 (3.5:1) as a white solid (321 mg, 81%): MS (M+H) 377.

Step 4: (+/−)-2-[3-(4-Chlorophenyl)ureido]-5,6,7,8-tetrahydro-4H-5,8-epiminocyclohepta[b]thiophene-3-carboxamide hydrochloride [(+/−)-X8 and (+/−)-X9, mixture of atropisomers]

To a stirred mixture of atropisomers (+/−)-X6 and (+/−)-X7 (3.5:1) (37 mg, 0.10 mmol) in methanol at room temperature was added 1 M hydrochloric acid (2.0 mL, 2.0 mmol). The mixture was sonicated for 20 min, diluted with water, and lyophilized to provide a mixture of atropisomers (+/−)-X8 and (+/−)-X9 (3.5:1) as a white solid (39 mg, 96%): $^1$H NMR (300 MHz, DMSO-$d_6$) δ 11.05 (s, 0.18H), 10.29 and 10.28 (2 s, 1H), 10.13 (s, 0.82H), 9.52 (bs, 1H), 9.23 and 9.21 (2 s, 0.18H), 9.01 and 8.98 (2 s, 0.82H), 7.55-7.20 (m, 6H), 5.00-4.95 (m, 1H), 4.31 (bs, 1H), 3.26-3.16 (m, 1H), 2.98-2.72 (m, 1H), 2.28-2.05 (m, 3H), 1.84-1.76 (m, 1H). MS (M+H) 377.

Example 123

Preparation of (+/−)-2-[3-(4-Chlorophenyl)ureido]-5,8-dimethyl-5,6,7,8-tetrahydro-4H-5,8-epiminocyclohepta[b]thiophene-3-carboxamide trifluoroacetate

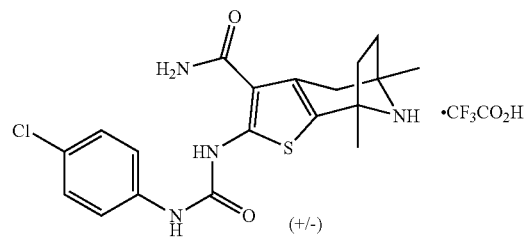 [SMILES: CC12CCC(C)(N1)c1sc(NC(=O)Nc3ccc(Cl)cc3)c(C(N)=O)c1C2 ; "·CF3CO2H"]

The title compound was prepared using a similar procedure as described in Example 122. MS (M+H) 405. $^1$H NMR (500 MHz, DMSO-$d_6$) δ 11.10 (s, 1H), 10.28 (s, 1H), 9.40-9.20 (m, 2H), 7.51-7.34 (m, 4H), 6.50 (bs, 2H), 3.20-3.05 (m, 2H), 2.25-1.90 (m, 4H), 1.76 (s, 3H), 1.57 (s, 3H).

Example 124

Preparation of (+/−)-2-[3-(4-chlorophenyl)ureido]-5,6,7,8-tetrahydro-4H-5,8-epiminocyclohepta[b]thiophene-3-carboxamide hydrochloride [(+/−)-X9, atropisomer B]

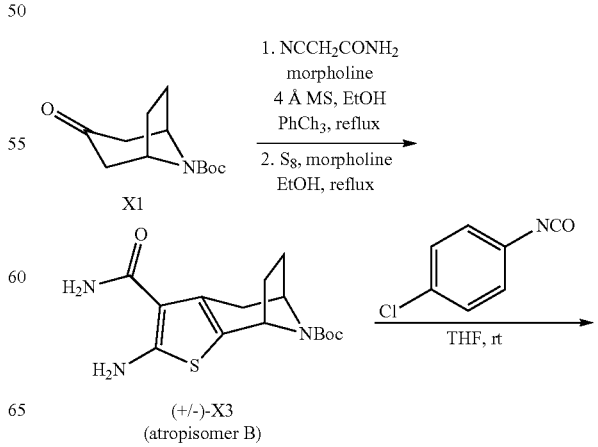

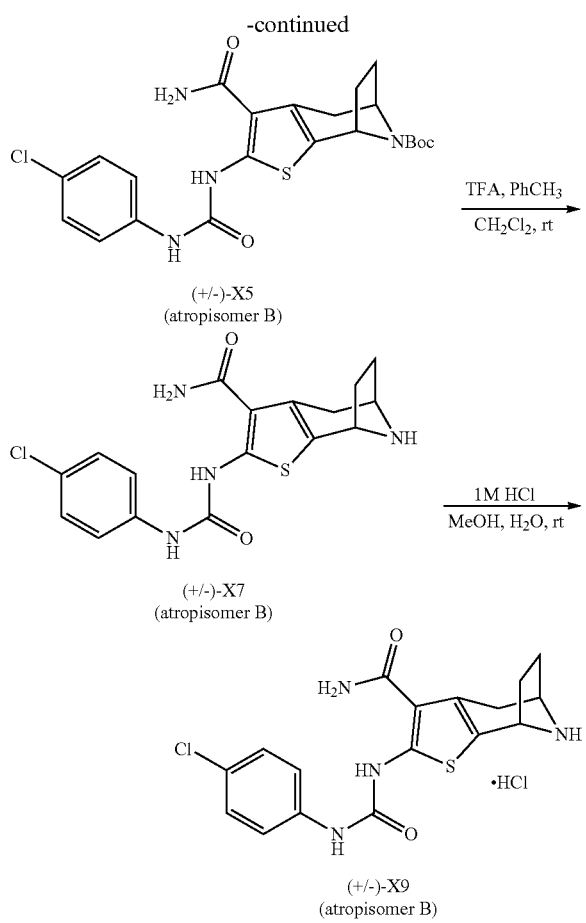

(+/−)-X5
(atropisomer B)

TFA, PhCH₃
CH₂Cl₂, rt (+/−)-X7
(atropisomer B)

1M HCl
MeOH, H₂O, rt (+/−)-X9
(atropisomer B)

Step 1: (+/−)-tert-Butyl 2-amino-3-carbamoyl-5,6,7,8-tetrahydro-4H-5,8-epiminocyclohepta[b]thiophene-9-carboxylate [(+/−)-X3, atropisomer B]

A stirred mixture of tert-butyl 3-oxo-8-azabicyclo[3.2.1]octane-8-carboxylate (X1, 7.50 g, 33.3 mmol), 2-cyanoacetamide (2.80 g, 33.3 mmol), 4 Å molecular sieves (8 g), and morpholine (4.35 g, 49.9 mmol) in ethanol (200 mL) and toluene (200 mL) was heated to reflux under nitrogen with Dean-Stark apparatus to remove water for 2 days. After this time, the reaction mixture was cooled to room temperature and filtered. The filter cake was washed with ethanol (30 mL). The combined filtrate was concentrated under reduced pressure. The resulting residue was purified by flash column chromatography on silica gel eluting with methanol/methylene chloride (1:9) to provide an intermediate as a yellow gum (1.67 g, 17%): ¹H NMR (300 MHz, DMSO-d₆) δ 7.93 (s, 1H), 7.74 (s, 1H), 4.26 (bs, 1H), 4.17 (bs, 1H), 2.79 (d, J=15.0 Hz, 1H), 2.65-2.50 (m, 2H), 2.40 (d, J=15.0 Hz, 1H), 1.92-1.83 (m, 2H), 1.50-1.39 (m, 11H). MS (M−H) 290.

A stirred mixture of the intermediate described above (6.51 g, 22.3 mmol), sulfur (931 mg, 29.0 mmol), and morpholine (5.84 g, 67.0 mmol) in ethanol (200 mL) was heated to reflux overnight under nitrogen. After this time, the reaction mixture was cooled to room temperature and concentrated under reduced pressure. The resulting residue was mixed with saturated aqueous sodium bicarbonate (300 mL) and extracted with methylene chloride (3×100 mL). The combined organic extracts were dried over anhydrous sodium sulfate, filtered, and concentrated under reduced pressure. The resulting residue was purified by flash column chromatography on silica gel eluting with ethyl acetate/hexanes (8:2) to provide atropisomer B (+/−)-X3 as a white solid (6.01 g, 83%): ¹H NMR (300 MHz, DMSO-d₆) δ 7.02 (s, 2H), 6.54 (bs, 2H), 4.62 (d, J=5.1 Hz, 1H), 4.30 (bs, 1H), 3.19 (d, J=15.3 Hz, 1H), 2.40-2.39 (m, 1H), 2.16-1.82 (m, 3H), 1.63-1.55 (m, 1H), 1.38 (s, 9H). MS (M+H) 324.

Step 2: (+/−)-tert-Butyl 3-carbamoyl-2-[3-(4-chlorophenyl)ureido]-5,6,7,8-tetrahydro-4H-5,8-epiminocyclohepta[b]thiophene-9-carboxylate [(+/−)-X5, atropisomer B]

To a stirred mixture of atropisomer (+/−)-X3 (2.00 g, 6.18 mmol) in tetrahydrofuran (100 mL) at room temperature under nitrogen was added 4-chlorophenyl isocyanate (1.14 g, 7.42 mmol). After addition, the reaction mixture was stirred overnight and concentrated under reduced pressure. The resulting residue was purified by flash column chromatography on silica gel eluting with ethyl acetate/hexanes (9:1) to provide atropisomer B (+/−)-X5 as pale yellow solid (2.69 g, 91%): ¹H NMR (300 MHz, DMSO-d₆) δ 11.09-11.01 (m, 1H), 10.20 (s, 1H), 7.62-6.70 (m, 6H), 4.82 (d, J=5.1 Hz, 1H), 4.38 (bs, 1H), 2.15-1.52 (m, 6H), 1.23 (bs, 9H). MS (M−H) 475.

Step 3: (+/−)-2-[3-(4-Chlorophenyl)ureido]-5,6,7,8-tetrahydro-4H-5,8-epiminocyclohepta[b]thiophene-3-carboxamide [(+/−)-X7, atropisomer B]

To a stirred mixture of atropisomer (+/−)-X5 (2.69 g, 5.64 mmol) in methylene chloride (50 mL) and toluene (20 mL) at room temperature was added trifluoroacetic acid (23.0 g, 202 mmol) dropwise over 5 min. After addition, the reaction mixture was stirred for 2.5 h and then concentrated under reduced pressure. The resulting residue was diluted with methylene chloride (200 mL) and then slowly quenched with saturated aqueous sodium bicarbonate (200 mL). The layers were separated and the aqueous layer was extracted with 5% methanol/methylene chloride (4×200 mL). The combined organics were dried over sodium sulfate, filtered, and concentrated under reduced pressure. The resulting residue was purified by flash column chromatography on silica gel eluting with ammonium hydroxide/methanol/methylene chloride (1:14:85) to provide atropisomer B (+/−)-X7 as a pale yellow solid (1.43 g, 67%): MS (M+H) 377.

Step 4: (+/−)-2-[3-(4-Chlorophenyl)ureido]-5,6,7,8-tetrahydro-4H-5,8-epiminocyclohepta[b]thiophene-3-carboxamide hydrochloride [(+/−)-X9, atropisomer B]

To a mixture of atropisomer (+/−)-X7 (226 mg, 0.600 mmol) in methanol (5 mL) at room temperature was added 1 M hydrochloric acid (1.20 mL, 1.20 mmol) dropwise over 2 min. After addition, the mixture was sonicated for 0.5 h, diluted with water (10 mL), and lyophilized to provide atropisomer B (+/−)-X9 as a white solid (243 mg, 98%): ¹H NMR (300 MHz, DMSO-d₆) δ 11.05 (s, 1H), 10.30 (s, 1H), 9.73 (bs, 1H), 9.26 and 9.23 (2 s, 1H), 7.70-6.75 (m, 6H), 4.94 (bs, 1H), 4.30 (bs, 1H), 3.35-3.27 (m, 1H), 3.00-2.91 (m, 1H), 2.26-2.05 (m, 3H), 1.89-1.80 (m, 1H). MS (M+H) 377.

Example 125

Preparation of (+/−)-2-[3-(4-chlorophenyl)ureido)-9-methyl-5,6,7,8-tetrahydro-4H-5,8-epiminocyclohepta[b]thiophene-3-carboxamide hydrochloride [(+/−)-Y4]

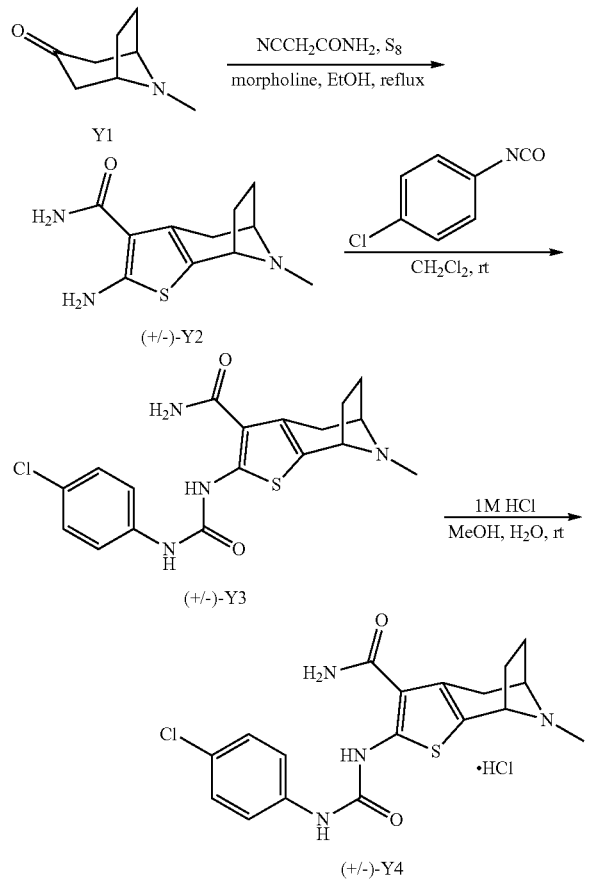

Step 1: (+/−)-2-Amino-9-methyl-5,6,7,8-tetrahydro-4H-5,8-epiminocyclohepta[b]thiophene-3-carboxamide [(+/−)-Y2]

A stirred mixture of tropinone (Y1, 3.00 g, 21.6 mmol), 2-cyanoacetamide (1.99 g, 23.7 mmol), sulphur (830 mg, 25.9 mmol), and morpholine (3.75 g, 43.0 mmol) in ethanol (80 mL) was heated to reflux under nitrogen for 4 h. After this time, the reaction mixture was cooled to room temperature and concentrated under reduced pressure. The resulting residue was diluted with saturated aqueous sodium bicarbonate (60 mL) and extracted with methylene chloride (3×150 mL). The combined organic extracts were dried over anhydrous sodium sulfate, filtered, and concentrated under reduced pressure. The resulting residue was purified by flash column chromatography on silica gel eluting with methanol/methylene chloride (1:9) to provide compound (+/−)-Y2 as a brown solid (396 mg, 8%): MS (M+H) 238.

Step 2: (+/−)-2-[3-(4-Chlorophenyl)ureido]-9-methyl-5,6,7,8-tetrahydro-4H-5,8-epiminocyclohepta[b]thiophene-3-carboxamide [(+/−)-Y3]

To a stirred mixture of compound (+/−)-Y2 (375 mg, 1.58 mmol) in methylene chloride (10 mL) at room temperature under nitrogen was added a solution of 4-chlorophenyl isocyanate (255 mg, 1.66 mmol) in methylene chloride (10 mL). The reaction mixture was stirred overnight and concentrated under reduced pressure. The resulting residue was purified by flash column chromatography on silica gel eluting with methanol/methylene chloride (15:85) to provide compound (+/−)-Y3 as an off-white solid (369 mg, 60%): $^1$H NMR (300 MHz, DMSO-d$_6$) δ 10.70 (bs, 1H), 10.05 (bs, 1H), 7.90-6.50 (m, 6H), 4.11 (bs, 1H), 2.99 (d, J=14.1 Hz, 1H), 2.35-1.95 (m, 7H), 1.79 (bs, 1H), 1.48 (bs, 1H). MS (M+H) 391.

Step 3: (+/−)-2-[3-(4-Chlorophenyl)ureido]-9-methyl-5,6,7,8-tetrahydro-4H-5,8-epiminocyclohepta[b]thiophene-3-carboxamide hydrochloride [(+/−)-Y4]

To a mixture of compound (+/−)-Y3 (78 mg, 0.20 mmol) in methanol (3 mL) at 0° C. was added 1 M hydrochloric acid (0.30 mL, 0.30 mmol). After addition, the mixture was stirred for 5 min, diluted with water (6 mL), and lyophilized to provide compound (+/−)-Y4 as a white solid (81 mg, 95%): $^1$H NMR (300 MHz, DMSO-d$_6$) δ 11.31 (bs, 0.38H), 10.34 and 10.32 (2 s, 1H), 10.22-10.18 (m, 1.62H), 7.60-7.33 (m, 6H), 4.94-4.82 (m, 1H), 4.19-4.09 (m, 1H), 3.38-3.16 (m, 1H), 2.86-2.68 (m, 4H), 2.49-2.08 (m, 3H), 1.89-1.79 (m, 1H). MS (M+H) 391.

Example 126

Preparation of (+/−)-2-[3-(4-Benzoylphenyl)ureido]-9-methyl-5,6,7,8-tetrahydro-4H-5,8-epiminocyclohepta[b]thiophene-3-carboxamide hydrochloride

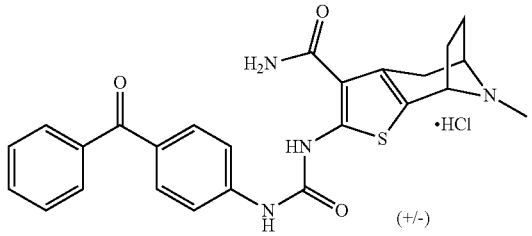 [SMILES: CN1C2CCC1c1sc(NC(=O)Nc3ccc(C(=O)c4ccccc4)cc3)c(C(N)=O)c1C2 ; Cl]

The title compound was prepared using a similar procedure as described in Example 125. MS (M+H) 461. $^1$H NMR (300 MHz, DMSO-d$_6$) δ 11.30 (bs, 0.37H), 10.53 and 10.50 (2 s, 1H), 10.44 and 10.42 (2 s, 1H), 10.23 (bs, 0.63H), 7.80-7.36 (m, 11H), 4.96-4.83 (m, 1H), 4.20-4.09 (m, 1H), 3.40-3.18 (m, 1H), 2.89-2.65 (m, 4H), 2.59-2.11 (m, 3H), 1.90-1.81 (m, 1H).

Example 127

Preparation of (−)-2-[3-(4-chlorophenyl)ureido]-9-methyl-5,6,7,8-tetrahydro-4H-5,8-epiminocyclohepta[b]thiophene-3-carboxamide hydrochloride [(−)-Z1]

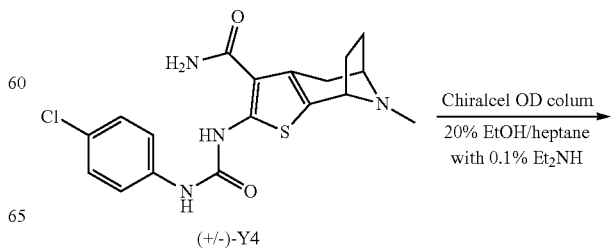

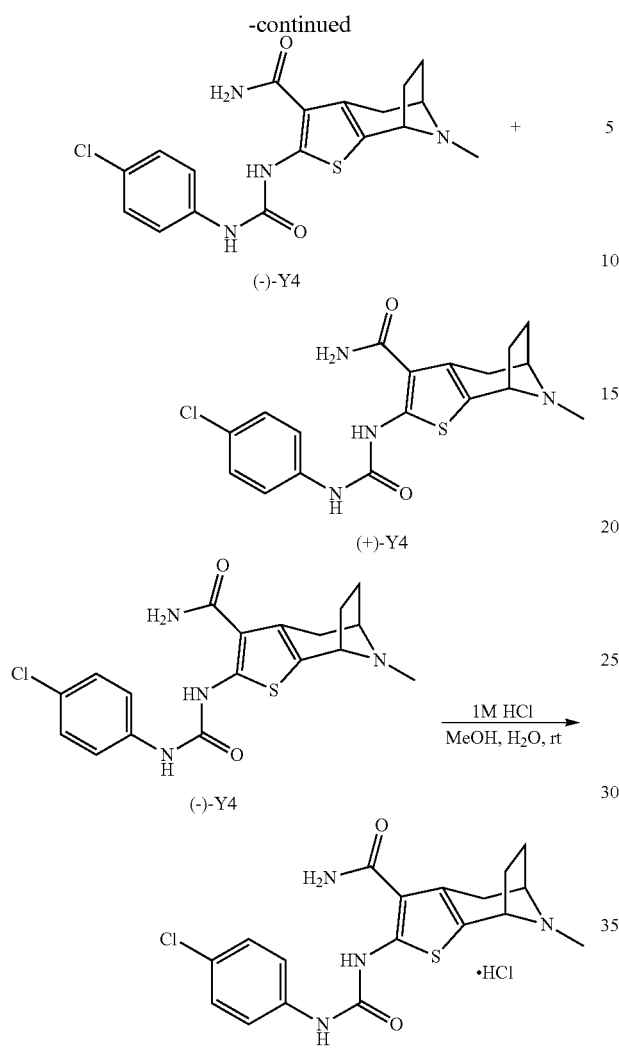

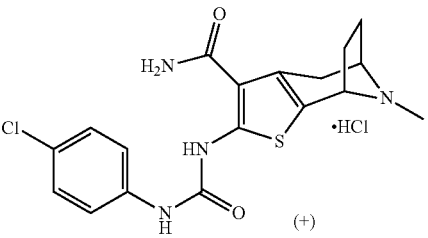 [SMILES: CN1C2CCC1c1sc(NC(=O)Nc3ccc(Cl)cc3)c(C(N)=O)c1C2 ; Cl]

Step 1: Chiral separation of (−)-2-[3-(4-chlorophenyl)ureido]-9-methyl-5,6,7,8-tetrahydro-4H-5,8-epiminocyclohepta[b]thiophene-3-carboxamide [(−)-Y4] and (+)-2-[3-(4-chlorophenyl)ureido]-9-methyl-5,6,7,8-tetrahydro-4H-5,8-epiminocyclohepta[b]thiophene-3-carboxamide [(+)-Y4]

Compound (+/−)-Y4 (720 mg) was separated by chiral preparative HPLC (20 μm CHIRALCEL OD, 5 cm×50 cm, 100 mL/min flow rate, 120 mg/injection) eluting with 0.1% diethylamine in 20% ethanol/heptane to provide (−)-Y4 as a white solid (268 mg, 37%); followed by (+)-Y4 (250 mg, 35%) as a white solid. Compound (−)-Y4: MS (M+H) 391. Compound (+)-Y4: MS (M+H) 391.

Step 2: (−)-2-[3-(4-Chlorophenyl)ureido]-9-methyl-5,6,7,8-tetrahydro-4H-5,8-epiminocyclohepta[b]thiophene-3-carboxamide hydrochloride [(−)-Z1]

To a stirred mixture of compound (−)-Y4 (240 mg, 0.610 mmol) in methanol (30 mL) at room temperature was added 1 M hydrochloric acid (1.25 mL, 1.25 mmol) dropwise. After addition, the mixture was stirred for 10 min. After this time, the mixture was diluted with water (10 mL) and lyophilized to provide compound (−)-Z1 as a white solid (255 mg, 97%): $^1$H NMR (300 MHz, DMSO-$d_6$) δ 11.24 (bs, 0.40H), 10.34 and 10.32 (2 s, 1H), 10.19-10.16 (m, 1.60H), 7.51-7.48 (m, 4H), 7.35 (d, J=9.0 Hz, 2H), 4.95-4.82 (m, 1H), 4.19-4.08 (m, 1H), 3.43-3.17 (m, 1H), 2.88-2.68 (m, 4H), 2.45-2.09 (m, 3H), 1.89-1.80 (m, 1H). MS (M+H) 391.

Example 128

Preparation of (+)-2-[3-(4-Chlorophenyl)ureido]-9-methyl-5,6,7,8-tetrahydro-4H-5,8-epiminocyclohepta[b]thiophene-3-carboxamide hydrochloride

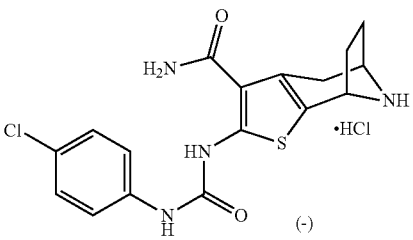 [SMILES: NC(=O)c1c(NC(=O)Nc2ccc(Cl)cc2)sc2c1CC1CCC2N1 ; Cl]

The title compound was prepared using a similar procedure as described in Example 127. MS (M+H) 391. $^1$H NMR (300 MHz, DMSO-$d_6$) δ 11.20 (bs, 0.34H), 10.34 and 10.31 (2 s, 1H), 10.18 (s, 1H), 10.16 (bs, 0.66H), 7.54-7.33 (m, 6H), 4.94-4.90 (m, 1H), 4.20-4.06 (m, 1H), 3.42-3.16 (m, 1H), 2.88-2.65 (m, 4H), 2.49-2.28 (m, 2H), 2.21-2.09 (m, 1H), 1.89-1.80 (m, 1H).

Example 129

Preparation of (−)-2-[3-(4-Chlorophenyl)ureido]-5,6,7,8-tetrahydro-4H-5,8-epiminocyclohepta[b]thiophene-3-carboxamide hydrochloride The title compound was prepared using a similar procedure as described in Example 127. MS (M+H) 377. $^1$H NMR (300 MHz, DMSO-$d_6$) δ 11.05 (s, 1H), 10.31 (s, 1H), 9.80 (bs, 1H), 9.26 (bs, 1H), 7.80-6.79 (m, 6H), 4.94 (bs, 1H), 4.30 (bs, 1H), 3.31 (d, J=15.3 Hz, 1H), 2.96 (d, J=16.5 Hz, 1H), 2.29-2.03 (m, 3H), 1.95-1.85 (m, 1H).

Example 130

Preparation of (+)-2-[3-(4-Chlorophenyl)ureido]-5,6,7,8-tetrahydro-4H-5,8-epiminocyclohepta[b]thiophene-3-carboxamide hydrochloride (atropisomer B)

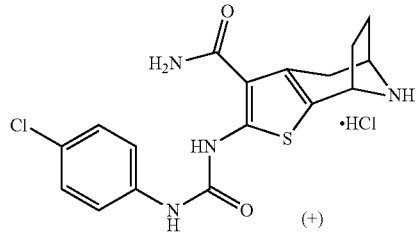

The title compound was prepared using a similar procedure as described in Example 127. MS (M+H) 377. ¹H NMR (300 MHz, DMSO-d₆) δ 11.04 (m, 1H), 10.31 (s, 1H), 9.83 (bs, 1H), 9.28 (bs, 1H), 7.75-6.90 (m, 6H), 4.94 (bs 1H), 4.30 (bs, 1H), 3.30-3.12 (m, 1H), 2.99-2.89 (m, 1H), 2.29-2.02 (m, 3H), 1.90-1.79 (m, 1H).

Example 131

Preparation of (+/−)-2-[3-(4-chlorophenyl)ureido]-9-(cyclohexylmethyl)-5,6,7,8-tetrahydro-4H-5,8-epiminocyclohepta[b]thiophene-3-carboxamide hydrochloride

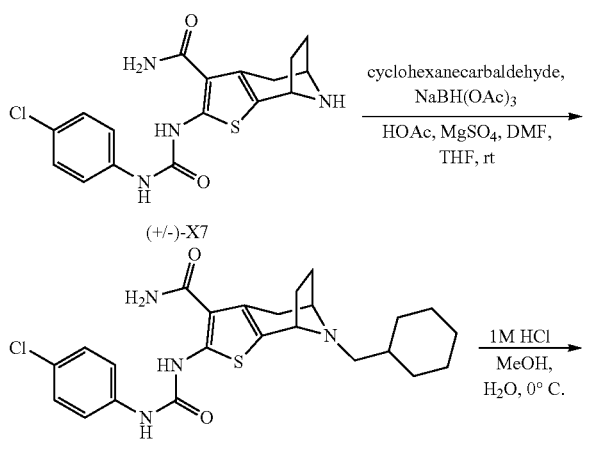

Step 1: (+/−)-2-[3-(4-Chlorophenyl)ureido]-9-(cyclohexylmethyl)-5,6,7,8-tetrahydro-4H-5,8-epiminocyclohepta[b]thiophene-3-carboxamide [(+/−)-AA1]

To a stirred mixture of compound (+/−)-X7 (151 mg, 0.401 mmol) in anhydrous tetrahydrofuran (6 mL) and anhydrous N,N-dimethylformamide (2 mL) at room temperature under nitrogen was added cyclohexanecarbaldehyde (225 mg, 2.00 mmol) followed with acetic acid (15.0 mg, 0.250 mmol) and anhydrous magnesium sulfate (1 g). The reaction mixture was stirred for 10 min. Then to the reaction mixture was added sodium triacetoxyborohydride (339 mg, 1.60 mmol) in one portion. The reaction mixture was stirred for another 2 h. After this time, the reaction was quenched by slow addition of saturated aqueous sodium bicarbonate (20 mL). The resulting mixture was filtered through a short silica gel plug. The filter cake was washed with 10% methanol/methylene chloride (3×20 mL) and filtered. The layers of the combined filtrate were separated and the aqueous layer was extracted with methylene chloride (3×30 mL). The combined organics were dried over anhydrous sodium sulfate, filtered, and concentrated under reduced pressure. The resulting residue was purified by flash column chromatography on silica gel eluting with methanol/methylene chloride (1:9) to provide compound (+/−)-AA1 as a white solid (128 mg, 68%): ¹H NMR (300 MHz, DMSO-d₆) δ 11.08 (s, 1H), 10.17 (s, 1H), 7.51 (dd, J=6.9 and 2.1 Hz, 2H), 7.49 (bs, 1H), 7.33 (dd, J=6.9 and 2.1 Hz, 2H), 6.77 (bs, 1H), 3.85 (d, J=3.9 Hz, 1H), 3.43-3.40 (m, 1H), 3.18-3.05 (m, 1H), 2.30-2.21 (m, 3H), 2.09-1.94 (m, 2H), 1.80-1.53 (m, 6H), 1.50-1.33 (m, 2H), 1.28-1.06 (m, 3H), 0.89-0.76 (m, 2H). MS (M+H) 473.

Step 2: (+/−)-2-[3-(4-Chlorophenyl)ureido)-9-(cyclohexylmethyl)-5,6,7,8-tetrahydro-4H-5,8-epiminocyclohepta[b]thiophene-3-carboxamide hydrochloride [(+/−)-AA2]

To a mixture of compound (+/−)-AA1 (120 mg, 0.250 mmol) in methanol (6 mL) at 0° C. was added 1 M hydrochloric acid (0.500 mL, 0.500 mmol). The mixture was stirred for 10 min, diluted with water (10 mL), lyophilized to provide compound (+/−)-AA2 as a white solid (118 mg, 91%): ¹H NMR (300 MHz, DMSO-d₆) δ 11.06 and 10.84 (2 s, 1H), 10.31 and 10.30 (2 s, 1H), 10.24 and 9.88 (2 bs, 1H), 7.70-6.70 (m, 6H), 5.00-4.96 (m, 1H), 4.23 (bs, 1H), 3.48-3.38 (m, 1H), 3.16-2.72 (m, 3H), 2.43-2.27 (m, 2H), 2.13-2.00 (m, 1H), 1.95-1.55 (m, 7H), 1.32-0.85 (m, 5H). MS (M+H) 473.

Example 132

Preparation of (+/−)-2-[3-(4-Chlorophenyl)ureido]-9-(cyclobutylmethyl)-5,6,7,8-tetrahydro-4H-5,8-epiminocyclohepta[b]thiophene-3-carboxamide hydrochloride

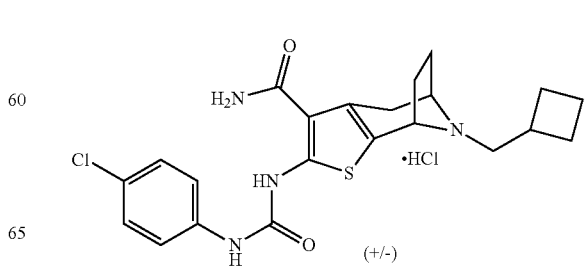

The title compound was prepared using a similar procedure as described in Example 131. MS (M+H) 445. $^1$H NMR (300 MHz, DMSO-d$_6$) δ 10.84 (bs, 0.69H), 10.32-9.94 (m, 2.31H), 7.59-7.00 (m, 6H), 4.89-4.78 (m, 1H), 4.21-4.12 (m, 1H), 3.25-2.72 (m, 5H), 2.48-1.53 (m, 10H).

Example 133

Preparation of (+/−)-2-[3-(4-Chlorophenyl)ureido]-9-ethyl-5,6,7,8-tetrahydro-4H-5,8-epiminocyclohepta[b]thiophene-3-carboxamide hydrochloride

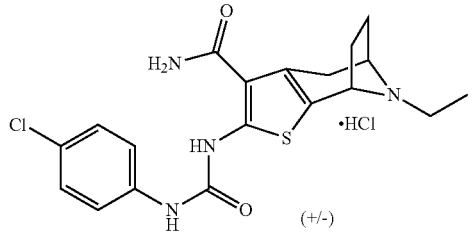 [SMILES: CCN1C2CCC1c1sc(NC(=O)Nc3ccc(Cl)cc3)c(C(N)=O)c1C2 ; Cl]

The title compound was prepared using a similar procedure as described in Example 131. MS (M+H) 405. $^1$H NMR (300 MHz, DMSO-d$_6$) δ 11.07 (s, 0.42H), 10.85 (bs, 0.58H), 10.82 (s, 0.58H), 10.31 and 10.29 (2 s, 1H), 10.14 (bs, 0.42H), 7.70-6.86 (m, 6H), 4.98 (bs, 1H), 4.31-4.19 (m, 1H), 3.41-3.32 (m, 1H), 3.16-3.00 (m, 3H), 2.38-2.20 (m, 2H), 2.15-2.05 (m, 1H), 1.89-1.82 (m, 1H), 1.30-1.21 (m, 3H).

Example 134

Preparation of (+/−)-Methyl 3-{3-carbamoyl-2-[3-(4-chlorophenyl)ureido]-5,6,7,8-tetrahydro-4H-5,8-epiminocyclohepta[b]thiophen-9-yl}-2,2-dimethyl-propanoate hydrochloride

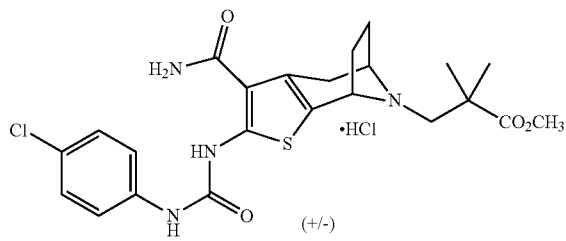 [SMILES: COC(=O)C(C)(C)CN1C2CCC1c1sc(NC(=O)Nc3ccc(Cl)cc3)c(C(N)=O)c1C2 ; Cl]

The title compound was prepared using a similar procedure as described in Example 131. MS (M+H) 491. $^1$H NMR (300 MHz, DMSO-d$_6$) δ 11.05 (s, 0.48H), 10.83 (s, 0.52H), 10.32 and 10.31 (2 s, 1H), 9.79 (bs, 0.52H), 9.66 (bs, 0.48H), 7.79-6.85 (m, 6H), 4.95-4.84 (m, 1H), 4.27 (bs, 1H), 3.70-3.51 (m, 3H), 3.49-2.86 (m, 4H), 2.55-1.85 (m, 4H), 1.33 and 1.31 (2 s, 3H), 1.27 (s, 3H).

Example 135

Preparation of 3-carbamoyl-2-[3-(4-chlorophenyl)ureido]-6-isobutyl-6-methyl-4,5,6,7-tetrahydrothieno[2,3-c]pyridin-6-ium iodide (BB2)

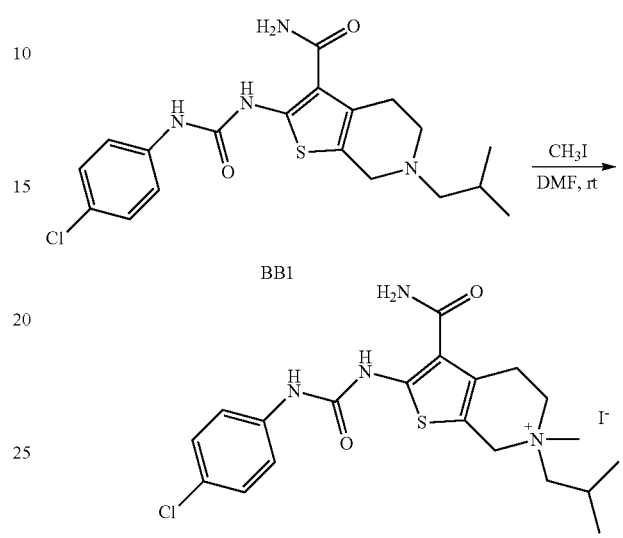

A solution of compound BB1 (30 mg, 0.074 mmol) and iodomethane (14 mg, 0.096 mmol) in N,N-dimethylformamide (1.5 mL) was stirred at room temperature for 18 h. After this time, the reaction mixture was concentrated under reduced pressure. The resulting residue was triturated with methylene chloride to afford compound BB2 as a light yellow solid (27 mg, 68%): $^1$H NMR (500 MHz, DMSO-d$_6$) δ 10.81 (s, 1H), 10.26 (s, 1H), 7.80-6.90 (m, 6H), 4.59 (s, 2H), 3.70-3.63 (m, 2H), 3.41-3.31 (m, 2H), 3.19-3.12 (m, 2H), 3.10 (s, 3H), 2.36-2.34 (m, 1H), 1.08 (d, J=6.8 Hz, 3H), 1.05 (d, J=6.8 Hz, 3H). MS (M) 421.

Example 136

Preparation of 3-Carbamoyl-2-[3-(4-chlorophenyl)ureido]-6-ethyl-6-methyl-4,5,6,7-tetrahydrothieno[2,3-c]pyridin-6-ium iodide

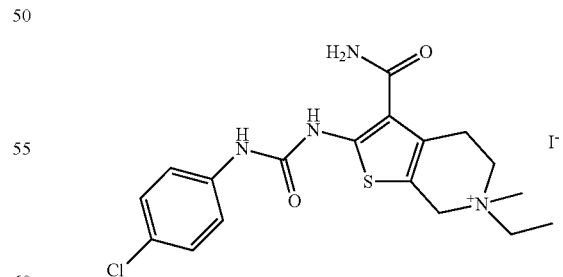

The title compound was prepared using a similar procedure as described in Example 135. MS (M) 393. $^1$H NMR (500 MHz, DMSO-d$_6$) δ 10.80 (s, 1H), 10.26 (s, 1H), 7.72-7.29 (m, 5H), 7.14 (bs, 1H), 4.59-4.52 (m, 2H), 3.71-3.58 (m, 2H), 3.51-3.42 (m, 2H), 3.20-3.10 (m, 2H), 3.05 (s, 3H), 1.34 (t, J=7.0 Hz, 3H).

Example 137

Preparation of 3-Carbamoyl-2-[3-(4-chlorophenyl)ureido]-5-ethyl-5-methyl-5,6-dihydro-4H-thieno[2,3-c]pyrrol-5-ium iodide

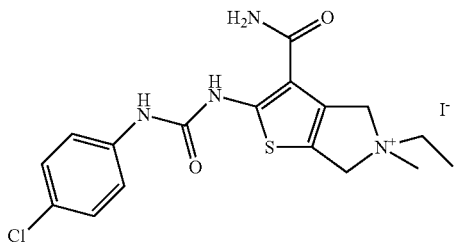 [SMILES: CC[N+]1(C)Cc2sc(NC(=O)Nc3ccc(Cl)cc3)c(C(N)=O)c2C1 ; [I-]]

The title compound was prepared using a similar procedure as described in Example 135. MS (M) 379. $^1$H NMR (500 MHz, DMSO-$d_6$) δ 11.14 (s, 1H), 10.37 (s, 1H), 7.70-6.90 (m, 6H), 5.00-4.97 (m, 1H), 4.88-4.82 (m, 2H), 4.73-4.68 (m, 1H), 3.72-3.66 (m, 2H), 3.25 (s, 3H), 1.31 (t, J=7.0 Hz, 3H).

Example 138

Preparation of 3'-Carbamoyl-2'-[3-(4-chlorophenyl)ureido]-5',7'-dihydro-4'H-spiro[pyrrolidine-1,6'-thieno[2,3-c]pyridin]-1-ium bromide

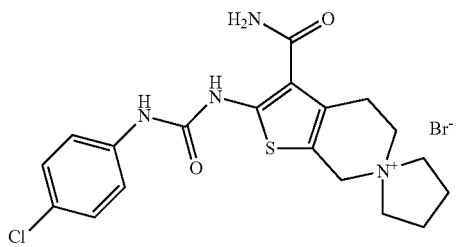 [SMILES: NC(=O)c1c(NC(=O)Nc2ccc(Cl)cc2)sc2c1CC[N+]1(CCCC1)C2 ; [Br-]]

The title compound was prepared using a similar procedure as described in Example 135. MS (M) 405. $^1$H NMR (500 MHz, DMSO-$d_6$) δ 10.81 (s, 1H), 10.26 (s, 1H), 7.71-6.99 (m, 6H), 4.60 (s, 2H), 3.74-3.69 (m, 2H), 3.63-3.50 (m, 4H), 3.22-3.16 (m, 2H), 2.18-2.10 (m, 4H).

Example 139

Preparation of 3-Carbamoyl-2-[3-(4-chlorophenyl)ureido]-6,6-diethyl-4,5,6,7-tetrahydrothieno[2,3-c]pyridin-6-ium iodide

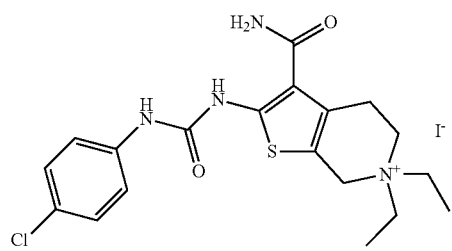 [SMILES: CC[N+]1(CC)CCc2c(sc(NC(=O)Nc3ccc(Cl)cc3)c2C(N)=O)C1 ; [I-]]

The title compound was prepared using a similar procedure as described in Example 135. MS (M) 407. $^1$H NMR (500 MHz, DMSO-$d_6$) δ 10.79 (s, 1H), 10.26 (s, 1H), 7.80-7.00 (m, 6H), 4.56 (s, 2H), 3.65-3.35 (m, 6H), 3.13-3.10 (m, 2H), 1.28 (t, J=7.5 Hz, 6H).

Example 140

Preparation of 3-Carbamoyl-2-[3-(4-chlorophenyl)ureido]-6-(cyclopropylmethyl)-6-methyl-4,5,6,7-tetrahydrothieno[2,3-c]pyridin-6-ium iodide

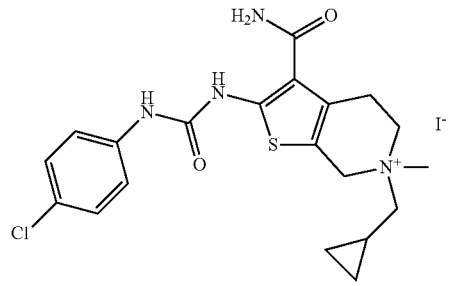 [SMILES: C[N+]1(CC2CC2)CCc2c(sc(NC(=O)Nc3ccc(Cl)cc3)c2C(N)=O)C1 ; [I-]]

The title compound was prepared using a similar procedure as described in Example 135. MS (M) 419. $^1$H NMR (500 MHz, DMSO-$d_6$) δ 10.80 (s, 1H), 10.26 (s, 1H), 7.80-7.00 (m, 6H), 4.62 (ABq, J=15.0 Hz, 2H), 3.75-3.41 (m, 3H), 3.28-3.12 (m, 6H), 1.26-1.23 (m, 1H), 0.75 (bs, 2H), 0.41 (bs, 2H).

Example 141

Preparation of 3-Carbamoyl-2-[3-(4-chlorophenyl)ureido]-6-(3-methoxypropyl)-6-methyl-4,5,6,7-tetrahydrothieno[2,3-c]pyridin-6-ium iodide

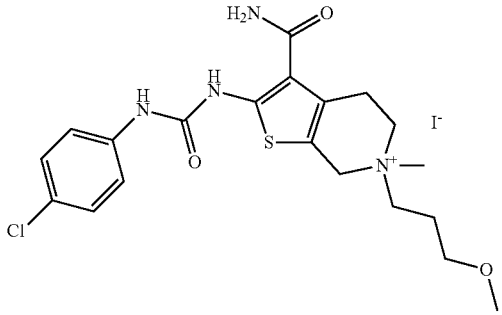 [SMILES: COCCC[N+]1(C)CCc2c(sc(NC(=O)Nc3ccc(Cl)cc3)c2C(N)=O)C1 ; [I-]]

The title compound was prepared using a similar procedure as described in Example 135. MS (M) 437. $^1$H NMR (500 MHz, DMSO-$d_6$) δ 10.81 (s, 1H), 10.26 (s, 1H), 7.70-7.00 (m, 6H), 4.65-4.59 (m, 2H), 3.69-3.41 (m, 6H), 3.26 (s, 3H), 3.16-3.14 (m, 2H), 3.09 (s, 3H), 2.09-2.02 (m, 2H).

Example 142

Preparation of 3-Carbamoyl-2-[3-(4-chlorophenyl)ureido]-6-methyl-6-(oxetan-3-yl)-4,5,6,7-tetrahydrothieno[2,3-c]pyridin-6-ium iodide

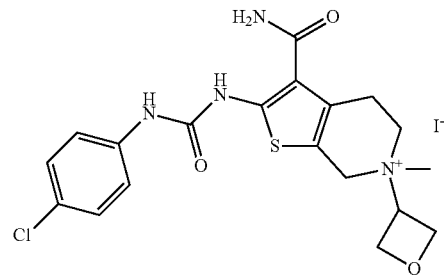 [SMILES: C[N+]1(C2COC2)CCc2c(sc(NC(=O)Nc3ccc(Cl)cc3)c2C(N)=O)C1 ; [I-]]

The title compound was prepared using a similar procedure as described in Example 135. MS (M) 421. $^1$H NMR (500 MHz, DMSO-$d_6$) δ 10.80 (s, 1H), 10.27 (s, 1H), 7.80-7.00 (m, 6H), 5.05-4.61 (m, 7H), 3.71-3.58 (m, 2H), 3.25-3.08 (m, 5H).

Example 143

Preparation of 3-Carbamoyl-2-[3-(4-chlorophenyl) ureido]-6-methyl-6-(tetrahydro-2H-pyran-4-yl)-4,5,6,7-tetrahydrothieno[2,3-c]pyridin-6-ium iodide

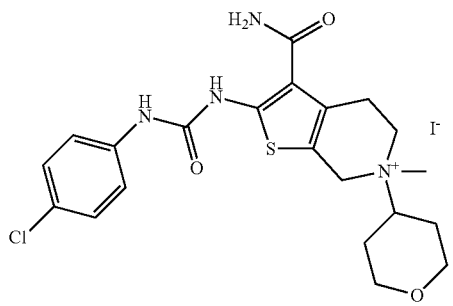 [SMILES: C[N+]1(C2CCOCC2)CCc2c(sc(NC(=O)Nc3ccc(Cl)cc3)c2C(N)=O)C1 ; [I-]]

The title compound was prepared using a similar procedure as described in Example 135. MS (M) 449. $^1$H NMR (500 MHz, DMSO-$d_6$) δ 10.82 (s, 1H), 10.27 (s, 1H), 7.80-7.00 (m, 6H), 4.71-4.48 (m, 2H), 4.07-3.35 (m, 7H), 3.16 (bs, 2H), 2.98 (s, 3H), 2.14-1.80 (m, 4H).

Example 144

Preparation of 3-Carbamoyl-2-[3-(4-chlorophenyl) ureido]-6-(2-hydroxyethyl)-6-methyl-4,5,6,7-tetrahydrothieno[2,3-c]pyridin-6-ium iodide

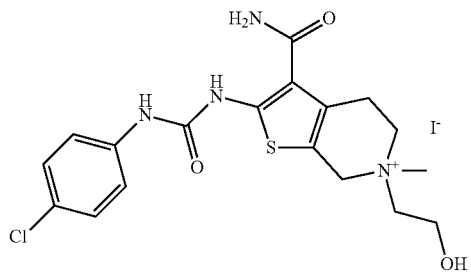 [SMILES: C[N+]1(CCO)CCc2c(sc(NC(=O)Nc3ccc(Cl)cc3)c2C(N)=O)C1 ; [I-]]

The title compound was prepared using a similar procedure as described in Example 135. MS (M) 409. $^1$H NMR (500 MHz, DMSO-$d_6$) δ 10.82 (s, 1H), 10.26 (s, 1H), 7.80-7.00 (m, 6H), 5.35 (s, 1H), 4.65 (ABq, J=15.5 Hz, 2H), 3.93-3.49 (m, 6H), 3.18-3.16 (m, 5H).

Example 145

Preparation of 3-Carbamoyl-2-[3-(4-chlorophenyl) ureido]-6-(cyclobutylmethyl)-6-methyl-4,5,6,7-tetrahydrothieno[2,3-c]pyridin-6-ium iodide

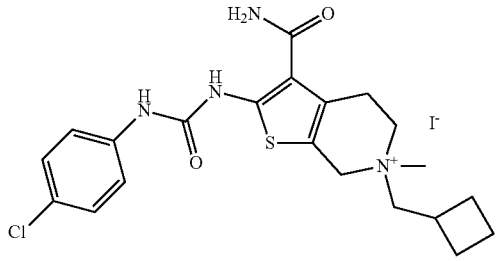 [SMILES: C[N+]1(CC2CCC2)CCc2c(sc(NC(=O)Nc3ccc(Cl)cc3)c2C(N)=O)C1 ; [I-]]

The title compound was prepared using a similar procedure as described in Example 135. MS (M) 433. $^1$H NMR (500 MHz, DMSO-$d_6$) δ 10.80 (s, 1H), 10.26 (s, 1H), 7.80-7.00 (m, 6H), 4.51 (s, 2H), 3.65-3.45 (m, 4H), 3.14 (bs, 2H), 3.03 (s, 3H), 2.98-2.90 (m, 1H), 2.20-1.70 (m, 6H).

Example 146

Preparation of 3'-Carbamoyl-2'-[3-(4-chlorophenyl) ureido]-5',7'-dihydro-4'H-spiro[morpholine-4,6'-thieno[2,3-c]pyridin]-4-ium iodide

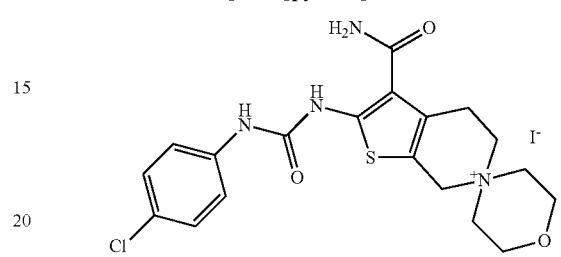

The title compound was prepared using a similar procedure as described in Example 135. MS (M) 421. $^1$H NMR (500 MHz, DMSO-$d_6$) δ 10.80 (s, 1H), 10.27 (s, 1H), 7.80-6.90 (m, 6H), 4.80 (s, 2H), 4.15-3.85 (m, 6H), 3.58-3.50 (m, 4H), 3.18 (bs, 2H).

Example 147

Preparation of 6-(2-tert-Butoxy-2-oxoethyl)-3-carbamoyl-2-[3-(4-chlorophenyl)ureido]-6-methyl-4,5,6,7-tetrahydrothieno[2,3-c]pyridin-6-ium iodide

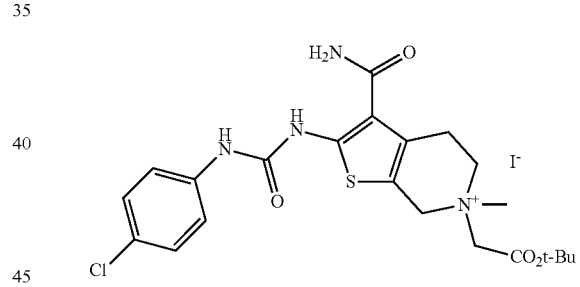

The title compound was prepared using a similar procedure as described in Example 135. MS (M) 479. $^1$H NMR (500 MHz, DMSO-$d_6$) δ 10.79 (s, 1H), 10.27 (s, 1H), 7.80-7.00 (m, 6H), 4.74 (ABq, J=16.0 Hz, 2H), 4.38 (s, 2H), 3.96-3.74 (m, 2H), 3.29 (s, 3H), 3.19-3.16 (m, 2H), 1.48 (s, 9H).

Example 148

Preparation of 3-Carbamoyl-2-[3-(4-chlorobenzyl) ureido]-6-ethyl-6-methyl-4,5,6,7-tetrahydrothieno[2,3-c]pyridin-6-ium iodide

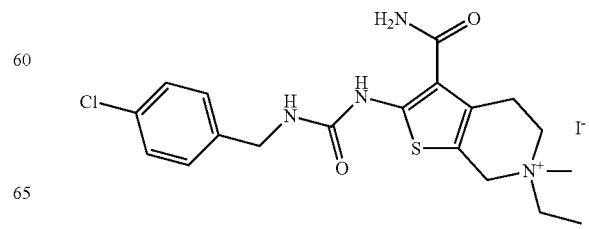

The title compound was prepared using a similar procedure as described in Example 135. MS (M) 407. $^1$H NMR (500 MHz, DMSO-d$_6$) δ 10.52 (s, 1H), 8.27 (s, 1H), 7.80-6.90 (m, 6H), 4.55-4.45 (m, 2H), 4.28 (s, 2H), 3.66-3.43 (m, 4H), 3.11-3.09 (m, 2H), 3.03 (s, 3H), 1.32 (t, J=7.0 Hz, 3H).

Example 149

Preparation of 3-Carbamoyl-6-(3-carboxypropyl)-2-[3-(4-chlorophenyl)ureido]-6-methyl-4,5,6,7-tetrahydrothieno[2,3-c]pyridin-6-ium trifluoroacetate

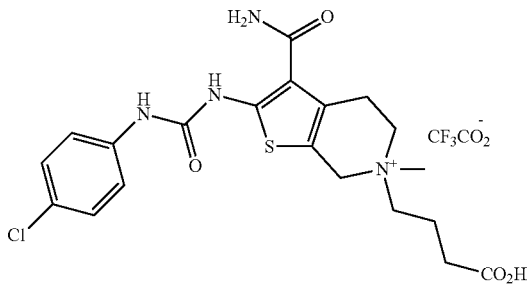

The title compound was prepared using a similar procedure as described in Example 135. MS (M) 451. $^1$H NMR (500 MHz, DMSO-d$_6$) δ 12.26 (bs, 1H), 10.84 (s, 1H), 10.27 (s, 1H), 7.80-7.00 (m, 6H), 4.60 (s, 2H), 3.70-3.35 (m, 4H), 3.15 (bs, 2H), 3.11 (s, 3H), 2.36-1.95 (m, 4H).

Example 150

Preparation of 3-Carbamoyl-2-[3-(4-cyanophenyl)ureido]-6-ethyl-6-methyl-4,5,6,7-tetrahydrothieno[2,3-c]pyridin-6-ium iodide

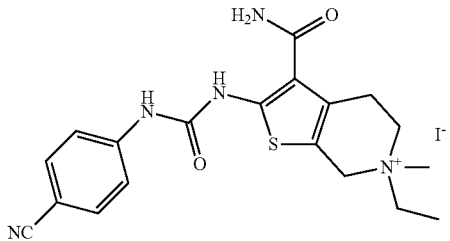 [SMILES: CC[N+]1(C)CCc2c(sc(NC(=O)Nc3ccc(C#N)cc3)c2C(N)=O)C1 ; [I-]]

The title compound was prepared using a similar procedure as described in Example 135. MS (M) 384. $^1$H NMR (500 MHz, DMSO-d$_6$) δ 9.94 (s, 1H), 9.09 (s, 1H), 7.75-7.54 (m, 4H), 6.54 (bs, 1H), 4.41-4.33 (m, 2H), 3.60-3.35 (m, 4H), 3.29-3.10 (m, 2H), 3.00 (s, 3H), 1.31 (t, J=7.5 Hz, 3H).

Example 151

Preparation of 6-(3-tert-Butoxy-3-oxopropyl)-3-carbamoyl-2-[3-(4-chlorophenyl)ureido]-6-methyl-4,5,6,7-tetrahydrothieno[2,3-c]pyridin-6-ium iodide

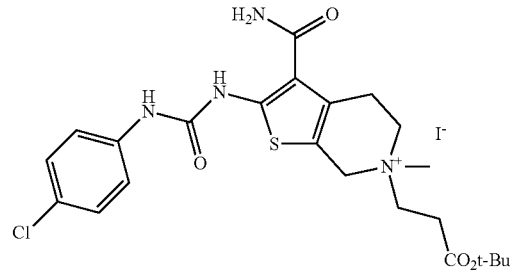 [SMILES: CC(C)(C)OC(=O)CC[N+]1(C)CCc2c(sc(NC(=O)Nc3ccc(Cl)cc3)c2C(N)=O)C1 ; [I-]]

The title compound was prepared using a similar procedure as described in Example 135. MS (M) 493. $^1$H NMR (500 MHz, DMSO-d$_6$) δ 10.81 (s, 1H), 10.27 (s, 1H), 7.80-6.90 (m, 6H), 4.60 (ABq, J=16.0 Hz, 2H), 3.75-3.60 (m, 4H), 3.17-3.15 (m, 2H), 3.08 (s, 3H), 2.97-2.94 (m, 2H), 1.44 (s, 9H).

Example 152

Preparation of 3-Carbamoyl-2-[3-(4-chlorophenyl)ureido]-6-(cyclohexylmethyl)-6-methyl-4,5,6,7-tetrahydrothieno[2,3-c]pyridin-6-ium iodide

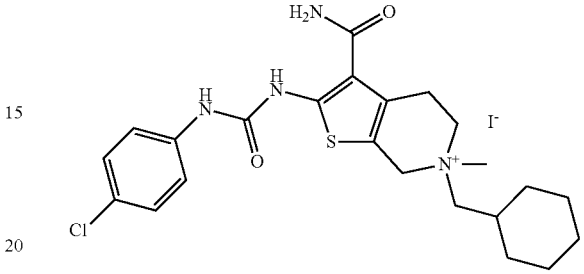

The title compound was prepared using a similar procedure as described in Example 135. MS (M) 461. $^1$H NMR (500 MHz, DMSO-d$_6$) δ 10.81 (s, 1H), 10.26 (s, 1H), 7.80-7.00 (m, 6H), 4.58 (s, 2H), 3.75-3.60 (m, 2H), 3.28-3.12 (m, 4H), 3.09 (s, 3H), 2.10-1.55 (m, 6H), 1.40-1.00 (m, 5H).

Example 153

Preparation of 3-Carbamoyl-2-[3-(4-chlorophenyl)ureido]-6-(cyclopentylmethyl)-6-methyl-4,5,6,7-tetrahydrothieno[2,3-c]pyridin-6-ium iodide

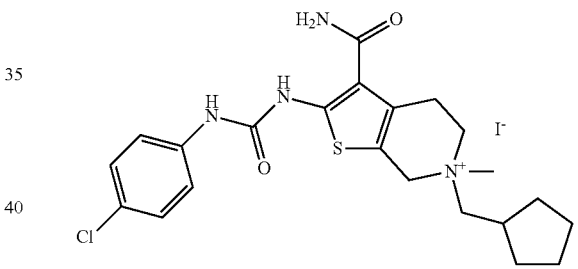

The title compound was prepared using a similar procedure as described in Example 135. MS (M) 447. $^1$H NMR (500 MHz, DMSO-d$_6$) δ 10.81 (s, 1H), 10.26 (s, 1H), 7.80-7.00 (m, 6H), 4.58 (s, 2H), 3.70-3.46 (m, 4H), 3.17-3.14 (m, 2H), 3.10 (s, 3H), 2.42-2.39 (m, 1H), 1.99-1.20 (m, 8H).

Example 154

Preparation of 6-(4-tert-Butoxy-4-oxobutyl)-3-carbamoyl-2-[3-(4-chlorophenyl)ureido]-6-methyl-4,5,6,7-tetrahydrothieno[2,3-c]pyridin-6-ium trifluoroacetate

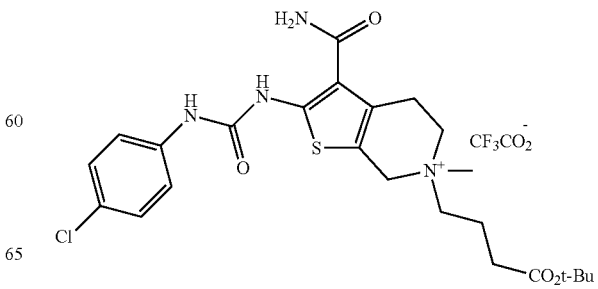

The title compound was prepared using a similar procedure as described in Example 135. MS (M) 507. $^1$H NMR (500 MHz, DMSO-d$_6$) δ 10.83 (s, 1H), 10.27 (s, 1H), 7.80-6.90 (m, 6H), 4.59 (s, 2H), 3.68-3.37 (m, 4H), 3.16-3.14 (m, 2H), 3.11 (s, 3H), 2.35-1.97 (m, 4H), 1.41 (s, 9H).

Example 155

Preparation of 6-(5-tert-Butoxy-5-oxopentyl)-3-carbamoyl-2-[3-(4-chlorophenyl)ureido]-6-methyl-4,5,6,7-tetrahydrothieno[2,3-c]pyridin-6-ium iodide

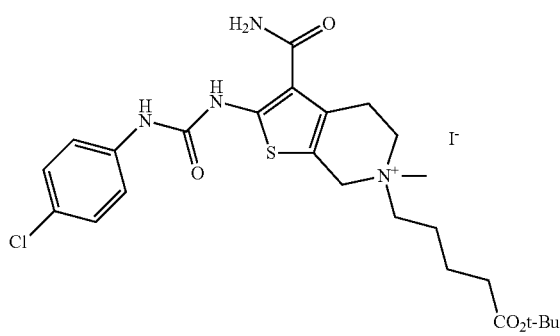 [SMILES: CC(C)(C)OC(=O)CCCC[N+]1(C)CCc2c(sc(NC(=O)Nc3ccc(Cl)cc3)c2C(N)=O)C1 ; [I-]]

The title compound was prepared using a similar procedure as described in Example 135. MS (M) 521. $^1$H NMR (500 MHz, DMSO-d$_6$) δ 10.80 (s, 1H), 10.26 (s, 1H), 7.80-6.90 (m, 6H), 4.56 (s, 2H), 3.70-3.36 (m, 4H), 3.15 (bs, 2H), 3.08 (s, 3H), 2.30-2.27 (m, 2H), 1.80-1.50 (m, 4H), 1.41 (s, 9H).

Example 156

Preparation of 6-(6-tert-Butoxy-6-oxohexyl)-3-carbamoyl-2-[3-(4-chlorophenyl)ureido]-6-methyl-4,5,6,7-tetrahydrothieno[2,3-c]pyridin-6-ium iodide

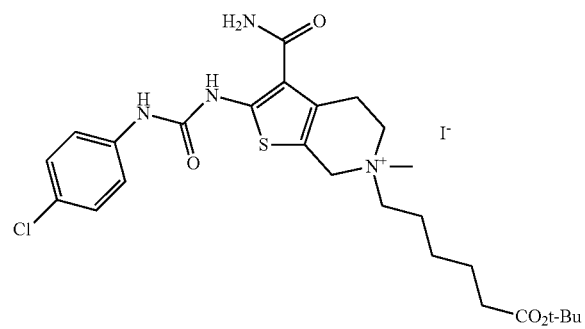 [SMILES: CC(C)(C)OC(=O)CCCCC[N+]1(C)CCc2c(sc(NC(=O)Nc3ccc(Cl)cc3)c2C(N)=O)C1 ; [I-]]

The title compound was prepared using a similar procedure as described in Example 135. MS (M) 535. $^1$H NMR (500 MHz, DMSO-d$_6$) δ 10.81 (s, 1H), 10.26 (s, 1H), 7.80-7.00 (m, 6H), 4.60-4.50 (m, 2H), 3.68-3.35 (m, 4H), 3.15 (bs, 2H), 3.08 (s, 3H), 2.25-2.22 (m, 2H), 1.78-1.53 (m, 4H), 1.40 (s, 9H), 1.32-1.27 (m, 2H).

Example 157

Preparation of 6-(3-Amino-3-oxopropyl)-3-carbamoyl-2-[3-(4-chlorophenyl)ureido]-6-methyl-4,5,6,7-tetrahydrothieno[2,3-c]pyridin-6-ium iodide

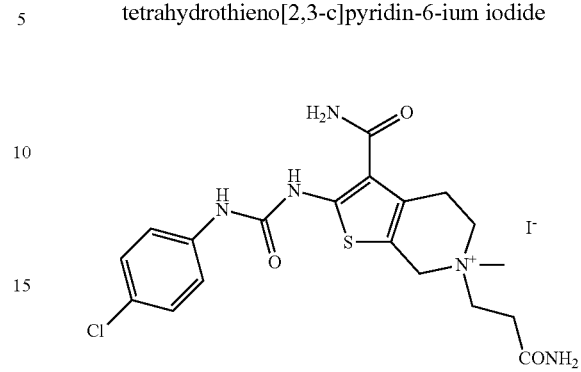

The title compound was prepared using a similar procedure as described in Example 135. MS (M) 436. $^1$H NMR (500 MHz, DMSO-d$_6$) δ 10.80 (s, 1H), 10.26 (s, 1H), 7.80-7.00 (m, 8H), 4.63-4.55 (m, 2H), 3.73-3.61 (m, 4H), 3.16 (bs, 2H), 3.07 (s, 3H), 2.74-2.69 (m, 2H).

Example 158

Preparation of 3-Carbamoyl-2-[3-(4-chlorophenyl)ureido]-6-(4-methoxy-4-oxobutyl)-6-methyl-4,5,6,7-tetrahydrothieno[2,3-c]pyridin-6-ium iodide

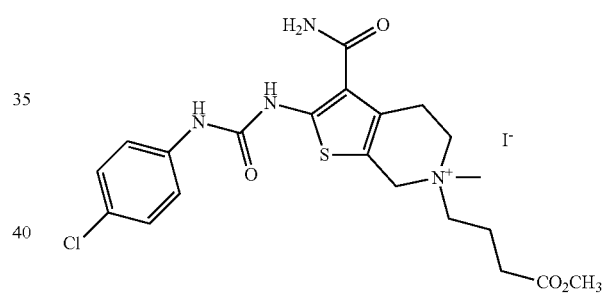

The title compound was prepared using a similar procedure as described in Example 135. MS (M) 465. $^1$H NMR (500 MHz, DMSO-d$_6$) δ 10.82 (s, 1H), 10.26 (s, 1H), 7.80-7.00 (m, 6H), 4.59 (s, 2H), 3.67-3.62 (m, 5H), 3.40-3.37 (m, 2H), 3.15 (bs, 2H), 3.11 (s, 3H), 2.47-2.03 (m, 4H).

Example 159

Preparation of 3-Carbamoyl-2-[3-(4-chlorophenyl)ureido]-6-(3-isopropoxy-3-oxopropyl)-6-methyl-4,5,6,7-tetrahydrothieno[2,3-c]pyridin-6-ium iodide

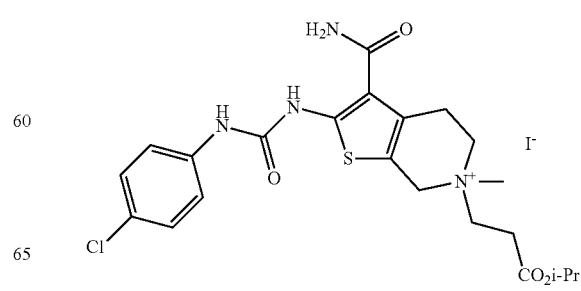

151

The title compound was prepared using a similar procedure as described in Example 135. MS (M) 479. $^1$H NMR (500 MHz, DMSO-d$_6$) δ 10.81 (s, 1H), 10.27 (s, 1H), 7.80-7.00 (m, 6H), 4.99-4.91 (m, 1H), 4.62 (ABq, J=15.0 Hz, 2H), 3.73-3.65 (m, 4H), 3.16 (s, 2H), 3.08 (s, 3H), 3.03-2.99 (m, 2H), 1.22 (d, J=6.5 Hz, 6H).

Example 160

Preparation of 3-Carbamoyl-2-[3-(4-chlorophenyl)ureido]-6-(3-ethoxy-3-oxopropyl)-6-methyl-4,5,6,7-tetrahydrothieno[2,3-c]pyridin-6-ium chloride iodide

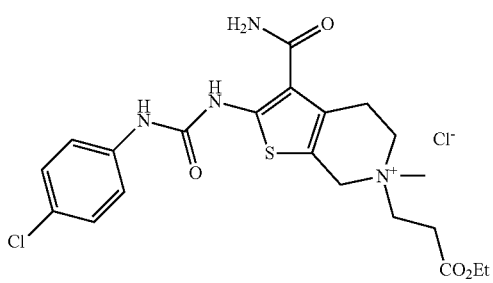 [SMILES: CCOC(=O)CC[N+]1(C)CCc2c(sc(NC(=O)Nc3ccc(Cl)cc3)c2C(N)=O)C1 ; [Cl-]]

The title compound was prepared using a similar procedure as described in Example 135. MS (M) 465. $^1$H NMR (500 MHz, DMSO-d$_6$) δ 10.79 (s, 1H), 10.31 (s, 1H), 7.80-7.00 (m, 6H), 4.68-4.59 (m, 2H), 4.13 (q, J=7.0 Hz, 2H), 3.74-3.64 (m, 4H), 3.17 (s, 2H), 3.10 (s, 3H), 3.06-3.03 (m, 2H), 1.22 (t, J=7.0 Hz, 3H).

Example 161

Preparation of 3-Carbamoyl-2-[3-(4-chlorophenyl)ureido]-6-(4-ethoxy-4-oxobutyl)-6-methyl-4,5,6,7-tetrahydrothieno[2,3-c]pyridin-6-ium iodide

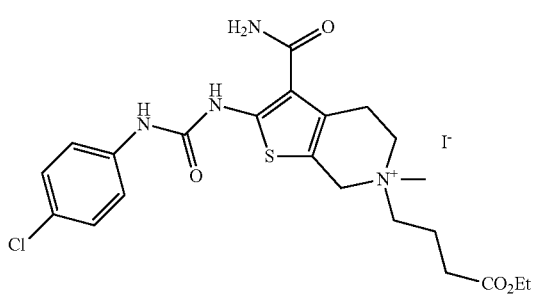 [SMILES: CCOC(=O)CCC[N+]1(C)CCc2c(sc(NC(=O)Nc3ccc(Cl)cc3)c2C(N)=O)C1 ; [I-]]

The title compound was prepared using a similar procedure as described in Example 135. MS (M) 479. $^1$H NMR (500 MHz, DMSO-d$_6$) δ 10.82 (s, 1H), 10.26 (s, 1H), 7.80-6.90 (m, 6H), 4.59 (bs, 2H), 4.08 (q, J=7.0 Hz, 2H), 3.67-3.37 (m, 4H), 3.15 (bs, 2H), 3.11 (s, 3H), 2.44-2.03 (m, 4H), 1.19 (t, J=7.0 Hz, 3H).

152

Example 162

Preparation of 3-Carbamoyl-2-[3-(4-chlorophenyl)ureido]-6,6-dimethyl-4,5,6,7-tetrahydrothieno[2,3-c]pyridin-6-ium trifluoroacetate

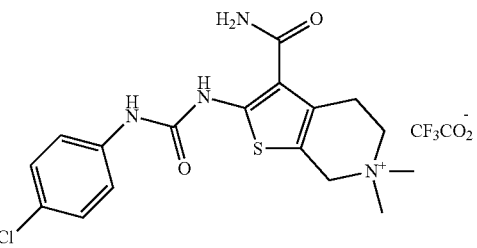

The title compound was prepared using a similar procedure as described in Example 135. MS (M) 379. $^1$H NMR (500 MHz, DMSO-d$_6$) δ 10.81 (s, 1H), 10.27 (s, 1H), 7.80-6.90 (m, 6H), 4.57 (s, 2H), 3.65-3.63 (m, 2H), 3.17-3.15 (m, 8H).

Example 163

Preparation of 6-[3-(tert-Butoxycarbonyl)cyclobutyl]-3-carbamoyl-2-[3-(4-chlorophenyl)ureido]-6-methyl-4,5,6,7-tetrahydrothieno[2,3-c]pyridin-6-ium iodide

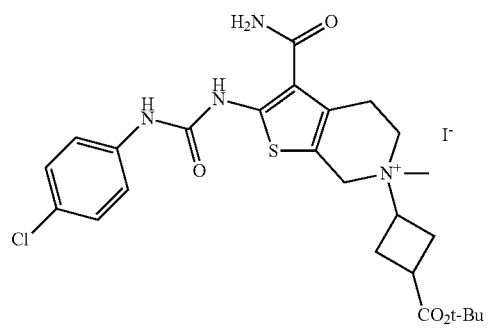 [SMILES: CC(C)(C)OC(=O)C1CC([N+]2(C)CCc3c(sc(NC(=O)Nc4ccc(Cl)cc4)c3C(N)=O)C2)C1 ; [I-]]

The title compound was prepared using a similar procedure as described in Example 135. MS (M) 519. $^1$H NMR (500 MHz, DMSO-d$_6$) δ 10.79 (s, 1H), 10.26 (s, 1H), 7.80-6.90 (m, 6H), 4.55-4.45 (m, 2H), 4.18-3.47 (m, 3H), 3.20-3.05 (m, 2H), 3.01 (s, 3H), 2.81-2.59 (m, 3H), 2.43-2.36 (m, 2H), 1.43 (s, 9H).

Example 164

Preparation of 3-Carbamoyl-2-[3-(4-chlorophenyl)ureido]-6-[3-(isopropylamino)-3-oxopropyl]-6-methyl-4,5,6,7-tetrahydrothieno[2,3-c]pyridin-6-ium trifluoroacetate

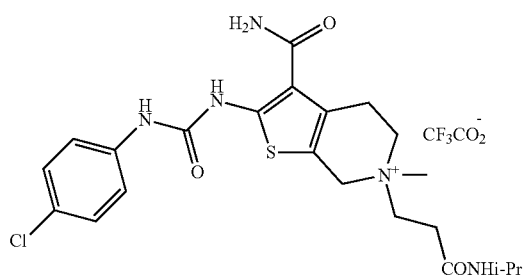

The title compound was prepared using a similar procedure as described in Example 135. MS (M) 478. ¹H NMR (500 MHz, DMSO-d₆) δ 10.81 (s, 1H), 10.27 (s, 1H), 8.02 (d, J=6.0 Hz, 1H), 7.80-7.00 (m, 6H), 4.59-4.53 (m, 2H), 3.87-3.62 (m, 5H), 3.17 (bs, 2H), 3.06 (s, 3H), 2.71-2.65 (m, 2H), 1.07 (d, J=6.5 Hz, 6H).

Example 165

Preparation of 3-Carbamoyl-2-[3-(4-chlorophenyl)ureido]-6-[4-(dimethylamino)-4-oxobutyl]-6-methyl-4,5,6,7-tetrahydrothieno[2,3-c]pyridin-6-ium trifluoroacetate

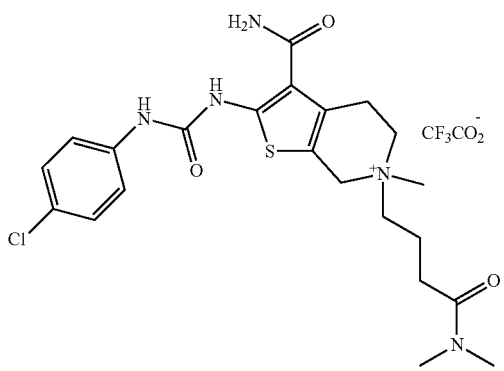

The title compound was prepared using a similar procedure as described in Example 135. MS (M) 478. ¹H NMR (500 MHz, DMSO-d₆) δ 10.82 (s, 1H), 10.27 (s, 1H), 7.80-6.90 (m, 6H), 4.60 (s, 2H), 3.68-3.15 (m, 6H), 3.11 (s, 3H), 2.95 (s, 3H), 2.83 (s, 3H), 2.42-1.98 (m, 4H).

Example 166

Preparation of 3-Carbamoyl-2-[3-(4-chlorophenyl)ureido]-6-[4-(isopropylamino)-4-oxobutyl]-6-methyl-4,5,6,7-tetrahydrothieno[2,3-c]pyridin-6-ium trifluoroacetate

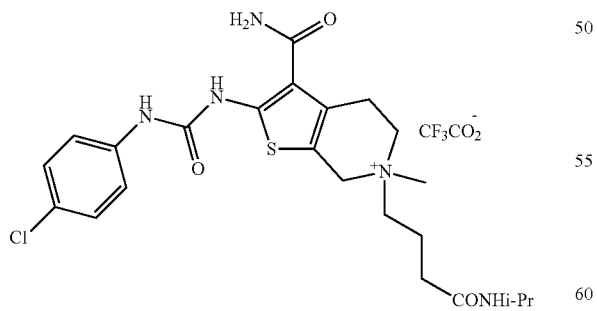

The title compound was prepared using a similar procedure as described in Example 135. MS (M) 492. ¹H NMR (500 MHz, DMSO-d₆) δ 10.82 (s, 1H), 10.27 (s, 1H), 7.80-6.90 (m, 7H), 4.59 (s, 2H), 3.86-3.38 (m, 5H), 3.17-3.15 (m, 2H), 3.10 (s, 3H), 2.15-1.95 (m, 4H), 1.05-1.02 (m, 6H).

Example 167

Preparation of 6-(4-Amino-4-oxobutyl)-3-carbamoyl-2-[3-(4-chlorophenyl)ureido]-6-methyl-4,5,6,7-tetrahydrothieno[2,3-c]pyridin-6-ium trifluoroacetate

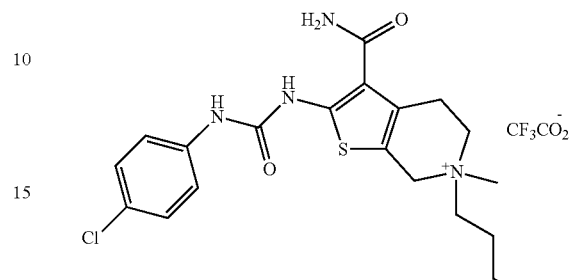

The title compound was prepared using a similar procedure as described in Example 135. MS (M) 450. ¹H NMR (500 MHz, DMSO-d₆) δ 10.81 (s, 1H), 10.27 (s, 1H), 7.80-6.80 (m, 8H), 4.59 (s, 2H), 3.68-3.39 (m, 4H), 3.16 (bs, 2H), 3.10 (s, 3H), 2.18-1.95 (m, 4H).

Example 168

Preparation of 2-[3-(4-Benzoylphenyl)ureido]-3-carbamoyl-6-ethyl-6-methyl-4,5,6,7-tetrahydrothieno[2,3-c]pyridin-6-ium iodide

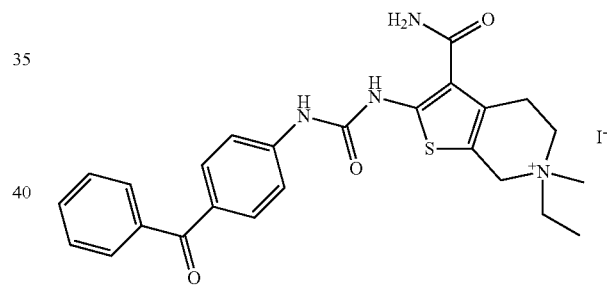

The title compound was prepared using a similar procedure as described in Example 135. MS (M) 463. ¹H NMR (500 MHz, DMSO-d₆) δ 10.89 (s, 1H), 10.59 (s, 1H), 7.80-7.00 (m, 11H), 4.57 (bs, 2H), 3.69-3.44 (m, 4H), 3.16 (bs, 2H), 3.06 (s, 3H), 1.34 (t, J=7.0 Hz, 3H).

Example 169

Preparation of 3-Carbamoyl-2-[3-(4-chlorophenyl)ureido]-N,N,N-trimethyl-4,5,6,7-tetrahydrobenzo[b]thiophen-6-aminium iodide

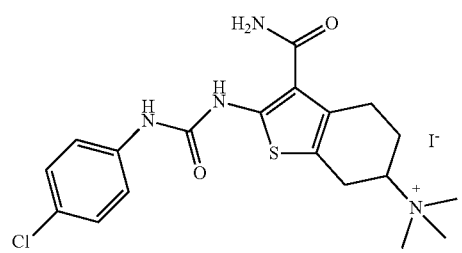

The title compound was prepared using a similar procedure as described in Example 135. MS (M) 407. ¹H NMR (300 MHz, DMSO-d₆) δ 10.94 (s, 1H), 10.20 (s, 1H), 7.80-6.70 (m, 6H), 3.76 (bs, 1H), 3.29-2.80 (m, 13H), 2.27 (bs, 1H), 1.77-1.74 (m, 1H).

Example 170

Preparation of 1-{3-Carbamoyl-2-[3-(4-chlorophenyl)ureido]-4,5,6,7-tetrahydrobenzo[b]thiophen-6-yl}-1-methylazetidin-1-ium iodide

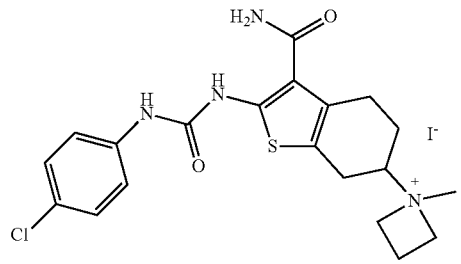

The title compound was prepared using a similar procedure as described in Example 135. MS (M) 419. ¹H NMR (300 MHz, DMSO-d₆) δ 10.94 (s, 1H), 10.20 (s, 1H), 7.80-6.70 (m, 6H), 4.67-3.89 (m, 5H), 3.12-2.70 (m, 8H), 2.35-1.65 (m, 3H).

Example 171

Preparation of 3-Carbamoyl-2-[3-(4-chlorophenyl)ureido]-6-methyl-6-neopentyl-4,5,6,7-tetrahydrothieno[2,3-c]pyridin-6-ium iodide

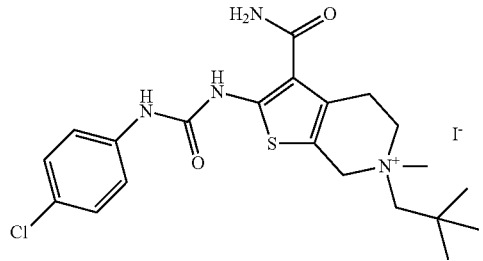 [SMILES: CC(C)(C)C[N+]1(C)CCc2c(sc(NC(=O)Nc3ccc(Cl)cc3)c2C(N)=O)C1 ; [I-]]

The title compound was prepared using a similar procedure as described in Example 135. MS (M) 435. ¹H NMR (500 MHz, DMSO-d₆) δ 10.81 (s, 1H), 10.26 (s, 1H), 7.80-6.90 (m, 6H), 4.68-4.63 (m, 2H), 3.71-3.67 (m, 2H), 3.18-3.09 (m, 7H), 1.18 (s, 9H).

Example 172

Preparation of 5-Carbamoyl-6-[3-(4-chlorophenyl)ureido]-2-ethyl-2-methyl-1,2,3,4-tetrahydroisoquinolin-2-ium iodide

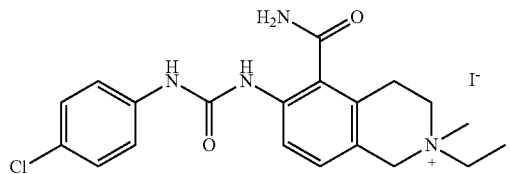

The title compound was prepared using a similar procedure as described in Example 135. MS (M) 387. ¹H NMR (500 MHz, DMSO-d₆) δ 9.65 (s, 1H), 8.13 (s, 1H), 8.07 (s, 1H), 7.89 (s, 1H), 7.87 (d, J=8.6 Hz, 1H), 7.48-7.32 (m, 4H), 7.18 (d, J=8.6 Hz, 1H), 4.55 (s, 2H), 3.70-3.42 (m, 4H), 3.15-3.05 (m, 5H), 1.34 (t, J=7.2 Hz, 3H).

Example 173

Preparation of 3-Carbamoyl-2-[3-(4-chlorophenyl)ureido]-7-ethyl-7-methyl-5,6,7,8-tetrahydro-4H-thieno[2,3-c]azepin-7-ium iodide

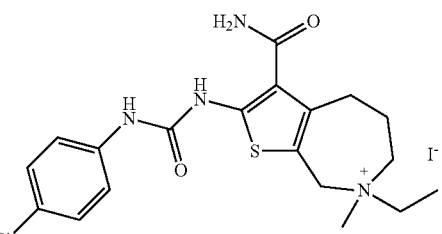

The title compound was prepared using a similar procedure as described in Example 135. MS (M) 407. ¹H NMR (500 MHz, DMSO-d₆) δ 10.18 (s, 1H), 10.12 (s, 1H), 7.75-7.34 (m, 6H), 4.75-4.60 (m, 2H), 3.63 (bs, 2H), 3.27 (bs, 1H), 3.05-2.90 (m, 5H), 2.55 (s, 1H), 2.00 (bs, 2H), 1.28 (t, J=7.2 Hz, 3H).

Example 174

Preparation of 3-Carbamoyl-2-[3-(4-chlorophenyl)ureido]-6-ethyl-6-methyl-5,6,7,8-tetrahydro-4H-thieno[2,3-d]azepin-6-ium iodide

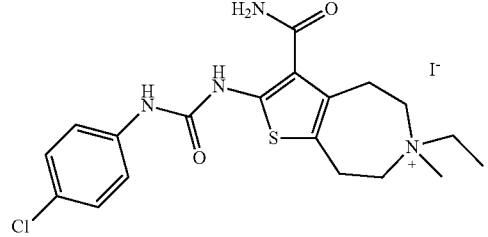
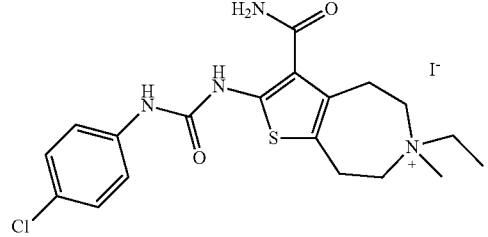

The title compound was prepared using a similar procedure as described in Example 135. MS (M) 407. ¹H NMR (500 MHz, DMSO-d₆) δ 10.17 (s, 1H), 10.06 (s, 1H), 7.80-7.10 (m, 6H), 3.65-3.50 (m, 6H), 3.25-3.09 (m, 7H), 1.30 (t, J=7.1 Hz, 3H).

Example 175

Preparation of 3-Carbamoyl-6-isobutyl-6-methyl-2-[3-(naphthalen-2-yl)ureido]-4,5,6,7-tetrahydrothieno[2,3-c]pyridin-6-ium iodide

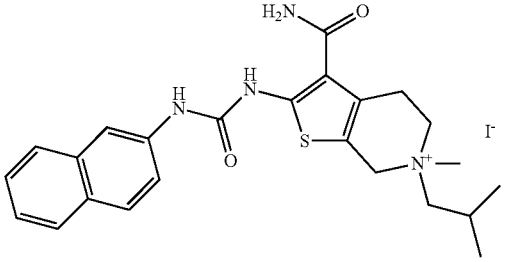 [SMILES: CC(C)C[N+]1(C)CCc2c(sc(NC(=O)Nc3ccc4ccccc4c3)c2C(N)=O)C1 ; [I-]]

The title compound was prepared using a similar procedure as described in Example 135. MS (M) 437. $^1$H NMR (300 MHz, DMSO-$d_6$) δ 10.86 (s, 1H), 10.37 (s, 1H), 8.14-7.00 (m, 9H), 4.61 (bs, 2H), 3.75-3.60 (m, 2H), 3.29-3.05 (m, 7H), 2.39-2.34 (m, 1H), 1.10-1.04 (m, 6H).

Example 176

Preparation of 3-Carbamoyl-6-(cyclobutylmethyl)-6-methyl-2-[3-(naphthalen-2-yl)ureido]-4,5,6,7-tetrahydrothieno[2,3-c]pyridin-6-ium iodide

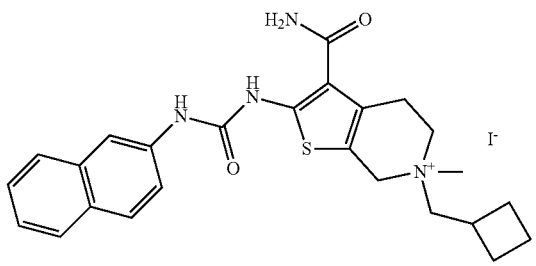 [SMILES: C[N+]1(CC2CCC2)CCc2c(sc(NC(=O)Nc3ccc4ccccc4c3)c2C(N)=O)C1 ; [I-]]

The title compound was prepared using a similar procedure as described in Example 135. MS (M) 449. $^1$H NMR (300 MHz, DMSO-$d_6$) δ 10.85 (s, 1H), 10.36 (s, 1H), 8.14-7.00 (m, 9H), 4.53 (bs, 2H), 3.62-3.33 (m, 4H), 3.20-2.90 (m, 6H), 2.20-1.75 (m, 6H).

Example 177

Preparation of (+/−)-3-Carbamoyl-2-[3-(4-chlorophenyl)ureido]-9-methyl-4,4a,5,6,7,8,9,10-octahydrothieno[3,2-b]quinolizin-9-ium iodide

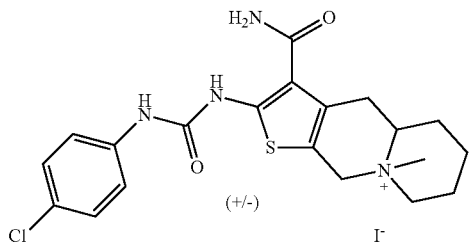

The title compound was prepared using a similar procedure as described in Example 135. MS (M) 419. $^1$H NMR (300 MHz, DMSO-$d_6$) δ 10.81 and 10.79 (2 s, 1H), 10.28 (s, 1H), 7.80-6.90 (m, 6H), 4.90-4.75 (m, 1H), 4.00-3.36 (m, 3H), 3.29-2.90 (m, 5H), 2.20-1.50 (m, 7H).

Example 178

Preparation of (+/−)-3-Carbamoyl-2-[3-(4-chlorophenyl)ureido]-6-methyl-4,5,6,7,8,9,10,10a-octahydrothieno[2,3-a]quinolizin-6-ium chloride

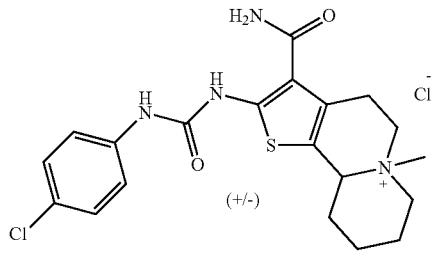

The title compound was prepared using a similar procedure as described in Example 135. MS (M) 419. $^1$H NMR (300 MHz, DMSO-$d_6$) δ 10.85 (s, 1H), 10.31 (s, 1H), 7.80-6.90 (m, 6H), 4.65-4.54 (m, 2H), 3.80-3.49 (m, 3H), 3.15-2.85 (m, 5H), 2.15-1.50 (m, 6H).

Example 179

Preparation of 2-[3-(4-Chlorophenyl)ureido]-6-ethyl-6-methyl-3-(morpholine-4-carbonyl)-4,5,6,7-tetrahydrothieno[2,3-c]pyridin-6-ium chloride

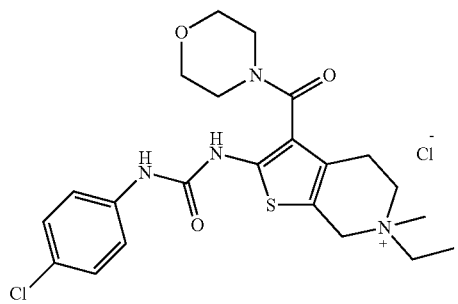

The title compound was prepared using a similar procedure as described in Example 135. MS (M) 463. $^1$H NMR (300 MHz, DMSO-$d_6$) δ 10.08 (s, 1H), 9.70 (s, 1H), 7.51-7.34 (m, 4H), 4.56 (bs, 2H), 3.80-3.35 (m, 12H), 3.03 (s, 3H), 2.81 (bs, 2H), 1.33 (t, J=7.0 Hz, 3H).

Example 180

Preparation of 3-Carbamoyl-6-ethyl-2-[3-(6-fluoronaphthalen-2-yl)ureido]-6-methyl-4,5,6,7-tetrahydrothieno[2,3-c]pyridin-6-ium iodide

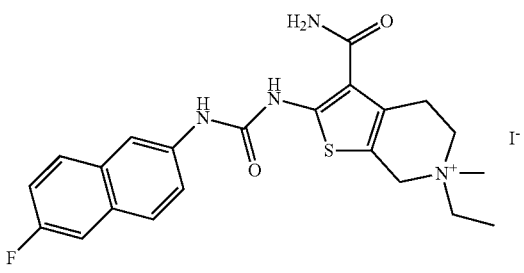 [SMILES: CC[N+]1(C)CCc2c(sc(NC(=O)Nc3ccc4cc(F)ccc4c3)c2C(N)=O)C1 ; [I-]]

The title compound was prepared using a similar procedure as described in Example 135. MS (M) 427. $^1$H NMR (300 MHz, DMSO-$d_6$) δ 10.85 (s, 1H), 10.39 (s, 1H), 8.18 (s, 1H), 7.95-7.00 (m, 7H), 4.57 (s, 2H), 3.69-3.55 (m, 2H), 3.50-3.41 (m, 2H), 3.20-3.11 (m, 2H), 3.07 (s, 3H), 1.35 (t, J=7.1 Hz, 3H).

Example 181

Preparation of 3-Carbamoyl-2-[3-(4-chloronaphthalen-1-yl)ureido]-6-isobutyl-6-methyl-4,5,6,7-tetrahydrothieno[2,3-c]pyridin-6-ium iodide

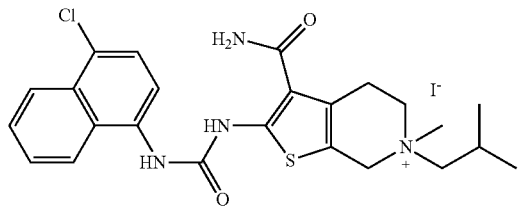

The title compound was prepared using a similar procedure as described in Example 135. MS (M) 471. ¹H NMR (300 MHz, DMSO-d₆) δ 10.90 (s, 1H), 10.12 (s, 1H), 8.31-7.11 (m, 8H), 4.59 (s, 2H), 3.67 (bs, 2H), 3.30-3.03 (m, 7H), 2.40-2.29 (m, 1H), 1.08 (d, J=7.2 Hz, 3H), 1.05 (d, J=7.2 Hz, 3H).

Example 182

Preparation of 3-Carbamoyl-2-[3-(4-chloronaphthalen-1-yl)ureido]-6-(cyclobutylmethyl)-6-methyl-4,5,6,7-tetrahydrothieno[2,3-c]pyridin-6-ium chloride

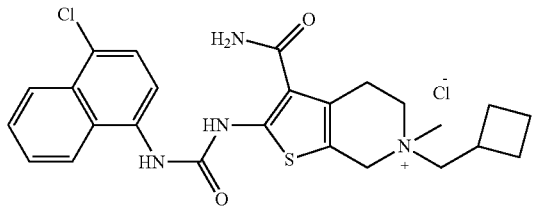

The title compound was prepared using a similar procedure as described in Example 135. MS (M) 483. ¹H NMR (300 MHz, DMSO-d₆) δ 10.89 (s, 1H), 10.14 (s, 1H), 8.29-8.20 (m, 2H), 7.89-7.14 (m, 6H), 4.52 (s, 2H), 3.62 (bs, 2H), 3.46 (bs, 2H), 3.20-2.91 (m, 6H), 2.10-2.07 (m, 2H), 1.98-1.75 (m, 4H).

Example 183

Preparation of 3-Carbamoyl-2-[3-(4-chloronaphthalen-1-yl)ureido]-6-methyl-6-neopentyl-4,5,6,7-tetrahydrothieno[2,3-c]pyridin-6-ium chloride

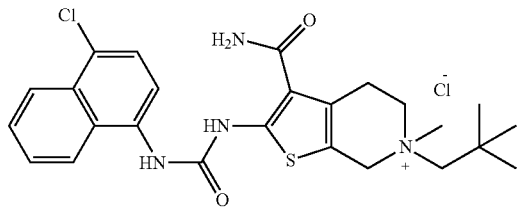

The title compound was prepared using a similar procedure as described in Example 135. MS (M) 485. ¹H NMR (300 MHz, DMSO-d₆) δ 10.90 (s, 1H), 10.14 (s, 1H), 8.27 (d, J=8.4 Hz, 1H), 8.22 (d, J=8.4 Hz, 1H), 7.87 (d, J=8.1 Hz, 1H), 7.78-7.10 (m, 5H), 4.68 (s, 2H), 3.70 (bs, 2H), 3.40 (bs, 2H), 3.25-3.05 (m, 5H), 1.18 (s, 9H).

Example 184

Preparation of 3-Carbamoyl-6-ethyl-6-methyl-2-ureido-4,5,6,7-tetrahydrothieno[2,3-c]pyridin-6-ium iodide

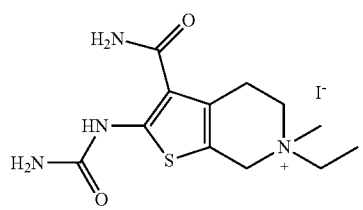

The title compound was prepared using a similar procedure as described in Example 135. MS (M) 283. ¹H NMR (300 MHz, DMSO-d₆) δ 10.30 (s, 1H), 7.92-6.68 (m, 4H), 4.50 (s, 2H), 3.68-3.52 (m, 2H), 3.48-3.40 (m, 2H), 3.15-3.10 (m, 2H), 3.04 (s, 3H), 1.32 (t, J=7.2 Hz, 3H).

Example 185

Preparation of 3-Carbamoyl-2-[3-(4-chlorophenyl)-3-methylureido]-6-ethyl-6-methyl-4,5,6,7-tetrahydrothieno[2,3-c]pyridin-6-ium chloride

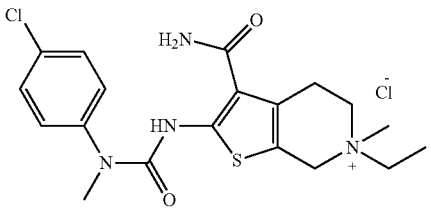

The title compound was prepared using a similar procedure as described in Example 135. MS (M) 407. ¹H NMR (300 MHz, DMSO-d₆) δ 11.28 (s, 1H), 7.95-6.80 (m, 6H), 4.53 (s, 2H), 3.69-3.51 (m, 2H), 3.26-3.01 (m, 10H), 1.31 (bs, 3H).

Example 186

Preparation of (+/−)-3-Carbamoyl-2-[3-(4-chlorophenyl)ureido]-1',1'-dimethyl-5,7-dihydro-4H-spiro(benzo[b]thiophene-6,2'-pyrrolidin)-1'-ium trifluoroacetate

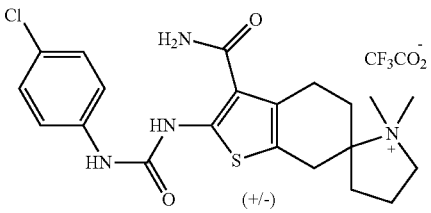

The title compound was prepared using a similar procedure as described in Example 135. MS (M) 433. ¹H NMR (300 MHz, DMSO-d₆) δ 10.84 (s, 1H), 10.21 (s, 1H), 7.61-6.80 (m, 6H), 3.90-3.45 (m, 2H), 3.27-3.15 (m, 1H), 3.06-2.85 (m, 9H), 1.29-1.22 (m, 1H), 2.10-1.85 (m, 5H).

Example 187

Preparation of (+/−)-3-Carbamoyl-2-[3-(4-chlorophenyl)ureido]-9-ethyl-9-methyl-5,6,7,8-tetrahydro-4H-thienocyclohepten-5,8-iminium chloride

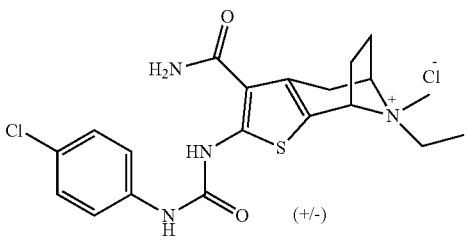

The title compound was prepared using a similar procedure as described in Example 135. MS (M) 419. ¹H NMR (300 MHz, DMSO-d₆) δ 10.30 (s, 1H), 10.18 (s, 1H), 7.61-7.40 (m, 4H), 7.36 (d, J=8.7 Hz, 2H), 4.98-4.91 (m, 1H), 4.27 (bs, 1H), 3.50-2.95 (m, 9H), 2.25-1.90 (m, 2H), 1.38-1.21 (m, 3H).

Example 188

Preparation of (+/−)-3-Carbamoyl-2-[3-(4-chlorophenyl)ureido]-9,9-dimethyl-5,6,7,8-tetrahydro-4H-thienocyclohepten-5,8-iminium iodide

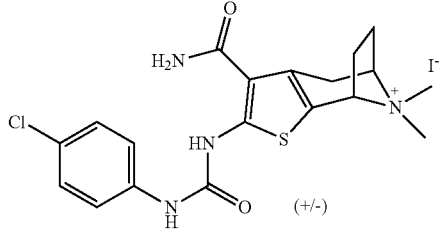

The title compound was prepared using a similar procedure as described in Example 135. MS (M) 405. $^1$H NMR (300 MHz, DMSO-d$_6$) δ 10.26 (s, 1H), 10.08 (s, 1H), 7.65-7.30 (m, 6H), 5.02-4.90 (m, 1H), 4.23 (bs, 1H), 3.40-2.96 (m, 8H), 2.65-2.58 (m, 2H), 2.25-2.15 (m, 1H), 2.03-1.93 (m, 1H).

Example 189

Preparation of (+/−)-3-Carbamoyl-2-[3-(4-chlorophenyl)ureido]-9-(cyclobutylmethyl)-9-methyl-5,6,7,8-tetrahydro-4H-thienocyclohepten-5,8-iminium trifluoroacetate

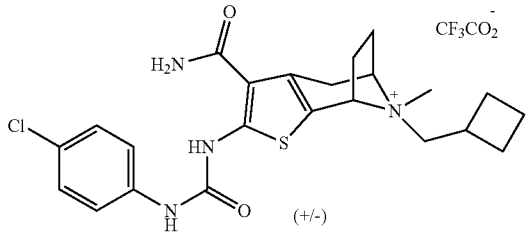

The title compound was prepared using a similar procedure as described in Example 135. MS (M) 459. $^1$H NMR (300 MHz, DMSO-d$_6$) δ 10.86 (s, 0.24H), 10.33 (s, 0.24H), 10.19 (s, 0.76H), 10.10 (s, 0.76H), 7.55-7.37 (m, 4H), 7.36 (d, J=8.7 Hz, 2H), 4.91-4.87 (m, 1H), 4.28-4.18 (m, 1H), 3.41-3.22 (m, 3H), 3.10-2.72 (m, 5H), 2.25-0.85 (m, 10H).

Example 190

Preparation of 3-carbamoyl-2-[3-(4-chlorophenyl)ureido]-6-(cyclobutylmethyl)-6-ethyl-4,5,6,7-tetrahydrothieno[2,3-c]pyridin-6-ium chloride (CC2)

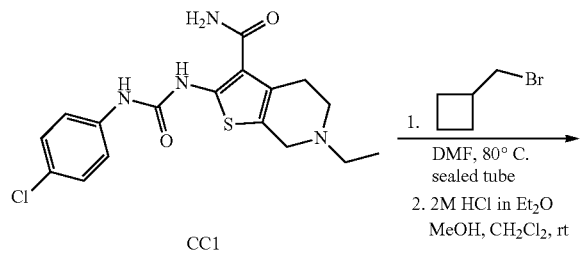

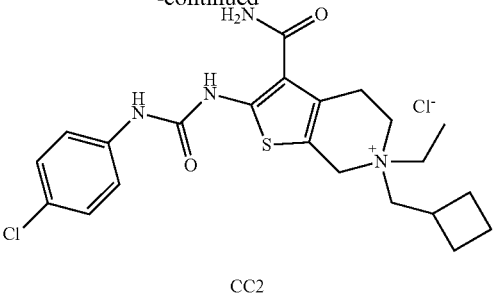

A solution of compound CC1 (400 mg, 1.06 mmol) and (bromomethyl)cyclobutane (1.59 g, 10.7 mmol) in N,N-dimethylformamide (5 mL) was heated to 80° C. in a sealed tube for 22 h. After this time, the reaction mixture was cooled to room temperature and concentrated under reduced pressure. The resulting residue was purified by flash column chromatography on silica gel eluting with methanol to 5% ammonium hydroxide/methanol followed by reverse phase semi-preparative HPLC eluting with 0.05% TFA in acetonitrile/water (gradient from 10% to 100%, Phenomenex Luna column). The product was dissolved in a mixture of methanol (2 mL), methylene chloride (5 mL), and hydrochloride (2 M in diethyl ether, 1 mL). The resulting solution was concentrated under reduced pressure to afford compound CC2 as an off-white solid (55 mg, 11%): $^1$H NMR (500 MHz, DMSO-d$_6$) δ 10.79 (s, 1H), 10.29 (s, 1H), 7.70-6.90 (m, 6H), 4.55-4.45 (m, 2H), 3.61-3.58 (m, 2H), 3.41-3.35 (m, 4H), 3.20-3.05 (m, 2H), 2.90-2.80 (m, 1H), 2.20-1.70 (m, 6H), 1.28 (t, J=7.1 Hz, 3H). MS (M) 447.

Example 191

Preparation of 3-Carbamoyl-2-[3-(4-chlorophenyl)ureido]-6-isopropyl-6-methyl-4,5,6,7-tetrahydrothieno[2,3-c]pyridin-6-ium iodide

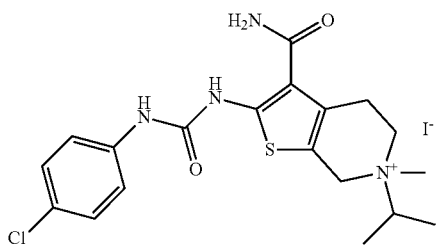 [SMILES: CC(C)[N+]1(C)CCc2c(sc(NC(=O)Nc3ccc(Cl)cc3)c2C(N)=O)C1 ; [I-]]

The title compound was prepared using a similar procedure as described in Example 190. MS (M) 407. $^1$H NMR (500 MHz, DMSO-d$_6$) δ 10.80 (s, 1H), 10.26 (s, 1H), 7.80-7.00 (m, 6H), 4.66-4.47 (m, 2H), 3.85-3.54 (m, 3H), 3.14 (bs, 2H), 2.92 (s, 3H), 1.41-1.36 (m, 6H).

Example 192

Preparation of 3-Carbamoyl-2-[3-(4-chlorophenyl)ureido]-6-methyl-6-(2,2,2-trifluoroethyl)-4,5,6,7-tetrahydrothieno[2,3-c]pyridin-6-ium iodide

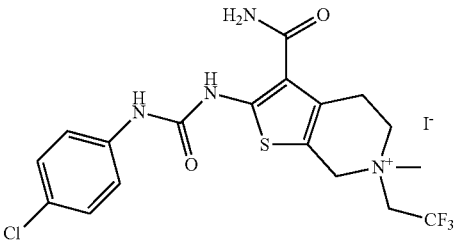 [SMILES: C[N+]1(CC(F)(F)F)CCc2c(sc(NC(=O)Nc3ccc(Cl)cc3)c2C(N)=O)C1 ; [I-]]

The title compound was prepared using a similar procedure as described in Example 190. MS (M) 447. $^1$H NMR (500 MHz, DMSO-d$_6$) δ 10.72 (s, 1H), 10.27 (s, 1H), 7.80-7.00 (m, 6H), 4.85-4.62 (m, 4H), 3.89-3.86 (m, 2H), 3.36 (s, 3H), 3.27-3.23 (m, 2H).

Example 193

Preparation of 3-Carbamoyl-6-methyl-2-(3-naphthalen-2-ylureido)-6-neopentyl-4,5,6,7-tetrahydrothieno[2,3-c]pyridin-6-ium trifluoroacetate

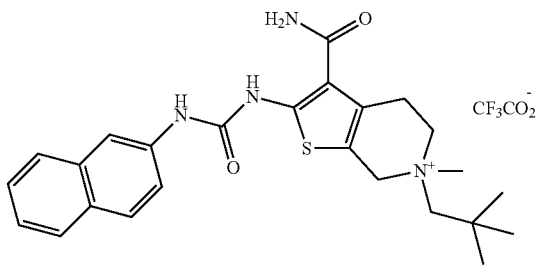

The title compound was prepared using a similar procedure as described in Example 190. MS (M) 451. $^1$H NMR (500 MHz, DMSO-d$_6$) δ 10.85 (s, 1H), 10.37 (s, 1H), 8.13-7.00 (m, 9H), 4.73-4.64 (m, 2H), 3.71 (bs, 2H), 3.41 (s, 2H), 3.20 (bs, 5H), 1.19 (s, 9H).

Example 194

Preparation of 3-Carbamoyl-2-[3-(4-chlorophenyl)ureido]-6-[3-(dimethylamino)-3-oxopropyl]-6-methyl-4,5,6,7-tetrahydrothieno[2,3-c]pyridin-6-ium chloride

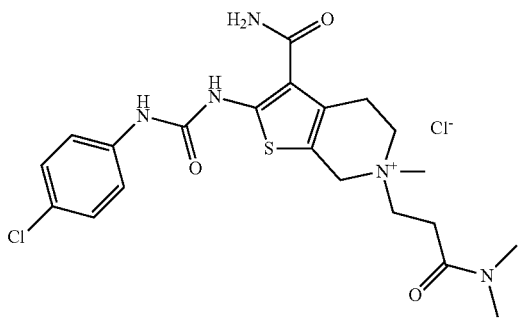 [SMILES: CN(C)C(=O)CC[N+]1(C)CCc2c(sc(NC(=O)Nc3ccc(Cl)cc3)c2C(N)=O)C1 ; [Cl-]]

The title compound was prepared using a similar procedure as described in Example 190. MS (M) 464. $^1$H NMR (300 MHz, DMSO-d$_6$) δ 10.79 (s, 1H), 10.34 (s, 1H), 7.80-7.10 (m, 6H), 4.71-4.59 (m, 2H), 3.60-2.93 (m, 14H), 2.84 (s, 3H).

Example 195

Preparation of 3-Carbamoyl-2-[3-(4-chlorophenyl)ureido]-6-(cyclohexylmethyl)-6-ethyl-4,5,6,7-tetrahydrothieno[2,3-c]pyridin-6-ium trifluoroacetate

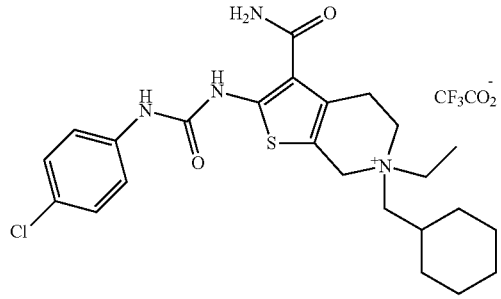

The title compound was prepared using a similar procedure as described in Example 190. MS (M) 475. $^1$H NMR (500 MHz, DMSO-d$_6$) δ 10.81 (s, 1H), 10.27 (s, 1H), 7.80-7.00 (m, 6H), 4.65-4.56 (m, 2H), 3.70-3.40 (m, 4H), 3.28-3.05 (m, 4H), 2.05-1.55 (m, 6H), 1.40-1.05 (m, 8H).

Example 196

Preparation of 3-Carbamoyl-2-[3-(4-chlorophenyl)ureido]-6-methyl-6-[(1-methylcyclopropyl)methyl]-4,5,6,7-tetrahydrothieno[2,3-c]pyridin-6-ium trifluoroacetate

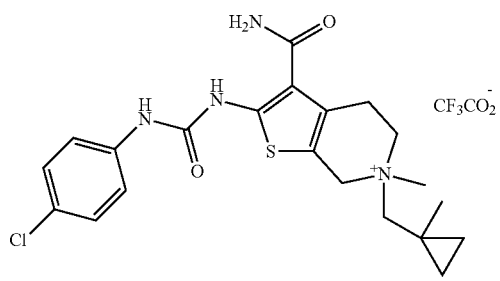

The title compound was prepared using a similar procedure as described in Example 190. MS (M) 433. $^1$H NMR (300 MHz, DMSO-d$_6$) δ 10.80 (s, 1H), 10.28 (s, 1H), 7.80-7.00 (m, 6H), 4.70-4.56 (m, 2H), 3.70-3.10 (m, 9H), 1.32 (s, 3H), 0.75-0.50 (m, 4H).

Example 197

Preparation of 6-[(3r,5r,7r)-Adamantan-1-ylmethyl]-3-carbamoyl-2-[3-(4-chlorophenyl)ureido]-6-methyl-4,5,6,7-tetrahydrothieno[2,3-c]pyridin-6-ium chloride

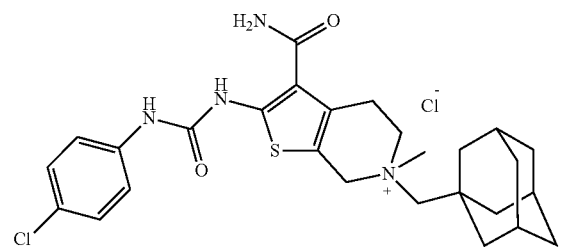

The title compound was prepared using a similar procedure as described in Example 190. MS (M) 513. $^1$H NMR (500 MHz, DMSO-d$_6$) δ 10.80 (s, 1H), 10.28 (s, 1H), 7.80-7.00 (m, 6H), 4.69-4.65 (m, 2H), 3.96 (bs, 2H), 3.25-3.12 (m, 7H), 1.99-1.68 (m, 15H).

Example 198

Preparation of 6-[4-(tert-Butoxy)-4-oxobutyl]-3-carbamoyl-2-[3-(4-chlorophenyl)ureido]-6-ethyl-4,5,6,7-tetrahydrothieno[2,3-c]pyridin-6-ium trifluoroacetate

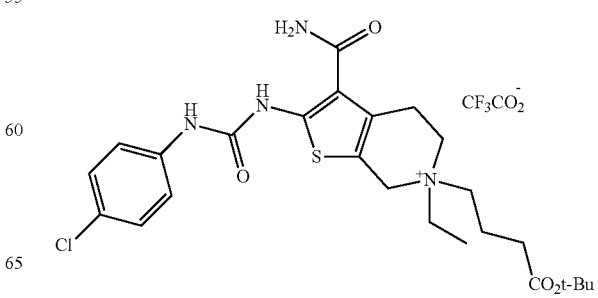

The title compound was prepared using a similar procedure as described in Example 190. MS (M) 521. ¹H NMR (500 MHz, DMSO-d₆) δ 10.81 (s, 1H), 10.27 (s, 1H), 7.80-7.00 (m, 6H), 4.65-4.56 (m, 2H), 3.75-3.10 (m, 8H), 2.38-2.34 (m, 2H), 2.00-1.85 (m, 2H), 1.41 (s, 9H), 1.32 (t, J=7.0 Hz, 3H).

Example 199

Preparation of 6-[4-(tert-Butoxy)-4-oxobutyl]-3-carbamoyl-2-[3-(4-chlorophenyl)ureido]-6-(cyclobutylmethyl)-4,5,6,7-tetrahydrothieno[2,3-c]pyridin-6-ium trifluoroacetate

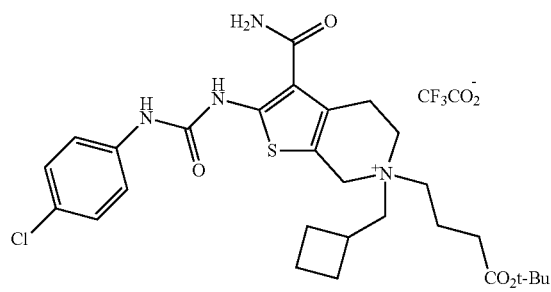

The title compound was prepared using a similar procedure as described in Example 190. MS (M) 561. ¹H NMR (500 MHz, DMSO-d₆) δ 10.84 (s, 1H), 10.27 (s, 1H), 7.80-6.90 (m, 6H), 4.54 (s, 2H), 3.65-2.90 (m, 8H), 2.40-1.75 (m, 11H), 1.40 (s, 9H).

Example 200

Preparation of 3-Carbamoyl-2-[3-(4-chlorophenyl)ureido]-6-ethyl-6-isobutyl-4,5,6,7-tetrahydrothieno[2,3-c]pyridin-6-ium chloride

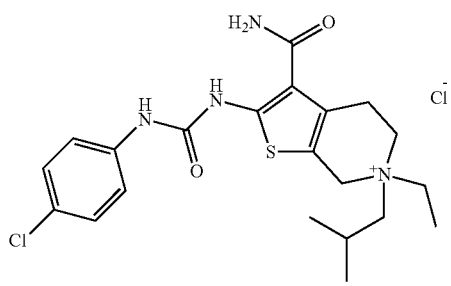

The title compound was prepared using a similar procedure as described in Example 190. MS (M) 435. ¹H NMR (500 MHz, DMSO-d₆) δ 10.80 (s, 1H), 10.29 (s, 1H), 7.80-7.00 (m, 6H), 4.62 (bs, 2H), 3.66-3.45 (m, 4H), 3.29-3.05 (m, 4H), 2.35-2.25 (m, 1H), 1.29 (t, J=7.2 Hz, 3H), 1.08-1.05 (m, 6H).

Example 201

Preparation of 3-Carbamoyl-2-[3-(4-chlorophenyl)ureido]-6,6-bis(3-hydroxypropyl)-4,5,6,7-tetrahydrothieno[2,3-c]pyridin-6-ium chloride

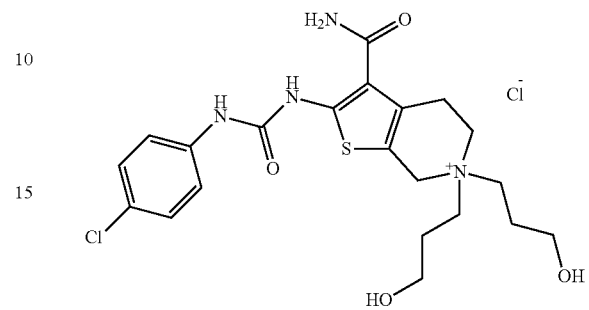

The title compound was prepared using a similar procedure as described in Example 190. MS (M) 467. ¹H NMR (300 MHz, DMSO-d₆) δ 10.82 (s, 1H), 10.31 (s, 1H), 7.80-7.00 (m, 6H), 4.85 (bs, 2H), 4.65 (s, 2H), 3.75-3.35 (m, 10H), 3.14 (bs, 2H), 2.00-1.80 (m, 4H).

Example 202

Preparation of 3-Carbamoyl-2-[3-(4-chlorophenyl)ureido]-6-(2-hydroxy-2-methylpropyl)-6-methyl-4,5,6,7-tetrahydrothieno[2,3-c]pyridin-6-ium iodide

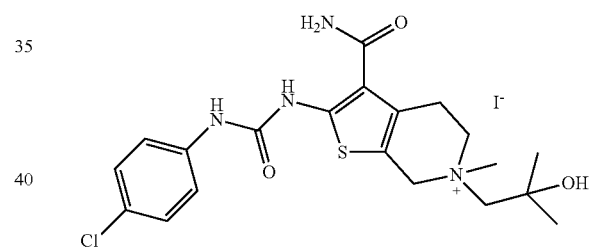

The title compound was prepared using a similar procedure as described in Example 190. MS (M) 437. ¹H NMR (300 MHz, DMSO-d₆) δ 11.95 (s, 0.25H), 11.24 (s, 0.24H), 10.83 (s, 0.72H), 10.29 (s, 0.74H), 7.80-7.00 (m, 6H), 5.44-5.42 (m, 1H), 4.87-4.59 (m, 2H), 3.77-3.42 (m, 4H), 3.28-3.18 (m, 5H), 1.35-1.33 (m, 6H).

Example 203

Preparation of (+/−)-3-Carbamoyl-2-[3-(4-chlorophenyl)ureido]-6-(1-cyclobutylethyl)-6-methyl-4,5,6,7-tetrahydrothieno[2,3-c]pyridin-6-ium chloride

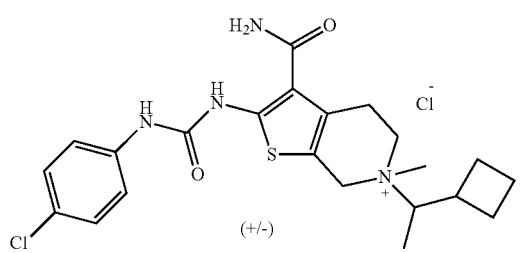

The title compound was prepared using a similar procedure as described in Example 190. MS (M) 447. ¹H NMR (300 MHz, DMSO-d₆) δ 10.79 (s, 1H), 10.32 (s, 1H), 7.80-7.00 (m, 6H), 4.55-4.40 (m, 2H), 3.80-3.50 (m, 3H), 3.20-2.80 (6H), 2.15-1.60 (m, 6H), 1.30-1.20 (m, 3H).

Example 204

Preparation of (+/−)-3-Carbamoyl-2-[3-(4-chlorophenyl)ureido]-6-methyl-6-(3-methylbutan-2-yl)-4,5,6,7-tetrahydrothieno[2,3-c]pyridine-6-ium chloride

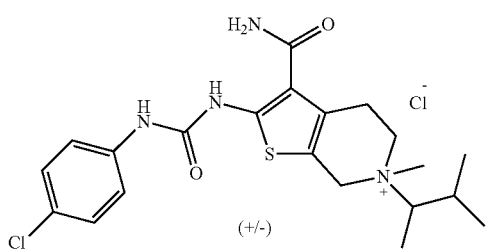

The title compound was prepared using a similar procedure as described in Example 190. MS (M) 435. ¹H NMR (300 MHz, DMSO-d₆) δ 10.79 (s, 1H), 10.30 (s, 1H), 7.80-7.00 (m, 6H), 4.80-4.39 (m, 2H), 3.90-3.50 (m, 3H), 3.90-2.58 (m, 6H), 1.35-0.85 (m, 9H).

Example 205

Preparation of tert-butyl N-[3-(3-carbamoyl-2-{[(4-chlorophenyl)carbamoyl]amino}-4H,5H,6H,7H-thieno[2,3-c]pyridin-6-yl)propyl]carbamate (F)

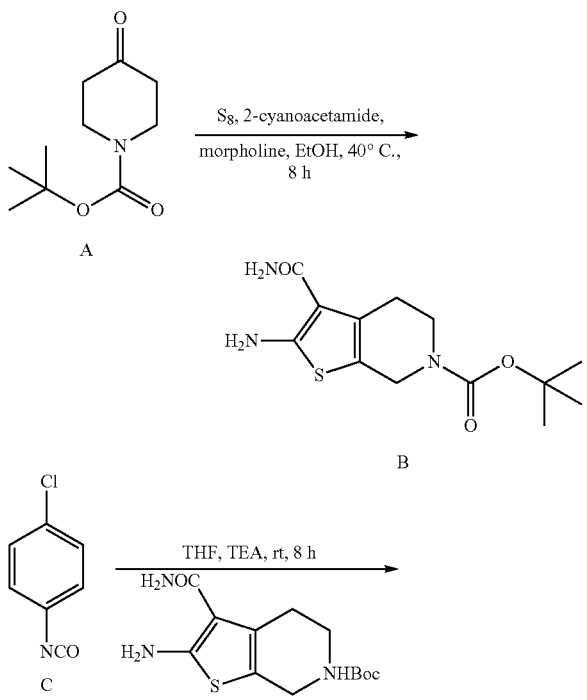

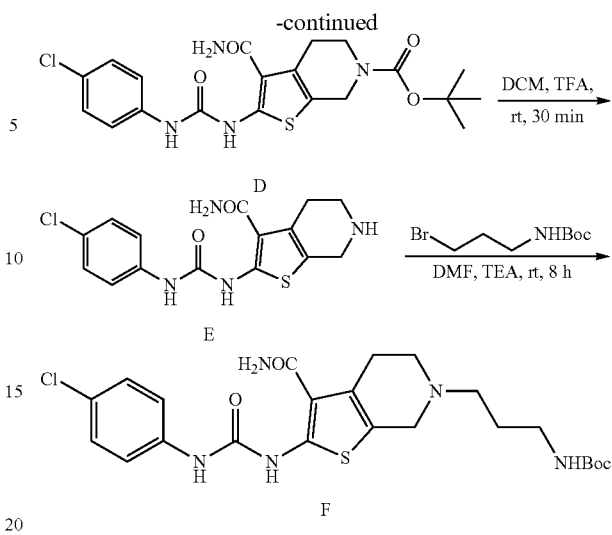

Step 1: tert-Butyl 2-amino-3-carbamoyl-4,5-dihydrothieno[2,3-c]pyridine-6(7H)-carboxylate (B)

A round bottom flask fitted with a stir bar, was charged with sulfur (196 mg, 6.114 mmol) followed by morpholine (704 μL, 8.14 mmol) and the suspension was stirred at 40° C. for 1 h or until sulfur dissolved in morpholine. The solution was diluted with anhydrous EtOH, whereupon 4-N-Boc-piperidinone (1.20 g, 6.02 mmol) and cyanamide (506 mg, 6.02 mmol) were added and the reaction mixture stirred at room temperature overnight. Upon completion, the reaction mixture was concentrated in vacuo to afford viscous orange oil. The resultant product was diluted with MeOH and then 10% EtOAc in Hexane was added until precipitation of the product was complete. The product was filtered to afford the title compound as a tan solid (1.8 g, quantitative yield). ¹H NMR (300 MHz, MeOH-d₄) δ 4.35 (bs, 2H), 3.68-3.55 (m, 2H), 2.71-2.68 (m, 2H), 1.49 (s, 9H). LRMS [M+H]298.

Step 2: tert-Butyl 3-carbamoyl-2-[3-(4-chlorophenyl)ureido]-4,5-dihydrothieno[2,3-c]pyridine-6(7H)-carboxylate (D)

To a stirred solution of 4-chlorophenyl isocyanate (325 mg, 2.12 mmol) and triethylamine (444 μL, 3.18 mmol) in anhydrous THF (10 mL) was added tert-butyl 2-amino-3-carbamoyl-4,5-dihydrothieno[2,3-c]pyridine-6(7H)-carboxylate (632 mg, 2.12 mmol) and the reaction mixture was stirred at rt for 8 h. The reaction mixture was concentrated in vacuo to afford oil, which was taken up in DCM and washed with water (×2). The organics were then dried with anhydrous Na₂SO₄ and concentrated in vacuo. The product was purified by Isolera system (SiO₂ gel as stationary phase, 25 g HP column, dry loading) using DCM-DCM/MeOH (0%-8% MeOH in DCM) to afford the title compound as a tan solid (633 mg, 57% yield). LRMS [M+H]451.

Step 3: 2-[3-(4-Chlorophenyl)ureido]-4,5,6,7-tetrahydrothieno[2,3-c]pyridine-3-carboxamide trifluoroacetate (E)

A stirred suspension of tert-butyl 3-carbamoyl-2-[3-(4-chlorophenyl)ureido]-4,5-dihydrothieno[2,3-c]pyridine-6(7H)-carboxylate (697 mg, 1.55 mmol) in 6 mL of DCM at rt was treated with 3 mL of TFA. The resultant solution was stirred at rt for 25 min whereupon it was concentrated in a rotary evaporator. The product was taken up in MeOH and the solution concentrated in vacuo (×2) to afford the title compound as a tan solid in quantitative yield. LRMS [M+H]351.

Step 4: tert-Butyl N-[3-(3-carbamoyl-2-{[(4-chlorophenyl)carbamoyl]amino}-4H,5H,6H,7H-thieno[2,3-c]pyridin-6-yl)propyl]carbamate (F)

A solution of 2-[3-(4-Chlorophenyl)ureido]-4,5,6,7-tetrahydrothieno[2,3-c]pyridine-3-carboxamide trifluoroacetate (0.48 mmol) in anhydrous DMF was treated with triethyl amine (200 μL, 1.43 mmol) and N-Boc-bromopropylamine (114 mg, 0.48 mmol) and the reaction mixture was allowed to stir at room temperature for 14 h. Analytical HPLC showed close to 50% progression. Another 100 μL of triethyl amine and 70 mg of N-Boc-bromopropylamine were added and the reaction mixture was stirred at room temperature. Upon completion (48 h), DMF was removed under vacuo and the resultant crude mixture was diluted with DCM and washed with water (×2). The organic layer was dried (anhydrous $Na_2SO_4$) and concentrated to afford an oil which was purified by flash chromatography Isolera system ($SiO_2$ gel as stationary phase, 40 g HP column, dry loading) using DCM-DCM/MeOH (0%-15% MeOH in DCM) to afford the title compound as a light brown solid (144 mg, 60% yield). $^1$H NMR (300 MHz, dmso-$d_6$) δ 10.95 (s, 1H), 10.18 (s, 1H), 7.55-7.43 (m, 2H), 7.37-7.27 (m, 2H), 6.82 (s, 1H), 3.53-3.43 (m, 2H), 3.03-2.90 (m, 2H), 2.85-2.57 (m, 4H), 2.50-2.40 (m, 2H), 1.69-1.53 (m, 2H), 1.37 (s, 9H). LRMS [M+H]508.

Example 206

Preparation of tert-Butyl N-[3-(3-carbamoyl-2-{[(naphthalen-2-yl)carbamoyl]amino}-4H,5H,6H,7H-thieno[2,3-c]pyridin-6-yl)propyl]carbamate

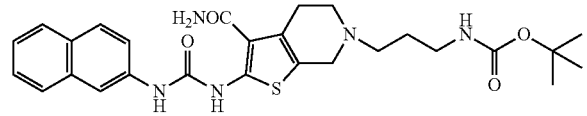 [SMILES: CC(C)(C)OC(=O)NCCCN1CCc2c(sc(NC(=O)Nc3ccc4ccccc4c3)c2C(N)=O)C1]

The title compound was prepared using a similar procedure as described in Example 205. MS (M+H) 524. $^1$H NMR (300 MHz, dmso-$d_6$) δ 11.00 (s, 1H), 10.28 (s, 1H), 8.15 (s, 1H), 7.88-7.76 (m, 3H), 7.56-7.28 (m, 4H), 6.83 (s, 1H), 3.55-3.45 (m, 2H), 3.04-2.92 (m, 2H), 2.84-2.60 (m, 4H), 2.50-2.40 (m, 2H), 1.68-1.54 (m, 2H), 1.48 (s, 9H).

Example 207

Preparation of tert-Butyl 6-[3-(benzyloxy)propyl]-2-{[(4-iodophenyl)carbamoyl]amino}-4H,5H,6H,7H-thieno[2,3-c]pyridine-3-carboxamide

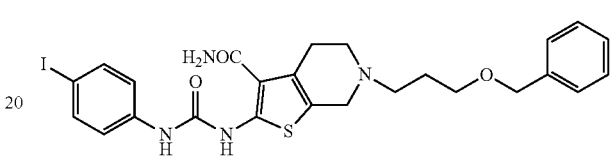

The title compound was prepared using a similar procedure as described in Example 205. MS (M+H) 591. $^1$H NMR (300 MHz, dmso-$d_6$) δ 10.94 (s, 1H), 10.16 (s, 1H), 7.66-7.56 (m, 2H), 7.39-7.23 (m, 7H), 4.45 (s, 2H), 3.57-3.40 (m, 3H), 2.84-2.54 (m, 5H), 2.54-2.44 (m, 2H), 1.86-1.71 (m, 2H).

Example 208

Preparation of tert-Butyl N-[3-(2-{[(4-benzoylphenyl)carbamoyl]amino}-3-carbamoyl-4H,5H,6H,7H-thieno[2,3-c]pyridin-6-yl)propyl]carbamate

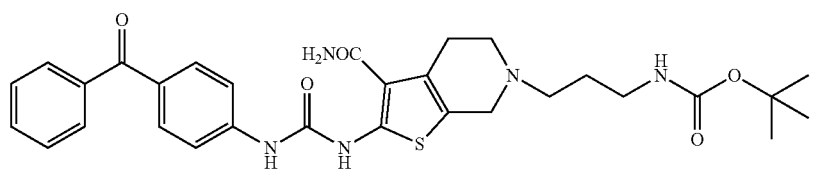 [SMILES: CC(C)(C)OC(=O)NCCCN1CCc2c(sc(NC(=O)Nc3ccc(C(=O)c4ccccc4)cc3)c2C(N)=O)C1]

The title compound was prepared using a similar procedure as described in Example 205. MS (M+H) 578.

Example 209

Preparation of 2-{[(4-chlorophenyl)carbamoyl]amino}-6-{3-[3-(1H-indol-3-yl)propanamido]propyl}-4H,5H,6H,7H-thieno[2,3-c]pyridine-3-carboxamide

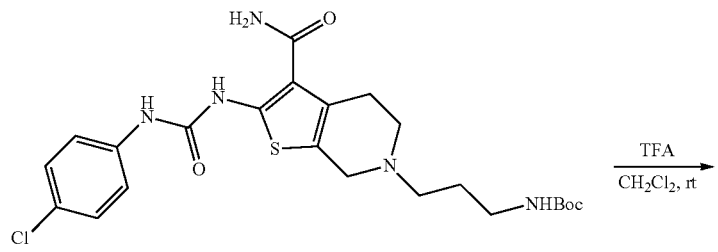

F

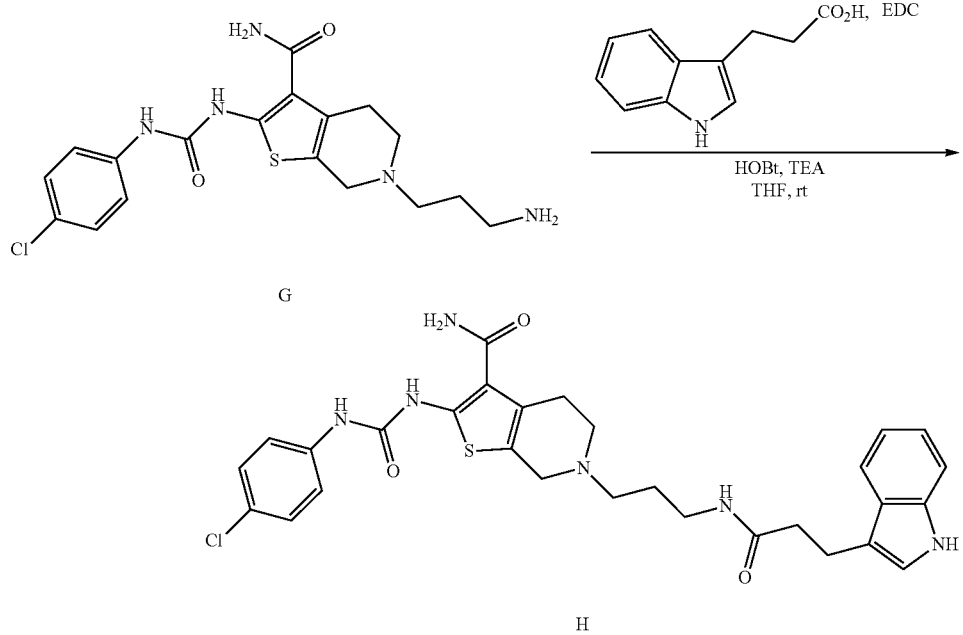

G

H

Step 1: 6-(3-aminopropyl)-2-{[(4-chlorophenyl)carbamoyl]amino}-4H,5H,6H,7H-thieno[2,3-c]pyridine-3-carboxamide (G)

A stirred suspension of tert-butyl-N-[3-(2-{[(4-benzoylphenyl)carbamoyl]amino}-3-carbamoyl-4H,5H,6H,7H-thieno[2,3-c]pyridin-6-yl)propyl]carbamate (70 mg, 0.14 mmol) in 4 mL of DCM at rt was treated with 2 mL of TFA. The resultant solution was stirred at rt for 40 min whereupon it was concentrated in a rotary evaporator. The product was taken up in MeOH and the solution concentrated in vacuo (×2) to afford the title compound as a light tan solid in quantitative yield. LRMS [M+H]408.

Step 2: 2-{[(4-chlorophenyl)carbamoyl]amino}-6-{3-[3-(1H-indol-3-yl)propanamido]propyl}-4H,5H,6H,7H-thieno[2,3-c]pyridine-3-carboxamide (H)

To a stirred solution of 6-(3-aminopropyl)-2-{[(4-chlorophenyl)carbamoyl]amino}-4H,5H,6H,7H-thieno[2,3-c]pyridine-3-carboxamide (0.14 mmol) in anhydrous THF (1.5) were added triethyl amine (93 µL, 0.66 mmol), 3-indolepropionic acid (31 mg, 0.16 mmol), EDC.HCl (31 mg, 0.16 mmol), HOBt (25 mg, 0.16 mmol) and the resultant mixture was stirred at room temperature for 8 h. Upon completion, the solvent was removed in vacuo and the oil was taken up in DCM. The organics were washed with water (×2) and dried (anhydrous Na$_2$SO$_4$) and evaporated to afford the crude product which was purified by flash chromatography Isolera system (SiO$_2$ gel as stationary phase, 12 g HP column, dry loading) using DCM-DCM/MeOH (0%-12% MeOH in DCM) to afford the title compound as a brown solid (31 mg, 37% yield). $^1$H NMR (300 MHz, MeOH-d$_4$) δ 7.55 (d, J=15.5 Hz, 1H), 7.50-7.43 (m, 2H), 7.34-7.24 (m, 3H), 7.12-6.95 (m, 3H), 3.38 (bs, 2H), 3.17 (t, J=6.7 Hz, 2H), 3.06 (t, J=7.2 Hz, 2H), 2.82-2.74 (m, 2H), 2.68-2.61 (m, 2H), 2.55 (t, J=7.2 Hz, 2H), 2.36-2.27 (m, 2H), 1.67-1.54 (m, 2H). LRMS [M+H] 579.

Example 210

Preparation of 2-{[(4-chlorophenyl)carbamoyl]amino}-6-[3-(3-phenylpropanamido)propyl]-4H,5H,6H,7H-thieno[2,3-c]pyridine-3-carboxamide

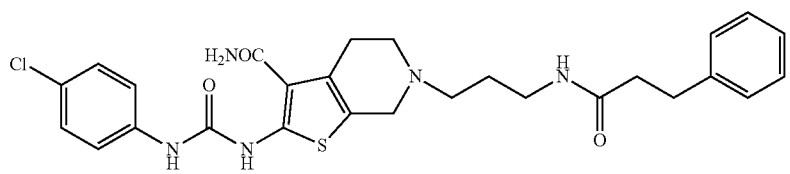 [SMILES: NC(=O)c1c(NC(=O)Nc2ccc(Cl)cc2)sc2c1CCN(CCCNC(=O)CCc1ccccc1)C2]

The title compound was prepared using a similar procedure as described in Example 209. MS (M+H) 540. $^1$H NMR (300 MHz, dmso-d$_6$) δ 10.94 (s, 1H), 10.33 (s, 1H), 8.15 (s, 1H), 7.51 (d, J=8.8 Hz, 2H), 7.35 (d, J=8.8 Hz, 2H), 7.31-7.13 (m, 5H), 4.47 (d, J=14.4 Hz, 1H), 4.18 (d, J=13.4 Hz, 1H), 3.63-3.23 (m, 4H), 3.18-2.98 (m, 5H), 2.78-2.76 (m, 2H), 2.45-2.31 (m, 2H), 1.95-1.87 (m, 2H).

Example 211

Preparation of 2-{[(4-chlorophenyl)carbamoyl]amino}-6-{3-[3-(pyridin-3-yl)propanamido]propyl}-4H,5H,6H,7H-thieno[2,3-c]pyridine-3-carboxamide

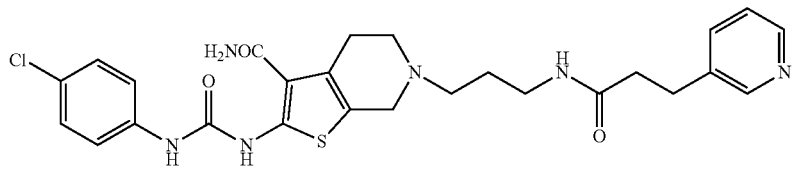 [SMILES: NC(=O)c1c(NC(=O)Nc2ccc(Cl)cc2)sc2c1CCN(CCCNC(=O)CCc1cccnc1)C2]

The title compound was prepared using a similar procedure as described in Example 209. MS (M+H) 541.

Example 212

Preparation of 2-{[(4-chlorophenyl)carbamoyl]amino}-6-[3-(phenylformamido)propyl]-4H,5H,6H,7H-thieno[2,3-c]pyridine-3-carboxamide

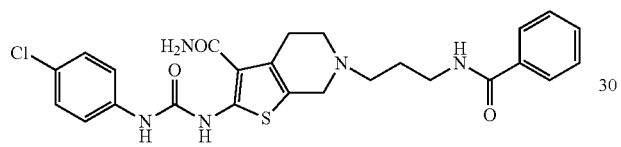

The title compound was prepared using a similar procedure as described in Example 209. MS (M+H) 512. $^1$H NMR (300 MHz, MeOH-$d_4$) δ 7.82-7.74 (m, 2H), 7.54-7.36 (m, 5H), 7.31-7.18 (m, 2H), 3.85 (bs, 2H), 3.54-3.45 (m, 2H), 3.11-2.83 (m, 6H), 2.05-1.94 (m, 2H).

Example 213

Preparation of 6-{3-[3-(4-tert-butylphenyl)propanamido]propyl}-2-{[(4-chlorophenyl)carbamoyl]amino}-4H,5H,6H,7H-thieno[2,3-c]pyridine-3-carboxamide

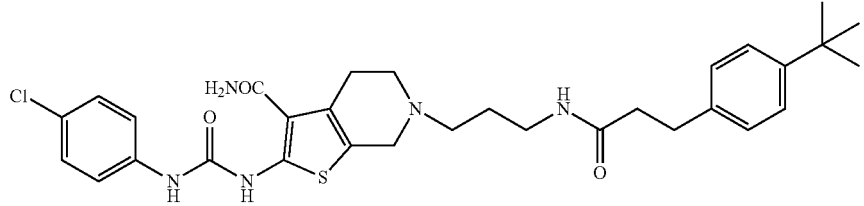 [SMILES: CC(C)(C)c1ccc(CCC(=O)NCCCN2CCc3c(sc(NC(=O)Nc4ccc(Cl)cc4)c3C(N)=O)C2)cc1]

The title compound was prepared using a similar procedure as described in Example 209. MS (M+H) 596. $^1$H NMR (300 MHz, MeOH-$d_4$) δ 7.52-7.43 (m, 2H), 7.36-7.23 (m, 4H), 7.15-7.06 (m, 2H), 3.61 (bs, 2H), 3.27-3.15 (m, 2H), 2.93-2.78 (m, 5H), 2.62-2.52 (m, 2H), 2.50-2.39 (m, 2H), 1.82-1.66 (m, 2H), 1.26 (s, H).

Example 214

Preparation of 2-{[(4-chlorophenyl)carbamoyl]amino}-6-{3-[3-(naphthalen-1-yl)propanamido]propyl}-4H,5H,6H,7H-thieno[2,3-c]pyridine-3-carboxamide

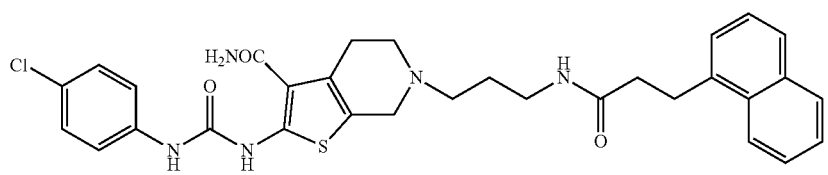 [SMILES: NC(=O)c1c(NC(=O)Nc2ccc(Cl)cc2)sc2c1CCN(CCCNC(=O)CCc1cccc3ccccc13)C2]

The title compound was prepared using a similar procedure as described in Example 209. MS (M+H) 590. $^1$H NMR (300 MHz, MeOH-d$_4$) δ 8.13-8.04 (m, 1H), 7.88-7.81 (m, 1H), 7.75-7.68 (m, 1H), 7.57-7.22 (m, 8H), 3.52 (bs, 2H), 3.42-3.33 (m, 2H), 3.18 (t, J=6.6 Hz, 2H), 2.87-2.72 (m, 4H), 2.65-2.56 (m, 2H), 2.48-2.40 (m, 2H), 1.73-1.59 (m, 2H).

Example 215

Preparation of 2-{[(4-chlorophenyl)carbamoyl]amino}-6-[3-(cyclopropylformamido)propyl]-4H,5H,6H,7H-thieno[2,3-c]pyridine-3-carboxamide

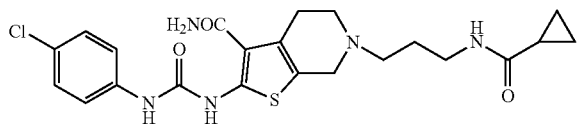 [SMILES: NC(=O)c1c(NC(=O)Nc2ccc(Cl)cc2)sc2c1CCN(CCCNC(=O)C1CC1)C2]

The title compound was prepared using a similar procedure as described in Example 209. MS (M+H) 488.

Example 216

Preparation of 2-{[(4-chlorophenyl)carbamoyl]amino}-6-[3-(pent-4-ynamido)propyl]-4H,5H,6H,7H-thieno[2,3-c]pyridine-3-carboxamide

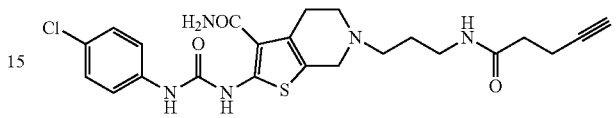

The title compound was prepared using a similar procedure as described in Example 209. MS (M+H) 488.

Example 217

Preparation of 2-{[(4-chlorophenyl)carbamoyl]amino}-6-{3-[(2E)-3-phenylprop-2-enamido]propyl}-4H,5H,6H,7H-thieno[2,3-c]pyridine-3-carboxamide

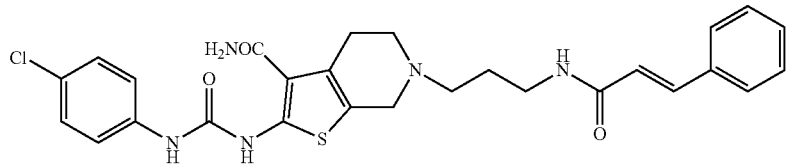 [SMILES: NC(=O)c1c(NC(=O)Nc2ccc(Cl)cc2)sc2c1CCN(CCCNC(=O)/C=C/c1ccccc1)C2]

The title compound was prepared using a similar procedure as described in Example 209. MS (M+H) 538. $^1$H NMR (300 MHz, dmso-d$_6$) δ 10.95 (s, 1H), 10.26 (s, 1H), 9.85 (s, 1H), 8.35 (s, 1H), 7.61-7.27 (m, 10H), 6.64 (d, J=15.8 Hz, 1H), 3.32-3.25 (m, 3H), 3.14-2.96 (m, 7H), 2.00-1.78 (m, 2H).

Example 218

Preparation of 2-{[(4-chlorophenyl)carbamoyl]amino}-6-(3-{3-[4-(trifluoromethyl)phenyl]propanamido}propyl)-4H,5H,6H,7H-thieno[2,3-c]pyridine-3-carboxamide

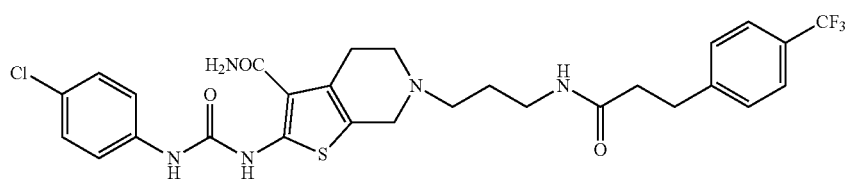 [SMILES: NC(=O)c1c(NC(=O)Nc2ccc(Cl)cc2)sc2c1CCN(CCCNC(=O)CCc1ccc(C(F)(F)F)cc1)C2]

The title compound was prepared using a similar procedure as described in Example 209. MS (M+H) 608.

Example 219

Preparation of 6-butyl-3-carbamoyl-2-{[(4-chlorophenyl)carbamoyl]amino}-6-methyl-4H,5H,6H,7H-thieno[2,3-c]pyridin-6-ium

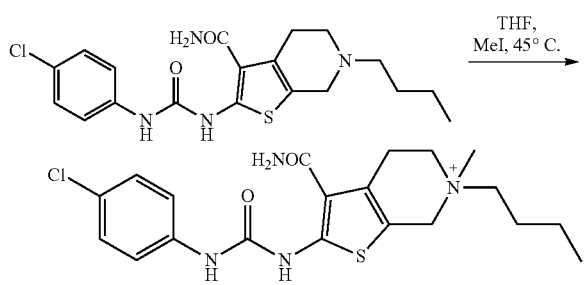

A stirred solution of 6-butyl-2-(3-(4-chlorophenyl)ureido)-4,5,6,7-tetrahydrothieno[2,3-c]pyridine-3-carboxamide (16.0 mg, 0.04 mmol) in anhydrous THF was treated with MeI (2.4 µL, 0.4 mmol) and the reaction mixture was heated at 45° C. Upon completion, as judged by LC-MS, the solvent was removed under vacuo. The resultant solid was washed with DCM and the washings were discarded. The remaining solid was diluted with MeOH and the reaction mixture concentrated (×2) to afford the title compound as a light brown solid in quantitative yield. MS (M) 421.

Example 220

Preparation of 2-{[(4-bromophenyl)carbamoyl]amino}-3-carbamoyl-6-ethyl-6-methyl-4H,5H,6H,7H-thieno[2,3-c]pyridin-6-ium

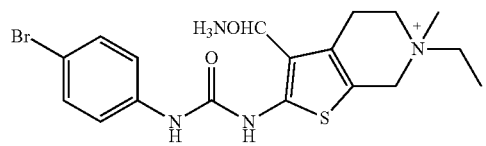

The title compound was prepared using a similar procedure as described in Example 219. MS (M) 439.

Example 221

Preparation of 6-ethyl-2-({[4-(trifluoromethyl)phenyl]carbamoyl}amino)-4H,5H,6H,7H-thieno[2,3-c]pyridine-3-carboxamide

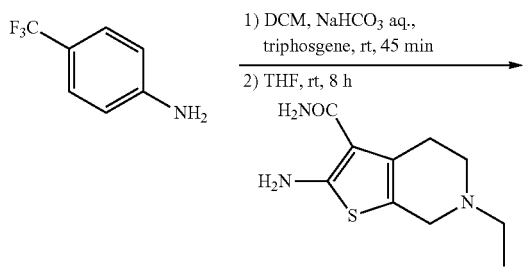

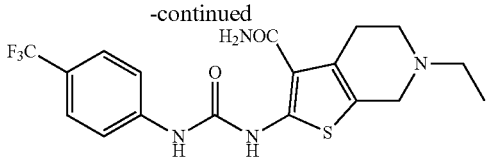

A vigorously stirred solution of 4-trifluoromethyl aniline (161 mg, 1.0 mmol) in DCM (3 mL) at room temperature was treated with aq. NaHCO₃ (3 mL) and triphosgene (98 mg, 0.33 mmol) and the reaction mixture was vigorously stirred at room temperature for 45 min. 2-Amino-6-ethyl-4,5,6,7-tetrahydrothieno[2,3-c]pyridine-3-carboxamide (225 mg, 1.0 mmol) was next added followed by THF and the reaction mixture was stirred at room temperature for 8 h. The solvent was then removed under vacuo and the resultant crude product was diluted with methanol and the insoluble solid was filtered off. Upon evaporation of MeOH, the crude oil was taken up in DCM and washed with water (×2), and the aqueous layer was back extracted with DCM. All organics were combined, dried (Na₂SO₄) and concentrated using a rotary evaporator. The crude product was purified by flash chromatography, Isolera system (SiO₂ gel as stationary phase, 12 g HP column, dry loading) using DCM-DCM/MeOH (0%-10% MeOH in DCM) to afford the title compound as a brown solid (128 mg, 31% yield). MS (M+H) 413.

Example 222

Preparation of 2-{[(4-bromophenyl)carbamoyl]amino}-6-ethyl-4H,5H,6H,7H-thieno[2,3-c]pyridine-3-carboxamide

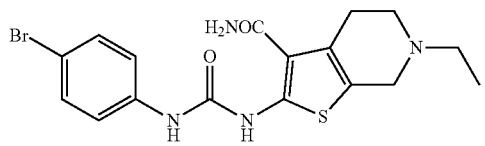 [SMILES: CCN1CCc2c(sc(NC(=O)Nc3ccc(Br)cc3)c2C(N)=O)C1]

The title compound was prepared using a similar procedure as described in Example 221. MS (M+H) 423.

Example 223

Preparation of 6-ethyl-2-{[(naphthalen-2-yl)carbamoyl]amino}-4H,5H,6H,7H-thieno[2,3-c]pyridine-3-carboxamide

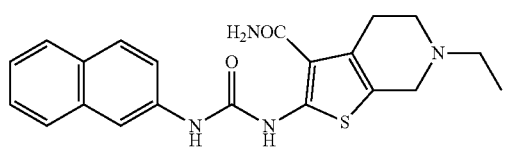 [SMILES: CCN1CCc2c(sc(NC(=O)Nc3ccc4ccccc4c3)c2C(N)=O)C1]

The title compound was prepared using a similar procedure as described in Example 221. MS (M+H) 395. ¹H NMR (300 MHz, dmso-d₆) δ 11.00 (s, 1H), 10.26 (s, 1H), 8.78-8.18 (s, 1H), 7.87-7.74 (m, 3H), 7.67-7.31 (m, 4H), 3.31-3.41 (m, 2H), 2.83-2.72 (m, 7H), 2.70-2.60 (m, 2H), 2.58-2.48 (m, 2H), 1.08 (t, J=7.1 Hz, 2H).

Example 224

Preparation of 6-ethyl-2-{[(4-iodophenyl)carbamoyl]amino}-4H,5H,6H,7H-thieno[2,3-c]pyridine-3-carboxamide

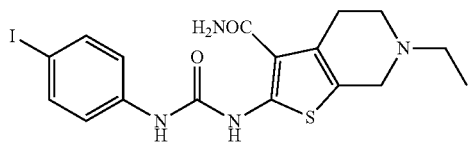 [SMILES: CCN1CCc2c(sc(NC(=O)Nc3ccc(I)cc3)c2C(N)=O)C1]

The title compound was prepared using a similar procedure as described in Example 221. MS (M+H) 471. $^1$H NMR (300 MHz, dmso-d$_6$) δ 10.95 (s, 1H), 10.16 (s, 1H), 7.60 (d, J=8.8 Hz, 2H), 7.32 (t, J=8.8 Hz, 2H), 7.67-7.31 (m, 4H), 3.61-3.39 (m, 2H), 2.88-2.63 (m, 4H), 2.61-2.45 (m, 2H), 1.08 (t, J=7.1 Hz, 2H).

Example 225

Preparation of 6-ethyl-2-{[(4-phenoxyphenyl)carbamoyl]amino}-4H,5H,6H,7H-thieno[2,3-c]pyridine-3-carboxamide

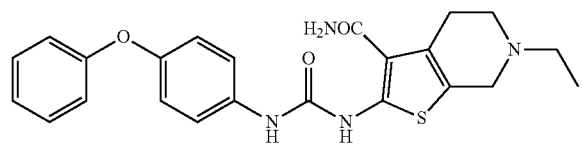 [SMILES: CCN1CCc2c(sc(NC(=O)Nc3ccc(Oc4ccccc4)cc3)c2C(N)=O)C1]

The title compound was prepared using a similar procedure as described in Example 221. MS (M+H) 437.

Example 226

Preparation of 2-{[(4-benzylphenyl)carbamoyl]amino}-6-ethyl-4H,5H,6H,7H-thieno[2,3-c]pyridine-3-carboxamide

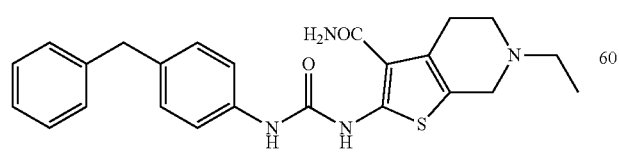

The title compound was prepared using a similar procedure as described in Example 221. MS (M+H) 435.

Example 227

Preparation of 6-ethyl-2-{[(5,6,7,8-tetrahydronaphthalen-2-yl)carbamoyl]amino}-4H,5H,6H,7H-thieno[2,3-c]pyridine-3-carboxamide

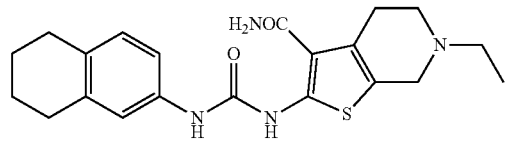 [SMILES: CCN1CCc2c(sc(NC(=O)Nc3ccc4c(c3)CCCC4)c2C(N)=O)C1]

The title compound was prepared using a similar procedure as described in Example 221. MS (M+H) 399.

Example 228

Preparation of 2-{[(4-chloronaphthalen-1-yl)carbamoyl]amino}-6-ethyl-4H,5H,6H,7H-thieno[2,3-c]pyridine-3-carboxamide

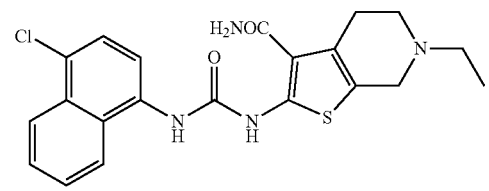 [SMILES: CCN1CCc2c(sc(NC(=O)Nc3ccc(Cl)c4ccccc34)c2C(N)=O)C1]

The title compound was prepared using a similar procedure as described in Example 221. MS (M+H) 430. $^1$H NMR (300 MHz, dmso-d$_6$) δ 10.99 (s, 1H), 10.18 (s, 1H), 8.32-8.15 (m, 2H), 7.92-7.81 (m, 1H), 7.77-7.64 (m, 3H), 3.54-3.40 (m, 2H), 2.84-2.59 (m, 4H), 2.58-2.45 (m, 2H), 1.08 (t, J=7.1 Hz, 2H).

Example 229

Preparation of 2-{[(2,4-dichlorophenyl)carbamoyl]amino}-6-ethyl-4H,5H,6H,7H-thieno[2,3-c]pyridine-3-carboxamide

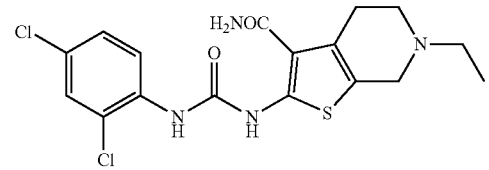 [SMILES: CCN1CCc2c(sc(NC(=O)Nc3ccc(Cl)cc3Cl)c2C(N)=O)C1]

The title compound was prepared using a similar procedure as described in Example 221. MS (M+H) 413.

Example 230

Preparation of 6-ethyl-2-{[(4-methoxyphenyl)carbamoyl]amino}-4H,5H,6H,7H-thieno[2,3-c]pyridine-3-carboxamide

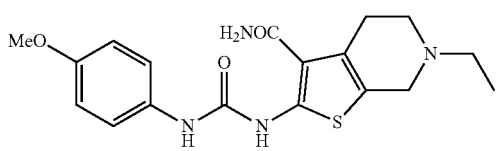 [SMILES: CCN1CCc2c(sc(NC(=O)Nc3ccc(OC)cc3)c2C(N)=O)C1]

The title compound was prepared using a similar procedure as described in Example 221. MS (M+H) 375.

Example 231

Hair Cell Toxicity Assay in Zebrafish

Zebrafish are bred and newly fertilized embryos are collected the week prior and raised at 28.5° C. in petri dishes containing embryo medium. Newly hatched free-swimming larvae are fed paramecium and dry fish food at 4 days post fertilization (dpf) with lights on. For treatment, fish 5-7 dpf are transferred to cell culture baskets and place within a well of a 6-well plate containing 7 milliliters of 1× embryo medium. Typically, tests are done with ten fish per basket but work well with up to 50 fish. All treatment and wash volumes are 7 milliliters.

1. Fish are pre-treated with test compound for 1 hour. Concentrations between 0.010 to 25 micromolar of test compound are tested.
2. Treat with 200 micromolar neomycin (neomycin sulfate, Sigma, St. Louis, Mo., catalog #N1142)+test compound for 30 minutes.
3. Rinse fish briefly 4 times in embryo medium and add 700 μl of 0.05% DASPEI (2-{4-(dimethylamino)styryl}-N-ethylpyridinium iodide, Molecular Probes, Eugene, Oreg.) and allowed to stain for 15 minutes.
4. Rinse twice in embryo medium and add 350 μl MS222 (0.55 ug/ml final concentration, 3-aminobenzoic acid ethyl ester, methansulfoneate salt, Sigma, St. Louis, Mo.) to anesthetize.
5. View with epifluorescence dissecting microscope equipped with a DAPSEI filter set (excitation 450-490 nM and barrier 515 nM, Chroma Technologies, Brattleboro, Vt.). For assessment of initial dose response curves, fish are transferred to wide depression slide with wide-bore pipette. The DASPEI staining of ten neuromasts (SO1, SO2, IO1, IO2, IO3, IO4, M2, MI1, MI2 and O2) on one side of an animal are evaluated. Each neuromast is scored for presence of DASPEI staining (score=2), reduced DASPEI staining (score=1) or absence of DASPEI staining (score=0). Total scores for an animal are tabulated, to give a composite score that can range from 0 to 20. Average scores and standard deviations are calculated for animals in each treatment group. Scores are normalized to control group (vehicle only, no drug, no neomycin) and expressed as % hair cell survival. HCmax is the maximum protection (hair cell survival) observed.
6. If at least 50% hair cells survive, the HC50 (concentration that would produce 50% hair cell survival) is calculated as a linear extrapolation from the nearest concentrations of protective drug that produce hair cell survival below and above 50%. If less than 50% hair cells survive, the HC50 is not determined.

1× embryo media (standard lab EM):
1 mM $MgSO_4$,
0.15 mM $KH_2PO_4$,
0.05 mM $Na_2HPO_4$,
1 mM $CaCl_2$,
0.5 mM KCl
15 mM NaCl
0.7 mM $NaHCO_3$

TABLE 1

| Example | $HC_{50}$ (μM) | Max HC Protection |
|---|---|---|
| 1 | B | 92% @ 25 μM |
| 2 | B | 84% @ 25 μM |
| 3 | B | 76% @ 25 μM |
| 4 | B | 56% @ 8.3 μM |
| 5 | B | 89% @ 8.3 μM |
| 6 | B | 72% @ 25 μM |
| 7 | B | 78% @ 25 μM |
| 8 | C | 84% @ 25 μM |
| 9 | B | 82% @ 25 μM |
| 10 | ND | 13% @ 8.3 μM |
| 11 | B | 68% @ 25 μM |
| 12 | B | 73% @ 8.3 μM |
| 13 | ND | 17% @ 8.3 μM |
| 14 | A | 83% @ 8.3 μM |
| 15 | C | 57% @ 25 μM |
| 16 | B | 57% @ 2.8 μM |
| 17 | B | 65% @ 8.3 μM |
| 18 | A | 64% @ 2.8 μM |
| 19 | A | 68% @ 8.3 μM |
| 20 | B | 65% @ 25 μM |
| 21 | B | 57% @ 2.8 μM |
| 22 | ND | 22% @ 2.8 μM |
| 23 | ND | 43% @ 2.8 μM |
| 24 | B | 54% @ 2.8 μM |
| 25 | B | 57% @ 2.8 μM |
| 26 | B | 68% @ 8.3 μM |
| 27 | B | 79% @ 25 μM |
| 28 | B | 58% @ 8.3 μM |
| 29 | B | 75% @ 25 μM |
| 30 | B | 58% @ 25 μM |
| 31 | ND | 22% @ 25 μM |
| 32 | ND | 19% @ 25 μM |
| 33 | ND | 9% @ 0.93 μM |
| 34 | B | 87% @ 25 μM |
| 35 | ND | 42% @ 2.8 μM |
| 36 | ND | 13% @ 8.3 μM |
| 37 | B | 105% @ 25 μM |
| 38 | ND | 14% @ 2.8 μM |
| 39 | C | 56% @ 25 μM |
| 40 | B | 62% @ 8.3 μM |
| 41 | ND | 39% @ 8.3 μM |
| 42 | B | 90% @ 25 μM |
| 43 | B | 93% @ 25 μM |
| 44 | B | 98% @ 25 μM |
| 45 | B | 78% @ 25 μM |
| 46 | C | 79% @ 25μM |
| 47 | A | 73% @ 2.8 μM |
| 48 | B | 72% @ 25 μM |
| 49 | B | 64% @ 2.8 μM |
| 50 | B | 82% @ 25 μM |
| 51 | B | 55% @ 8.3 μM |
| 52 | ND | 33% @ 25 μM |
| 53 | B | 103% @ 25 μM |
| 54 | B | 58% @ 25 μM |
| 55 | ND | 17% @ 2.8 μM |
| 56 | ND | 48% @ 2.8 μM |
| 57 | B | 50% @ 2.8 μM |
| 58 | ND | 7% @ 2.8 μM |
| 59 | ND | 40% @ 8.3 μM |
| 60 | B | 71% @ 25 μM |
| 61 | ND | 24% @ 25 μM |
| 62 | ND | 29% @ 25 μM |

TABLE 1-continued

| Example | HC$_{50}$ (µM) | Max HC Protection |
|---|---|---|
| 63 | B | 54% @ 2.8 µM |
| 64 | B | 77% @ 25 µM |
| 65 | ND | 17% @ 2.8 µM |
| 66 | C | 57% @ 25 µM |
| 67 | ND | 20% @ 8.3 µM |
| 68 | ND | 5% @ 25 µM |
| 69 | ND | 12% @ 25 µM |
| 70 | B | 64% @ 25 µM |
| 71 | ND | 45% @ 25 µM |
| 72 | B | 68% @ 25 µM |
| 73 | C | 51% @ 25 µM |
| 74 | C | 54% @ 25 µM |
| 75 | ND | 24% @ 25 µM |
| 76 | ND | 40% @ 25 µM |
| 77 | ND | 45% @ 25 µM |
| 78 | C | 52% @ 25 µM |
| 79 | ND | 34% @ 0.3 µM |
| 80 | ND | 36% @ 8.3 µM |
| 81 | ND | 32% @ 8.3 µM |
| 82 | ND | 23% @ 25 µM |
| 83 | B | 63% @ 25 µM |
| 84 | ND | 4% @ 25 µM |
| 85 | B | 63% @ 25 µM |
| 86 | B | 51% @ 8.3 µM |
| 87 | ND | 11% @ 25 µM |
| 88 | B | 88% @ 25 µM |
| 89 | ND | 18% @ 8.3 µM |
| 90 | B | 99% @ 8.3 µM |
| 91 | ND | 15% @ 0.9 µM |
| 92 | ND | 22% @ 2.8 µM |
| 93 | B | 97% @ 25 µM |
| 94 | C | 69% @ 25 µM |
| 95 | B | 78% @ 25 µM |
| 96 | B | 57% @ 8.3 µM |
| 97 | ND | 37% @ 8.3 µM |
| 98 | C | 52% @ 25 µM |
| 99 | ND | 18% @ 2.8 µM |
| 100 | B | 59% @ 25 µM |
| 101 | B | 74% @ 25 µM |
| 102 | ND | 22% @ 25 µM |
| 103 | ND | 12% @ 0.9 µM |
| 104 | ND | 0% @ 25 µM |
| 105 | ND | 7% @ 25 µM |
| 106 | ND | 23% @ 25 µM |
| 107 | ND | 36% @ 2.8 µM |
| 108 | ND | 13% @ 0.9 µM |
| 109 | ND | 22% @ 25 µM |
| 110 | C | 69% @ 25 µM |
| 111 | B | 55% @ 2.8 µM |
| 112 | ND | 49% @ 25 µM |
| 113 | ND | 12% @ 2.8 µM |
| 114 | B | 97% @ 25 µM |
| 115 | B | 99% @ 25 µM |
| 116 | B | 82% @ 25 µM |
| 117 | B | 78% @ 25 µM |
| 118 | B | 99% @ 25 µM |
| 119 | B | 65% @ 25 µM |
| 120 | B | 81% @ 2.8 µM |
| 121 | ND | 6% @ 03 µM |
| 122 | A | 91% @ 25 µM |
| 123 | A | 60% @ 2.8 µM |
| 124 | A | 91% @ 25 µM |
| 125 | A | 99% @ 8.3 µM |
| 126 | ND | 41% @ 2.8 µM |
| 127 | B | 55% @ 2.8 µM |
| 128 | A | 93% @ 2.8 µM |
| 129 | A | 81% @ 2.8 µM |
| 130 | ND | 40% @ 2.8 µM |
| 131 | A | 88% @ 2.8 µM |
| 132 | A | 97% @ 2.8 µM |
| 133 | A | 76% @ 25 µM |
| 134 | ND | 11% @ 0.9 µM |
| 135 | A | 107% @ 25 µM |
| 136 | B | 76% @ 25 µM |
| 137 | B | 85% @ 25 µM |
| 138 | A | 94% @ 25 µM |
| 139 | A | 99% @ 25 µM |
| 140 | A | 92% @ 25 µM |
| 141 | A | 77% @ 2.8 µM |
| 142 | B | 82% @ 25 µM |
| 143 | B | 96% @ 25 µM |
| 144 | B | 78% @ 25 µM |
| 145 | A | 95% @ 8.3 µM |
| 146 | B | 96% @ 25 µM |
| 147 | A | 90% @ 2.8 µM |
| 148 | C | 51% @ 25 µM |
| 149 | ND | 24% @ 25 µM |
| 150 | ND | 43% @ 25 µM |
| 151 | A | 105% @ 2.8 µM |
| 152 | A | 78% @ 0.9 µM |
| 153 | A | 98% @ 8.3 µM |
| 154 | A | 96% @ 2.8 µM |
| 155 | A | 75% @ 2.8 µM |
| 156 | A | 96% @ 2.8 µM |
| 157 | B | 94% @ 25 µM |
| 158 | B | 80% @ 25 µM |
| 159 | A | 84% @ 2.8 µM |
| 160 | B | 70% @ 2.8 µM |
| 161 | A | 87% @ 2.8 µM |
| 162 | ND | 36% @ 2.8 µM |
| 163 | A | 88% @ 8.3 µM |
| 164 | B | 60% @ 2.8 µM |
| 165 | B | 52% @ 2.8 µM |
| 166 | B | 63% @ 2.8 µM |
| 167 | ND | 21% @ 2.8 µM |
| 168 | ND | 20% @ 2.8 µM |
| 169 | B | 101% @ 25 µM |
| 170 | B | 85% @ 25 µM |
| 171 | A | 92% @ 2.8 µM |
| 172 | C | 66% @ 25 µM |
| 173 | B | 102% @ 25 µM |
| 174 | B | 74% @ 25 µM |
| 175 | A | 111% @ 25 µM |
| 176 | A | 100% @ 8.3 µM |
| 177 | B | 97% @ 25 µM |
| 178 | B | 102% @ 25 µM |
| 179 | ND | 38% @ 8.3 µM |
| 180 | B | 102% @ 25 µM |
| 181 | B | 93% @ 25 µM |
| 182 | B | 76% @ 83 µM |
| 183 | B | 70% @ 8.3 µM |
| 184 | ND | 30% @ 25 µM |
| 185 | ND | 16% @ 2.8 µM |
| 186 | A | 65% @ 2.8 µM |
| 187 | B | 72% @ 25 µM |
| 188 | B | 59% @ 25 µM |
| 189 | B | 96% @ 25 µM |
| 190 | A | 100% @ 2.8 µM |
| 191 | A | 80% @ 8.3 µM |
| 192 | A | 88% @ 25 µM |
| 193 | A | 98% @ 25 µM |
| 194 | ND | 36% @ 2.8 µM |
| 195 | A | 74% @ 0.9 µM |
| 196 | A | 85% @ 2.8 µM |
| 197 | A | 93% @ 2.8 µM |
| 198 | A | 89% @ 2.8 µM |
| 199 | A | 68% @ 0.3 µM |
| 200 | A | 97% @ 2.8 µM |
| 201 | A | 102% @ 2.5 µM |
| 202 | A | 85% @ 8.3 µM |
| 203 | A | 75% @ 2.8 µM |
| 204 | ND | 77% @ 8.3 µM |
| 205 | B | 81% @ 6.3 µM |
| 206 | B | 88% @ 6.3 µM |
| 207 | B | 66% @ 25 µM |
| 208 | B | 56% @ 2.8 µM |
| 209 | A | 98% @ 2.8 µM |
| 210 | A | 99% @ 25 µM |
| 211 | A | 95% @ 25 µM |
| 212 | B | 103% @ 25 µM |
| 213 | A | 92% @ 2.8 µM |
| 214 | A | 95% @ 2.8 µM |
| 215 | B | 95% @ 25 µM |
| 216 | B | 97% @ 25 µM |

TABLE 1-continued

| Example | HC$_{50}$ (μM) | Max HC Protection |
|---|---|---|
| 217 | A | 93% @ 2.8 μM |
| 218 | A | 103% @ 2.8 μM |
| 219 | A | 92% @ 25 μM |
| 220 | A | 98% @ 25 μM |
| 221 | B | 68% @ 25 μM |
| 222 | B | 90% @ 25 μM |
| 223 | B | 104% @ 25 μM |
| 224 | B | 94% @ 12.5 μM |
| 225 | B | 91% @ 25 μM |
| 226 | B | 68% @ 8.3 μM |
| 227 | B | 80% @ 25 μM |
| 228 | B | 93% @ 25 μM |
| 229 | C | 54% @ 25 μM |
| 230 | ND | 48% @ 25 μM |

A: HC50 < 1 μM;
B: 1 μM ≤ HC50 ≤ 10 μM;
C: HC50 > 10 μM;
ND: not determined.

Example 232

Figure 2:
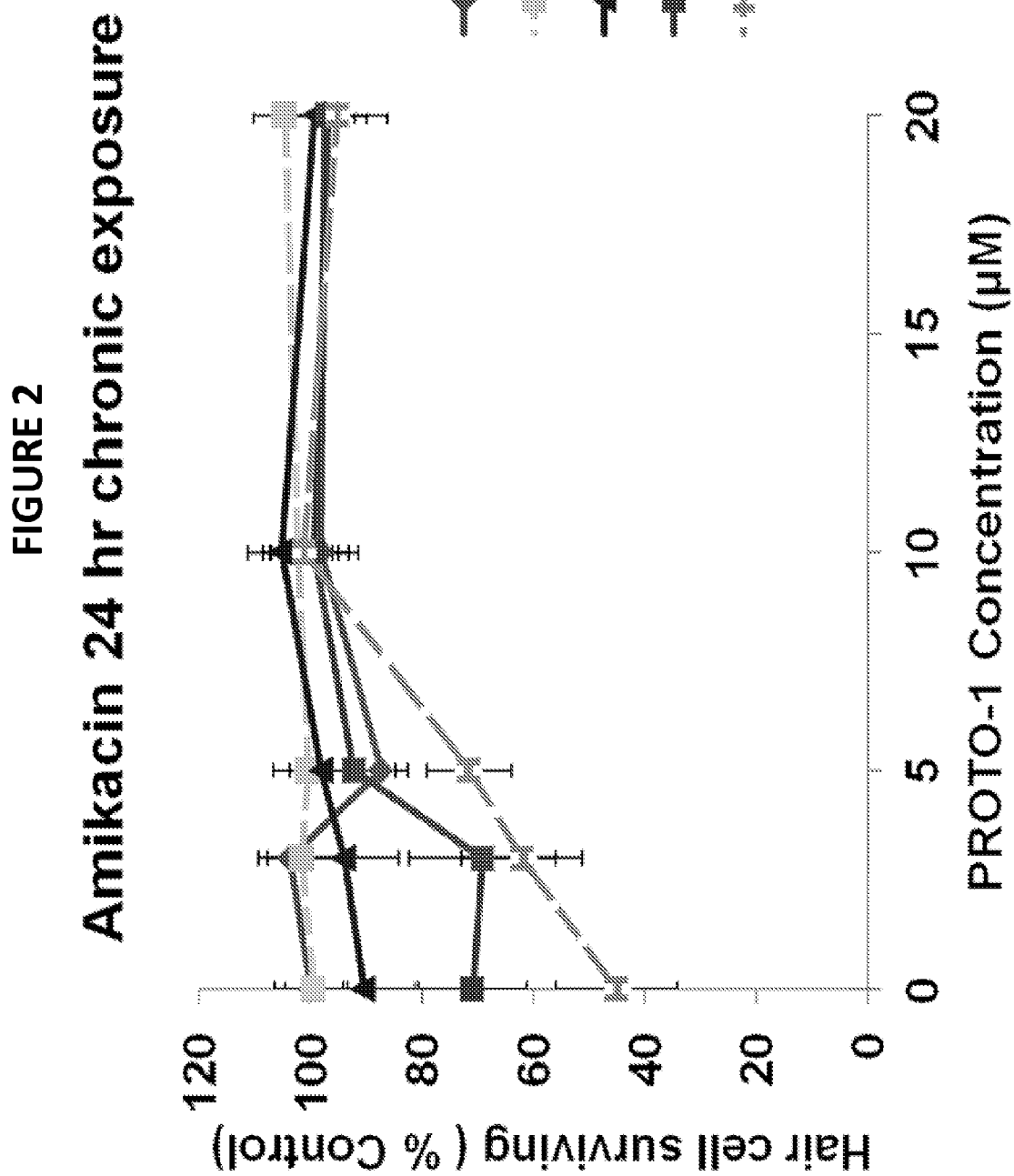
FIG. 2 shows hair cell survival in the zebrafish assay following treatment with amikacin and PROTO-1.
Figure 3:
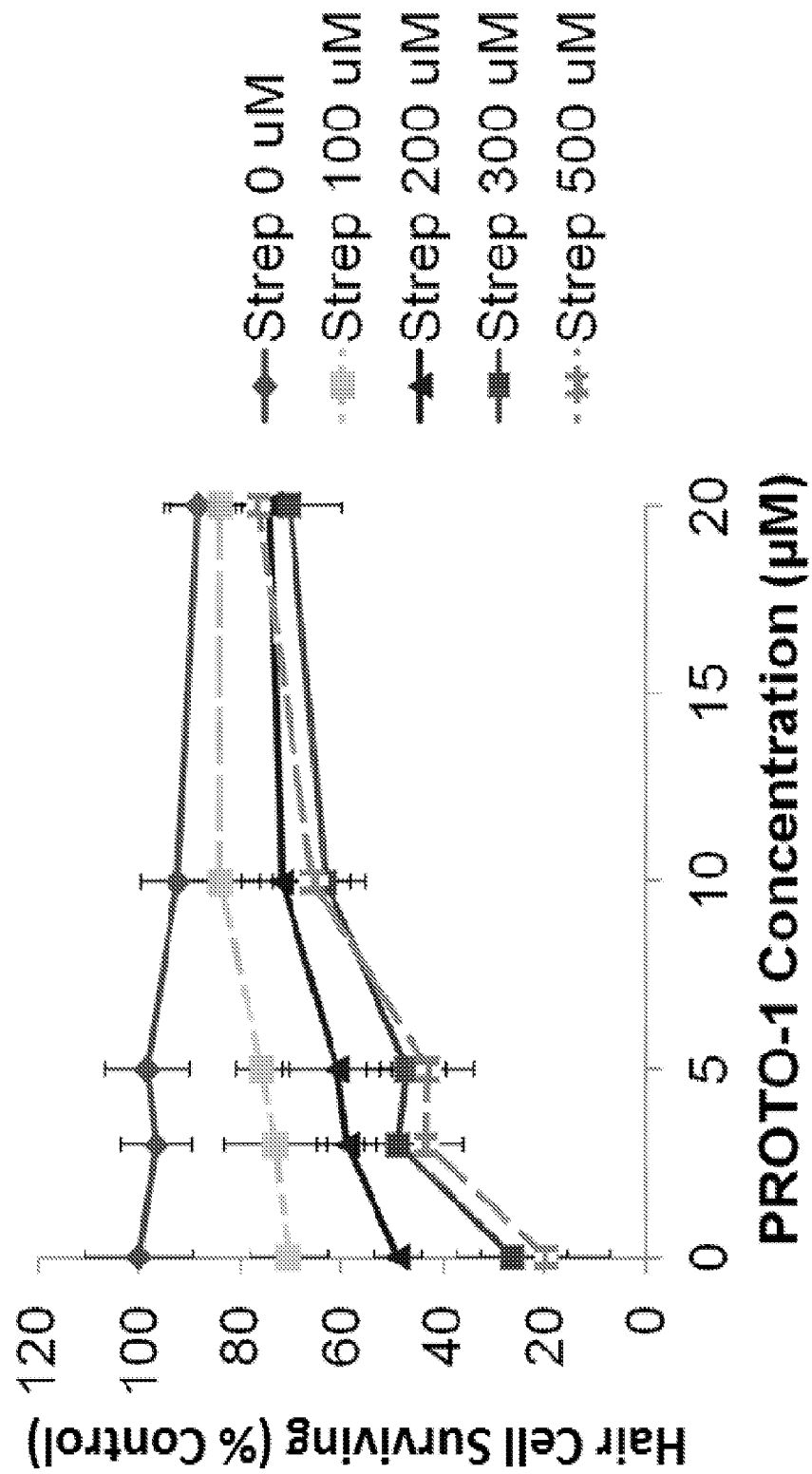
FIG. 3 shows hair cell survival in the zebrafish assay following treatment with streptomycin and PROTO-1.
Figure 4:
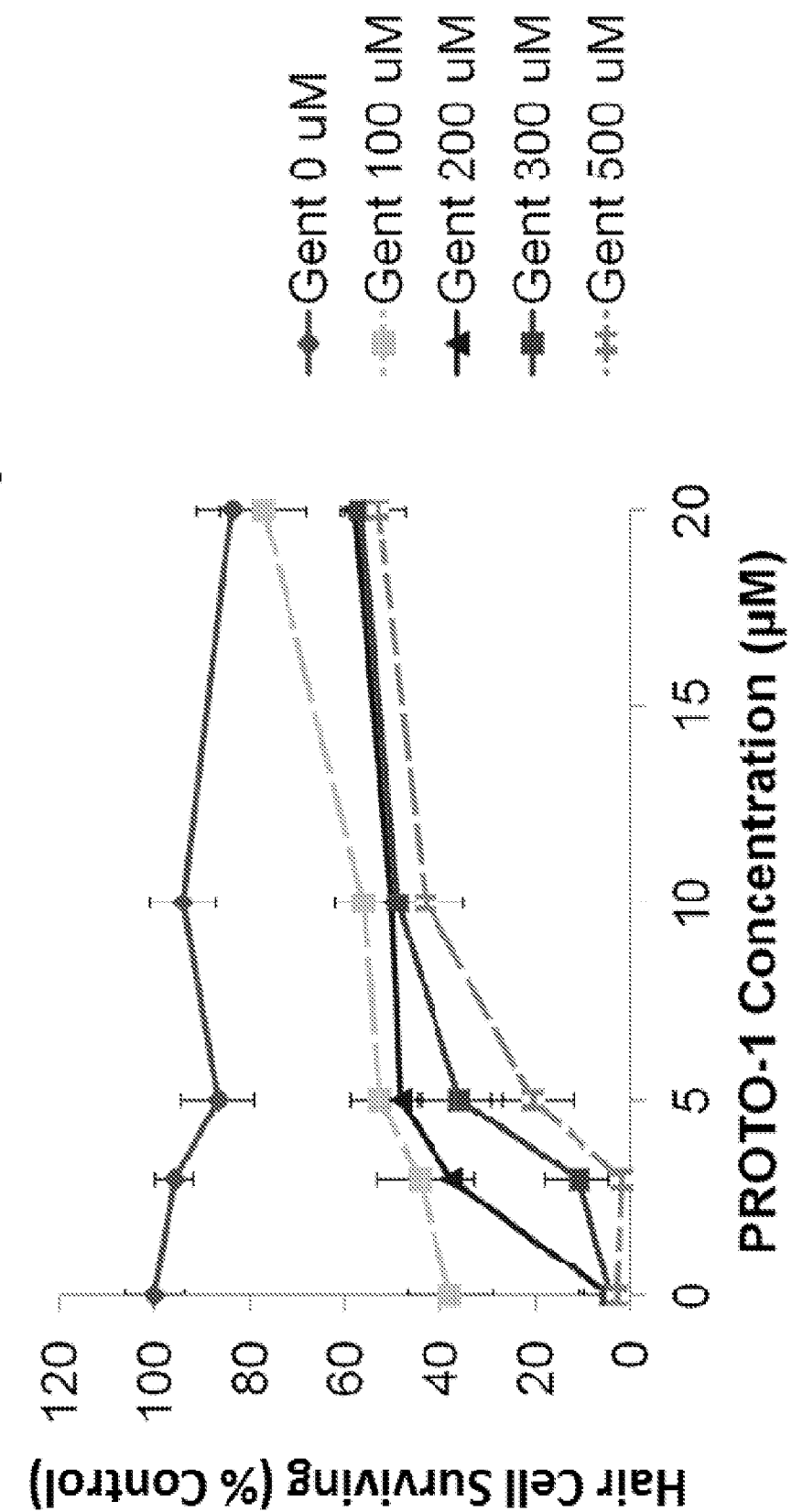
FIG. 4 shows hair cell survival in the zebrafish assay following treatment with gentamicin and PROTO-1.
Figure 5:
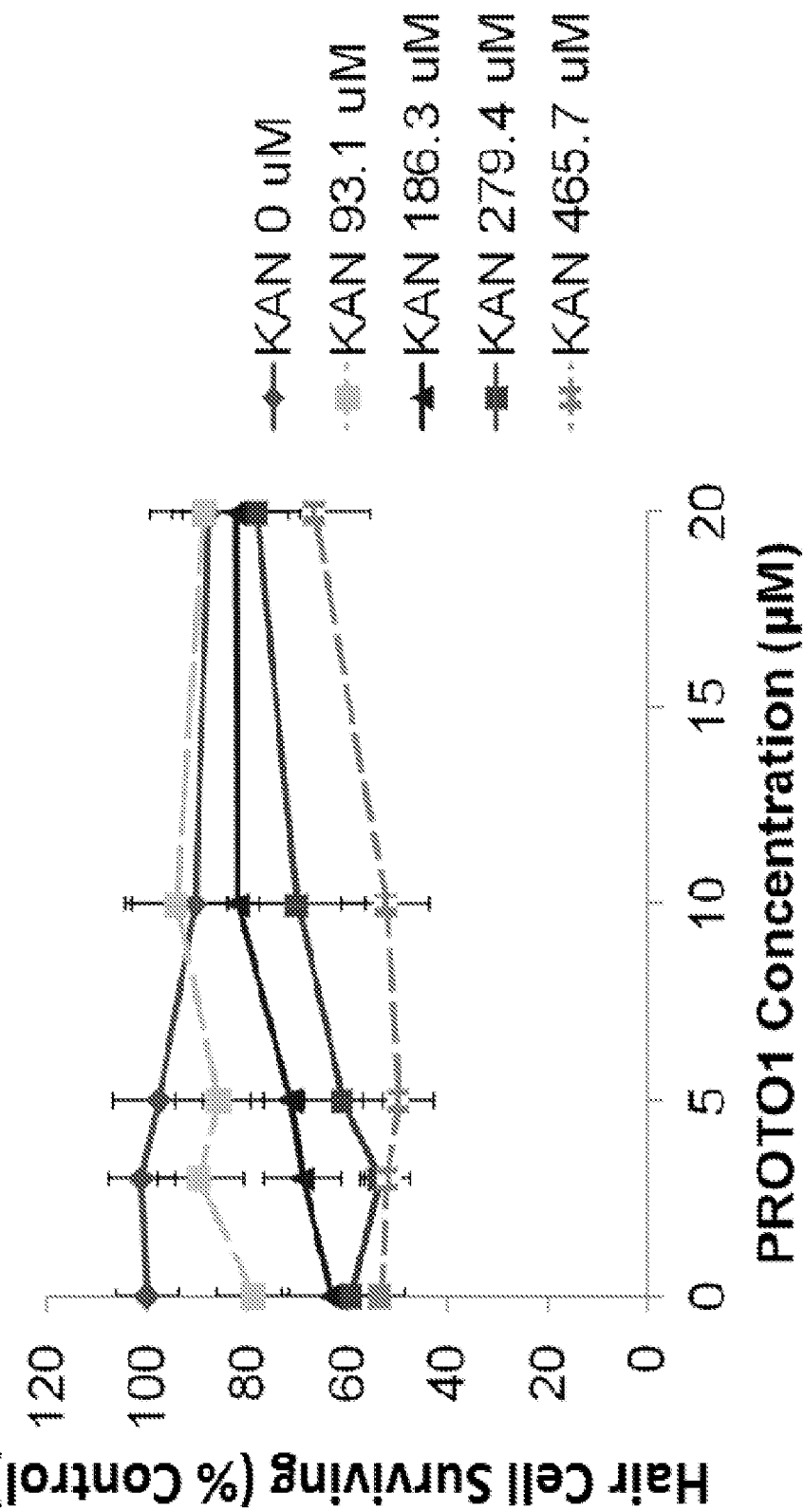
FIG. 5 shows hair cell survival in the zebrafish assay following treatment with kanamycin and PROTO-1.

Hair Cell Toxicity Assay in Zebrafish Treated with Various Aminoglycoside Antibiotics The assay is performed as described in Example 231 with neomycin (FIG. 1), substituting neomycin with amikacin (FIG. 2), substituting neomycin with streptomycin (FIG. 3), substituting neomycin with gentamicin (FIG. 4), and substituting neomycin with kanamycin (FIG. 5), using PROTO-1 (2-(3-(4-chlorophenyl)ureido)-6-ethyl-4,5,6,7-tetrahydrothieno[2,3-c]pyridine-3-carboxamide) as the test compound and varying the concentrations of the aminoglycoside antibiotic.

Example 233

Clinical Trial of the Protective Effect of a Compound of Formula (I)-(VII) Against Ototoxicity Peritonitis is currently one of the leading complications of continuous ambulatory peritoneal dialysis (CAPD). Aminoglycosides and vancomycin are used in the treatment of CAPD peritonitis despite their potential risk for ototoxicity. The purpose of this study is to examine whether ototoxicity due to antibiotics used in the treatment of CAPD peritonitis can be prevented by a compound of Formula (I)-(VII).

Patients: Eligible subjects will be men and women 18-65 years of age.

Inclusion Criteria
  End-stage renal disease
  Undergoing continuous ambulatory peritoneal dialysis as a renal replacement therapy
  Developing the first continuous ambulatory peritoneal dialysis related peritonitis episode Exclusion Criteria
  Being treated with aminoglycoside antibiotics and vancomycine within the previous 3 months
  Detection of mechanical occlusion of external ear
  Having signs of disturbed integrity of tympanic membrane on otoscopy or tympanometry
  History of a continuous ambulatory peritoneal dialysis related peritonitis Study Design:

| Arms | Assigned Interventions |
|---|---|
| Experimental: Compound of Formula (I)-(VII) Compound of Formula (I)-(VII) 600 mg twice daily + vancomycine and/or amikacin | Drug: Compound of Formula (I)-(VII) Compound of Formula (I)-(VII) 600 mg twice a day, one week after administration of antibiotics |
| No Intervention: Control Vancomycine and/or amikacin alone | Drug: Compound of Formula (I)-(VII) Compound of Formula (I)-(VII) 600 mg twice a day, one week after administration of antibiotics |

Primary Outcome Measures
Threshold hearing levels (Time Frame: 4 weeks)

What is claimed is:
1. A compound having the structure of Formula (III):

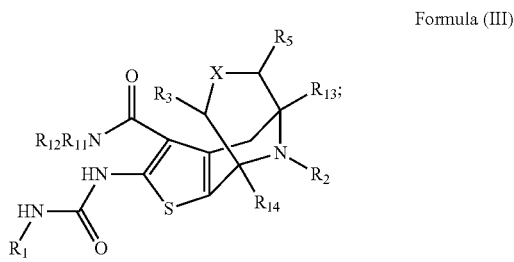

Formula (III)

wherein:
X is a single bond, double bond, —CH$_2$—, or —O—;
R$_1$ is C$_6$-C$_{10}$aryl or C$_3$-C$_9$heteroaryl, wherein C$_6$-C$_{10}$aryl and C$_3$-C$_9$heteroaryl are optionally substituted with one or more R$_4$;
R$_2$ is H, C$_1$-C$_6$alkyl, C$_1$-C$_6$alkyl-OR$_6$, C$_1$-C$_6$alkylC$_3$-C$_6$cycloalkyl, C$_1$-C$_6$alkylC$_2$-C$_7$heterocycloalkyl, C$_1$-C$_6$alkyl-CO$_2$R$_6$, optionally substituted C$_1$-C$_6$alkylC$_6$-C$_{10}$aryl, or optionally substituted C$_1$-C$_6$alkylC$_3$-C$_9$heteroaryl;
R$_3$ are R$_5$ are each independently H, or C$_1$-C$_6$alkyl; or
R$_3$ and R$_5$ together form an optionally substituted C$_3$-C$_6$cycloalkyl ring, optionally substituted C$_2$-C$_7$heterocycloalkyl ring, optionally substituted C$_6$-C$_{10}$aryl ring, or an optionally substituted C$_3$-C$_9$heteroaryl ring;
each R$_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, —C(O)NR$_8$R$_9$, —N(R$_8$)C(O)R$_{10}$, —N(R$_8$)CO$_2$R$_{10}$, —NHS(O)$_2$R$_{10}$, —S(O)$_2$NR$_8$R$_9$, C$_1$-C$_6$alkyl, C$_3$-C$_6$cycloalkyl, C$_1$-C$_6$heteroalkyl, C$_1$-C$_6$haloalkyl, C$_2$-C$_7$heterocycloalkyl, C$_6$-C$_{10}$aryl, and C$_3$-C$_9$heteroaryl;
R$_6$ is H, or C$_1$-C$_6$alkyl;
R$_8$ is H, or C$_1$-C$_6$alkyl;
R$_9$ is H, C$_1$-C$_6$alkyl, C$_3$-C$_6$cycloalkyl, C$_2$-C$_7$heterocycloalkyl, C$_6$-C$_{10}$aryl, C$_3$-C$_9$heteroaryl, C$_1$-C$_6$alkylC$_6$-C$_{10}$aryl, or C$_1$-C$_6$alkylC$_3$-C$_9$heteroaryl;
R$_{10}$ is C$_1$-C$_6$alkyl, C$_3$-C$_6$cycloalkyl, C$_2$-C$_7$heterocycloalkyl, C$_6$-C$_{10}$aryl, C$_3$-C$_9$heteroaryl, C$_1$-C$_6$alkylC$_6$-C$_{10}$aryl, or C$_1$-C$_6$alkylC$_3$-C$_9$heteroaryl;

$R_{11}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

or $R_{11}$ and $R_{12}$ together with the nitrogen to which they are attached form an optionally substituted $C_2$-$C_7$heterocycloalkyl ring; and $R_{13}$ are $R_{14}$ are each independently H, or $C_1$-$C_6$alkyl;

or a pharmaceutically acceptable salt, pharmaceutically acceptable solvate or hydrate, pharmaceutically acceptable salt hydrate, or pharmaceutically acceptable prodrug thereof.

2. The compound of claim 1 wherein $R_1$ is phenyl optionally substituted with one or more $R_4$.

3. The compound of claim 2 wherein $R_1$ is substituted with one $R_4$, wherein $R_4$ is selected from F, Cl, Br, I, —CN, —CF$_3$, —OR$_9$, —OCF$_3$, —C(O)R$_{10}$, —CO$_2$R$_9$, and $C_1$-$C_6$alkyl.

4. The compound of claim 3 wherein $R_{11}$ and $R_{12}$ are each H.

5. The compound of claim 4 wherein $R_3$ and $R_5$ are each H.

6. The compound of claim 5 wherein $R_{13}$ and $R_{14}$ are each CH$_3$.

7. The compound of claim 5 wherein $R_{13}$ and $R_{14}$ are each H.

8. The compound of claim 7 wherein X is a single bond.

9. The compound of claim 8 wherein $R_1$ is 4-chlorophenyl.

10. The compound of claim 9 wherein $R_2$ is H.

11. The compound of claim 9 wherein $R_2$ is $C_1$-$C_6$alkyl.

12. The compound of claim 11 wherein $R_2$ is CH$_3$.

13. The compound of claim 9 wherein $R_2$ is $C_1$-$C_6$alkyl$C_3$-$C_6$cycloalkyl.

14. The compound of claim 13 wherein $R_2$ is —CH$_2$$C_3$-$C_6$cycloalkyl.

15. A pharmaceutical composition comprising a therapeutically effective amount of a compound of claim 1, and a pharmaceutically acceptable excipient.

16. The pharmaceutical composition of claim 15 further comprising an aminoglycoside antibiotic.

17. A method for preventing, treating, and/or protecting against sensory hair cell death in an individual comprising administering to the individual a therapeutically effective amount of a compound of claim 1.

18. The method of claim 17 wherein the sensory hair cell death is associated with exposure to an ototoxic agent.

19. The method of claim 18 wherein the ototoxic agent is an aminoglycoside antibiotic.

20. A compound having the structure of Formula (I):

Formula (I)

wherein:

$R_1$ is $C_6$-$C_{10}$aryl or $C_3$-$C_9$heteroaryl, wherein $C_6$-$C_{10}$aryl and $C_3$-$C_9$heteroaryl are optionally substituted with one or more $R_4$;

$R_2$ is H, $C_1$-$C_4$alkyl, or $C_2$-$C_4$alkenyl;

$R_3$ is $C_2$-$C_6$alkyl, $C_2$-$C_6$alkenyl, $C_1$-$C_4$haloalkyl, optionally substituted $C_3$-$C_6$cycloalkyl, optionally substituted $C_2$-$C_7$heterocycloalkyl, optionally substituted $C_6$-$C_{10}$aryl, —OR$_6$, —NR$_5$R$_6$, —C(O)R$_7$, —CO$_2$R$_6$, —C(O)NR$_5$R$_6$, —N(R$_5$)C(O)R$_7$, —N(R$_5$)CO$_2$R$_7$, —NHS(O)$_2$R$_7$, —S(O)$_2$NR$_5$R$_6$, or $R_2$ and $R_3$ together form an optionally substituted $C_2$-$C_7$heterocycloalkyl ring;

each $R_4$ is independently selected from F, Cl, Br, I, —CN, —NO$_2$, —CF$_3$, —OR$_9$, —OCF$_3$, —NR$_8$R$_9$, —C(O)R$_{10}$, —CO$_2$R$_9$, —C(O)NR$_8$R$_9$, —N(R$_8$)C(O)R$_{10}$, —N(R$_8$)CO$_2$R$_{10}$, —NHS(O)$_2$R$_{10}$, —S(O)$_2$NR$_8$R$_9$, $C_1$-$C_6$alkyl, $C_3$-$C_6$cycloalkyl, $C_1$-$C_6$heteroalkyl, $C_1$-$C_6$haloalkyl, $C_2$-$C_7$heterocycloalkyl, $C_6$-$C_{10}$aryl, and $C_3$-$C_9$heteroaryl;

$R_5$ is H, or $C_1$-$C_6$alkyl;

$R_6$ is H, $C_1$-$C_6$alkyl, optionally substituted $C_3$-$C_6$cycloalkyl, optionally substituted $C_2$-$C_7$heterocycloalkyl, optionally substituted $C_6$-$C_{10}$aryl, optionally substituted $C_3$-$C_9$heteroaryl, optionally substituted $C_1$-$C_6$alkyl$C_6$-$C_{10}$aryl, or optionally substituted $C_1$-$C_6$alkyl$C_3$-$C_9$heteroaryl;

$R_7$ is $C_1$-$C_6$alkyl, optionally substituted $C_3$-$C_6$cycloalkyl, optionally substituted $C_2$-$C_7$heterocycloalkyl, optionally substituted $C_6$-$C_{10}$aryl, $C_3$-$C_9$heteroaryl, optionally substituted $C_1$-$C_6$alkyl$C_6$-$C_{10}$aryl, or optionally substituted $C_1$-$C_6$alkyl$C_3$-$C_9$heteroaryl;

$R_8$ is H, or $C_1$-$C_6$alkyl;

$R_9$ is H, $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

$R_{10}$ is $C_1$-$C_6$alkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_6$-$C_{10}$aryl, or $C_1$-$C_6$alkyl$C_3$-$C_9$heteroaryl;

$R_{11}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl;

$R_{12}$ is H, $C_1$-$C_6$alkyl, $C_1$-$C_6$haloalkyl, $C_3$-$C_6$cycloalkyl, $C_2$-$C_7$heterocycloalkyl, $C_6$-$C_{10}$aryl, $C_3$-$C_9$heteroaryl, $C_1$-$C_6$alkyl$C_3$-$C_6$cycloalkyl, $C_1$-$C_6$alkyl$C_6$-$C_{10}$aryl, or $C_1$-$C_6$alkyl$C_3$-$C_9$heteroaryl; or $R_{11}$ and $R_{12}$ together with the nitrogen to which they are attached form an optionally substituted $C_2$-$C_7$heterocycloalkyl ring;

$R_{13}$, $R_{14}$, $R_{15}$, and $R_{16}$ are each independently H, or $C_1$-$C_4$alkyl;

n is an integer selected from 0-4;

p is an integer selected from 0-3; and
q is an integer selected from 0-3;
or a pharmaceutically acceptable salt, pharmaceutically acceptable solvate or hydrate, pharmaceutically acceptable salt hydrate, or pharmaceutically acceptable prodrug thereof.

* * * * *